(12) United States Patent
Brace et al.

(10) Patent No.: US 10,287,299 B2
(45) Date of Patent: May 14, 2019

(54) SUBSTITUTED BENZO[B][1,4]OXAZINES AND PYRIDO[3,2-B][1,4]OXAZINES AS MODULATORS OF TUMOR NECROSIS FACTOR ACTIVITY

(71) Applicant: UCB Biopharma SPRL, Brussels (BE)

(72) Inventors: Gareth Neil Brace, Abingdon (GB); Prafulkumar Tulshibhai Chovatia, Abingdon (GB); Gregory Foulkes, Abingdon (GB); James Andrew Johnson, Slough (GB); Severine Danielle Jones, Abingdon (GB); Boris Kroeplien, Slough (GB); Fabien Claude Lecomte, Slough (GB); Pui Leng Loke, Abingdon (GB); Martin Alexander Lowe, Slough (GB); Ajay Mandal, Abingdon (GB); Timothy John Norman, Slough (GB); Christopher Francis Palmer, Abingdon (GB); Yolanda Pérez-Fuertes, Abingdon (GB); John Robert Porter, Slough (GB); Donald Smyth, Abingdon (GB); Giancarlo Trani, Abingdon (GB); Muhammed Uddin, Abingdon (GB); Zhaoning Zhu, Slough (GB)

(73) Assignee: UCB Biopharma SPRL, Brussels (BE)

( * ) Notice: Subject to any disclaimer, the term of this patent is extended or adjusted under 35 U.S.C. 154(b) by 0 days.

(21) Appl. No.: 15/580,059

(22) PCT Filed: Jun. 7, 2016

(86) PCT No.: PCT/EP2016/062900
§ 371 (c)(1),
(2) Date: Dec. 6, 2017

(87) PCT Pub. No.: WO2016/198400
PCT Pub. Date: Dec. 15, 2016

(65) Prior Publication Data
US 2018/0134728 A1 May 17, 2018

(30) Foreign Application Priority Data

Jun. 8, 2015 (GB) .................................. 1509893.2

(51) Int. Cl.
*A61K 31/5365* (2006.01)
*C07D 265/36* (2006.01)
(Continued)

(52) U.S. Cl.
CPC .......... *C07D 498/04* (2013.01); *A61K 31/423* (2013.01); *A61K 31/4375* (2013.01); *A61K 31/444* (2013.01); *A61K 31/4545* (2013.01); *A61K 31/473* (2013.01); *A61K 31/4725* (2013.01); *A61K 31/538* (2013.01); *A61K 31/5383* (2013.01); *A61K 31/55* (2013.01); *A61P 3/00* (2018.01); *A61P 9/00* (2018.01); *A61P 23/00* (2018.01); *A61P 25/00* (2018.01); *A61P 27/02* (2018.01); *A61P 29/00* (2018.01); *A61P 35/00* (2018.01); *C07D 401/06* (2013.01); *C07D 413/06* (2013.01); *C07D 413/12* (2013.01); *C07D 413/14* (2013.01); *C07D 471/04* (2013.01); *C07D 519/00* (2013.01)

(58) Field of Classification Search
CPC .............. A61K 31/536; A61K 31/5365; C07D 265/36; C07D 498/04
USPC ........................................ 514/230.5; 544/105
See application file for complete search history.

(56) References Cited

U.S. PATENT DOCUMENTS

| 4,902,335 | A | 2/1990 | Kume et al. |
| 5,084,084 | A | 1/1992 | Satow et al. |
| 2004/0097504 | A1 | 5/2004 | Bethiel |

FOREIGN PATENT DOCUMENTS

| WO | WO 01/030782 | * | 5/2001 |
| WO | WO 2013/186229 | | 12/2013 |

(Continued)

OTHER PUBLICATIONS

Yu, et al. Tetrahedron, 69(48), 2013, 10488-10496.*

(Continued)

*Primary Examiner* — Douglas M Willis
(74) *Attorney, Agent, or Firm* — McDonnell Boehnen Hulbert & Berghoff LLP

(57) ABSTRACT

A series of substituted 3,4-dihydro-2H-.1,4-benzoxazin-3-one derivatives, and analogs thereof, being potent modulators of human TNFa activity, are accordingly of benefit in the treatment and/or prevention of various human ailments, including autoimmune and inflammatory disorders; neurological and neuradegenerative disorders; pain and nociceptive disorders; cardiovascular disorders; metabolic disorders; ocular disorders; and oncological disorders.

6 Claims, No Drawings

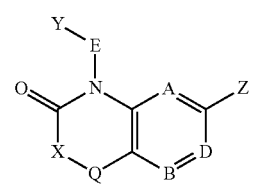

(51) Int. Cl.

| | |
|---|---|
| *C07D 498/04* | (2006.01) |
| *C07D 401/06* | (2006.01) |
| *C07D 413/06* | (2006.01) |
| *A61P 27/02* | (2006.01) |
| *A61P 3/00* | (2006.01) |
| *A61P 9/00* | (2006.01) |
| *A61P 23/00* | (2006.01) |
| *A61P 25/00* | (2006.01) |
| *A61P 29/00* | (2006.01) |
| *A61P 35/00* | (2006.01) |
| *A61K 31/423* | (2006.01) |
| *A61K 31/4375* | (2006.01) |
| *A61K 31/444* | (2006.01) |
| *A61K 31/4545* | (2006.01) |
| *A61K 31/4725* | (2006.01) |
| *A61K 31/473* | (2006.01) |
| *A61K 31/538* | (2006.01) |
| *A61K 31/5383* | (2006.01) |
| *A61K 31/55* | (2006.01) |
| *C07D 413/12* | (2006.01) |
| *C07D 413/14* | (2006.01) |
| *C07D 471/04* | (2006.01) |
| *C07D 519/00* | (2006.01) |

(56) References Cited

FOREIGN PATENT DOCUMENTS

| | | |
|---|---|---|
| WO | WO 2014/009295 | 1/2014 |
| WO | WO 2014/009296 | 1/2014 |
| WO | WO 2015/086506 | 6/2015 |

OTHER PUBLICATIONS

Jordan, V. C. Nature Reviews: Drug Discovery, 2, 2003, 205.*
Hackam, et al. JAMA, 296(14), 2006, 1731-1732.*
Tansey & Szymkowski, "The TNF superfamily in 2009: new pathways, new indications, and new drugs," Drug Discovery Today, Oct. 2009, 14:1082-1088.
Carneiro et al., "Emerging Role for TNF-a in Erectile Dysfunction," J. Sexual Medicine, Dec. 1, 2010, 7(12): 3823-3834.
Wu et al., "Do TNF Inhibitors Reduce the Risk of Myocardial Infarction in Psoriasis Patients?" JAMA, May 15, 2013, vol. 309, No. 19, pp. 2043-2044.
Van Hauwermeiren et al., "Safe TNF-based antitumor therapy following p55TNFR reduction in intestinal epithelium," J. Clin Invest., Jun. 2013, vol. 123, No. 6, pp. 2590-2603.
Haider et al., "Synthesis of novel 1,2,3-triazole based benzoxazolinones: Their TNF-a based molecular docking with in-vivo anti-inflammatory, antinociceptive activities and ulcerogenic risk evaluation,"European Journal of Medicinal Chemistry, 70 (May 30, 2013) 579-588.
Teno et al., "Novel type of plasmin inhibitors: Providing insight into P4 moiety and alternative scaffold to pyrrolopyrimidine," Bioorganic & Medicinal Chemistry 23 (Apr. 10, 2015) 3696-3704.

* cited by examiner

SUBSTITUTED BENZO[B][1,4]OXAZINES AND PYRIDO[3,2-B][1,4]OXAZINES AS MODULATORS OF TUMOR NECROSIS FACTOR ACTIVITY

CROSS-REFERENCE TO RELATED APPLICATIONS

This application is a U.S. national phase application under 35 USC 371 of International Patent Application no. PCT/EP2016/062900, filed Jun. 7, 2016, which claims the benefit of Great Britain Application no. 1509893.2, filed Jun. 8, 2015.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

(1) Field of the Invention

The present invention relates to a class of heterocyclic compounds, and to their use in therapy. More particularly, this invention is concerned with pharmacologically active substituted 3,4-dihydro-2H-1,4-benzoxazin-3-one derivatives, and analogues thereof. These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

(2) Description of Related Art

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

BRIEF SUMMARY OF THE INVENTION

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

Certain specific 1,2,3-triazol-4-ylmethyl-substituted 1,3-benzoxazol-2(3H)-one derivatives, one of which (referred to as compound 3i) is stated to show significant TNFα inhibitory activity as compared to indomethacin, are described by S. Haider et al. in *Eur. J. Med. Chem.*, 2013, 70, 579. There is, however, no disclosure in that publication of a compound wherein $R_1$ is anything other than hydrogen, chloro or methyl.

WO 2013/186229, WO 2014/009295 and WO 2014/009296 describe fused imidazole derivatives which are modulators of human TNFα activity.

Co-pending international patent application PCT/EP2014/076845, published on 18 Jun. 2015 as WO 2015/086506, describes fused imidazole and pyrazole derivatives which are modulators of human TNFα activity.

None of the prior art available to date, however, discloses or suggests the precise structural class of heterocyclic compounds as provided by the present invention.

BRIEF DESCRIPTION OF THE SEVERAL VIEWS OF THE DRAWING(S)

Not Applicable

DETAILED DESCRIPTION OF THE INVENTION

The present invention provides a compound of formula (I) or an N-oxide thereof, or a pharmaceutically acceptable salt thereof:

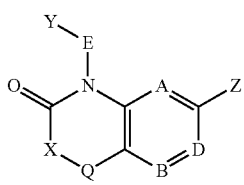

wherein

A represents C—R⁰ or N;

B represents C—R¹ or N;

D represents C—R² or N;

E represents a covalent bond; or E represents —O—, —S—, —S(O)—, —S(O)$_2$—, —S(O)(NR$^3$)— or —N(R$^3$)—; or E represents an optionally substituted straight or branched $C_{1-4}$ alkylene chain;

Q represents —O—, —S—, —S(O)—, —S(O)$_2$—, —S(O)(NR$^4$)—, —N(R$^4$)—, —C(O)— or —C(R$^{5a}$)(R$^{5b}$)—;

X represents a covalent bond; or X represents a group of formula —C(R$^{6a}$)(R$^{6b}$)—, —CH$_2$C(R$^{6a}$)(R$^{6b}$)— or —C(R$^{6a}$)(R$^{6b}$)CH$_2$—; or X represents —O— when Q represents —C(O)— or —C(R$^{5a}$)(R$^{5b}$)—;

Y represents heteroaryl, which group may be optionally substituted by one or more substituents;

Z represents $C_{3-7}$ cycloalkyl, $C_{4-7}$ cycloalkenyl, aryl, $C_{3-7}$ heterocycloalkyl, $C_{3-7}$ heterocycloalkenyl or heteroaryl, any of which groups may be optionally substituted by one or more substituents;

R⁰ represents hydrogen, halogen or $C_{1-6}$ alkyl;

R¹ and R² independently represent hydrogen, halogen, cyano, $C_{1-6}$ alkyl, fluoromethyl, difluoromethyl, trifluoromethyl, hydroxy, hydroxy($C_{1-6}$)alkyl, $C_{1-6}$ alkoxy, difluoromethoxy, trifluoromethoxy, pentafluorothio, $C_{1-6}$ alkylthio, $C_{1-6}$ alkylsulphinyl, $C_{1-6}$ alkylsulphonyl, amino, amino ($C_{1-6}$)alkyl, $C_{1-6}$ alkylamino, di($C_{1-6}$)alkylamino, formyl, $C_{2-6}$ alkylcarbonyl, carboxy, $C_{2-6}$ alkoxycarbonyl, aminocarbonyl, $C_{1-6}$ alkyl-aminocarbonyl, di($C_{1-6}$)alkylaminocarbonyl, aminosulphonyl, $C_{1-6}$ alkylaminosulphonyl, di($C_{1-6}$)alkylaminosulphonyl, ($C_{1-6}$)alkylsulphoximinyl or [($C_{1-6}$)alkyl][N—($C_{1-6}$)alkyl]-sulphoximinyl;

R³ represents hydrogen or $C_{1-6}$ alkyl;

R⁴ represents hydrogen or $C_{1-6}$ alkyl;

R$^{5a}$ and R$^{5b}$ independently represent hydrogen or $C_{1-6}$ alkyl; and

R$^{6a}$ and R$^{6b}$ independently represent hydrogen, halogen, trifluoromethyl or $C_{1-6}$ alkyl; or R$^{6a}$ and R$^{6b}$, when taken together with the carbon atom to which they are both attached, represent $C_{3-7}$ cycloalkyl or $C_{3-7}$ heterocycloalkyl, either of which groups may be optionally substituted by one or more substituents; or R$^{5a}$ and R$^{6a}$, when taken together with the two intervening carbon atoms, represent $C_{3-7}$ cycloalkyl or $C_{3-7}$ heterocycloalkyl, either of which groups may be optionally substituted by one or more substituents.

The present invention also provides a compound of formula (I) as defined above or an N-oxide thereof, or a pharmaceutically acceptable salt thereof, for use in therapy.

The present invention also provides a compound of formula (I) as defined above or an N-oxide thereof, or a pharmaceutically acceptable salt thereof, for use in the treatment and/or prevention of disorders for which the administration of a modulator of TNFα function is indicated.

In another aspect, the present invention provides a compound of formula (I) as defined above or an N-oxide thereof, or a pharmaceutically acceptable salt thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above or an N-oxide thereof, or a pharmaceutically acceptable salt thereof.

In another aspect, the present invention provides a method for the treatment and/or prevention of an inflammatory or autoimmune disorder, a neurological or neuro-degenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one, two or three substituents.

For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-4}$ alkylene chain" refers to a divalent straight or branched alkylene chain containing 1 to 4 carbon atoms. Typical examples include methylene, ethylene, methylmethylene, ethylmethylene and dimethylmethylene.

Suitable $C_{2-6}$ alkenyl groups include vinyl and allyl.

Suitable $C_{2-6}$ alkynyl groups include ethynyl, propargyl and butynyl.

The term "$C_{3-7}$ cycloalkyl" as used herein refers to monovalent groups of 3 to 7 carbon atoms derived from a saturated monocyclic hydrocarbon, and may comprise benzo-fused analogues thereof. Suitable $C_{3-7}$ cycloalkyl groups include cyclopropyl, cyclobutyl, benzocyclobutenyl, cyclopentyl, indanyl, cyclohexyl and cycloheptyl.

The term "$C_{4-7}$ cycloalkenyl" as used herein refers to monovalent groups of 4 to 7 carbon atoms derived from a partially unsaturated monocyclic hydrocarbon. Suitable $C_{4-7}$ cycloalkenyl groups include cyclobutenyl, cyclopentenyl, cyclohexenyl and cycloheptenyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, dihydrobenzoisothiazolyl, imidazolidinyl, tetrahydro-pyranyl, chromanyl, tetrahydrothiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]pyrazinyl, homopiperazinyl, morpholinyl, benzoxazinyl, thiomorpholinyl, azepanyl, oxazepanyl, diazepanyl, thiadiazepanyl and azocanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, isothiazolinyl, imidazolinyl, dihydropyranyl, dihydrothiopyranyl and 1,2,3,6-tetrahydropyridinyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, 4,5,6,7-tetrahydrobenzothienyl, thieno[2,3-c]-pyrazolyl, thieno[3,4-b][1,4]dioxinyl, 4,5,6,7,8-pentahydrothieno[3,2-c]azepinyl, dibenzothienyl, pyrrolyl, indolyl, pyrrolo[2,3-b]pyridinyl, pyrrolo[3,2-c]pyridinyl, pyrrolo[3,4-b]pyridinyl, pyrrolo[2,1-f][1,2,4]triazinyl, pyrazolyl, indazolyl, 4,5,6,7-tetrahydroindazolyl, pyrazolo[1,5-a]pyridinyl, pyrazolo[4,3-b]pyridinyl, pyrazolo[3,4-d]-pyrimidinyl, oxazolyl, benzoxazolyl, isoxazolyl, thiazolyl, benzothiazolyl, 4,5,6,7,8-pentahydrothiazolo[4,5-c]azepinyl, 4,5,6,7,8-pentahydrothiazolo[5,4-c]azepinyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔enol ($CH=CHOH$) tautomers or amide ($NHC=O$), hydroxyimine ($N=COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

Suitably, X represents a covalent bond, or a group of formula —$C(R^{6a})(R^{6b})$—.

In a first embodiment, X represents a covalent bond, whereby the integer Q is attached directly to the carbonyl (C=O) group.

In a second embodiment, X represents a group of formula —$C(R^{6a})(R^{6b})$—.

In a third embodiment, X represents a group of formula —$CH_2C(R^{6a})(R^{6b})$—.

In a fourth embodiment, X represents a group of formula —$C(R^{6a})(R^{6b})CH_2$—.

In a fifth embodiment, X represents —O— when Q represents —C(O)—.

In a sixth embodiment, X represents —O— when Q represents —$C(R^{5a})(R^{5b})$.

Specific sub-classes of compounds in accordance with the present invention are represented by the compounds of formula (IA), (IB), (IC), (ID), (IE) and (IF):

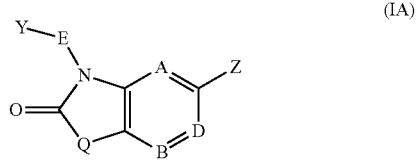

(IA)

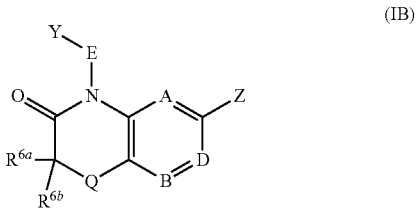

(IB)

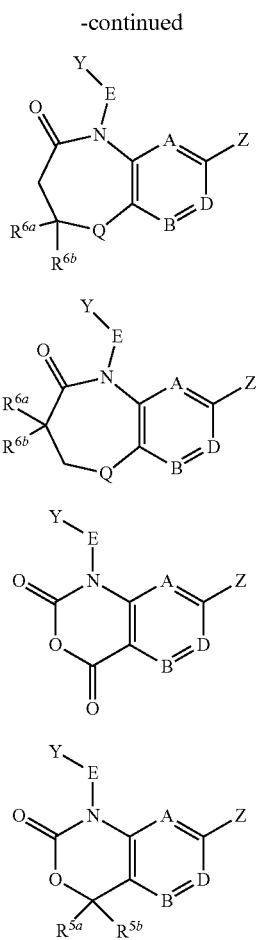

wherein A, B, D, E, Y, Z, $R^{5a}$, $R^{5b}$, $R^{6a}$ and $R^{6b}$ are as defined above.

Suitably, the present invention provides a compound of formula (IA) or (IB) as depicted above, or an N-oxide thereof, or a pharmaceutically acceptable salt thereof.

In a first embodiment, the present invention provides a compound of formula (IA) as depicted above, or an N-oxide thereof, or a pharmaceutically acceptable salt thereof.

In a second embodiment, the present invention provides a compound of formula (IB) as depicted above, or an N-oxide thereof, or a pharmaceutically acceptable salt thereof.

In a third embodiment, the present invention provides a compound of formula (IC) as depicted above, or an N-oxide thereof, or a pharmaceutically acceptable salt thereof.

In a fourth embodiment, the present invention provides a compound of formula (ID) as depicted above, or an N-oxide thereof, or a pharmaceutically acceptable salt thereof.

In a fifth embodiment, the present invention provides a compound of formula (IE) as depicted above, or an N-oxide thereof, or a pharmaceutically acceptable salt thereof.

In a sixth embodiment, the present invention provides a compound of formula (IF) as depicted above, or an N-oxide thereof, or a pharmaceutically acceptable salt thereof.

In one embodiment, A represents C—$R^0$. In another embodiment, A represents N.

In one embodiment, B represents C—$R^1$. In another embodiment, B represents N.

In one embodiment, D represents C—$R^2$. In another embodiment, D represents N.

In a first embodiment, A represents C—$R^0$, B represents C—$R^1$ and D represents C—$R^2$.

In a second embodiment, A represents C—$R^0$, B represents C—$R^1$ and D represents N.

In a third embodiment, A represents C—$R^0$, B represents N and D represents C—$R^2$.

In a fourth embodiment, A represents C—$R^0$, B represents N and D represents N.

In a fifth embodiment, A represents N, B represents C—$R^1$ and D represents C—$R^2$.

In a sixth embodiment, A represents N, B represents C—$R^1$ and D represents N.

In a seventh embodiment, A represents N, B represents N and D represents C—$R^2$.

In an eighth embodiment, A represents N, B represents N and D represents N.

Typically, A represents C—$R^0$, B represents C—$R^1$ and D represents C—$R^2$; or A represents C—$R^0$, B represents N and D represents C—$R^2$; or A represents N, B represents C—$R^1$ and D represents C—$R^2$.

Suitably, A represents C—$R^0$, B represents C—$R^1$ and D represents C—$R^2$; or A represents N, B represents C—$R^1$ and D represents C—$R^2$.

Where the compounds in accordance with the invention comprise an optionally substituted straight or branched alkylene chain, typical values thereof include methylene (—$CH_2$—), (methyl)methylene, ethylene (—$CH_2CH_2$—), (ethyl)methylene, (dimethyl)-methylene, (methyl)ethylene, propylene (—$CH_2CH_2CH_2$—), (propyl)methylene and (dimethyl)ethylene, any of which chains may be optionally substituted by one or more substituents. Suitably, such chains are unsubstituted, monosubstituted or disubstituted. Typically, such chains are unsubstituted or monosubstituted. In one embodiment, such chains are unsubstituted. In another embodiment, such chains are monosubstituted. In a further embodiment, such chains are disubstituted.

Examples of typical substituents on the alkylene chain which may be present in a compound in accordance with the invention include halogen, cyano, trifluoromethyl, oxo, hydroxy, $C_{1-6}$ alkoxy, carboxy($C_{1-6}$)alkoxy, trifluoromethoxy, amino, $C_{1-6}$ alkylamino, di($C_{1-6}$)alkylamino, $C_{2-6}$ alkylcarbonylamino, carboxy, benzyloxycarbonyl, tetrazolyl, aminocarbonyl, $C_{1-6}$ alkylaminocarbonyl and di($C_{1-6}$)alkylaminocarbonyl.

Specific examples of suitable substituents on the alkylene chain which may be present in a compound in accordance with the invention include fluoro, cyano, trifluoromethyl, oxo, hydroxy, methoxy, carboxymethoxy, amino, acetylamino, carboxy, benzyloxycarbonyl and tetrazolyl.

In a first embodiment, E represents a covalent bond, whereby the integer Y is attached directly to the nitrogen atom in the Q-containing ring.

In a second embodiment, E represents —O—, —S—, —S(O)—, —S(O)$_2$—, —S(O)(N$R^3$)— or —N($R^3$)—. In a first aspect of that embodiment, E represents —O—. In a second aspect of that embodiment, E represents —S—. In a third aspect of that embodiment, E represents —S(O)—. In a fourth aspect of that embodiment, E represents —S(O)$_2$—. In a fifth aspect of that embodiment, E represents —S(O)(N$R^3$)—. In a sixth aspect of that embodiment, E represents —N($R^3$)—.

In a third embodiment, E represents an optionally substituted straight or branched $C_{1-4}$ alkylene chain. In a first aspect of that embodiment, E represents an optionally substituted methylene (—$CH_2$—) linkage. In a second aspect of that embodiment, E represents an optionally substituted (methyl)methylene linkage. In a third aspect of that embodiment, E represents an optionally substituted (ethyl)methylene linkage.

Generally, E represents a covalent bond; or E represents —N(R³)—; or E represents an optionally substituted straight or branched C$_{1-4}$ alkylene chain.

Typically, E represents —N(R³)—; or E represents an optionally substituted straight or branched C$_{1-4}$ alkylene chain.

Suitably, E represents a covalent bond; or E represents —N(R³)—; or E represents methylene (—CH$_2$—), (methyl)methylene or (ethyl)methylene, any of which groups may be optionally substituted by one or more substituents.

Generally, E represents —N(R³)—; or E represents methylene (—CH$_2$—) or (methyl)methylene, either of which groups may be optionally substituted by one or more substituents.

Appositely, E represents methylene (—CH$_2$—) or (methyl)methylene, either of which groups may be optionally substituted by one or more substituents.

Selected examples of typical substituents on the linkage represented by E include halogen, trifluoromethyl, oxo, hydroxy, C$_{1-6}$ alkoxy, carboxy(C$_{1-6}$)alkoxy, trifluoromethoxy, amino, C$_{1-6}$ alkylamino, di(C$_{1-6}$)alkylamino, C$_{2-6}$ alkylcarbonylamino, carboxy, benzyloxycarbonyl and tetrazolyl.

Specific examples of typical substituents on the linkage represented by E include fluoro, trifluoromethyl, oxo, hydroxy, methoxy, carboxymethoxy, trifluoromethoxy, amino, methylamino, dimethylamino, acetylamino, carboxy, benzyloxycarbonyl and tetrazolyl.

Typical values of E include —N(R³)—, —CH$_2$—, —C(O)—, —CH(OH)—, —CH(OCH$_3$)—, —CH(OCH$_2$CO$_2$H)—, —CH(NH$_2$)—, —CH(NHCOCH$_3$)—, —CH(CO$_2$H)—, —CH(CO$_2$benzyl)-, —CH(CH$_3$)—, —C(CH$_3$)(OH)— and —CH(CH$_2$CH$_3$)—; or E may represent a covalent bond.

Suitable values of E include —CH$_2$— and —CH(CH$_3$)—.

In one embodiment, E represents —CH$_2$—.

In another embodiment, E represents —CH(CH$_3$)—.

Suitably, Q represents —O— or —C(R$^{5a}$)(R$^{5b}$)—.

In a first embodiment, Q represents —O—. In a second embodiment, Q represents —S—. In a third embodiment, Q represents —S(O)—. In a fourth embodiment, Q represents —S(O)$_2$—. In a fifth embodiment, Q represents —S(O)(NR$^4$)—. In a sixth embodiment, Q 5 represents —N(R$^4$)—. In a seventh embodiment, Q represents —C(O)—. In an eighth embodiment, Q represents —C(R$^{5a}$)(R$^{5b}$)—.

Particular sub-classes of compounds in accordance with the present invention include the compounds of formula (IA-1), (IB-1), (IB-2), (IB-3), (IB-4) and (IB-5):

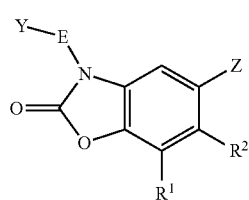
(IA-1)

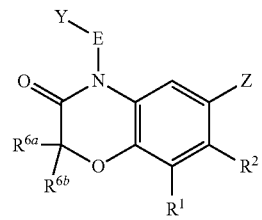
(IB-1)

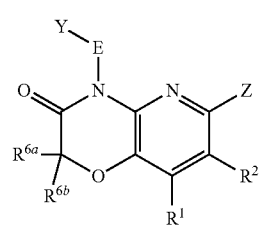
(IB-2)

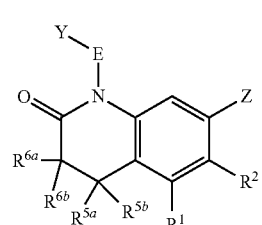
(IB-3)

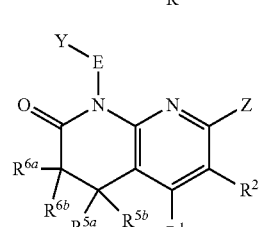
(IB-4)

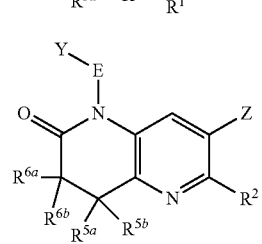
(IB-5)

wherein E, Y, Z, R$^1$, R$^2$, R$^{5a}$, R$^{5b}$, R$^{6a}$ and R$^{6b}$ are as defined above.

Suitably, the optionally substituted heteroaryl moiety Y may be an optionally substituted monocyclic heteroaryl ring; or an optionally substituted fused bicyclic heteroaryl ring system.

In a first embodiment, Y represents a monocyclic heteroaryl ring, which may be optionally substituted by one or more substituents. Typical examples of monocyclic heteroaryl rings for Y include pyrazolyl, isoxazolyl, imidazolyl, triazolyl, pyridinyl, pyridazinyl and pyrimidinyl.

In a second embodiment, Y represents a fused bicyclic heteroaryl ring system, which may be optionally substituted by one or more substituents. Typical examples of fused bicyclic heteroaryl ring systems for Y include imidazo[1,2-a]pyridinyl and imidazo[1,2-a]pyrazinyl.

Typically, the heteroaryl moiety Y may be unsubstituted, or substituted by one, two or three substituents. In a first embodiment, Y is unsubstituted. In a second embodiment, Y is monosubstituted. In a third embodiment, Y is disubstituted. In a fourth embodiment, where valency allows, Y is trisubstituted.

Typically, Y represents pyrazolyl, isoxazolyl, imidazolyl, imidazo[1,2-a]pyridinyl, imidazo[1,2-a]pyrazinyl, triazolyl, pyridinyl, pyridazinyl or pyrimidinyl, any of which groups may be optionally substituted by one or more substituents.

Typical examples of optional substituents on the heteroaryl moiety Y include halogen, $C_{1-6}$ alkyl, halo($C_{1-6}$) alkyl, $C_{1-6}$ alkoxy, difluoromethoxy, trifluoromethoxy, $C_{1-6}$ alkoxy($C_{1-6}$)alkyl, ($C_{1-6}$)alkoxy($C_{1-6}$)alkoxy($C_{1-6}$)alkyl, $C_{1-6}$ alkylthio, $C_{1-6}$ alkylsulfinyl, $C_{1-6}$ alkylsulfonyl, $C_{1-6}$ alkylsulfonylphenyl, hydroxy, hydroxy($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyl-oxy, amino, amino($C_{1-6}$)alkyl, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylamino-sulfonyl, ($C_{1-6}$)alkylsulphoximinyl, [($C_{1-6}$)alkyl][N—($C_{1-6}$)alkyl]sulphoximinyl, oxetanyl-oxy($C_{1-6}$)alkyl, ($C_{1-6}$)alkylheteroaryl, ($C_{1-6}$) alkoxyheteroaryl, hydroxy($C_{1-6}$)alkylheteroaryl, oxoheteroaryl and morpholinylheteroaryloxy($C_{1-6}$)alkyl.

Suitable examples of optional substituents on the heteroaryl moiety Y include halogen, $C_{1-6}$ alkyl, halo($C_{1-6}$) alkyl, $C_{1-6}$ alkoxy, ($C_{1-6}$)alkoxy($C_{1-6}$)alkoxy($C_{1-6}$)alkyl, $C_{1-6}$ alkylthio, $C_{1-6}$ alkylsulfonyl, $C_{1-6}$ alkylsulfonylphenyl, hydroxy($C_{1-6}$)alkyl, cyano, oxetanyloxy($C_{1-6}$)alkyl, ($C_{1-6}$) alkylheteroaryl, ($C_{1-6}$)alkoxyheteroaryl, hydroxy($C_{1-6}$) alkyl-heteroaryl, oxoheteroaryl and morpholinylheteroaryloxy($C_{1-6}$)alkyl.

Typical examples of specific substituents on the heteroaryl moiety Y include fluoro, chloro, bromo, methyl, ethyl, isopropyl, fluoromethyl, methoxy, isopropoxy, difluoromethoxy, trifluoromethoxy, methoxymethyl, methoxymethoxymethyl, methoxy-ethoxymethyl, methylthio, ethylthio, methylsulfinyl, methylsulfonyl, methylsulfonyl-phenyl, hydroxy, hydroxymethyl, hydroxyethyl, hydroxyisopropyl, cyano, trifluoromethyl, oxo, acetyl, carboxy, methoxycarbonyl, ethoxycarbonyl, tert-butoxycarbonyl, acetoxy, amino, aminomethyl, methylamino, ethylamino, dimethylamino, phenylamino, pyridinyl-amino, acetylamino, acetylaminomethyl, tert-butoxycarbonylamino, methylsulfonyl-amino, aminocarbonyl, methylaminocarbonyl, dimethylaminocarbonyl, aminosulfonyl, methylaminosulfonyl, dimethylaminosulfonyl, methylsulphoximinyl, (methyl)(N-methyl)sulphoximinyl, oxetanyloxymethyl, methylpyrazolyl, methoxypyridinyl, hydroxyisopropylpyrimidinyl, oxopyridinyl and morpholinylpyrimidinyloxymethyl.

Suitable examples of specific substituents on the heteroaryl moiety Y include fluoro, chloro, bromo, methyl, fluoromethyl, methoxy, methoxymethoxymethyl, methoxyethoxymethyl, methylthio, methylsulfonyl, methylsulfonylphenyl, hydroxymethyl, cyano, oxetanyloxymethyl, methylpyrazolyl, methoxypyridinyl, hydroxyisopropylpyrimidinyl, oxopyridinyl and morpholinylpyrimidinyloxymethyl.

Typical values of Y include (chloro)(dimethyl)pyrazolyl, trimethylpyrazolyl, (dimethyl)(fluoromethyl)pyrazolyl, (dimethyl)(methoxymethoxymethyl)pyrazolyl, (dimethyl) (methoxyethoxymethyl)pyrazolyl, (dimethyl)(methylthio) pyrazolyl, (dimethyl)-(methylsulfonyl)pyrazolyl, (dimethyl) (hydroxymethyl)pyrazolyl, (dimethyl)-(oxetanyloxymethyl) pyrazolyl, (dimethyl)(methoxypyridinyl)pyrazolyl, (dimethyl)-(oxopyridinyl)pyrazolyl, (dimethyl)(morpholinylpyrimidinyloxymethyl)pyrazolyl, dimethylisoxazolyl, trimethylimidazolyl, methylimidazo[1,2-a]pyridinyl, methylsulfonyl-phenylimidazo[1,2-a]pyridinyl, (fluoro)(methyl) imidazo[1,2-a]pyridinyl, (bromo)-(methyl)imidazo[1,2-a] pyridinyl, (cyano)(methyl)imidazo[1,2-a]pyridinyl, (methoxy-pyridinyl)(methyl)imidazo[1,2-a]pyridinyl, (oxopyridinyl)(methyl)imidazo[1,2-a]-pyridinyl, (bromo) (fluoro)(methyl)imidazo[1,2-a]pyridinyl, (cyano)(fluoro) (methyl)-imidazo[1,2-a]pyridinyl, (fluoro)(methyl) (methylpyrazolyl)imidazo[1,2-a]pyridinyl, (fluoro) (hydroxyisopropylpyrimidinyl)(methyl)imidazo[1,2-a] pyridinyl, methyl-imidazo[1,2-a]pyrazinyl, (cyano)(methyl) imidazo[1,2-a]pyrazinyl, (methoxy)(methyl)-imidazo[1,2-a] pyrazinyl, dimethyltriazolyl, methylpyridinyl, dimethylpyridinyl, dimethyl-pyridazinyl and dimethylpyrimidinyl.

Suitably, Z represents aryl, $C_{3-7}$ heterocycloalkyl, $C_{3-7}$ heterocycloalkenyl or heteroaryl, any of which groups may be optionally substituted by one or more substituents.

Alternatively, Z represents aryl or heteroaryl, either of which groups may be optionally substituted by one or more substituents.

Where Z represents optionally substituted aryl, this may typically be optionally substituted phenyl.

Where Z represents optionally substituted $C_{3-7}$ heterocycloalkyl, this may typically be pyrrolidinyl, dihydrobenzoisothiazolyl, piperidinyl, 1,2,3,4-tetrahydroquinolinyl or 1,2,3,4-tetrahydroisoquinolinyl, any of which groups may be optionally substituted by one or more substituents.

Where Z represents optionally substituted $C_{3-7}$ heterocycloalkenyl, this may typically be optionally substituted 1,2,3,6-tetrahydropyridinyl.

Where Z represents optionally substituted heteroaryl, this may typically be 4,5,6,7-tetrahydrobenzothienyl, 4,5,6,7,8-pentahydrothieno[3,2-c]azepinyl, indolyl, pyrrolo[2,1-f]-[1,2,4]triazinyl, pyrazolyl, indazolyl, pyrazolo[4,3-b]pyridinyl, 4,5,6,7,8-pentahydro-thiazolo[4,5-c]azepinyl, 4,5,6,7,8-pentahydrothiazolo[5,4-c]azepinyl, pyridinyl, quinolinyl, phthalazinyl or pyrimidinyl, any of which groups may be optionally substituted by one or more substituents.

Typically, Z may be unsubstituted, or substituted by one, two or three substituents. In a first embodiment, Z is unsubstituted. In a second embodiment, Z is monosubstituted. In a third embodiment, Z is disubstituted. In a fourth embodiment, where valency allows, Z is trisubstituted.

Typically, Z represents phenyl, pyrrolidinyl, dihydrobenzoisothiazolyl, piperidinyl, 1,2,3,4-tetrahydroquinolinyl, 1,2,3,4-tetrahydroisoquinolinyl, 1,2,3,6-tetrahydropyridinyl, 4,5,6,7-tetrahydrobenzothienyl, 4,5,6,7,8-pentahydrothieno[3,2-c]azepinyl, indolyl, pyrrolo[2,1-f][1,2,4]triazinyl, pyrazolyl, indazolyl, pyrazolo[4,3-b]pyridinyl, 4,5,6,7,8-pentahydrothiazolo[4,5-c]azepinyl, 4,5,6,7,8-pentahydrothiazolo[5,4-c]azepinyl, pyridinyl, quinolinyl, phthalazinyl or pyrimidinyl, any of which groups may be optionally substituted by one or more substituents.

Typical examples of optional substituents on Z include halogen, $C_{1-6}$ alkyl, halo($C_{1-6}$)alkyl, $C_{1-6}$ alkoxy, difluoromethoxy, trifluoromethoxy, $C_{1-6}$ alkoxy($C_{1-6}$)alkyl, ($C_{1-6}$) alkoxy($C_{1-6}$)alkoxy($C_{1-6}$)alkyl, $C_{1-6}$ alkylthio, $C_{1-6}$ alkylsulfinyl, $C_{1-6}$ alkylsulfonyl, cyclopropylthio, cyclopropylsulfinyl, cyclopropylsulfonyl, $C_{1-6}$ alkylsulfonylphenyl, hydroxy, hydroxy($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, amino($C_{1-6}$)alkyl, $C_{1-6}$ alkylamino, di-($C_{1-6}$)alkylamino, phenylamino, pyridinylamino, $C_{2-6}$ alkylcarbonylamino, $C_{2-6}$ alkyl-carbonylamino($C_{1-6}$)alkyl, $C_{2-6}$ alkoxycarbonylamino, $C_{1-6}$ alkylsulfonylamino, amino-carbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl, ($C_{1-6}$)alkylsulphoximinyl, [($C_{1-6}$)alkyl]-[N—($C_{1-6}$)alkyl]sulphoximinyl, benzyl, morpholinyl, heteroaryl, ($C_{1-6}$)alkylheteroaryl, ($C_{1-6}$)alkoxyheteroaryl, hydroxy($C_{1-6}$)alkylheteroaryl and oxo-heteroaryl.

Suitable examples of optional substituents on Z include halogen, $C_{1-6}$ alkyl, $C_{1-6}$ alkoxy, difluoromethoxy, $C_{1-6}$ alkylthio, $C_{1-6}$ alkylsulfinyl, $C_{1-6}$ alkylsulfonyl, cyclopropylthio, cyclopropylsulfinyl, cyclopropylsulfonyl, hydroxy($C_{1-6}$)alkyl, oxo, $C_{2-6}$ alkyl-carbonyl, $C_{2-6}$ alkoxycarbonyl, aminocarbonyl, aminosulfonyl, ($C_{1-6}$)alkylsulphoximinyl, benzyl, morpholinyl and heteroaryl.

Typical examples of specific substituents on Z include fluoro, chloro, bromo, methyl, ethyl, isopropyl, fluoromethyl, methoxy, isopropoxy, difluoromethoxy, trifluoromethoxy, methoxymethyl, methoxymethoxymethyl, methoxyethoxymethyl, methylthio, ethylthio, methylsulfinyl, methylsulfonyl, cyclopropylthio, cyclopropylsulfinyl, cyclopropylsulfonyl, methylsulfonylphenyl, hydroxy, hydroxymethyl, hydroxyethyl, hydroxyisopropyl, cyano, trifluoromethyl, oxo, acetyl, carboxy, methoxycarbonyl, ethoxycarbonyl, tert-butoxycarbonyl, acetoxy, amino, aminomethyl, methylamino, ethylamino, dimethylamino, phenylamino, pyridinylamino, acetylamino, acetylaminomethyl, tert-butoxycarbonylamino, methylsulfonylamino, aminocarbonyl, methylamino-carbonyl, dimethylaminocarbonyl, aminosulfonyl, methylaminosulfonyl, dimethylamino-sulfonyl, methylsulphoximinyl, (methyl)(N-methyl)sulphoximinyl, benzyl, morpholinyl, pyrazolyl, methylpyrazolyl, methoxypyridinyl, hydroxyisopropylpyrimidinyl and oxopyridinyl.

Suitable examples of specific substituents on Z include fluoro, methyl, methoxy, difluoromethoxy, methylthio, methylsulfinyl, methylsulfonyl, cyclopropylthio, cyclopropylsulfinyl, cyclopropylsulfonyl, hydroxymethyl, oxo, acetyl, ethoxycarbonyl, tert-butoxycarbonyl, aminocarbonyl, aminosulfonyl, methylsulphoximinyl, benzyl, morpholinyl and pyrazolyl.

Typical values of Z include methoxyphenyl, difluoromethoxyphenyl, methylthio-phenyl, methylsulfinylphenyl, methylsulfonylphenyl, cyclopropylthiophenyl, cyclopropyl-sulfinylphenyl, cyclopropylsulfonylphenyl, acetylphenyl, aminocarbonylphenyl, amino-sulfonylphenyl, methylsulphoximinylphenyl, pyrazolylphenyl, (hydroxymethyl)(methyl-sulfinyl)phenyl, (aminosulfonyl)(fluoro)phenyl, (fluoro)(methylsulphoximinyl)phenyl, pyrrolidinyl, methylsulfonylpyrrolidinyl, acetylpyrrolidinyl, (acetyl)(difluoro)pyrrolidinyl, dioxodihydrobenzoisothiazolyl, piperidinyl, methylsulfonylpiperidinyl, acetylpiperidinyl, tert-butoxycarbonylpiperidinyl, aminocarbonylpiperidinyl, (ethoxycarbonyl)(methyl)-piperidinyl, (aminocarbonyl)(methyl)piperidinyl, (fluoro)(oxo)-1,2,3,4-tetrahydro-quinolinyl, oxo-1,2,3,4-tetrahydroisoquinolinyl, (fluoro)(oxo)-1,2,3,4-tetrahydro-isoquinolinyl, acetyl-1,2,3,6-tetrahydropyridinyl, tert-butoxycarbonyl-1,2,3,6-tetrahydro-pyridinyl, benzyl-1,2,3,6-tetrahydropyridinyl, oxo-4,5,6,7-tetrahydrobenzothienyl, oxo-4,5,6,7,8-pentahydrothieno[3,2-c]azepinyl, indolyl, oxopyrrolo[2,1-f][1,2,4]triazinyl, methylpyrazolyl, methoxyindazolyl, methylsulfonylindazolyl, pyrazolo[4,3-b]pyridinyl, methylpyrazolo[4,3-b]pyridinyl, oxo-4,5,6,7-pentahydrothiazolo[4,5-c]azepinyl, (dimethyl)(oxo)-4,5,6,7,8-pentahydrothiazolo[5,4-c]azepinyl, pyridinyl, fluoropyridinyl, methylpyridinyl, methoxypyridinyl, (fluoro)(methoxy)pyridinyl, quinolinyl, oxophthalazinyl and morpholinylpyrimidinyl.

Suitably, $R^0$ represents hydrogen, fluoro or methyl.

In a first embodiment, $R^0$ represents hydrogen. In a second embodiment, $R^0$ represents halogen, especially fluoro. In a third embodiment, $R^0$ represents $C_{1-6}$ alkyl, especially methyl.

Typically, $R^1$ represents hydrogen, halogen, $C_{1-6}$ alkyl or trifluoromethyl.

Typical values of $R^1$ include hydrogen, fluoro, chloro, bromo, cyano, methyl, fluoromethyl, difluoromethyl, trifluoromethyl, hydroxy, hydroxymethyl, hydroxyethyl, hydroxyisopropyl, methoxy, difluoromethoxy, trifluoromethoxy, pentafluorothio, methylthio, methylsulphinyl, methylsulphonyl, amino, aminomethyl, methylamino, dimethylamino, formyl, acetyl, carboxy, methoxycarbonyl, ethoxycarbonyl, tert-butoxycarbonyl, aminocarbonyl, methylaminocarbonyl, dimethylaminocarbonyl, aminosulphonyl, methylaminosulphonyl, dimethylaminosulphonyl, methylsulphoximinyl and (methyl)(N-methyl)sulphoximinyl.

Illustrative values of $R^1$ include hydrogen, fluoro, methyl and trifluoromethyl.

Suitably, $R^1$ represents hydrogen or halogen. In a first embodiment, $R^1$ represents hydrogen. In a second embodiment, $R^1$ represents halogen, especially fluoro.

Typically, $R^2$ represents hydrogen or trifluoromethyl.

Typical values of $R^2$ include hydrogen, fluoro, chloro, bromo, cyano, methyl, fluoromethyl, difluoromethyl, trifluoromethyl, hydroxy, hydroxymethyl, hydroxyethyl, hydroxyisopropyl, methoxy, difluoromethoxy, trifluoromethoxy, pentafluorothio, methylthio, methylsulphinyl, methylsulphonyl, amino, aminomethyl, methylamino, dimethylamino, formyl, acetyl, carboxy, methoxycarbonyl, ethoxycarbonyl, tert-butoxycarbonyl, aminocarbonyl, methylaminocarbonyl, dimethylaminocarbonyl, aminosulphonyl, methylaminosulphonyl, dimethylaminosulphonyl, methylsulphoximinyl and (methyl)(N-methyl)sulphoximinyl.

In a first embodiment, $R^2$ represents hydrogen. In a second embodiment, $R^2$ represents trifluoromethyl.

Suitably, $R^3$ represents hydrogen or methyl.

In a first embodiment, $R^3$ represents hydrogen. In a second embodiment, $R^3$ represents $C_{1-6}$ alkyl, especially methyl.

Suitably, $R^4$ represents hydrogen or methyl.

In a first embodiment, $R^4$ represents hydrogen. In a second embodiment, $R^4$ represents $C_{1-6}$ alkyl, especially methyl.

Suitably, $R^{5a}$ represents hydrogen or methyl.

In a first embodiment, $R^{5a}$ represents hydrogen. In a second embodiment, $R^{5a}$ represents $C_{1-6}$ alkyl, especially methyl.

Suitably, $R^{5b}$ represents hydrogen or methyl.

In a first embodiment, $R^{5b}$ represents hydrogen. In a second embodiment, $R^{5b}$ represents $C_{1-6}$ alkyl, especially methyl.

Typically, $R^{6a}$ represents hydrogen, fluoro, trifluoromethyl or methyl.

Suitably, $R^{6a}$ represents hydrogen, fluoro or methyl.

In a first embodiment, $R^{6a}$ represents hydrogen. In a second embodiment, $R^{6a}$ represents halogen. In one aspect of that embodiment, $R^{6a}$ represents fluoro. In a third embodiment, $R^{6a}$ represents trifluoromethyl. In a fourth embodiment, $R^{6a}$ represents $C_{1-6}$ alkyl. In one aspect of that embodiment, $R^{6a}$ represents methyl.

Typically, $R^{6b}$ represents hydrogen, fluoro or methyl.

Suitably, $R^{6b}$ represents hydrogen or fluoro.

In a first embodiment, $R^{6b}$ represents hydrogen. In a second embodiment, $R^{6b}$ represents halogen. In one aspect of that embodiment, $R^{6b}$ represents fluoro. In a third embodiment, $R^{6b}$ represents trifluoromethyl. In a fourth embodiment, $R^{6b}$ represents $C_{1-6}$ alkyl. In one aspect of that embodiment, $R^{6b}$ represents methyl.

Alternatively, $R^{6a}$ and $R^{6b}$ may together form an optionally substituted spiro linkage. Thus, $R^{6a}$ and $R^{6b}$, when taken together with the carbon atom to which they are both attached, may represent $C_{3-7}$ cycloalkyl or $C_{3-7}$ heterocycloalkyl, either of which groups may be unsubstituted, or substituted by one or more substituents, typically by one or two substituents. In one embodiment, $R^{6a}$ and $R^{6b}$, when taken together with the carbon atom to which they are both attached, may suitably represent an optionally substituted cyclopropyl ring. In another embodiment, $R^{6a}$ and $R^{6b}$, when taken together with the carbon atom to which they are both attached, may suitably represent an optionally substituted oxetanyl ring.

Typical examples of optional substituents on the spirocycle formed by $R^{6a}$ and $R^{6b}$ include $C_{1-6}$ alkyl, halogen, cyano, trifluoromethyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino and di($C_{1-6}$)alkylamino.

Typical examples of particular substituents on the spirocycle formed by $R^{6a}$ and $R^{6b}$ include methyl, fluoro, chloro, bromo, cyano, trifluoromethyl, hydroxy, methoxy, methylthio, methylsulphinyl, methylsulphonyl, acetyl, amino, methylamino and dimethylamino.

Alternatively, $R^{5a}$ and $R^{6a}$ may together form an optionally substituted fused bicyclic ring system. Thus, $R^5$ and $R^{6a}$, when taken together with the two intervening carbon atoms, may represent $C_{3-7}$ cycloalkyl or $C_{3-7}$ heterocycloalkyl, either of which groups may be unsubstituted, or substituted by one or more substituents, typically by one or two substituents. In one embodiment, $R^{5a}$ and $R^{6a}$, when taken together with the two intervening carbon atoms, may suitably represent an optionally substituted cyclopropyl ring. In another embodiment, $R^{5a}$ and $R^{6a}$, when taken together with the two intervening carbon atoms, may suitably represent an optionally substituted oxetanyl ring.

Typical examples of optional substituents on the fused bicyclic ring system formed by $R^5$ and $R^{6a}$ include $C_{1-6}$ alkyl, halogen, cyano, trifluoromethyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino and di($C_{1-6}$)alkylamino.

Typical examples of particular substituents on the fused bicyclic ring system formed by $R^{5a}$ and $R^{6a}$ include methyl, fluoro, chloro, bromo, cyano, trifluoromethyl, hydroxy, methoxy, methylthio, methylsulphinyl, methylsulphonyl, acetyl, amino, methylamino and dimethylamino.

An illustrative sub-class of compounds according to the invention is represented by the compounds of formula (IIA) and N-oxides thereof, and pharmaceutically acceptable salts thereof:

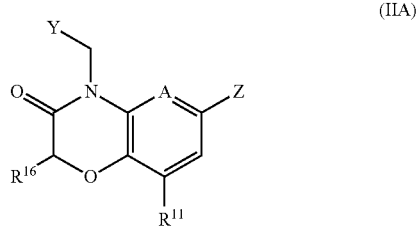

(IIA)

wherein
$R^{11}$ represents hydrogen, halogen or $C_{1-6}$ alkyl;
$R^{16}$ represents hydrogen, halogen or $C_{1-6}$ alkyl; and
A, Y and Z are as defined above.

Suitably, $R^{11}$ represents hydrogen or halogen.

In a first embodiment, $R^{11}$ represents hydrogen. In a second embodiment, $R^{11}$ represents halogen. In one aspect of that embodiment, $R^{11}$ represents fluoro. In a third embodiment, $R^{11}$ represents $C_{1-6}$ alkyl. In one aspect of that embodiment, $R^{11}$ represents methyl.

Suitable values of $R^{11}$ include hydrogen, fluoro and methyl.

Particular values of $R^{11}$ include hydrogen and fluoro.

Suitably, $R^{16}$ represents hydrogen or $C_{1-6}$ alkyl.

In a first embodiment, $R^{16}$ represents hydrogen. In a second embodiment, $R^{16}$ represents halogen. In one aspect of that embodiment, $R^{16}$ represents fluoro. In a third embodiment, $R^{16}$ represents $C_{1-6}$ alkyl. In one aspect of that embodiment, $R^{16}$ represents methyl.

Suitable values of $R^{16}$ include hydrogen, fluoro and methyl.

Particular values of $R^{16}$ include hydrogen and methyl.

Another illustrative sub-class of compounds according to the invention is represented by the compounds of formula (IIB) and N-oxides thereof, and pharmaceutically acceptable salts thereof:

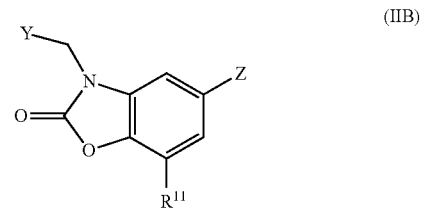

(IIB)

wherein
Y, Z and $R^{11}$ are as defined above.

Specific novel compounds in accordance with the present invention include each of the compounds whose preparation is described in the accompanying Examples, and pharmaceutically acceptable salts thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, polymyositis, scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (I) above may be prepared by a process which comprises reacting a compound of formula Z—H or Z-$M^1$ with a compound of formula (III):

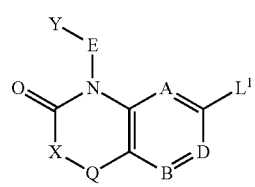

(III)

wherein A, B, D, E, Q, X, Y and Z are as defined above, $L^1$ represents a suitable leaving group, and $M^1$ represents a boronic acid moiety —$B(OH)_2$ or a cyclic ester thereof formed with an organic diol, e.g. pinacol, 1,3-propanediol or neopentyl glycol, or $M^1$ represents —$Sn(Alk)_3$ in which Alk represents a $C_{1-6}$ alkyl group, typically n-butyl or methyl, or $M^1$ represents —ZnHal in which Hal represents a halogen atom, e.g. chloro; in the presence of a transition metal catalyst.

The leaving group $L^1$ is typically a halogen atom, e.g. bromo or chloro.

A suitable transition metal catalyst for use in the above reaction may be selected from [1,1'-bis(di-tert-butylphosphino)ferrocene]dichloropalladium(II), tris(dibenzylideneacetone)dipalladium(0), tetrakis(triphenylphosphine)palladium(0), bis(triphenyl-phosphine)dichloropalladium(II) and palladium(II) acetate. The reaction is conveniently carried out at an elevated temperature in a suitable solvent, e.g. a cyclic ether such as 1,4-dioxane, typically in the presence of a base, e.g. an inorganic base such as sodium carbonate, potassium carbonate or cesium carbonate. Where appropriate, a reagent such as 2-dicyclohexylphosphino-2',4',6'-triisopropylbiphenyl (X-Phos) or 2-dicyclohexyl-phosphino-2',6'-diisopropoxybiphenyl may additionally be included in the reaction mixture.

Where a C—N bond is formed in the above reaction, a suitable transition metal catalyst may be copper(I) iodide, in which case the reaction is typically performed in the presence of 1,3-di(pyridin-2-yl)propane-1,3-dione. The reaction is conveniently carried out at an elevated temperature in a suitable solvent, e.g. N,N-dimethylformamide, typically in the presence of a base, e.g. an inorganic base such as potassium carbonate.

In an alternative procedure, the compounds of formula (I) above may be prepared by a process which comprises reacting a compound of formula Z-$L^1$ with a compound of formula (IV):

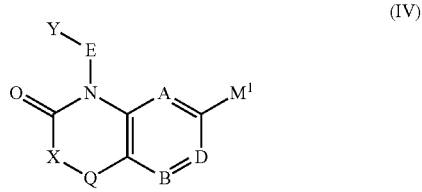

(IV)

wherein A, B, D, E, Q, X, Y, Z, $L^1$ and $M^1$ are as defined above; under conditions analogous to those described above for the reaction between compound (III) and a compound of formula Z—H or Z-$M^1$.

The intermediates of formula (IV) above wherein $M^1$ represents the pinacol ester of a boronic acid moiety may be prepared by reacting bis(pinacol)diboron with a compound of formula (III) as defined above; under conditions analogous to those described above for the reaction between compound (III) and a compound of formula Z—H or Z-$M^1$.

In another procedure, the compounds of formula (I) above may be prepared by a process which comprises reacting a compound of formula Y-E-OH with a compound of formula (V):

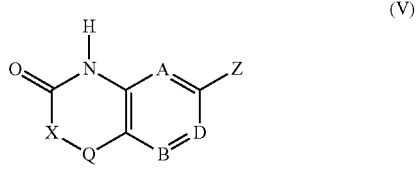

(V)

wherein A, B, D, E, Q, X, Y and Z are as defined above.

The procedure is suitably effected in the presence of triphenylphosphine and a $C_{1-6}$ alkyl ester of azodicarboxylic acid, e.g. diisopropyl azodicarboxylate. Alternatively, the procedure may be effected in the presence of (cyanomethylene)tributylphosphorane. The reaction is conveniently carried out in a suitable solvent, e.g. a cyclic ether such as tetrahydrofuran, or a chlorinated solvent such as dichloromethane, or an organic nitrile such as acetonitrile.

Alternatively, the procedure may be effected in the presence of a sulphonic acid derivative, e.g. a $C_{1-6}$ alkylsulphonic acid such as methanesulphonic acid. The reaction is conveniently carried out at an elevated temperature in a suitable solvent, e.g. a cyclic ether such as 1,4-dioxane.

In an alternative procedure, the compounds of formula (I) above may be prepared by a process which comprises reacting a compound of formula Y-E-L² with a compound of formula (V) as defined above.

The leaving group $L^2$ is suitably a halogen atom, e.g. chloro; or a sulphonate derivative, e.g. a $C_{1-6}$ alkylsulphonate such as methylsulphonate.

Where $L^2$ is halo, the procedure is suitably effected in the presence of a base, e.g. an alkali metal hydride such as sodium hydride, or an alkali metal carbonate such as cesium carbonate or potassium carbonate. The reaction is conveniently effected in a suitable solvent, e.g. a dipolar aprotic solvent such as N,N-dimethylformamide or N,N-dimethylacetamide.

Where $L^2$ is a sulphonate derivative, e.g. methylsulphonate, the procedure is suitably effected in the presence of a base, e.g. an alkali metal hydride such as sodium hydride. The reaction is conveniently carried out at an elevated temperature in a suitable solvent, e.g. a dipolar aprotic solvent such as N,N-dimethylformamide.

The intermediates of formula Y-E-L² wherein $L^2$ is chloro may be prepared from the corresponding compound of formula Y-E-OH by treatment with a chlorinating agent such as thionyl chloride. The reaction is conveniently carried out in a suitable solvent, e.g. a cyclic ether such as tetrahydrofuran, or a chlorinated solvent such as dichloromethane.

The intermediates of formula Y-E-L² wherein $L^2$ is methylsulphonate may be prepared from the corresponding compound of formula Y-E-OH by treatment with methanesulphonic anhydride, typically in the presence of a base, e.g. an alkali metal hydride such as sodium hydride. The reaction is conveniently carried out at an elevated temperature in a suitable solvent, e.g. a dipolar aprotic solvent such as N,N-dimethyl-formamide.

The intermediates of formula (III) above may be prepared by reacting a compound of formula Y-E-OH with a compound of formula (VI):

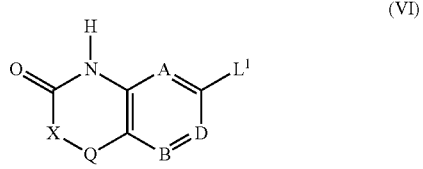

(VI)

wherein A, B, D, E, Q, X, Y and $L^1$ are as defined above; under conditions analogous to those described above for the reaction between compound (V) and a compound of formula Y-E-OH.

Alternatively, the intermediates of formula (III) above may be prepared by reacting a compound of formula Y-E-L² with a compound of formula (VI) as defined above; under conditions analogous to those described above for the reaction between compound (V) and a compound of formula Y-E-L².

The intermediates of formula (V) above may be prepared by reacting a compound of formula Z-M¹ with a compound of formula (VI) as defined above; under conditions analogous to those described above for the reaction between compound (III) and a compound of formula Z-M¹.

Where they are not commercially available, the starting materials of formula (VI) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound wherein E represents —C(O)— may be converted into the corresponding compound wherein E represents —CH(OH)— by treatment with a reducing agent such as sodium borohydride.

A compound wherein E represents —CH(OH)— may be converted into the corresponding compound wherein E represents —CH₂— by heating with elemental iodine and phosphinic acid in acetic acid; or by treating with triethylsilane and an acid, e.g. an organic acid such as trifluoroacetic acid, or a Lewis acid such as boron trifluoride diethyl etherate; or by treating with chlorotrimethylsilane and sodium iodide; or by a two-step procedure which comprises: (i) treatment with thionyl bromide; and (ii) treatment of the product thereby obtained with a transition metal catalyst, e.g. (2,2'-bipyridine)dichloro-ruthenium(II) hydrate, in the presence of diethyl 1,4-dihydro-2,6-dimethyl-3,5-pyridine-dicarboxylate (Hantzsch ester) and a base, e.g. an organic base such as N,N-diisopropyl-ethylamine.

A compound wherein E represents —CH₂— may be converted into the corresponding compound wherein E represents —CH(CH₃)— by treatment with a methyl halide, e.g. methyl iodide, in the presence of a base such as lithium hexamethyldisilazide.

A compound which contains a methoxymethoxymethyl group may be converted into the corresponding compound containing a hydroxymethyl group by heating with a mineral acid, e.g. hydrochloric acid.

A compound which contains a hydroxy group may be alkylated by treatment with the appropriate alkyl halide in the presence of a base, e.g. sodium hydride, or silver oxide. A compound which contains hydroxy may be converted into the corresponding fluoro-substituted compound by treatment with diethylaminosulfur trifluoride (DAST) or bis(2-methoxyethyl)aminosulfur trifluoride (BAST). A compound which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound containing an N-benzyl moiety may be converted into the corresponding compound containing an N—H moiety by catalytic hydrogenation, typically by treatment with a hydrogenation catalyst, e.g. palladium on charcoal, or palladium hydroxide on carbon, under an atmosphere of hydrogen gas.

A compound which contains an N—H moiety may be alkylated by treatment with the appropriate alkyl halide, typically at an elevated temperature in an organic solvent such as acetonitrile; or at ambient temperature in the presence of a base, e.g. an alkali metal carbonate such as potassium carbonate or cesium carbonate, in a suitable solvent, e.g. a dipolar aprotic solvent such as N,N-dimethylformamide. Alternatively, a compound which contains an N—H moiety may be alkylated by treatment with the appropriate alkyl tosylate in the presence of a base, e.g. an inorganic base such as sodium hydride, or an organic base such as 1,8-diazabicyclo[5.4.0]undec-7-ene (DBU).

A compound which contains an N—H moiety may be methylated by treatment with formaldehyde in the presence of a reducing agent, e.g. sodium triacetoxyborohydride.

A compound which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine or pyridine.

A compound which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonyl chloride, e.g. methanesulphonyl chloride, or with the appropriate $C_{1-6}$ alkylsulphonic acid anhydride, e.g. methanesulphonic anhydride, typically at ambient temperature in the presence of a base, e.g. an organic base such as triethylamine, N,N-diisopropylethylamine or pyridine.

A compound which contains an N—H moiety may be converted into the corresponding compound wherein the nitrogen atom is substituted by aminocarbonyl by treatment with potassium cyanate.

A compound substituted by amino (—NH$_2$) may be converted into the corresponding compound substituted by $C_{1-6}$ alkylsulphonylamino, e.g. methylsulphonylamino, or bis[($C_{1-6}$)alkylsulphonyl]amino, e.g. bis(methylsulphonyl)amino, by treatment with the appropriate $C_{1-6}$ alkylsulphonyl halide, e.g. a $C_{1-6}$ alkylsulphonyl chloride such as methanesulphonyl chloride. Similarly, a compound substituted by hydroxy (—OH) may be converted into the corresponding compound substituted by $C_{1-6}$ alkylsulphonyloxy, e.g. methylsulphonyloxy, by treatment with the appropriate $C_{1-6}$ alkylsulphonyl halide, e.g. a $C_{1-6}$ alkylsulphonyl chloride such as methanesulphonyl chloride.

A compound containing the moiety —S— may be converted into the corresponding compound containing the moiety —S(O)— by treatment with 3-chloroperoxybenzoic acid. Likewise, a compound containing the moiety —S(O)— may be converted into the corresponding compound containing the moiety —S(O)$_2$— by treatment with 3-chloroperoxy-benzoic acid. Alternatively, a compound containing the moiety —S— may be converted into the corresponding compound containing the moiety —S(O)$_2$— by treatment with Oxone® (potassium peroxymonosulfate).

A compound containing a ($C_{1-6}$)alkylsulfinyl group may be converted into the corresponding compound containing a ($C_{1-6}$)alkylsulfoximinyl group via a two-step procedure which comprises: (i) treatment with 2,2,2-trifluoroacetamide in the presence of magnesium oxide, rhodium(II) acetate dimer and iodobenzene I,I-diacetate; and (ii) treatment of the material thereby obtained with a base such as sodium carbonate.

A compound containing an aromatic nitrogen atom may be converted into the corresponding N-oxide derivative by treatment with 3-chloroperoxybenzoic acid.

A bromophenyl derivative may be converted into the corresponding optionally substituted 2-oxopyrrolidin-1-yl-phenyl or 2-oxooxazolidin-3-ylphenyl derivative by treatment with pyrrolidin-2-one or oxazolidin-2-one, or an appropriately substituted analogue thereof. The reaction is conveniently effected at an elevated temperature in the presence of copper(I) iodide, trans-N,N'-dimethylcyclohexane-1,2-diamine and an inorganic base such as potassium carbonate.

An aryl or heteroaryl compound containing a halogen atom, e.g. bromo or iodo, may be converted into the corresponding compound containing an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected in the presence of a transition metal catalyst, e.g. [1,1'-bis(diphenylphosphino)ferrocene]dichloropalladium (II), [1,1'-bis(di-tert-butylphosphino)ferrocene]dichloropalladium(II), tetrakis(triphenyl-phosphine)palladium(0), or dichlorobis(triphenylphosphine)palladium(II), and a base, e.g. an inorganic base such as sodium carbonate or potassium carbonate, or potassium phosphate, or potassium fluoride.

An aryl or heteroaryl compound containing a halogen atom, e.g. bromo or iodo, may be converted into the corresponding compound containing a cyano group by heating with copper(I) cyanide.

An aryl or heteroaryl compound containing a halogen atom, e.g. bromo or iodo, may be dehalogenated by treatment with a hydrogenation catalyst, e.g. palladium on charcoal, in the presence of a hydrogen transfer reagent such as ammonium formate.

In general, a compound containing a —C≡C— functionality may be converted into the corresponding compound containing a —CH—CH— functionality by catalytic hydrogenation, typically by treatment with a hydrogenation catalyst, e.g. palladium on charcoal, or palladium hydroxide on carbon, under an atmosphere of hydrogen gas, optionally in the presence of a base, e.g. an alkali metal hydroxide such as sodium hydroxide, or an organic base such as triethylamine.

A compound containing a pyridinyl group may be converted into the corresponding compound containing a piperidinyl group by catalytic hydrogenation, generally by treatment with a hydrogenation catalyst, e.g. platinum(IV) oxide, under an atmosphere of hydrogen gas, typically in the presence of a mineral acid, e.g. hydrochloric acid.

A compound containing a 6-methoxypyridin-3-yl group may be converted into the corresponding compound containing a 2-oxo-1,2-dihydropyridin-5-yl group by treatment with pyridine hydrochloride; or by heating with a mineral acid such as hydrochloric acid. By utilising similar methodology, a compound containing a 6-methoxy-4-methyl-pyridin-3-yl group may be converted into the corresponding compound containing a 4-methyl-2-oxo-1,2-dihydropyridin-5-yl group; and a compound containing a 6-methoxy-5-methylpyridin-3-yl group may be converted into the corresponding compound containing a 3-methyl-2-oxo-1,2-dihydropyridin-5-yl group.

A compound containing a 2-oxo-1,2-dihydropyridin-5-yl group may be converted into the corresponding compound containing a 2-oxopiperidin-5-yl group by catalytic hydrogenation, typically by treatment with gaseous hydrogen in the presence of a hydrogenation catalyst such as platinum (IV) oxide.

A compound containing an ester moiety, e.g. a $C_{2-6}$ alkoxycarbonyl group such as methoxycarbonyl or ethoxycarbonyl, may be converted into the corresponding compound containing a carboxy (—CO$_2$H) moiety by treatment with an acid, e.g. a mineral acid such as hydrochloric acid.

A compound containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

A compound containing an ester moiety, e.g. a $C_{2-6}$ alkoxycarbonyl group such as methoxycarbonyl or ethoxycarbonyl, may alternatively be converted into the corresponding compound containing a carboxy (—$CO_2H$) moiety by treatment with a base, e.g. an alkali metal hydroxide selected from lithium hydroxide, sodium hydroxide and potassium hydroxide; or an organic base such as sodium methoxide or sodium ethoxide.

A compound containing a carboxy (—$CO_2H$) moiety may be converted into the corresponding compound containing an amide moiety by treatment with ammonium chloride, or with the appropriate amine, in the presence of a condensing agent such as 1-ethyl-3-(3-dimethylaminopropyl)carbodiimide, or a coupling agent such as 1-[bis(dimethylamino)methylene]-1H-1,2,3-triazolo[4,5-b]pyridinium 3-oxide hexafluorophosphate (HATU).

A compound containing a carbonyl (C=O) moiety may be converted into the corresponding compound containing a —$C(CH_3)(OH)$— moiety by treatment with methylmagnesium bromide. Similarly, a compound containing a carbonyl (C=O) moiety may be converted into the corresponding compound containing a —$C(CF_3)(OH)$— moiety by treatment with (trifluoromethyl)trimethylsilane and cesium fluoride. A compound containing a carbonyl (C=O) moiety may be converted into the corresponding compound containing a —$C(CH_2NO_2)(OH)$— moiety by treatment with nitromethane.

A compound containing a hydroxymethyl moiety may be converted into the corresponding compound containing a formyl (—CHO) moiety by treatment with an oxidising agent such as Dess-Martin periodinane. A compound containing a hydroxymethyl moiety may be converted into the corresponding compound containing a carboxy moiety by treatment with an oxidising agent such as tetrapropylammonium perruthenate. Similarly, a compound containing a —CH(OH)— moiety may be converted into the corresponding compound containing a —C(O)— moiety by treatment with an oxidising agent such as tetrapropylammonium perruthenate.

A compound containing an oxo moiety can be converted into the corresponding compound containing an ethoxycarbonylmethylidene moiety by treatment with triethyl phosphonoacetate in the presence of a base such as sodium hydride.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I), this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T.W. Greene & P.G.M. Wuts, *Protective Groups in Organic Synthesis*, John Wiley & Sons, $3^{rd}$ edition, 1999. The protecting groups may be removed at any convenient subsequent stage utilising methods known from the art.

The following Examples illustrate the preparation of compounds according to the invention.

The compounds in accordance with the present invention potently inhibit the binding of a fluorescence conjugate to TNFα when tested in the fluorescence polarisation assay described herein. Indeed, when tested in that assay, the compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ FIGURE denotes a more active compound).

Certain compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, certain compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 20 nM or less (as before, the skilled person will appreciate that a lower $IC_{50}$ FIGURE denotes a more active compound).

Fluorescence Polarisation Assay

Preparation of Compound (A)

1-(2,5-Dimethylbenzyl)-6-[4-(piperazin-1-ylmethyl)phenyl]-2-(pyridin-4-yl-methyl)-1H-benzimidazole—hereinafter referred to as "Compound (A)"—can be prepared by the procedure described in Example 499 of WO 2013/186229; or by a procedure analogous thereto.

Preparation of Fluorescence Conjugate

Compound (A) (27.02 mg, 0.0538 mmol) was dissolved in DMSO (2 mL). 5 (−6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 μL aliquot was removed and diluted in a 80:20 mixture of AcOH:$H_2O$ for LC-MS analysis on the 1200RR-6140 LC- MS system. The chromatogram showed two closely eluting peaks at retention times of 1.42 and 1.50 minutes, both with mass (M+H)$^+$=860.8 amu, corresponding to the two products formed with the 5- and 6-substituted carboxyfluorescein group. A further peak at retention time 2.21 minutes had a mass of (M+H)$^+$=502.8 amu, corresponding to Compound (A). No peak was observed for unreacted 5(–6) carboxyfluorescein succinimyl ester. The peak areas were 22.0%, 39.6% and 31.4% for the three signals, indicating a 61.6% conversion to the two isomers of the desired fluorescence conjugate at that time-point. Further 20 μL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα

Compounds were tested at 10 concentrations starting from 25 μM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 μL. Plates were read on a plate reader capable of detecting fluorescence polarisation (e.g. an Analyst HT plate reader; or an Envision plate reader). An IC$_{50}$ value was calculated using XLfit™ (4 parameter logistic model) in ActivityBase.

When tested in the fluorescence polarisation assay, the compounds of the accompanying Examples were all found to exhibit IC$_{50}$ values of 50 μM or better.

Thus, when tested in the fluorescence polarisation assay, compounds of the accompanying Examples exhibit IC$_{50}$ values generally in the range of about 0.01 nM to about 50 μM, usually in the range of about 0.01 nM to about 20 μM, typically in the range of about 0.01 nM to about 5 μM, suitably in the range of about 0.01 nM to about 1 μM, appositely in the range of about 0.01 nM to about 500 nM, ideally in the range of about 0.01 nM to about 100 nM, and preferably in the range of about 0.01 nM to about 25 nM.

Reporter Gene Assay
Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (e.g. 30,000 nM to 2 nM final concentration). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using a colorimetric substrate, e.g. QUANTI-Blue™ or HEK-Blue™ Detection media (InvivoGen). Percentage inhibitions for compound dilutions were calculated between a DMSO control and maximum inhibition (by excess control compound) and an IC$_{50}$ value calculated using XLfit™ (4 parameter logistic model) in ActivityBase.

When tested in the reporter gene assay, certain compounds of the accompanying Examples were found to exhibit IC$_{50}$ values of 50 μM or better.

Thus, when tested in the reporter gene assay, compounds of the accompanying Examples exhibit IC$_{50}$ values generally in the range of about 0.01 nM to about 50 μM, usually in the range of about 0.01 nM to about 20 μM, typically in the range of about 0.01 nM to about 5 μM, suitably in the range of about 0.01 nM to about 1 μM, appositely in the range of about 0.01 nM to about 500 nM, ideally in the range of about 0.01 nM to about 100 nM, and preferably in the range of about 0.01 nM to about 25 nM.

EXAMPLES

Abbreviations

DCM: dichloromethane EtOAc: ethyl acetate
MeOH: methanol DMSO: dimethylsulfoxide
EtOH: ethanol DIPEA: N,N-diisopropylethylamine
DMF: N,N-dimethylformamide THF: tetrahydrofuran
Et$_2$O: diethyl ether CDI: 1,1'-carbonyldiimidazole
AcOH: acetic acid IPA: isopropanol
DIAD: diisopropyl azodicarboxylate PCC: pyridinium chlorochromate
LDA: lithium diisopropylamide LiHMDS: lithium bis(trimethylsilyl)amide
DEA: diethylamine TEA: triethylamine
AIBN: 2,2'-(E)-diazene-1,2-diylbis(2-methylpropanenitrile)
TBAB: tri-tert-butylphosphonium tetrafluoroborate
Pd(dppf)Cl$_2$: [1,1'-bis(diphenylphosphino)ferrocene]dichloropalladium(II)
Pd$_2$(dba)$_3$: tris(dibenzylideneacetone)dipalladium(0)
X-Phos: 2-Dicyclohexylphosphino-2',4',6'-triisopropylbiphenyl
Ir(fppy)$_3$: tris[2-(4,6-difluorophenyl)pyridinato-C$^2$,N] iridium(III)
Pearlman's catalyst: palladium hydroxide on carbon
HATU: 1-[bis(dimethylamino)methylene]-1H-1,2,3-triazolo[4,5-b]pyridinium 3-oxide hexafluorophosphate
Sudan III: 1-[(E)-{4-[(Z)-phenyldiazenyl]phenyl}diazenyl]naphthalen-2-ol
h: hour M: mass
r.t. room temperature RT: retention time
HPLC: High Performance Liquid Chromatography
LCMS: Liquid Chromatography Mass Spectrometry Nomenclature Compounds were named with the aid of ACD/Name Batch (Network) version 12.0.

Analytical Conditions

All reactions involving air- or moisture-sensitive reagents were performed under a nitrogen atmosphere using dried solvents and glassware.

LCMS data were determined by using Methods A-F or HPLC-MS. Preparative HPLC for all compounds that required it was performed using Preparative Methods A-D.

Method A

Column: Waters Atlantis dC18, 2.1×100 mm, 3 m
Mobile phase A: 0.1% formic acid/water
Mobile phase B: 0.1% formic acid/acetonitrile Gradient program (flow rate 0.6 mL/minute, column temperature 40° C.):

| Time | A % | B % |
|---|---|---|
| 0.00 | 95.0 | 5.0 |
| 5.00 | 0.0 | 100 |
| 5.42 | 95.0 | 5.0 |
| 7.00 | 95.0 | 5.0 |

Method B
Column: Waters Atlantis dC18, 2.1×50 mm, 3 μm
Mobile phase A: 0.1% formic acid/water
Mobile phase B: 0.1% formic acid/acetonitrile
Gradient program (flow rate 1.0 mL/minute, column temperature 40° C.):

| Time | A % | B % |
|---|---|---|
| 0.0 | 95.0 | 5.0 |
| 2.5 | 0.0 | 100 |
| 2.7 | 0.0 | 100 |
| 3.0 | 95.0 | 5.0 |

Method C
Column: Waters Atlantis dC18, 2.1×30 mm, 3 m
Mobile phase A: 0.1% formic acid/water
Mobile phase B: 0.1% formic acid/acetonitrile
Gradient program (flow rate 1.0 mL/minute, column temperature 40° C.):

| Time | A % | B % |
|---|---|---|
| 0.0 | 95.0 | 5.0 |
| 1.5 | 0 | 100 |
| 1.6 | 95.0 | 5.0 |
| 2.0 | 95.0 | 5.0 |

Method D
Column: Phenomenex Kinetex-XB C18, 2.1×100 mm, 1.7 m
Mobile phase A: 0.1% formic acid/water
Mobile phase B: 0.1% formic acid/acetonitrile
Gradient program (flow rate 0.6 mL/minute, column temperature 40° C.):

| Time | A % | B % |
|---|---|---|
| 0.0 | 95.0 | 5.0 |
| 5.3 | 0 | 100 |
| 5.8 | 0 | 100 |
| 5.9 | 95.0 | 5.0 |

Method E
Column: Phenomenex Gemini C18, 2.0 mm×100 mm, 3 μm
Mobile phase A: 2 mM ammonium bicarbonate/water
Mobile phase B: acetonitrile
Gradient program (flow rate 0.5 mL/minute, column temperature 50° C.):

| Time | A % | B % |
|---|---|---|
| 0.0 | 95.0 | 5.0 |
| 5.5 | 0 | 100 |
| 5.9 | 0 | 100 |
| 6.0 | 95.0 | 5.0 |

Method F
Column: Phenomenex Gemini C18, 2.0 mm×50 mm, 3 m
Mobile phase A: 2 mM ammonium bicarbonate/water
Mobile phase B: acetonitrile
Gradient program (flow rate 1.0 mL/minute, column temperature 60° C.):

| Time | A % | B % |
|---|---|---|
| 0.0 | 99.0 | 1.0 |
| 1.8 | 0 | 100 |
| 2.1 | 0 | 100 |
| 2.3 | 99.0 | 1.0 |

HPLC-MS
Column: Waters Acquity UPLC, BEH C18, 2.1×50 mm, 1.7 m
Mobile phase A: 10 mM ammonium formate+0.1% ammonia
Mobile phase B: acetonitrile+5% water+0.1% ammonia
Gradient program (flow rate 1.0 mL/minute, column temperature 40° C.):

| Time | A % | B % |
|---|---|---|
| 0.00 | 95.0 | 5.0 |
| 0.5 | 95.0 | 5.0 |
| 1.75 | 5.0 | 95.0 |
| 2.00 | 5.0 | 95.0 |
| 2.75 | 95.0 | 5.0 |

Preparative Method A
Column: Waters Sunfire, C18, 30 mm×100 mm, 10 m
Mobile phase A: 0.1% formic acid/water
Mobile phase B: 0.1% formic acid/acetonitrile
Gradient program (flow rate 40 mL/minute):

| Time | A % | B % |
|---|---|---|
| 0.0 | 75.0 | 25.0 |
| 2.0 | 75.0 | 25.0 |
| 2.5 | 70.0 | 30.0 |
| 18.5 | 0 | 100 |
| 21.5 | 0 | 100 |
| 22.5 | 99.0 | 1.0 |
| 23.0 | 99.0 | 1.0 |

Preparative Method B
Column: Waters Sunfire, C18, 30 mm×100 mm, 10 m
Mobile phase A: 0.1% formic acid/water
Mobile phase B: 0.1% formic acid/acetonitrile
Gradient program (flow rate 40 mL/minute):

| Time | A % | B % |
|---|---|---|
| 0.0 | 95.0 | 5.0 |
| 2.0 | 95.0 | 5.0 |
| 2.5 | 90.0 | 10.0 |
| 18.5 | 0 | 100 |
| 21.5 | 0 | 100 |
| 22.5 | 95.0 | 5.0 |
| 25.5 | 95.0 | 5.0 |

Preparative Method C
Column: Waters Sunfire, C18, 19 mm×100 mm, 5 μm
Mobile phase A: water
Mobile phase B: acetonitrile Gradient program (flow rate 20 mL/minute):

| Time | A % | B % |
|---|---|---|
| 0.0 | 95.0 | 5.0 |
| 2.0 | 95.0 | 5.0 |
| 2.5 | 90.0 | 10.0 |
| 14.5 | 0 | 100 |
| 16.5 | 0 | 100 |
| 17.0 | 95.0 | 5.0 |
| 19.0 | 95.0 | 5.0 |

Preparative Method D
Column: Waters Sunfire, C-18, 30 mm×100 mm, 5 m
Mobile phase A: 0.2% ammonium hydroxide/water
Mobile phase B: 0.2% ammonium hydroxide/acetonitrile
Isocratic program (flow rate 40 mL/minute):

| Time | A % | B % |
|---|---|---|
| 0.0 | 95.0 | 5.0 |
| 2.0 | 85.0 | 15.0 |
| 12.0 | 70.0 | 30.0 |
| 12.5 | 5.0 | 95.0 |
| 15.0 | 5.0 | 95.0 |
| 15.5 | 95.0 | 5.0 |

Intermediate 1

(2,4-Dimethylpyridin-3-yl)methanol

To a solution of ethyl 2,4-dimethylpyridine-3-carboxylate (2 g, 11.2 mmol) in anhydrous THF (10 mL), previously cooled to −10° C., was added 2.4M lithium aluminium hydride (9.3 mL, 22.4 mmol) portionwise. Stirring was continued for 16 h. Water (0.8 mL) was added dropwise, followed by 15% aqueous sodium hydroxide solution (0.8 mL), then more water (2.4 mL). The reaction mixture was stirred at r.t. for 1 h, then extracted with DCM (2×100 mL). The organic phases were combined, dried over $Na_2SO_4$ and filtered. The solvent was removed in vacuo to give the title compound (1.53 g, 100%) as a white solid. Method B HPLC-MS: MH+ m/z 138, RT 0.26 minutes.

Intermediate 2

(1,4-Dimethyl-1H-1,2,3-triazol-5-yl)methanol

Prepared from ethyl 1,4-dimethyl-1H-1,2,3-triazole-5-carboxylate by a method similar to that used to prepare Intermediate 1. $\delta_H$ (500 MHz, CDCl$_3$) 4.50 (s, 2H), 3.87 (s, 3H), 2.08 (s, 3H).

Intermediate 3

(1,2,4-Trimethyl-1H-imidazol-5-yl) methanol

Prepared from Intermediate 18 by a method similar to that used to prepare Intermediate 1. $\delta_H$ (500 MHz, CDCl$_3$) 4.55 (s, 2H), 3.54 (s, 3H), 2.34 (s, 3H), 2.14 (s, 3H). Method B HPLC-MS: MH+ m/z 141, RT 0.25 minutes (100%).

Intermediate 4

(3,5-Dimethylpyridazin-4-yl)methanol

Prepared from Intermediate 14 by a method similar to that used to prepare Intermediate 1. $\delta_H$ (500 MHz, CDCl$_3$) 8.85 (s, 1H), 4.78 (s, 2H), 2.81 (s, 3H), 2.48 (s, 3H).

Intermediate 5

(6-Chloropyrazin-2-yl)methanol

Prepared from methyl 6-chloropyrazine-2-carboxylate by a method similar to that used to prepare Intermediate 1. Method B HPLC-MS: MH+ m/z 145-147, RT 0.84 minutes (83%).

Intermediate 6

{5-[(methoxymethoxy)methyl]-1,3-dimethyl-1H-pyrazol-4-yl}methanol

Prepared from Intermediate 19 by a method similar to that used to prepare Intermediate 1. $\delta_H$ (500 MHz, CDCl$_3$) 4.62 (s, 2H), 4.60 (s, 2H), 4.48 (s, 2H), 3.84 (s, 3H), 3.34 (s, 3H), 2.28 (s, 4H). Method B HPLC-MS: MH+ m/z 201, RT 0.97 minutes (100%).

Intermediate 7

[1,5-Dimethyl-3-(methylsulfanyl)pyrazol-4-yl]methanol

Prepared from Intermediate 34 by a method similar to that used to prepare Intermediate 1. HPLC-MS: MH+ m/z 173, RT 0.16 minutes.

Intermediate 8

Ethyl (2E)-2-acetyl-3-methoxybut-2-enoate

To a solution of ethyl 2-acetyl-3-oxobutanoate (4.53 mL, 29.04 mmol) in MeOH (20 mL) and THF (30 mL) was added 2M (diazomethyl)(trimethyl)silane (36.3 mL) at r.t. The reaction mixture was stirred at 40° C. for 2 h, then quenched with acetic acid (5 mL). The solvent was removed in vacuo. The residue was dissolved in DCM (30 mL) and washed sequentially with saturated aqueous NaHCO$_3$ (20 mL) and brine (20 mL), then dried over Na$_2$SO$_4$. The crude material was purified by column chromatography, with a gradient of 0-70% EtOAc in heptane, to afford the title compound (3 g, 55%) as a clear oil. Method B HPLC-MS: MH+ m/z 187, RT 1.40 minutes (90%).

Intermediate 9

Ethyl 4,6-dimethyl-2-(methylsulfanyl)pyrimidine-5-carboxylate

To a solution of Intermediate 8 (3 g, 16.11 mmol) in EtOH (20 mL) were added potassium carbonate (2.45 g, 17.72 mmol) and methyl carbamimidothioate sulfate (2:1) (3.5 mL, 16.11 mmol). The reaction mixture was stirred at 80° C. for 2 h, then at r.t. overnight. The mixture was concentrated in vacuo. The residue was dissolved in EtOAc (30 mL) and washed sequentially with water (20 mL) and brine (15 mL), then dried over Na$_2$SO$_4$. The solvent was removed in vacuo.

The resulting crude yellow oil was purified by column chromatography, with a gradient of 0-25% EtOAc in heptane, to afford the title compound (2 g, 55%) as a clear oil. Method B HPLC-MS: MH+ m/z 227, RT 1.97 minutes (97%).

Intermediate 10

[4,6-Dimethyl-2-(methylsulfanyl)pyrimidin-5-yl]methanol

To a solution of Intermediate 9 (2 g, 8.84 mmol) in anhydrous THF (20 mL), cooled to 0° C., was added 2M lithium aluminium hydride (4.42 mL, 8.84 mmol) slowly with stirring. The reaction mixture was stirred at 0° C. for 1 h, then quenched with slow sequential addition of water (0.3 mL), 1M aqueous sodium hydroxide solution (0.3 mL), and further water (0.9 mL), at 10 minute intervals. The resulting fine white precipitate was removed via filtration and washed with EtOAc (2×20 mL). The filtrate was collected and dried over $Na_2SO_4$, then the solvent was removed in vacuo. The resulting crude clear oil was purified by column chromatography, with a gradient of 0-100% EtOAc in heptane, to afford the title compound (1 g, 55%) as a clear oil which crystallised upon standing. Method B HPLC-MS: MH+ m/z 185, RT 1.25 minutes (87%).

Intermediate 11

(4,6-Dimethylpyrimidin-5-yl)methanol

To a solution of Intermediate 10 (800 mg, 3.9 mmol) in EtOH (30 mL) was added Raney nickel (slurry in water, 4 mL, 23.45 mmol) and the mixture was stirred at 80° C. under an atmosphere of nitrogen for 15 h. More Raney nickel (8 mL, 47 mmol) was added and the mixture was heated at 100° C. for 3 h, then cooled to r.t., filtered through a celite pad and washed with MeOH (100 mL). The residue was purified by column chromatography, with a gradient of 0-10% MeOH in DCM, to afford the title compound (276 mg, 51%) as a white solid. $\delta_H$ (250 MHz, $CDCl_3$) 8.87 (s, 1H), 4.80 (s, 2H), 2.62 (s, 6H). Method B HPLC-MS: MH+ m/z 139, RT 0.44 minutes (>95%).

Intermediate 12

Ethyl 3-oxo-2-(2-oxoethyl)butanoate

To a stirred solution of ethyl 2-acetylpent-4-enoate (90%, 4 g, 21.15 mmol) in a mixture of DCM (120 mL) and MeOH (12 mL) was added Sudan III (4 mg), producing a red/pink-coloured solution. The reaction mixture was cooled to −78° C., then ozone gas was bubbled through until the bright orange colour had disappeared (for approximately 4 h). Polymer-supported triphenylphosphine (16 g, 1.4-2.0 mmol/g loading) was then added as a single portion and the reaction mixture was left to warm to ambient temperature. Stirring was continued for another 2 h, then the polymer was removed by filtration. The filtrate was concentrated in vacuo. The residue was purified by biotage chromatography, using a EtOAc/heptane gradient, to give the title compound (1.25 g, 31%) as a yellow oil. $\delta_H$ (250 MHz, $CDCl_3$) 9.75 (s, 1H), 4.21 (q, J 7.1 Hz, 2H), 4.03 (dd, J 7.9, 5.7 Hz, 1H), 3.19 (dd, J 19.2, 7.9 Hz, 1H), 3.00 (dd, J 19.2, 5.7 Hz, 1H), 2.37 (s, 3H), 1.28 (t, J 7.1 Hz, 3H). Method B HPLC-MS: MH+ m/z 173, RT 1.33 minutes (85%).

Intermediate 13

Ethyl 3-methylpyridazine-4-carboxylate

To a stirred solution of Intermediate 12 (1.24 g, 0.01 mol) in EtOH (14 mL) was added dropwise, at 0° C., a solution of hydrazine hydrate (1:1) (0.32 mL, 0.01 mol) in EtOH (6 mL). The reaction mixture was left to warm to ambient temperature and stirring was continued for a further 2 h. Sodium nitrite (0.76 g, 0.01 mol) in water (0.5 mL) was added, followed by acetic acid (3 mL), and stirring was continued for another 2.5 h. Saturated aqueous $NaHCO_3$ solution was added until pH 8, then the reaction mixture was extracted with EtOAc (3×20 mL). The organic extracts were combined, and washed with a 1:1 mixture of water and brine (30 mL), then brine (15 mL), then dried over $MgSO_4$ and filtered. The solvent was removed in vacuo. The residue was purified by Biotage chromatography, using a EtOAc/heptane gradient, to afford the title compound (535 mg, 45%) as a red solid. $\delta_H$ (500 MHz, $CDCl_3$) 9.26 (d, J 5.1 Hz, 1H), 7.86 (d, J 5.1 Hz, 1H), 4.44 (q, J 7.1 Hz, 2H), 3.01 (s, 3H), 1.43 (t, J 7.1 Hz, 3H). Method B HPLC-MS: MH+ m/z 167, RT 1.29 minutes (100%).

Intermediate 14

Ethyl 3,5-dimethylpyridazine-4-carboxylate

Iron(II) sulfate hydrate (1:1:7) (720 mg, 2.59 mmol) previously dissolved in water (1 mL) and tert-butyl hydroperoxide (6M in nonane, 0.4 mL) were added simultaneously, dropwise, to a stirred solution of Intermediate 13 (430 mg, 2.59 mmol) in 10% aqueous sulfuric acid (8 mL) at ambient temperature. Stirring was continued for a further 1 h, then the solution was basified with concentrated aqueous ammonia and extracted with DCM (2×50 mL). The combined organic extracts were washed with brine (20 mL), dried over $Na_2SO_4$ and filtered. The solvent was removed in vacuo to give the title compound (458 mg, 86%) that was used in the next step without further purification. $\delta_H$ (500 MHz, $CDCl_3$) 8.99 (s, 1H), 4.47 (q, J 7.2 Hz, 2H), 2.73 (s, 3H), 2.36 (s, 3H), 1.42 (t, J 7.1 Hz, 3H). Method B HPLC-MS: MH+ m/z 181, RT 1.38 minutes (93%).

Intermediate 15

Ethyl 2-{[(tert-butoxy)carbonyl](methyl)amino}acetate

Ethyl 2-(methylamino)acetate hydrochloride (5.0 g, 32.6 mmol) was dissolved in DMF (55 mL) and triethylamine (5 mL, 35.8 mmol) was added. The resulting solution was cooled to 0° C. and di-tert-butyl dicarbonate (8.53 g, 39.1 mmol) was added portionwise over 5 minutes. The reaction mixture was stirred at 0° C. for 30 minutes, then allowed to warm to ambient temperature and left stirring overnight. After 18 h, the reaction mixture was diluted with water (50 mL) and extracted with EtOAc (3×50 mL). The combined organic layers were washed with water (15 mL), saturated aqueous ammonium chloride solution (15 mL), water (15 mL), saturated aqueous ammonium chloride solution (15 mL), water (15 mL) and brine (15 mL), then dried over $MgSO_4$. The crude material was purified by column chromatography, with a gradient of 0-30% EtOAc in heptane, to afford the title compound (6.42 g, 91%) as a pale yellow oil.

$\delta_H$ (500 MHz, CDCl$_3$) 4.30-4.14 (m, 2H), 4.07-3.75 (m, 2H), 3.01-2.85 (m, 3H), 1.53-1.38 (m, 9H), 1.34-1.19 (m, 3H).

Intermediate 16

Ethyl 2-{[(tert-butoxy)carbonyl](methyl)amino}-3-oxobutanoate

To a solution of LiHMDS (1M in THF, 62 mL, 62 mmol), cooled to −78° C. under nitrogen, was added a solution of Intermediate 15 (6.4 g, 29.5 mmol) in anhydrous THF (10 mL) dropwise. The mixture was brought to −40° C. and stirred for 1 h. Acetyl chloride (2.33 mL, 32.4 mmol) was added and the mixture was allowed to warm to r.t., then stirred for 16 h. Saturated aqueous ammonium chloride solution (70 mL) was added, followed by EtOAc (100 mL), and the layers were separated. The aqueous phase was extracted with EtOAc (2×30 mL) and the combined organic layers were washed with water (30 mL) and brine (30 mL), then dried over MgSO$_4$. The crude material was purified by column chromatography, with a gradient of 0-30% EtOAc in heptane, to afford the title compound (3.46 g, 68% pure, 27% yield). Method B HPLC-MS: [M−tBu]+ m/z 160, RT 2.03 minutes (68%).

Intermediate 17

Ethyl (2E)-3-hydroxy-2-(N-methylacetamido)but-2-enoate

Intermediate 16 (3 g, 11.6 mmol) was treated with hydrochloric acid (4M in 1,4-dioxane) (40 mL, 160 mmol) at r.t. The solvent was removed, and the residue was azeotroped several times with EtOAc, then the resulting yellow oil was dissolved in water (30 mL). Acetic anhydride (5.4 mL, 57.9 mmol) was added, followed by sodium acetate (2.85 g, 34.7 mmol), and the mixture was stirred at r.t. overnight. The mixture was extracted with EtOAc (3×50 mL) and dried over MgSO$_4$, then filtered and concentrated, to afford the title compound, which was used in the next step without further purification. Method B HPLC-MS: MH+ m/z 202, RT 1.49 minutes (75%).

Intermediate 18

Ethyl 1,2,4-trimethyl-1H-imidazole-5-carboxylate

To a solution of Intermediate 17 (2.33 g, 11.6 mmol) in acetic acid (50 mL) was added ammonium acetate (8.8 g, 116 mmol) and the mixture was stirred at 110° C. After 15 h, more ammonium acetate (3 g, 39 mmol) was added and stirring was continued at 110° C. for a total of 64 h. The mixture was then cooled to r.t., then the solvent was removed by rotary evaporation. The residue was taken up in EtOAc (50 mL) and washed with saturated aqueous NaHCO$_3$ solution. The aqueous layer was extracted with EtOAc (2×30 mL) and the combined organic layers were washed with saturated aqueous NaHCO$_3$ solution (20 mL), water (20 mL) and brine (20 mL), then dried over MgSO$_4$. The crude material was purified by column chromatography, with a gradient of 0-100% EtOAc in heptane, followed by a gradient of 0-10% MeOH in EtOAc, to afford the title compound (650 mg, 31%) as a yellow oil. $\delta_H$ (500 MHz, CDCl$_3$) 4.32 (d, J 7.1 Hz, 2H), 3.78 (s, 3H), 2.45 (s, 3H), 2.40 (s, 3H), 1.37 (t, J 7.1 Hz, 3H). Method B HPLC-MS: MH+ m/z 183, RT 0.65 minutes (97%).

Intermediate 19

Ethyl 5-[(methoxymethoxy)methyl]-1,3-dimethyl-1H-pyrazole-4-carboxylate

To a solution of ethyl 5-(hydroxymethyl)-1,3-dimethyl-1H-pyrazole-4-carboxylate (prepared according to the method described in *J. Heterocyclic Chem.*, 1979, 16, 1117) (1.06 g, 5.32 mmol) and DIPEA (1.85 mL, 10.64 mmol) in anhydrous DCM (26 mL) at 0° C. was added chloro(methoxy)methane (0.61 mL, 7.98 mmol) over 2 minutes. The mixture was stirred at 0° C. for 1 h, then allowed to warm to r.t. overnight. More DIPEA (1.85 mL, 10.64 mmol) was added, followed by the addition of chloro(methoxy)methane (0.61 mL, 7.98 mmol), and the mixture was left stirring at r.t. overnight. The reaction mixture was diluted with DCM (50 mL) and washed with water (2×50 mL). The combined aqueous washes were further extracted with DCM (25 mL). The combined organic extracts were dried over MgSO$_4$, filtered and concentrated. The crude material was purified by column chromatography, with a gradient of 20-100% EtOAc in heptane, to afford the title compound (1.13 g, 73%) as a light yellow oil. Method B HPLC-MS: MH+ m/z 243, RT 1.59 minutes (100%).

Intermediate 20

1,3-Dimethyl-5-[(oxetan-3-yloxy)methyl]-1H-pyrazole

To a solution of oxetan-3-ol (0.273 mL, 4.14 mmol) in dry DMF (5 mL) was added sodium hydride (60% in mineral oil, 265.5 mg, 5.53 mmol), and the mixture was stirred at r.t. for about 1 h. 5-(Chloromethyl)-1,3-dimethyl-1H-pyrazole (400 mg, 2.76 mmol) in DMF (5 mL) was added and the reaction mixture was stirred for 16 h at r.t. After removal of DMF under vacuum, the residue was dissolved in DCM (50 mL) and water (20 mL). The aqueous layer was extracted with DCM and the combined organic extracts were washed with brine, then dried over Na$_2$SO$_4$ and evaporated to dryness. The crude residue was purified by column chromatography, with a gradient of 25-100% EtOAc in heptane, to afford the title compound (349 mg, 69%). Method B HPLC-MS: MH+ m/z 183, RT 1.09 minutes (100%).

Intermediate 21

{1,3-Dimethyl-5-[(oxetan-3-yloxy)methyl]-1H-pyrazol-4-yl}methanol

To a stirred suspension of Intermediate 20 (349 mg, 1.91 mmol) in water (6 mL) was added formaldehyde (2.85 mL, 38.3 mmol) in one portion, then p-toluenesulfonic acid (36 mg, 0.19 mmol) was added and the reaction mixture was heated at 80° C. for 16 h in a sealed tube. More formaldehyde (2 mL) was added, and heating was continued for another 10 h. To the reaction mixture were added DCM (20 mL), water (10 mL) and 6M hydrochloric acid (10 mL), then the layers were separated. The aqueous phase was basified with solid NaHCO$_3$, then extracted twice with DCM and once with isopropanol/chloroform (1:1). The combined organic extracts were washed with brine, dried over Na$_2$SO$_4$ and evaporated to dryness. The crude material was purified by column chromatography, with a gradient of 1-10% MeOH in DCM, to afford the title compound (155 mg, 38%). $\delta_H$ (500 MHz, CDCl$_3$) 4.75-4.70 (m, 2H), 4.65-4.59

(m, 1H), 4.57-4.53 (m, 2H), 4.50 (s, 2H), 4.48 (s, 2H), 3.84 (s, 3H), 2.25 (s, 3H). Method B HPLC-MS: MH+ m/z 213, RT 0.86 minutes (94%).

Intermediate 22

{5-[(2-Meth oxy)methyl]-1,3-dimethyl-1H-pyrazol-4-yl}methanol

Prepared from Intermediate 28 in a similar manner to that described for Intermediate 21. Method B HPLC-MS: MH+ m/z 215, RT 0.97 minutes (87%).

Intermediate 23

[1,3-Dimethyl-5-({[2-(morpholin-4-yl)pyrimidin-5-yl]oxy}methyl)-1H-pyrazol-4-yl]-methanol Prepared from Intermediate 31 in a similar manner to that described for Intermediate 21. Method B HPLC-MS: MH+ m/z 320, RT 1.67 minutes (100%).

Intermediate 24

3-(Hydroxymethyl)-2-methylimidazo[1,2-a]pyridine-6-carbonitrile

Prepared from Intermediate 32 in a similar manner to that described for Intermediate 21. $\delta_H$ (500 MHz, DMSO-d$_6$) 9.10 (s, 1H), 7.62 (d, J 9.3 Hz, 1H), 7.48 (dd, J 9.3, 1.6 Hz, 1H), 5.23 (s, 1H), 4.82 (s, 2H), 2.38 (s, 3H). Method B HPLC-MS: MH+ m/z 188, RT 0.95 minutes (100%).

Intermediate 25

(6-Bromo-2-methylimidazo[1,2-a]pyridin-3-yl)methanol

Prepared from 6-bromo-2-methylimidazo[1,2-a]pyridine in a similar manner to that described for Intermediate 21. $\delta_H$ (250 MHz, CDCl$_3$) 8.36 (s, 1H), 7.41 (d, J 9.4 Hz, 1H), 7.28 (d, J 1.7 Hz, 1H), 4.93 (s, 2H), 2.42 (s, 3H). Method B HPLC-MS: MH+ m/z 241-243, RT 0.26 minutes (>90%).

Intermediate 26

{2-Methylimidazo[1,2-a]pyrazin-3-yl}methanol

Prepared from 2-methylimidazo[1,2-a]pyrazine in a similar manner to that described for Intermediate 21. $\delta_H$ (500 MHz, DMSO-d$_6$) 8.93 (d, J 1.4 Hz, 1H), 8.39 (dd, J 4.6, 1.4 Hz, 1H), 7.89 (d, J 4.6 Hz, 1H), 5.26 (t, J 5.3 Hz, 1H), 4.81 (d, J 4.9 Hz, 2H), 2.42 (s, 3H). Method E HPLC-MS: MH+ m/z 164, RT 0.98 minutes (100%).

Intermediate 27

{6-Bromo-7-fluoro-2-methylimidazo[1,2-a]pyridin-3-yl}methanol

Prepared from Intermediate 33 in a similar manner to that described for Intermediate 21. $\delta_H$ (500 MHz, DMSO-d$_6$) 8.70 (d, J 6.9 Hz, 1H), 7.55 (d, J 9.7 Hz, 1H), 5.14 (t, J 5.5 Hz, 1H), 4.75 (d, J 5.4 Hz, 2H), 2.31 (s, 3H).

Intermediate 28

5-[(2-Methoxyethoxy)methyl]-1,3-dimethyl-1H-pyrazole

To a solution of (1,3-dimethyl-1H-pyrazol-5-yl)methanol (400 mg, 3.17 mmol) in dry DMF (10 mL) was added NaH (60% in mineral oil, 228 mg, 4.75 mmol), and the mixture was stirred at r.t. for about 1 h. 1-Bromo-2-methoxyethane (0.596 mL, 6.34 mmol) was added and the reaction mixture was stirred for 16 h at r.t., then heated at 60° C. for 3 h. After removal of DMF under vacuum, the residue was dissolved in DCM (50 mL) and water (20 mL). The layers were separated and the aqueous phase was extracted with DCM. The combined organic extracts were washed with brine, dried over Na$_2$SO$_4$ and evaporated to dryness. The crude residue was purified by column chromatography, with a gradient of 25-100% EtOAc in heptane, to afford the title compound (330 mg, 55%). Method B HPLC-MS: MH+ m/z 185, RT 1.19 minutes (98%).

Intermediate 29

[6-(4-Methanesulfonylphenyl)-2-methylimidazo[1,2-a]pyridin-3-yl]methanol

To a degassed mixture of Intermediate 25 (5 g, 20.74 mmol), [4-(methylsulfonyl)-phenyl]boronic acid (4.26 g, 21.3 mmol) and 2M aqueous Na$_2$CO$_3$ solution (33 mL) in 1,4-dioxane (200 mL) was added bis[3-(diphenylphosphanyl)cyclopenta-2,4-dien-1-yl]-iron DCM dichloropalladium (0.85 g, 1.04 mmol). The reaction mixture was further degassed with nitrogen before heating at 100° C. for 3 h. The cooled mixture was filtered over kieselguhr and washed with 1,4-dioxane (3×30 mL). The solid was collected, washed with water (3×300 mL) and acetone (3×20 mL), then dried, to afford the title compound (4.52 g, 69%) as a beige solid. $\delta_H$ (500 MHz, DMSO-d$_6$) 8.71 (s, 1H), 8.03 (s, 4H), 7.64 (dd, J 9.3, 1.8 Hz, 1H), 7.59 (d, J 9.4 Hz, 1H), 5.17 (d, J 5.5 Hz, 1H), 4.86 (d, J 5.3 Hz, 2H), 3.27 (s, 3H), 2.37 (s, 3H). Method E HPLC-MS: MH+ m/z 317, RT 1.06 minutes (100%).

Intermediate 30

2-Chloro-5-[(1,3-dimethyl-1H-pyrazol-5-yl)methoxy]pyrimidine

A stirred mixture of 2-chloro-5-hydroxypyrimidine (0.2 g, 1.53 mmol) and cesium carbonate (1.5 g, 4.6 mmol) in anhydrous DMF (50 mL) under nitrogen was heated at 60° C. for 15 minutes, then a solution of 5-(chloromethyl)-1,3-dimethyl-1H-pyrazole (0.22 g, 1.53 mmol) in anhydrous DMF (20 mL) was added dropwise. The mixture was stirred at 60° C. for 1.3 h. The resulting white solid was removed by filtration, and the filtrate was concentrated under reduced pressure, to give the title compound (0.4 g, >99%) as a dark yellow solid. Method B HPLC-MS: MH+ m/z 239/241, RT 1.54 minutes (100%).

Intermediate 31

4-{5-[(1,3-Dimethyl-1H-pyrazol-5-yl)methoxy]pyrimidin-2-yl}morpholine

A mixture of Intermediate 30 (0.2 g, 0.84 mmol) and morpholine (0.22 mL, 2.51 mmol) in anhydrous 1,4-dioxane (2.7 mL) was heated at 100° C. with stirring in a microwave reactor for 1 h, followed by 2 h at 120° C. More morpholine (0.22 mL, 2.51 mmol) was added, and the mixture was heated in a microwave reactor at 120° C. for a further 4 h. The volatiles were evaporated under reduced pressure and the crude material was purified by column chromatography, eluting with a gradient of 17-100% EtOAc in heptane, to afford the title compound (0.23 g, 94.5%) as a light yellow solid. Method B HPLC-MS: MH+ m/z 290, RT 1.67 minutes (100%).

Intermediate 32

2-Methylimidazo[1,2-a]pyridine-6-carbonitrile

To a solution of 6-aminopyridine-3-carbonitrile (2 g, 16.79 mmol) in dry EtOH (30 mL) were added sodium bromide (0.86 g, 8.39 mmol) and chloroacetone (6.75 mL, 83.95 mmol) portionwise. The reaction mixture was heated at 80° C. for 17 h, then left to cool to ambient temperature. The salt was removed by filtration. The solvent was removed in vacuo and the residue was partitioned between EtOAc (50 mL) and saturated aqueous $Na_2CO_3$ solution (50 mL). The organic phase was collected and the aqueous phase was back-extracted with EtOAc (2×50 mL). The organic extracts were combined and washed with brine (50 mL), then dried over $MgSO_4$ and filtered. The solvent was removed in vacuo. The residue was purified by column chromatography, using an EtOAc/heptane gradient, to give the title compound (1.41 g, 53%). $\delta_H$ (500 MHz, DMSO-$d_6$) 9.27 (s, 1H), 7.80 (s, 1H), 7.60 (d, J 9.3 Hz, 1H), 7.43 (dd, J 9.3, 1.7 Hz, 1H), 2.37 (s, 3H). Method B HPLC-MS: MH+ m/z 158, RT 0.29 minutes (100%).

Intermediate 33

6-Bromo-7-fluoro-2-methylimidazo[1,2-a]pyridine

5-Bromo-4-fluoropyridin-2-amine (5 g, 26.18 mmol) was dissolved in EtOH (50 mL) and chloroacetone (4.25 mL, 52.82 mmol) was added. The reaction mixture was stirred at 90° C. for 16 h, then further chloroacetone (2.5 mL) was added and the reaction mixture was stirred for a further 4 h at 90° C. The reaction mixture was concentrated in vacuo and redissolved in EtOAc (15 mL), then washed with saturated aqueous $NaHCO_3$ solution (10 mL) and brine (10 mL). The aqueous layer was re-extracted with EtOAc (2×10 mL), then the combined organic phase was washed with brine (10 mL), dried over $Na_2SO_4$ and concentrated in vacuo. The crude residue was purified on silica (Biotage, 100 g), eluting with 0-100% EtOAc in heptanes, to afford the title compound (1.18 g, 20%) as a white solid. $\delta_H$ (500 MHz, DMSO-$d_6$) 8.97 (d, J 7.0 Hz, 1H), 7.62 (s, 1H), 7.51 (d, J 9.8 Hz, 1H), 2.30 (s, 3H).

Intermediate 34

Ethyl 1,5-dimethyl-3-(methylsulfanyl)pyrazole-4-carboxylate

Ethyl 5-methyl-3-(methylsulfanyl)-1H-pyrazole-4-carboxylate (1.0 g, 5.0 mmol) was dissolved in DMF (20 mL) and cooled in an ice bath before sodium hydride (0.24 g, 6.0 mmol) was added. After five minutes, iodomethane (0.85 g, 6.0 mmol) was added and the reaction mixture was stirred for 3 h, then separated between EtOAc (25 mL) and water (25 mL). The organic layer was washed with water (5×50 mL), then dried (phase separator) and evaporated in vacuo, to obtain the title compound (750 mg, 70%). HPLC-MS: MH+ m/z 215, RT 0.78 minutes.

Intermediate 35

3-(Chloromethyl)-2,4-dimethylpyridine

To a solution of Intermediate 1 (0.99 g, 7.2 mmol) in DCM (15 mL) was added thionyl chloride (4.75 mL, 65.49 mmol) dropwise at r.t. The mixture was stirred at 55° C. for 55 minutes, then concentrated in vacuo. The residue was azeotroped five times with DCM until a solid was obtained. The material was used without further purification.

Intermediate 36

4-(Chloromethyl)-1,3,5-trimethyl-1H-pyrazole

Prepared from (1,3,5-trimethyl-1H-pyrazol-4-yl)methanol in a similar manner to that described for Intermediate 35.

Intermediate 37

3-(Chloromethyl)-2-methylpyridine

Prepared from (2-methylpyridin-3-yl)methanol in a similar manner to that described for Intermediate 35.

Intermediate 38

4-(Chloromethyl)-3,5-dimethylpyridazine

Prepared from Intermediate 4 in a similar manner to that described for Intermediate 35.

Intermediate 39

3-(Chloromethyl)-2-methylimidazo[1,2-a]pyridine

Prepared from (2-methylimidazo[1,2-a]pyridin-3-yl)methanol in a similar manner to that described for Intermediate 35.

Intermediate 40

6-Bromo-3-(chloromethyl)-2-methylimidazo[1,2-a]pyridine

Prepared from Intermediate 25 in a similar manner to that described for Intermediate 35.

Intermediate 41

5-(Chloromethyl)-1,2,4-trimethyl-1H-imidazole

Prepared from Intermediate 3 in a similar manner to that described for Intermediate 35.

Intermediate 42

4-(Chloromethyl)-5-[(2-methoxyethoxy)methyl]-1,3-dimethyl-1H-pyrazole Hydrochloride Prepared from Intermediate 22 in a similar manner to that described for Intermediate 35.

Intermediate 43

3-(Chloromethyl)-6-[4-(methanesulfonyl)phenyl]-2-methylimidazo[1,2-a]pyridine Hydrochloride Prepared from Intermediate 29 in a similar manner to that described for Intermediate 35.

Intermediate 44

5-(Chloromethyl)-1,4-dimethyltriazole

Prepared from Intermediate 2 in a similar manner to that described for Intermediate 35.

Intermediate 45

(R)-Methyl 2-[(6-bromo-2-nitropyridin-3-yl)oxy]propanoate

Under a nitrogen atmosphere, DIAD (19.2 mL, 98 mmol) was added dropwise to a solution of 6-bromo-2-nitropyridin-3-ol (21.5 g, 98 mmol), (S)-methyl 2-hydroxy-propanoate (10.2 g, 98 mmol) and triphenylphosphine (25.8 g, 98 mmol) in THF (dry, 300 mL) at 0° C. After 10 minutes, the reaction mixture was concentrated in vacuo, diluted with water and extracted with EtOAc. The combined organic layers were washed with brine, dried ($Na_2SO_4$) and evaporated in vacuo. The residue was triturated from diethyl ether (250 mL) for 30 minutes, then filtered and washed with diethyl ether (50 mL). The combined filtrates were evaporated in vacuo, then the residue was purified by column chromatography (silica; eluent: DCM), to afford the title compound (29.5 g, 98%). $\delta_H$ (300 MHz, $CDCl_3$) 7.64 (d, J 8.7 Hz, 1H), 7.33 (d, J 8.7 Hz, 1H), 4.85 (q, J 6.8 Hz, 1H), 3.78 (s, 3H), 1.69 (d, J 6.8 Hz, 3H).

Intermediate 46

(R)-6-Bromo-2-methyl-2H-pyrido[3,2-b][1,4]oxazin-3(4H)-one

Iron (27.0 g, 483 mmol) was added to a solution of Intermediate 45 (29.5 g, 97 mmol) in acetic acid (300 mL) and heated at 110° C. for 30 minutes. The reaction mixture was allowed to cool and filtered over kieselguhr, then the filtrate was concentrated in vacuo. The residue was added to saturated aqueous $NaHCO_3$ solution and extracted twice with EtOAc. The combined organic layers were washed with brine, dried ($Na_2SO_4$) and concentrated in vacuo. The residue was dissolved in a mixture of DCM and MeOH solution and absorbed on isolute, then purified twice by column chromatography (silica; eluent: 0 to 20% EtOAc in heptane and 20% EtOAc in heptane) and triturated from diethyl ether, yielding a first crop of the title compound (3.25 g, 14%). The kieselguhr filtercake was rinsed with acetic acid (approximately 1 L) and the filtrate was concentrated in vacuo. The residue was added to saturated aqueous $NaHCO_3$ solution and extracted twice with EtOAc. The combined organic layers were washed with brine, dried ($Na_2SO_4$) and concentrated in vacuo, yielding a second crop of the title compound (6.55 g, 28%). $\delta_H$ (300 MHz, $CDCl_3$) 8.33 (s, 1H), 7.14 (d, J 8.2 Hz, 1H), 7.09 (d, J 8.2 Hz, 1H), 4.71 (q, J 6.9 Hz, 1H), 1.61 (d, J 6.9 Hz, 3H). LCMS: $[M+H]^+$ 243/245, RT 2.377 minutes.

Intermediate 47

(S)-6-Bromo-2-methyl-2H-pyrido[3,2-b][1,4]oxazin-3(4H)-one

Prepared in a similar manner to that described for Intermediate 46 from (S)-methyl 2-[(6-bromo-2-nitropyridin-3-yl)oxy]propanoate to give the title compound (62%, two steps). $\delta_H$ (300 MHz, $CDCl_3$) 8.72 (s, 1H), 7.14 (d, J 8.2 Hz, 1H), 7.09 (d, J 8.2 Hz, 1H), 4.73 (q, J 6.9 Hz, 1H), 1.61 (d, J 6.9 Hz, 3H). LCMS: $[M+H]^+$ 243/245, RT 2.38 minutes.

Intermediate 48

4-Chloro-2-fluoro-6-nitrophenol

At 15° C., fuming nitric acid (100%, 2.9 mL, 71.6 mmol) was added dropwise to a solution of 4-chloro-2-fluorophenol (10 g, 68.2 mmol) in acetic acid (100 mL) under water-bath cooling (cold tap water, −11° C.) within 10 minutes. During the addition, the reaction temperature increased to 27° C. After the addition was complete, the reaction mixture was maintained under water-bath cooling at −25° C. for 1 h, then slowly poured into water (1.5 L) with stirring. After 1 h, the precipitate was filtered off and washed with water, then dried by air current on the filter, to afford the title compound (9.88 g, 76%). $\delta_H$ (300 MHz, $CDCl_3$) 10.36 (s, 1H), 7.94 (t, J 2.3 Hz, 1H), 7.44 (dd, J 9.5, 2.5 Hz, 1H).

Intermediate 49

(R)-Methyl 2-(4-chloro-2-fluoro-6-nitrophenoxy)propanoate

Prepared from Intermediate 48 in a similar manner to that described for Intermediate 45. $\delta_H$ (300 MHz, $CDCl_3$) 7.61 (t, J 2.2 Hz, 1H), 7.35 (dd, J 10.7, 2.6 Hz, 1H), 4.89 (q, J 6.8 Hz, 1H), 3.73 (s, 3H), 1.68 (d, J 6.8 Hz, 3H).

Intermediate 50

(R)-Methyl 2-[(6-chloro-2-nitropyridin-3-yl)oxy]propanoate

Prepared from Intermediate 51 in a similar manner to that described for Intermediate 45. $\delta_H$ (300 MHz, $CDCl_3$) 7.52 (d, J 8.7 Hz, 1H), 7.45 (d, J 8.7 Hz, 1H), 4.87 (q, J 6.8 Hz, 1H), 3.78 (s, 3H), 1.69 (d, J 6.8 Hz, 3H).

Intermediate 51

6-Chloro-2-nitropyridin-3-ol

At 5-10° C., fuming nitric acid (99 mL, 2.21 mol) was added dropwise to a solution of 6-chloropyridin-3-ol (220 g, 1.70 mol) in acetic acid (2 L) under water/ice-bath cooling within 45 minutes. After the addition was complete, the reaction mixture was maintained at r.t. overnight. The reaction mixture was purged with nitrogen, then concentrated in vacuo. The residue was triturated from water (150 mL), filtered and washed with diisopropyl ether (150 mL), then dried by air current on the filter, to afford the title compound (170.8 g, 57%). LCMS [M+H]⁺ 175/177, RT 1.35 minutes.

Intermediate 52

(R)-6-Chloro-8-fluoro-2-methyl-2H-benzo[b][1,4]oxazin-3(4H)-one

Prepared from Intermediate 49 in a similar manner to that described for Intermediate 46. $\delta_H$ (300 MHz, DMSO-d$_6$) 10.96 (s, 1H), 7.10 (dd, J 10.4, 2.4 Hz, 1H), 6.78-6.72 (m, 1H), 4.80 (q, J 6.8 Hz, 1H), 1.45 (d, J 6.8 Hz, 3H). LCMS [M+H]+ 216/218, RT 2.68 minutes.

Intermediate 53

(R)-6-Chloro-2-methyl-2H-pyrido[3,2-b][1,4]oxazin-3(4H)-one

Prepared from Intermediate 50 in a similar manner to that described for Intermediate 46. $\delta_H$ (300 MHz, CDCl$_3$) 9.08 (s, 1H), 7.23 (d, J 8.3 Hz, 1H), 6.94 (d, J 8.3 Hz, 1H), 4.73 (q, J 6.9 Hz, 1H), 1.61 (d, J 6.9 Hz, 3H). LCMS [M+H]⁺ 199/201, RT 2.30 minutes.

Intermediate 54

(R)-Ethyl 2-[(6-bromo-4-methyl-2-nitropyridin-3-yl)oxy]propanoate

Prepared from Intermediate 64 in a similar manner to that described for Intermediate 45. $\delta_H$ (300 MHz, CDCl$_3$) 7.56 (s, 1H), 4.60 (q, J 6.8 Hz, 1H), 4.16 (qd, J 7.1, 1.1 Hz, 2H), 2.46 (s, 3H), 1.62 (d, J 6.8 Hz, 3H), 1.24 (t, J 7.1 Hz, 3H).

Intermediate 55

(R)-Methyl 2-(4-bromo-2-fluoro-6-nitrophenoxy)propanoate

Prepared from 4-bromo-2-fluoro-6-nitrophenol in a similar manner to that described for Intermediate 45. $\delta_H$ (300 MHz, CDCl$_3$) 7.75 (t, J 2.2 Hz, 1H), 7.48 (dd, J 10.5, 2.4 Hz, 1H), 4.90 (q, J 6.9 Hz, 1H), 3.73 (s, 3H), 1.67 (dd, J 6.8, 0.7 Hz, 3H).

Intermediate 56

(R)-6-Bromo-2,8-dimethyl-2H-pyrido[3,2-b][1,4]oxazin-3(4H)-one

Prepared from Intermediate 54 in a similar manner to that described for Intermediate 46. $\delta_H$ (300 MHz, DMSO-d$_6$) 11.34 (s, 1H), 7.13 (s, 1H), 4.77 (q, J 6.8 Hz, 1H), 2.18 (s, 3H), 1.44 (d, J 6.8 Hz, 3H). LCMS [M+H]⁺ 257/259, RT 2.711 minutes.

Intermediate 57

(R)-6-Bromo-8-fluoro-2-methyl-2H-benzo[b][1,4]oxazin-3(4H)-one

Prepared from Intermediate 55 in a similar manner to that described for Intermediate 46. $\delta_H$ (300 MHz, DMSO-d$_6$) 10.95 (s, 1H), 7.21 (dd, J 10.1, 2.2 Hz, 1H), 6.88 (t, J 2.0 Hz, 1H), 4.80 (q, J 6.8 Hz, 1H), 1.45 (d, J 6.8 Hz, 3H). LCMS [M+H]+ 260/262, RT 2.761 minutes.

Intermediate 58

5-Bromobenzo[d]oxazol-2(3H)-one

A solution of 2-amino-4-bromophenol (50.1 g, 266 mmol) and 1,1'-carbonyl-diimidazole (51.9 g, 320 mmol) in THF (1 L) was stirred at reflux for 2 h. After cooling to r.t., the mixture was diluted with aqueous HCl (2M) and extracted with EtOAc. The organic layer was washed with saturated aqueous NaHCO$_3$ solution and brine, then dried (Na$_2$SO$_4$) and evaporated in vacuo. The residue was triturated from a mixture of EtOAc (30 mL) and heptane (3 mL) to afford a first crop of the title compound (32.5 g, 56%). Concentration of the mother liquor afforded a second crop of the title compound (24.5 g, 41%). $\delta_H$ (300 MHz, DMSO-d$_6$) 11.84 (s, 1H), 7.26 (s, 3H). LCMS [M–H]⁻ 212/214, RT 2.603 minutes.

Intermediate 59

2-Amino-4-bromo-6-fluorophenol

To a stirred solution of 4-bromo-2-fluoro-6-nitrophenol (15 g, 0.072 mol) in EtOH (750 mL) was added SnCl$_2$ (67.5 g, 0.36 mol). The reaction mixture was heated at 80° C. for 2 h, then poured into ice. The pH was adjusted to 7-8 using aqueous NaOH solution, then the aqueous layer was extracted with EtOAc (2×600 mL). The combined organic layer was dried over anhydrous Na$_2$SO$_4$, then concentrated, to afford the title compound (10.5 g, 70%) as a grey solid. $\delta_H$ (400 MHz, DMSO-d$_6$) 9.21 (s, 1H), 6.72-6.45 (m, 2H), 5.17 (br s, 2H).

Intermediate 60

5-Bromo-7-fluoro-3H-1,3-benzoxazol-2-one

To a stirred solution of Intermediate 59 (10.5 g, 0.050 mol) in THF (210 mL) was added CDI (9.8 g, 0.069 mol). The reaction mixture was heated at 60° C. for 15 h, then quenched with 2N HCl (5 mL) and extracted with EtOAc (2×850 mL). The combined organic layer was dried over anhydrous Na$_2$SO$_4$ and concentrated. The crude residue was purified by column chromatography (silica 100-200 mesh; 20% EtOAc in hexanes) to afford the title compound (9.5 g, 80%) as a grey solid. $\delta_H$ (400 MHz, DMSO-d$_6$) 12.18 (s, 1H), 7.37 (dd, J 10.0, 1.8 Hz, 1H), 7.15 (dd, J 1.8, 0.7 Hz, 1H).

Intermediate 61

4-Methylpyridin-3-yl Acetate

Acetic anhydride (1000 mL, 10.6 mol) was heated to reflux. The heating bath was removed and 4-methylpyridine 1-oxide (496 g, 4.55 mol) was added in portions to maintain reflux. After the addition was complete (1.5 h), the reaction mixture was allowed to cool to r.t. and concentrated in vacuo. The residue was stirred with saturated aqueous NaHCO$_3$ solution and extracted with DCM. The combined organic layers were dried (Na$_2$SO$_4$) and evaporated in vacuo to afford a dark oil (553.5 g) containing the title compound (67%).

Intermediate 62

4-Methylpyridin-3-ol

Lithium hydroxide monohydrate (32.1 g, 764 mmol) was added to Intermediate 61 (127 g, 841 mmol) in THF (500 mL) and water (500 mL). After 6 h, THF was removed in vacuo, then DCM and 1M aqueous sodium hydroxide solution were added. The layers were separated. The aqueous phase was acidified with concentrated HCl until the pH was approximately 4-5, then saturated with sodium chloride and extracted with EtOAc. The combined organic layers were washed with brine, dried ($Na_2SO_4$), and evaporated in vacuo, to afford the title compound (19 g, 21%). $\delta_H$ (300 MHz, $CDCl_3$) 10.72 (s, 1H), 8.16 (s, 1H), 7.93 (d, J 4.9 Hz, 1H), 7.14 (d, J 4.9 Hz, 1H), 2.31 (s, 3H).

Intermediate 63

4-Methyl-2-nitropyridin-3-ol

While cooling in an ice/water bath, Intermediate 62 (59 g, 545 mmol) was added portionwise to concentrated sulfuric acid (290 mL), keeping the temperature below 40° C. At 0° C., an ice-cooled mixture of fuming nitric acid (25.5 mL, 600 mmol) in concentrated sulfuric acid (58 mL) was added dropwise over about 45 minutes, keeping the temperature below 20° C. After the addition was complete, the reaction mixture was stirred at r.t. for 2 h, then poured into a mixture of ice and water (1.5 L). Ammonium hydroxide was added carefully to the resulting mixture until the pH was approximately 1-2. The resulting precipitate was filtered and dried to afford the title compound (69.5 g, 83%). $\delta_H$ (300 MHz, DMSO-$d_6$) 10.40 (s, 1H), 7.93 (d, J 4.5 Hz, 1H), 7.57 (d, J 4.5 Hz, 1H), 2.32 (s, 3H).

Intermediate 64

6-Bromo-4-methyl-2-nitropyridin-3-ol

Under a nitrogen atmosphere, sodium methoxide (30 wt % solution in MeOH, 85 mL, 454 mmol) was added to a solution of Intermediate 63 (70 g, 454 mmol) in MeOH (500 mL). The mixture was stirred for 15 minutes at r.t., then a solution of bromine (23.4 mL, 454 mmol) in MeOH (100 mL) was added dropwise whilst cooling in an ice bath. After stirring at r.t. for 2 h, the mixture was concentrated in vacuo. The residue was partitioned between water (600 mL) and EtOAc (600 mL), and the layers were separated. The aqueous phase was saturated with sodium chloride and extracted with EtOAc (600 mL). The combined organic layers were washed with brine, dried ($Na_2SO_4$), and evaporated in vacuo. The residue was crystallised from isopropyl alcohol to afford the title compound (65 g, 61%). $\delta_H$ (300 MHz, $CDCl_3$) 10.52 (s, 1H), 7.60 (s, 1H), 2.41 (d, J 0.8 Hz, 3H).

Intermediate 65

Ethyl (E)-3-(3-amino-5-chloropyridin-2-yl)prop-2-enoate

To a degassed solution of 2,5-dichloropyridin-3-amine (10 g, 0.0613 mmol), ethyl acrylate (12.9 g, 0.128 mmol), DIPEA (28.7 mL, 0.1655 mmol) and TBAB (19.7 g, 0.0613 mmol) in DMF (200 mL) was added 1,4-bis(diphenylphosphino)butane (5.2 g, 0.0122 mmol), followed by Pd(OAc)$_2$ (1.37 g, 0.00613 mmol). The reaction mixture was degassed for a further 30 minutes, heated at 140° C. for 30 h, then quenched with $H_2O$. The aqueous layer was extracted with EtOAc. The combined organic layer was dried over anhydrous $Na_2SO_4$ and concentrated, then purified by column chromatography (silica: 100-200 mesh; 50% EtOAc: hexanes), to afford the title compound (7.2 g, 52%). $\delta_H$ (400 MHz, DMSO-$d_6$) 7.95 (d, J 17.2 Hz, 1H), 7.81 (s, 1H), 7.19 (s, 2H), 6.75 (d, J 17.5 Hz, 1H), 6.19 (s, 1H), 4.21 (q, 2H), 1.21 (t, 3H). LCMS: m/z 227 (97.7% purity).

Intermediate 66

Ethyl 3-(3-amino-5-chloropyridin-2-yl)propanoate

To a solution of Intermediate 65 (10 g, 0.0441 mol) in MeOH (100 mL) was added NiCl$_2$ (2.85 g, 0.0220 mol), followed by NaBH$_4$ (3.3 g, 0.0882 mol). The reaction mixture was stirred at r.t. for 2 h, then filtered through Celite. The filtrate was washed with $H_2O$, dried over anhydrous $Na_2SO_4$ and concentrated. The crude residue was purified by column chromatography (silica: 100-200 mesh; 10% EtOAc in hexanes) to afford the title compound (8 g, 79%). $\delta_H$ (400 MHz, DMSO-$d_6$) 7.65 (d, J 2.2 Hz, 1H), 6.96 (d, J 2.2 Hz, 1H), 5.46 (s, 2H), 4.03 (q, J 7.1, 4.0 Hz, 2H), 2.78 (t, J 6.7, 1.1 Hz, 2H), 2.69 (t, J 6.7, 1.3 Hz, 2H), 1.16 (t, 3H). LCMS: m/z 229 (97.6% purity).

Intermediate 67

7-Chloro-3,4-dihydro-1H-1,5-naphthyridin-2-one

To a solution of Intermediate 66 (8 g, 0.0350 mol) in THF (80 mL) was added potassium tert-butoxide (5.88 g, 0.0524 mol). The reaction mixture was stirred for 1 h, then diluted with $H_2O$. The aqueous layer was extracted with EtOAc. The combined organic layer was dried over $Na_2SO_4$, then concentrated, to give the title compound (5.2 g, 81%), which was used without any further purification. $\delta_H$ (400 MHz, DMSO-$d_6$) 10.27 (s, 1H), 8.11 (d, J 2.2 Hz, 1H), 7.22 (d, J 2.3 Hz, 1H), 3.01 (dd, J 8.5, 7.0 Hz, 2H), 2.60 (dd, J 8.5, 6.9 Hz, 2H). LCMS: m/z 183 (95.6% purity).

Intermediate 68

2-Amino-6-chloropyridine-3-carboxylic Acid

A solution of 2,6-dichloropyridine-3-carboxylic acid (3 g, 0.0157 mol) in aqueous ammonia (30 mL) was heated in a sealed tube at 130° C. for 12 h. The reaction mixture was concentrated and the resulting crude solid was triturated with diethyl ether to afford the title compound (2.5 g, 93%). $\delta_H$ (400 MHz, DMSO-$d_6$) 8.02 (d, J 8.0 Hz, 1H), 7.55 (s, 2H), 6.62 (d, J 8.0 Hz, 1H). LCMS: m/z 173 (97.70%).

Intermediate 69

(2-Amino-6-chloropyridin-3-yl)methanol

To a solution of Intermediate 68 (10 g, 0.058 mol) in THF (100 mL), maintained at 0° C., was added 2M borane dimethyl sulphide complex in THF (87 mL, 0.174 mol). The reaction mixture was heated under reflux for 2 h, then quenched with a saturated aqueous solution of NH$_4$Cl. The aqueous layer was extracted with EtOAc. The combined organic layer was dried on $Na_2SO_4$ and concentrated. The crude residue was purified by column chromatography (silica: 100-200 mesh; 2% MeOH in DCM) to afford the title compound (2.5 g, 27%). δ$_H$ (400 MHz, DMSO-d$_6$) 7.39 (d, J 7.6 Hz, 1H), 6.54 (d, J 7.5 Hz, 1H), 6.12 (s, 2H), 5.19 (t, J 5.5 Hz, 1H), 4.53-4.08 (m, 2H). LCMS: m/z 159 (90.92%).

Intermediate 70

2-Amino-6-chloropyridine-3-carbaldehyde

To a solution of Intermediate 69 (5 g, 0.0316 mol) in DCM (100 mL), maintained at 0° C., was added PCC (20.41 g, 0.0949 mol). The reaction mixture was stirred at r.t. for 2 h, then diluted with diethyl ether (10 mL) and filtered through Celite. The organic layer was concentrated, and the resulting gummy solid was dissolved in EtOAc. The organic layer was washed with H$_2$O, then dried over anhydrous Na$_2$SO$_4$ and concentrated, to give the title compound (3.25 g, 66%). δ$_H$ (400 MHz, DMSO-d$_6$) 9.84 (s, 1H), 8.04 (d, J 7.9 Hz, 1H), 7.90 (s, 2H), 6.77 (d, J 7.9 Hz, 1H). LCMS: m/z 156.95 (91.80%).

Intermediate 71

Ethyl (E)-3-(2-amino-6-chloropyridin-3-yl)prop-2-enoate

To a suspension of NaH (2.53 g, 0.063 mol) in DMF (20 mL), maintained at 0° C., was added triethyl phosphonoacetate (14.19 g, 0.063 mol). The reaction mixture was stirred at 0° C. for 30 minutes. To the reaction mixture was added Intermediate 70 (6.5 g, 0.042 mol). The reaction mixture was stirred at r.t. for 1 h, then quenched with ice water. The aqueous layer was extracted with EtOAc. The organic layer was dried over Na$_2$SO$_4$ and concentrated to give the title compound (7 g, 72%), which was used without further purification. δ$_H$ (400 MHz, DMSO-d$_6$) 7.88 (d, J 8.0 Hz, 1H), 7.74 (d, J 15.7 Hz, 1H), 6.86 (s, 2H), 6.58 (dd, J 8.0, 0.6 Hz, 1H), 6.46 (s, 1H), 4.17 (q, J 7.1 Hz, 2H), 1.25 (t, J 7.1 Hz, 3H). LCMS: m/z 227.05 (82.91%).

Intermediate 72

Ethyl 3-(2-amino-6-chloropyridin-3-yl)propanoate

To a solution of Intermediate 71 (7 g, 0.030 mol) in MeOH (50 mL) was added NiCl$_2$ (0.788 g, 0.0061 mol), followed by NaBH$_4$ (2.34 g, 0.061 mol). The reaction mixture was stirred at r.t. for 1 h, then diluted with H$_2$O and extracted with EtOAc. The combined organic layer was dried on NaSO$_4$ and concentrated to give the title compound (6.5 g, 92%), which was used without any further purification. δ$_H$ (400 MHz, DMSO-d$_6$) 7.21 (d, J 7.6 Hz, 1H), 6.48 (d, J 7.6 Hz, 1H), 6.24 (s, 2H), 4.04 (q, J 7.1 Hz, 2H), 2.64 (t, J 7.4 Hz, 2H), 2.57-2.45 (m, 2H), 1.16 (t, J 7.1 Hz, 3H). LCMS: m/z 229.05 (90.65%).

Intermediate 73

7-Chloro-3,4-dihydro-1H-1,8-naphthyridin-2-one

To a solution of Intermediate 72 (6.65 g, 0.028 mol) in THF (50 mL) was added potassium tert-butoxide (4.7 g, 0.042 mol). The reaction mixture was stirred for 1 h, then diluted with H$_2$O. The aqueous layer was extracted with EtOAc. The combined organic layer was dried over Na$_2$SO$_4$ and concentrated to give the title compound (4.6 g, 90%), which was used without any further purification. δ$_H$ (400 MHz, DMSO-d$_6$) 10.68 (s, 1H), 7.63 (d, J 7.7 Hz, 1H), 7.03 (d, J 7.7 Hz, 1H), 2.87 (dd, J 8.3, 7.0 Hz, 2H), 2.50 (d, J 15.3 Hz, 2H). LCMS: m/z 225 (CH$_3$CN adduct; 91.18%).

Intermediate 74

7-Chloro-1-[(1,3,5-trimethylpyrazol-4-yl)methyl]-3,4-dihydro-1,8-naphthyridin-2-one To a suspension of NaH (6.5 g, 0.164 mol) in DMF (40 mL), maintained at 0° C., was added Intermediate 73 (4.6 g, 0.032 mol). The reaction mixture was stirred at 0° C. for 30 minutes. To the reaction mixture was added Intermediate 36 (12.7 g, 0.065 mol) and the resulting mixture was stirred at r.t. for 1 h, then quenched with H$_2$O. The aqueous layer was extracted with EtOAc. The combined organic layer was washed with brine, dried and concentrated, to give the title compound (5 g, 65%), which was used without further purification. δ$_H$ (400 MHz, DMSO-d$_6$) 7.65 (d, J 7.6 Hz, 1H), 7.08 (dd, J 7.7, 2.0 Hz, 1H), 4.93 (s, 2H), 3.54 (s, 3H), 2.80 (t, J 7.5 Hz, 2H), 2.65 (t, J 7.4 Hz, 2H), 2.23 (s, 3H), 2.07 (s, 3H). LCMS: m/z 305.10 (97.94%).

Intermediate 75

7-Chloro-1-[(1,3,5-trimethylpyrazol-4-yl)methyl]-3,4-dihydro-1,5-naphthyridin-2-one To a suspension of NaH (3.2 g, 0.1369 mol) in DMF (100 mL), maintained at 0° C., was added Intermediate 67 (5 g, 0.0273 mol). The reaction mixture was stirred at 0° C. for 30 minutes. To the reaction mixture was added Intermediate 36 (10.6 g, 0.0546 mol) and the resulting mixture was stirred at r.t. for 1 h, then quenched with H$_2$O. The aqueous layer was extracted with EtOAc. The combined organic layer was washed with brine, dried and concentrated, to give the title compound (5.9 g, 71%), which was used without any further purification. δ$_H$ (400 MHz, DMSO-d$_6$) 8.14 (d, J 2.1 Hz, 1H), 7.45 (d, J 2.1 Hz, 1H), 4.95 (s, 2H), 3.55 (s, 3H), 2.97 (dd, J 8.8, 6.2 Hz, 2H), 2.75 (dd, J 8.7, 6.2 Hz, 2H), 2.18 (s, 3H), 2.00 (s, 3H). LCMS: m/z 305 (93.3% purity).

Intermediate 76

7-Chloro-3-methyl-1-[(1,3,5-trimethylpyrazol-4-yl)methyl]-3,4-dihydro-1,5-naphthyridin-2-one To a solution of Intermediate 75 (2 g, 6.6 mmol) in THF (40 mL), maintained at −78° C., was added LDA (7.28 mL, 13 mmol), and the reaction mixture was stirred at −78° C. for 30 minutes. To the reaction mixture was added iodomethane (1.19 g, 8.3 mmol), and the resulting mixture was stirred for 2 h at r.t., then quenched with H$_2$O. The aqueous layer was extracted with EtOAc. The combined organic layer was dried over Na$_2$SO$_4$ and concentrated to give the title compound (2 g, 96%), which was used without any further purification. δ$_H$ (400 MHz, DMSO-d$_6$) 8.15 (d, 1H), 7.45 (d, 1H), 5.25 (d, J 15.8 Hz, 1H), 4.91 (d, J 15.8 Hz, 1H), 3.55 (s, 3H), 3.05 (m, 1H), 2.86 (m, 2H), 2.17 (s, 3H), 1.98 (s, 3H), 1.23-1.12 (m, 3H). LCMS: m/z 319 (89.3% purity).

Intermediate 77

7-Chloro-3-methyl-1-[(1,3,5-trimethylpyrazol-4-yl)methyl]-3,4-dihydro-1,8-naphthyridin-2-one To a solution of Intermediate 74 (3 g, 0.0098 mol) in THF (20 mL), maintained at −78° C., was added LDA (13.6 mL, 0.0245 mol), and the reaction mixture was stirred at −78° C. for 30 minutes. To the reaction mixture was added iodomethane (1 mL, 0.014 mol), and the resulting mixture was stirred for 2 h at r.t., then quenched with H$_2$O. The aqueous layer was extracted with EtOAc. The combined organic layer was dried over Na$_2$SO$_4$ and concentrated to give the title compound (2.3 g, 74%). $\delta_H$ (400 MHz, CDCl$_3$) 7.38 (d, J 7.6 Hz, 1H), 6.90 (dd, J 7.7 Hz, 1H), 5.20 (d, J 14.6 Hz, 1H), 5.00 (d, J 14.5 Hz, 1H), 3.64 (s, 3H), 2.84 (ddd, J 15.2, 5.3, 0.8 Hz, 1H), 2.71-2.61 (m, 1H), 2.53 (ddd, J 15.4, 11.1, 1.1 Hz, 1H), 2.34 (s, 3H), 2.19 (s, 3H), 1.27 (d, J 6.8 Hz, 3H). LCMS: m/z 319.10 (85.51%).

Intermediate 78

5-Bromo-7-fluoro-3-[(1,3,5-trimethylpyrazol-4-yl)methyl]-1,3-benzoxazol-2-one

Prepared from Intermediate 36 and Intermediate 60 in a similar manner to that described for Intermediate 74 to give the title compound (5.5 g, 72%) as an off-white solid. $\delta_H$ (400 MHz, DMSO-d$_6$) 7.48-7.40 (m, 1H), 7.30 (s, 1H), 4.81 (s, 2H), 3.62 (s, 3H), 2.25 (s, 3H), 2.08 (s, 3H). LCMS: m/z 354 (99.2%).

Intermediate 79

6-(3-Methoxyphenyl)-2H,3H,4H-pyrido[3,2-b][1,4]oxazin-3-one

A mixture of 6-bromo-2H,3H,4H-pyrido[3,2-b][1,4]oxazin-3-one (1.82 g, 7.95 mmol), 3-methoxyphenylboronic acid (1.45 g, 9.54 mmol), and 2M aqueous Na$_2$CO$_3$ solution (12 mL) in anhydrous 1,4-dioxane (80 mL) was degassed with nitrogen for 10 minutes. To the mixture was added bis(cyclopentyldiphenylphosphane) dichloro-palladium iron (294.7 mg, 0.4 mmol), and the resulting mixture was heated at 100° C. for 3 h. The reaction mixture was allowed to cool to r.t. before being diluted with EtOAc. The suspension was filtered through a pad of Celite, washing with EtOAc. The filtrate was concentrated in vacuo. Purification of the crude residue by column chromatography (0-40% EtOAc:heptane) gave the title compound (32%). $\delta_H$ (250 MHz, DMSO-d$_6$) 11.31 (s, 1H), 7.53 (m, 3H), 7.37 (dd, J 14.3, 8.0 Hz, 2H), 6.95 (m, 1H), 4.67 (s, 2H), 3.80 (s, 3H).
Method D HPLC-MS: MH+ m/z 257, RT 1.72 minutes.

Intermediate 80

(2R)-8-Fluoro-2-methyl-6-(pyridin-3-yl)-3,4-dihydro-2H-1,4-benzoxazin-3-one

A suspension of Intermediate 52 (5.0 g, 23.19 mmol) and pyridin-3-ylboronic acid (3.4 g, 27.66 mmol) in 2M aqueous Na$_2$CO$_3$ solution (35 mL) and 1,4-dioxane (100 mL) was degassed with nitrogen, then tris(dibenzylidineacetone)dipalladium(0) (531 mg, 0.58 mmol) and X-Phos (553 mg, 1.16 mmol) were added and the mixture was degassed with nitrogen. The mixture was heated at 100° C. for 16 h, then cooled and diluted with water (100 mL) and DCM (100 mL). Solids were removed by filtration through Celite, then the residue was washed with water (50 mL) and DCM (2×100 mL). The aqueous layer was extracted with DCM (2×100 mL). The combined organic layers were washed with brine (50 mL) and dried (MgSO$_4$), then the solvent was removed in vacuo. The resulting red solid was triturated with hot tert-butyl methyl ether (100 mL), and collected by filtration, to afford the title compound (4.66 g, 78%). $\delta_H$ (500 MHz, DMSO-d$_6$) 10.85 (br s, 1H), 8.80 (d, J 2.2 Hz, 1H), 8.56 (dd, J 4.7, 1.4 Hz, 1H), 7.98 (dt, J 8.0, 1.9 Hz, 1H), 7.48 (dd, J 7.9, 4.8 Hz, 1H), 7.32 (dd, J 11.7, 2.0 Hz, 1H), 7.01 (s, 1H), 4.83 (q, J 6.8 Hz, 1H), 1.48 (d, J 6.8 Hz, 3H). Method B HPLC-MS: MH+ m/z 259.1, RT 1.28 minutes (100%).

Intermediate 81

8-Fluoro-6-(pyridin-3-yl)-3-dihydro-2H-1,4-benzoxazin-3-one

A suspension of 6-bromo-8-fluoro-3,4-dihydro-2H-1,4-benzoxazin-3-one (500 mg, 2.03 mmol) and 2M aqueous Na$_2$CO$_3$ solution (2.03 mL, 4.06 mmol) in 1,4-dioxane (10 mL) was treated with pyridin-3-ylboronic acid (375 mg, 3.05 mmol), then Pd(dppf)Cl$_2$ (166 mg, 0.20 mmol) was added. The mixture was heated at 100° C. for 2 h, then cooled. Water (10 mL) and EtOAc (10 mL) were added. The solid was removed by filtration to afford the title compound (451 mg, 91%). $\delta_H$ (500 MHz, DMSO-d$_6$) 8.84-8.77 (m, 1H), 8.56 (d, J 4.1 Hz, 1H), 7.98 (d, J 7.9 Hz, 1H), 7.48 (dd, J 7.8, 4.8 Hz, 1H), 7.35-7.27 (m, 1H), 7.01 (s, 1H), 4.70 (s, 2H).

Intermediate 82

6-(1-Acetylpiperidin-3-yl)-8-fluoro-3,4-dihydro-2H-1,4-benzoxazin-3-one

A suspension of Intermediate 81 (445 mg, 1.82 mmol) in EtOH (15 mL) and water (1.7 mL) was treated with methanesulfonic acid (0.19 mL, 1.82 mmol). Platinum(IV) oxide (86 mg, 0.38 mmol) was added and the mixture was stirred under hydrogen for 1 day. The solid was removed by filtration through Kieselguhr, then washed with MeOH/water (2:1, 3×15 mL). The filtrate was treated with saturated aqueous NaHCO$_3$ solution (1 mL), then partitioned between EtOAc (50 mL) and water (20 mL). The organic layer was dried (MgSO$_4$) and the solvent was removed in vacuo. The residue was acetylated using acetic anhydride and DIPEA, following the procedure described for Intermediate 84, to give the title compound. $\delta_H$ (500 MHz, DMSO-d$_6$) 10.87 (s, 1H), 6.85 (d, 1H), 6.61 (s, 1H), 4.63 (s, 2H), 4.48-4.33 (m, 1H), 3.79 (d, J 31.5, 13.0 Hz, 1H), 3.11-2.92 (m, 1H), 2.85-2.53 (m, 1H), 2.02 (s, 3H), 1.94-0.87 (m, 5H). Method B HPLC-MS: MH+ m/z 293, RT 1.51 minutes (98%).

Intermediate 83

(2R)-8-Fluoro-2-methyl-6-(piperidin-3-yl)-3,4-dihydro-2H-1,4-benzoxazin-3-one

Prepared from Intermediate 80 in a similar manner to that described for Intermediate 82 (omitting the acetylation step) to afford the title compound (3.33 g, 88%) as an off-white powder. $\delta_H$ (500 MHz, DMSO-d$_6$) 10.78 (br s, 1H), 6.77 (dd, J 11.8, 1.4 Hz, 1H), 6.56 (s, 1H), 4.72 (q, J 6.8 Hz, 1H), 3.00-2.91 (m, 2H), 2.57-2.51 (obs m, 1H), 2.48-2.44 (obs m, 1H), 1.89-1.77 (m, 1H), 1.70-1.60 (m, 1H), 1.52-1.44 (m, 2H), 1.43 (d, J 6.8 Hz, 3H). Method E HPLC-MS: MH+ m/z 265.2, RT 1.58 minutes (100%).

Intermediate 84

(2R)-6-(1-Acetylpiperidin-3-yl)-8-fluoro-2-methyl-3,4-dihydro-2H-1,4-benzoxazin-3-one Acetic anhydride (0.79 mL, 8.36 mmol) was added to a suspension of Intermediate 83 (2.1 g, 7.55 mmol) and DIPEA (1.5 mL, 9.08 mmol) in DCM (40 mL). The mixture was stirred at 20° C. for 2 days, then partitioned between 0.5M aqueous hydrochloric acid (50 mL) and DCM (50 mL). The aqueous layer was extracted with DCM (2×50 mL) and the combined organic layers were washed with saturated aqueous $Na_2CO_3$ solution (30 mL) and brine (30 mL), then dried ($MgSO_4$). The solvent was removed in vacuo. The resulting off-white solid was purified by column chromatography ($SiO_2$; 50% EtOAc/heptane to 10% MeOH/EtOAc) to afford the title compound (1.99 g, 75%). $\delta_H$ (500 MHz, DMSO-$d_6$) 10.81 (s, 1H), 6.90 (d, J 11.9 Hz, 0.5H), 6.82 (dd, J 11.8, 1.5 Hz, 0.5H), 6.63 (s, 0.5H), 6.58 (s, 0.5H), 4.80-4.67 (m, 1H), 4.39 (app t, J 13.8 Hz, 1H), 3.88-3.71 (m, 1H), 3.08-2.94 (m, 1H), 2.69-2.56 (m, 0.5H), 2.54-2.41 (obs m, 1.5H), 2.01 (s, 1.5H), 2.00 (s, 1.5H), 1.87 (app d, J 11.8 Hz, 1H), 1.79-1.66 (m, 1H), 1.65-1.55 (m, 1H), 1.54-1.46 (m, 0.5H), 1.43 (d, J 6.8 Hz, 3H), 1.42-1.29 (m, 0.5H). Method B HPLC-MS: MH+ m/z 307.0, RT 1.64 minutes (87%).

Intermediate 84 was separated by chiral SFC using Lux Amylose 2 column, 250×21.2 mm, 5 m; eluent: MeOH (30%). No modifier was added and the flow rate was 50 mL/minute at a wavelength of 218 nm to give the separated isomers as Intermediate 84A (191 mg, 99% d.e.) and Intermediate 84B (576 mg, 98.5% d.e.).

Intermediate 85 tert-Butyl 3-[(2R)-8-fluoro-2-methyl-3-oxo-3,4-dihydro-2H-1,4-benzoxazin-6-yl]-1H-pyrrole-1-carboxylate To Intermediate 57 (4.44 g, 17.06 mmol) in 1,4-dioxane (100 mL) was added tert-butyl 3-(4,4,5,5-tetramethyl-1,3,2-dioxaborolan-2-yl)-1H-pyrrole-1-carboxylate (5 g, 17.06 mmol), followed by 2M aqueous $Na_2CO_3$ solution (25.58 mL). The resulting mixture was degassed for 5 minutes before the addition of Pd(dppf)$Cl_2$ (0.7 g, 0.85 mmol). The reaction mixture was degassed for a further 5 minutes, then heated for 2 h at 100° C., then left to cool to r.t. EtOAc (100 mL) and water (100 mL) were added and the layers were separated. The aqueous phase was extracted with more EtOAc (100 mL) and the combined organic fractions were washed with brine (100 mL). The organic layer was concentrated under vacuum. The resulting crude dark solid (10.96 g) was purified by column chromatography (eluting with an EtOAc/heptane gradient) to afford the title compound (3.92 g, 65%). $\delta_H$ (500 MHz, DMSO-$d_6$) 10.80 (s, 1H), 7.59 (t, J 1.9 Hz, 1H), 7.31 (dd, J 3.2, 2.2 Hz, 1H), 7.25 (dd, J 11.9, 1.9 Hz, 1H), 6.91 (s, 1H), 6.60 (dd, J 3.3, 1.8 Hz, 1H), 4.78 (q, J 6.8 Hz, 1H), 1.58 (s, 9H), 1.46 (d, J 6.8 Hz, 3H). Method B HPLC-MS: MH+ m/z 347.05, RT 2.30 minutes (91%).

Intermediate 86 tert-Butyl 3-[(2R)-8-fluoro-2-methyl-3-oxo-3,4-dihydro-2H-1,4-benzoxazin-6-yl]-pyrrolidine-1-carboxylate A suspension of 10% palladium on carbon (50% water wet) (2.95 g, 2.77 mmol) and Intermediate 85 (3.92 g, 11.09 mmol) in EtOH (50 mL) and THF (75 mL) was stirred under an atmosphere of hydrogen for 4.5 h at r.t. The catalyst was removed by suction filtration through a Celite pad, washing with EtOAc (100 mL) and THF (2×100 mL). The filtrate was concentrated under vacuum to afford the title compound (3.871 g, 91%). $\delta_H$ (500 MHz, DMSO-$d_6$) 10.80 (s, 1H), 6.87 (d, J 11.3 Hz, 1H), 6.62 (s, 1H), 4.74 (q, J 6.9 Hz, 1H), 3.66 (t, J 8.2 Hz, 1H), 3.44 (t, J 9.3 Hz, 1H), 3.31-3.21 (m, 2H), 3.08 (td, J 9.9, 4.3 Hz, 1H), 2.21-2.09 (m, 1H), 1.93-1.78 (m, 1H), 1.45 (s, 3H), 1.41 (d, J 4.8 Hz, 9H). Method D HPLC-MS: MH+ m/z 351.1, RT 3.36 minutes (90%).

Chiral chromatography (Column: Cellulose 3 25 cm; Mobile phase: 10% MeOH: 90% $CO_2$; Flow rate: 4 mL/minute; UV at 215 nm; Runtime: 7 minutes) shows two peaks at RT 4.03 minute and 5.40 minute corresponding to a 1:1 mixture of diastereomers.

Intermediate 87

(2R)-8-Fluoro-2-methyl-6-(pyrrolidin-3-yl)-3,4-dihydro-2H-1,4-benzoxazin-3-one hydrochloride To a solution of Intermediate 86 (1.4 g, 3.8 mmol) in EtOH (50 mL) was added 4M HCl in 1,4-dioxane (47.45 mL). The reaction mixture was heated under reflux for 2 h, then concentrated in vacuo, to afford the title compound (1.19 g, quantitative). $\delta_H$ (500 MHz, DMSO-$d_6$) 10.90 (s, 1H), 9.04 (s, 2H), 6.96 (dd, J 11.7, 1.7 Hz, 1H), 6.64 (s, 1H), 4.75 (q, J 6.7 Hz, 1H), 3.57 (m, 1H), 3.39 (m, 2H), 3.24-3.15 (m, 1H), 2.99 (td, J 10.9, 4.5 Hz, 1H), 2.30 (s, 1H), 1.87 (p, J 9.7 Hz, 1H), 1.45 (d, J 6.8 Hz, 3H). Method B HPLC-MS: MH+ m/z 250.95, RT 1.13 minutes (94%).

Intermediate 87A was prepared from Intermediate 87 in a similar manner to that described for Intermediate 88A to give a separate isomer as Intermediate 87A (0.85 g, 100%). $\delta_H$ (500 MHz, DMSO-$d_6$) 10.90 (s, 1H), 9.38 (s, 2H), 7.03-6.87 (m, 1H), 6.72-6.57 (m, 1H), 4.74 (q, J 6.8 Hz, 1H), 3.59-3.49 (m, 1H), 3.37-3.27 (m, 2H), 3.22-3.10 (m, 1H), 3.03-2.89 (m, 1H), 2.34-2.22 (m, 1H), 1.92-1.78 (m, 1H), 1.50-1.37 (m, 3H).

Method C HPLC-MS: MH+ m/z 251, RT 0.71 minutes (100%).

Intermediate 88

(2R)-6-(1-Acetylpyrrolidin-3-yl)-8-fluoro-2-methyl-3,4-dihydro-2H-1,4-benzoxazin-3-one Acetic anhydride (0.37 mL, 3.96 mmol) was added to a stirred suspension of Intermediate 87 (1090 mg, 3.57 mmol) and DIPEA (1.3 mL, 7.87 mmol) in DCM (100 mL). The reaction mixture was stirred for 80 minutes, then partitioned between 0.5M aqueous hydrochloric acid (50 mL) and DCM (50 mL). The organic phase was separated and the aqueous layer was extracted with DCM (2×50 mL). The combined organic extracts were washed with saturated aqueous $Na_2CO_3$ solution (50 mL) and brine (50 mL), then dried over $MgSO_4$, filtered and reduced under vacuum, to afford the title compound (1.15 g, quantitative). $\delta_H$ (500 MHz, DMSO-$d_6$) 10.91-10.70 (m, 1H), 6.98-6.74 (m, 1H), 6.72-6.55 (m, 1H), 4.74 (q, J 6.8 Hz, 1H), 3.87-3.73 (m, 1H), 3.66-3.44 (m, 2H), 3.29-3.06 (m, 2H), 2.31-2.12 (m, 1H), 1.98-1.94 (m, 3H), 1.94-1.77 (m, 1H), 1.49-1.39 (m, 3H). Method B HPLC-MS: MH+ m/z 293, RT 1.54 minutes (99%).

Intermediate 88 was separated by SFC (Chiralpak AS, 250×20 mm, 5 μm; eluent MeOH (20%); no modifier added; flow rate 50 mL/minute) to afford the separated isomers as Intermediate 88A (97% ee) and Intermediate 88B (97% ee).

Intermediate 88A: $\delta_H$ (500 MHz, DMSO-$d_6$) 10.91-10.78 (m, 1H), 7.00-6.81 (m, 1H), 6.72-6.54 (m, 1H), 4.74 (q, J 6.7 Hz, 1H), 3.90-3.81 (m, 0.5H), 3.81-3.72 (m, 0.5H), 3.67-

3.38 (m, 2H), 3.32-3.05 (m, 2H), 2.30-2.23 (m, 0.5H), 2.20-2.12 (m, 0.5H), 1.99-1.94 (m, 3H), 1.94 (s, 1H), 1.49-1.39 (m, 3H). Method B HPLC-MS: MH+ m/z 293, RT 1.05 minutes (97%).

Intermediate 89 tert-Butyl 3-(8-fluoro-3-oxo-3,4-dihydro-2H-1,4-benzoxazin-6-yl)-1H-pyrrole-1-carboxylate Prepared from 6-bromo-8-fluoro-4H-1,4-benzoxazin-3-one and tert-butyl 3-(4,4,5,5-tetramethyl-1,3,2-dioxaborolan-2-yl)-1H-pyrrole-1-carboxylate in a similar manner to that described for Intermediate 85 to give the title compound (37%). $\delta_H$ (500 MHz, DMSO-$d_6$) 10.85 (s, 1H), 7.59 (t, J 1.9 Hz, 1H), 7.31 (dd, J 3.2, 2.2 Hz, 1H), 7.25 (dd, J 11.9, 1.9 Hz, 1H), 6.92 (s, 1H), 6.60 (dd, J 3.3, 1.8 Hz, 1H), 4.66 (s, 2H), 1.58 (s, 9H). Method B HPLC-MS: MH+ m/z 333, RT 2.07 minutes (72%).

Intermediate 90 tert-Butyl 3-(8-fluoro-3-oxo-3,4-dihydro-2H-1,4-benzoxazin-6-yl)pyrrolidine-1-carboxylate Prepared from Intermediate 89 in a similar manner to that described for Intermediate 86 to give the title compound (1.0 g, 100%). $\delta_H$ (500 MHz, DMSO-$d_6$) 10.85 (s, 1H), 6.86 (d, J 11.7 Hz, 1H), 6.62 (s, 1H), 4.63 (s, 2H), 3.69-3.62 (m, 1H), 3.48-3.41 (m, 1H), 3.30-3.21 (m, 2H), 3.12-3.03 (m, 1H), 2.14-2.10 (m, 1H), 1.90-1.80 (m, 1H), 1.45-1.37 (m, 10H). Method B HPLC-MS: MH+ m/z 336, RT 1.95 minutes (99%).

Intermediate 91

8-Fluoro-6-(pyrrolidin-3-yl)-3,4-dihydro-2H-1,4-benzoxazin-3-one

Prepared from Intermediate 90 in a similar manner to that described for Intermediate 87 to give the title compound (209 mg, 33%). Method B HPLC-MS: MH+m/z 237, RT 0.91 minutes (93%).

Intermediate 92

6-(1-Acetylpyrrolidin-3-yl)-8-fluoro-3,4-dihydro-2H-1,4-benzoxazin-3-one

Prepared from Intermediate 91 in a similar manner to that described for Intermediate 88 to give the title compound (285 mg, 100%). $\delta_H$ (500 MHz, DMSO-$d_6$) 10.87 (s, 1H), 6.99-6.79 (m, 1H), 6.71-6.52 (m, 1H), 4.67-4.60 (m, 2H), 3.87-3.73 (m, 1H), 3.65-3.48 (m, 2H), 3.30-3.06 (m, 2H), 2.29-2.10 (m, 1H), 1.98-1.93 (m, 3H), 1.94-1.77 (m, 1H). Method B HPLC-MS: MH+ m/z 279, RT 1.45 minutes (94%).

Intermediate 93 tert-Butyl 3-(3-oxo-3,4-dihydro-2H-1,4-benzoxazin-6-yl)-1H-pyrrole-1-carboxylate Prepared from 6-bromo-2H-1,4-benzoxazin-3(4H)-one and tert-butyl 3-(4,4,5,5-tetramethyl-1,3,2-dioxaborolan-2-yl)-1H-pyrrole-1-carboxylate in a similar manner to that described for Intermediate 85 to give the title compound (52%). $\delta_H$ (500 MHz, DMSO-$d_6$) 10.64 (s, 1H), 7.48 (t, J 1.9 Hz, 1H), 7.32-7.27 (m, 1H), 7.19 (dd, J 8.3, 2.1 Hz, 1H), 7.08 (d, J 2.1 Hz, 1H), 6.93 (d, J 8.3 Hz, 1H), 6.56 (dd, J 3.2, 1.8 Hz, 1H), 4.57 (s, 2H), 1.57 (s, 9H). Method C HPLC-MS: MH+(-tert-butyl) m/z 259, RT 1.41 minutes (92%).

Intermediate 94 tert-Butyl 3-(3-oxo-3,4-dihydro-2H-1,4-benzoxazin-6-yl)pyrrolidine-1-carboxylate Prepared from Intermediate 93 in a similar manner to that described for Intermediate 86 to give the title compound (90%). $\delta_H$ (500 MHz, DMSO-$d_6$) 10.64-10.63 (s, 1H), 6.88 (d, J 8.2 Hz, 1H), 6.83 (dd, J 8.3, 2.0 Hz, 1H), 6.78 (s, 1H), 4.52 (s, 2H), 3.65 (dd, J 10.3, 7.7 Hz, 1H), 3.44 (t, J 9.2 Hz, 1H), 3.32 (s, 2H), 3.12-3.01 (m, 1H), 2.22-2.08 (m, 1H), 1.84 (h, J 11.1 Hz, 1H), 1.41-1.40 (s, 9H). Method C HPLC-MS: MH+(-tert-butyl) m/z 263, RT 1.31 minutes (92%).

Intermediate 95

6-(Pyrrolidin-3-yl)-3,4-dihydro-2H-1,4-benzoxazin-3-one Hydrochloride

Prepared from Intermediate 94 in a similar manner to that described for Intermediate 87 to give the title compound (100%). $\delta_H$ (500 MHz, DMSO-$d_6$) 10.74 (s, 1H), 9.42 (br s, 2H), 6.94-6.88 (m, 2H), 6.82 (d, J 1.5 Hz, 1H), 4.54 (s, 2H), 3.76-3.27 (obs m, 3H), 3.23-3.12 (m, 1H), 3.00-2.88 (m, 1H), 2.33-2.23 (m, 1H), 1.92-1.77 (m, 1H). Method D HPLC-MS: MH+ m/z 219, RT 1.31 minutes (87%).

Intermediate 96

6-(1-Acetylpyrrolidin-3-yl)-3,4-dihydro-2H-1,4-benzoxazin-3-one

Prepared from Intermediate 95 in a similar manner to that described for Intermediate 88 to give the title compound (87%). $\delta_H$ (500 MHz, DMSO-$d_6$) 10.65 (s, 1H), 6.92-6.81 (m, 2H), 6.81-6.76 (m, 1H), 4.53 (s, 2H), 3.88-3.72 (m, 1H), 3.64-3.51 (m, 1H), 3.51-3.06 (obs m, 3H), 2.30-2.11 (m, 1H), 1.98-1.94 (m, 3H), 1.93-1.75 (m, 1H). Method C HPLC-MS: MH+ m/z 261, RT 0.93 minutes (99%).

Intermediate 97

8-Fluoro-6-[3-(methanesulfinyl)phenyl]-3,4-dihydro-2H-1,4-benzoxazin-3-one

A mixture of 6-bromo-8-fluoro-4H-1,4-benzoxazin-3-one (500 mg, 2.03 mmol) and 3-(methanesulfinyl)phenylboronic acid (90%, 457.08 mg, 2.24 mmol) in 1,4-dioxane (24 mL) and 2M aqueous Na$_2$CO$_3$ solution (3.05 mL) was degassed by bubbling through nitrogen for 10 minutes. The reaction mixture was charged with bis[3-(diphenyl-phosphanyl)cyclopenta-2,4-dien-1-yl]iron DCM dichloropalladium (82.98 mg, 0.1 mmol) and degassed for an additional 5 minutes. The reaction mixture was heated at 100° C. under reflux for 4 h, then partitioned between EtOAc (30 mL) and water (30 mL). The organic phase was separated and the aqueous layer was extracted with EtOAc (2×30 mL). The combined organic extracts were washed with brine (20 mL) and dried over MgSO$_4$, then filtered and concentrated in vacuo. The crude material was purified by column chromatography, with a gradient of 0-100% EtOAc in heptane, to afford the title compound (396 mg, 54%). $\delta_H$ (500 MHz, DMSO-d$_6$) 10.97 (s, 1H), 7.87 (s, 1H), 7.78-7.72 (m, 1H), 7.68 (m, 2H), 7.34 (dd, J 11.8, 2.0 Hz, 1H), 7.07 (s, 1H), 4.73 (s, 2H), 2.81 (s, 3H). Method C HPLC-MS: MH+ m/z 306, RT 1.08 minutes (84%).

Intermediate 98

(2R)-6-[3-(Methanesulfinyl)phenyl]-2-methyl-2H,3H,4H-pyrido[3,2-b][1,4]oxazin-3-one Prepared from Intermediate 46 and 3-(methanesulfinyl) phenylboronic acid in a similar manner to that described for Intermediate 97 to afford the title compound (261 mg, 42%) as a yellow solid. $\delta_H$ (500 MHz, DMSO-d$_6$) 11.37 (s, 1H), 8.31 (m, 1H), 8.13 (dt, J 4.9, 1.7 Hz, 1H), 7.68 (m, 1H), 7.67 (m, 1H), 7.65 (m, 1H), 7.50 (m, 1H), 4.83 (q, J 6.8 Hz, 1H), 2.80 (s, 3H), 1.48 (d, J 6.8 Hz, 3H). Method C HPLC-MS: MH+ m/z 303, RT 1.03 minutes (100%).

Intermediate 99

2,2,2-Trifluoro-N-{[3-(8-fluoro-3-oxo-3,4-dihydro-2H-1,4-benzoxazin-6-yl)phenyl](methyl)(oxo)-λ$^6$-sulfanylidene}acetamide To a suspension of Intermediate 97 (84%, 200 mg, 0.55 mmol), 2,2,2-trifluoro-acetamide (124.4 mg, 1.1 mmol), MgO (88.71 mg, 2.2 mmol) and rhodium(II) acetate dimer (6.08 mg, 0.01 mmol) in DCM (5.5 mL) was added iodobenzene I,I-diacetate (265.84 mg, 0.83 mmol) at r.t., and the mixture was stirred for 17.75 h. The resulting suspension was filtered through a pad of celite and washed with DCM (20 mL), then the filtrate was concentrated in vacuo. The residue was purified by column chromatography, using a gradient of 0-100% EtOAc in heptane, to afford the title compound (131 mg, 50%). $\delta_H$ (500 MHz, DMSO-d$_6$) 11.04 (s, 1H), 8.17 (s, 1H), 8.03 (m, 2H), 7.84 (t, J 7.9 Hz, 1H), 7.41 (dd, J 11.7, 2.0 Hz, 1H), 7.08 (s, 1H), 4.74 (s, 2H), 3.86 (s, 3H). Method E HPLC-MS: MH+ m/z 417, RT 1.43 minutes (87%).

Intermediate 100

2,2,2-Trifluoro-N—[(methyl) {3-[(2R)-2-methyl-3-oxo-2H,3H,4H-pyrido[3,2-b][1,4]-oxazin-6-yl]phenyl}(oxo)-λ$^6$-sulfanylidene]acetamide Prepared from Intermediate 98 and 2,2,2-trifluoroacetamide in a similar manner to that described for Intermediate 99 to afford the title compound (127 mg, 35%) as a clear oil. 6H (500 MHz, DMSO-d$_6$) 11.44 (s, 1H), 8.61 (s, 1H), 8.41 (d, J 7.0 Hz, 1H), 8.01 (d, J 8.2 Hz, 1H), 7.84 (t, J 7.9 Hz, 1H), 7.72 (dd, J 8.2, 3.0 Hz, 1H), 7.54 (d, J 8.2 Hz, 1H), 4.86 (q, J 6.7 Hz, 1H), 3.83 (s, 3H), 1.49 (d, J 6.8 Hz, 3H). Method C HPLC-MS: MH+m/z 414, RT 1.30 minutes (99%).

Intermediate 101

(2R)-6-Chloro-8-fluoro-2-methyl-4-[(1,3,5-trimethyl-1H-pyrazol-4-yl)methyl]-3,4-dihydro-2H-1,4-benzoxazin-3-one To a suspension of Intermediate 52 (2.0 g, 9.28 mmol) and cesium carbonate (9.0 g) in DMF (20 mL) was added a solution of Intermediate 36 (1.6 g, 10.2 mmol) in DMF (15 mL) dropwise at 0° C. The mixture was stirred at r.t. for 2 h. The solvent was removed in vacuo and the residue was dissolved in EtOAc (100 mL), then washed with water (2×50 mL) and brine. The aqueous layers were extracted with EtOAc (2×50 mL) and the combined organic layers were dried with Na$_2$SO$_4$, then the solvent was removed in vacuo. Trituration from DCM, followed by purification by column chromatography (SiO$_2$; DCM), gave the title compound (2.0 g, 60%). $\delta_H$ (DMSO-d$_6$) 7.20 (dd, J 10.1, 2.2 Hz, 1H), 7.01 (d, J 1.8 Hz, 1H), 5.09 (d, J 15.8 Hz, 1H), 4.90 (q, J 6.7 Hz, 1H), 4.84 (d, J 15.8 Hz, 1H), 3.56 (s, 3H), 2.18 (s, 4H), 1.99 (s, 3H), 1.49 (d, J 6.7 Hz, 3H). Method B HPLC-MS: MH+ m/z 338/340, RT 1.92 minutes.

Intermediate 102

6-Bromo-4-[(2,4-dimethylpyridin-3-yl)methyl]-2H,3H,4H-pyrido[3,2-b][1,4]oxazin-3-one Prepared from Intermediate 35 and 6-bromo-2H,3H,4H-pyrido[3,2-b][1,4]oxazin-3-one in a similar manner to that described for Intermediate 101. $\delta_H$ (250 MHz, DMSO-d$_6$) 8.30 (d, J 4.9 Hz, 1H), 7.52 (d, J 8.2 Hz, 1H), 7.34 (d, J 8.2 Hz, 1H), 7.15 (d, J 5.0 Hz, 1H), 5.33 (s, 2H), 5.00 (s, 2H), 2.69 (s, 3H), 2.55 (s, 3H).

Intermediate 103

(2R)-6-Bromo-8-fluoro-2-methyl-4-[(2-methylpyridin-3-yl)methyl]-3,4-dihydro-2H-1,4-benzoxazin-3-one Prepared from Intermediates 37 and 57 in a similar manner to that described for Intermediate 101. Method B HPLC-MS: MH+ m/z 365/367, RT 1.51 minutes (96%).

Intermediate 104

(2R)-6-Bromo-4-[(2,4-dimethylpyridin-3-yl)methyl]-2-methyl-2H,3H,4H-pyrido[3,2-b]-[1,4]oxazin-3-one Prepared from Intermediates 35 and 46 in a similar manner to that described for Intermediate 101.

Intermediate 105

(2R)-6-Bromo-2-methyl-4-[(2-methylpyridin-3-yl)methyl]-2H,3H,4H-pyrido[3,2-b][1,4]-oxazin-3-one Prepared from Intermediates 37 and 46 in a similar manner to that described for Intermediate 101.

Intermediate 106

6-Bromo-2-methyl-4-[(2-methylpyridin-3-yl)methyl]-2H,3H,4H-pyrido[3,2-b][1,4]-oxazin-3-one Prepared from 6-bromo-2-methyl-2H,3H,4H-pyrido[3,2-b][1,4]oxazin-3-one and Intermediate 37 in a similar manner to that described for Intermediate 101. $\delta_H$ (500 MHz, DMSO-d$_6$) 1.53 (3H, d, J 6.87 Hz), 2.62 (3H, s), 5.06 (1H, d, J 6.87 Hz), 5.12 (2H, d, J 4.12 Hz), 7.14 (1H, dd, J 7.78, 4.73 Hz), 7.26 (1H, d, J 8.24 Hz), 7.35-7.39 (1H, m), 7.43

(1H, d, J 8.24 Hz), 8.32 (1H, dd, J 4.81, 1.45 Hz). Method B HPLC-MS: MH+ m/z 348/350, RT 1.37 minutes.

Intermediate 107

6-Bromo-2-methyl-4-[(1,3,5-trimethyl-1H-pyrazol-4-yl)methyl]-2H,3H,4H-pyrido[3,2-b][1,4]oxazin-3-one Prepared from 6-bromo-2-methyl-2H,3H,4H-pyrido[3,2-b][1,4]oxazin-3-one and Intermediate 36 in a similar manner to that described for Intermediate 101. Method A HPLC-MS: MH+ m/z 365/367, RT 1.37 minutes.

Intermediate 108

(2R)-6-Bromo-4-[(3,5-dimethylpyridazin-4-yl)methyl]-2-methyl-2H,3H,4H-pyrido[3,2-b][1,4]oxazin-3-one Prepared from Intermediates 38 and 46 in a similar manner to that described for Intermediate 101. $\delta_H$ (500 MHz, DMSO-$d_6$) 8.83 (s, 1H), 7.39 (d, J 8.2 Hz, 1H), 7.21 (d, J 8.2 Hz, 1H), 5.26 (d, J 15.2 Hz, 1H), 5.09 (d, J 15.2 Hz, 1H), 4.97 (q, J 6.8 Hz, 1H), 2.66 (s, 3H), 2.33 (s, 3H), 1.51 (d, J 6.8 Hz, 3H). Method B HPLC-MS: MH+ m/z 363/365, RT 1.64 minutes.

Intermediate 109

6-Bromo-4-[(2-methylpyridin-3-yl)methyl]-2H-pyrido[3,2-b][1,4]oxazin-3-one

Prepared from 6-bromo-2H,3H,4H-pyrido[3,2-b][1,4]oxazin-3-one and Intermediate 37 in a similar manner to that described for Intermediate 101. $\delta_H$ (500 MHz, DMSO-$d_6$) 2.62 (3H, s), 4.93 (2H, s), 5.12 (2H, s), 7.14 (1H, dd, J 7.71, 4.81 Hz), 7.25 (1H, d, J 8.24 Hz), 7.40 (1H, d, J 8.09 Hz), 7.42-7.47 (1H, m), 8.32 (1H, dd, J 4.73, 1.53 Hz). Method B HPLC-MS: MH+ m/z 336, RT 1.17 minutes.

Intermediate 110

6-Bromo-2-methyl-4-[(2-methylimidazo[1,2-a]pyridin-3-yl)methyl]-2H,3H,4H-pyrido-[3,2-b][1,4]oxazin-3-one Prepared from 6-bromo-2-methyl-2H,3H,4H-pyrido[3,2-b][1,4]oxazin-3-one and Intermediate 39 in a similar manner to that described for Intermediate 101. Method B HPLC-MS: MH+ m/z 387/389, RT 1.44 minutes.

Intermediate 110A (2R)-6-Bromo-2-methyl-4-[(2-methylimidazo[1,2-a]pyridin-3-yl)methyl]-2H,3H,4H-pyrido[3,2-b][1,4]oxazin-3-one Prepared from Intermediates 39 and 46 in a similar manner to that described for Intermediate 101. Method B HPLC-MS: MH+ m/z 387/389, RT 1.46 minutes.

Intermediate 111

6-Bromo-4-(2-methylimidazo[1,2-a]pyridin-3-ylmethyl)-4H-pyrido[3,2-b][1,4]oxazin-3-one Prepared from 6-bromo-2H,3H,4H-pyrido[3,2-b][1,4]oxazin-3-one and (2-methyl-imidazo[1,2-a]pyridin-3-yl) methanol in a similar manner to that described for Intermediate 143. $\delta_H$ (500 MHz, DMSO-$d_6$) 2.53 (3H, s), 4.87 (2H, s), 5.49 (2H, s), 6.92 (1H, td, J 6.82, 1.02 Hz), 7.14-7.23 (1H, m), 7.26 (1H, d, J 8.20 Hz), 7.36 (1H, d, J 8.20 Hz), 7.43 (1H, d, J 8.98 Hz), 8.56 (1H, d, J 6.94 Hz).

Intermediate 112

6-Bromo-4-[(1,3,5-trimethyl-1H-pyrazol-4-yl)methyl]-2H,3H,4H-pyrido[3,2-b][1,4]-oxazin-3-one Prepared from Intermediate 36 and 6-bromo-2H,3H,4H-pyrido[3,2-b][1,4]oxazin-3-one in a similar manner to that described for Intermediate 101. $\delta_H$ (300 MHz, DMSO-$d_6$) 7.34 (d, J 8.2 Hz, 1H), 7.22 (d, J 8.2 Hz, 1H), 4.91 (s, 2H), 4.80 (s, 2H), 3.56 (s, 3H), 2.26 (s, 3H), 2.10 (s, 3H).

Also prepared from 6-bromo-2H,3H,4H-pyrido[3,2-b][1,4]oxazin-3-one and (1,3,5-trimethyl-1H-pyrazol-4-yl) methanol in a similar manner to that described for Intermediate 143. Method B HPLC-MS: MH+ m/z 351-353, RT 1.86 minutes.

Intermediate 113

6-Bromo-4-[(4,6-dimethylpyrimidin-5-yl)methyl]-8-fluoro-3,4-dihydro-2H-1,4-benzoxazin-3-one Prepared from 6-bromo-8-fluoro-3,4-dihydro-2H-1,4-benzoxazin-3-one and Intermediate 11 in a similar manner to that described for Intermediate 143. Method B HPLC-MS: MH+ m/z 366-368, RT 1.73 minutes.

Intermediate 114

(2R)-6-Bromo-2,8-dimethyl-4-[(1,3,5-trimethyl-1H-pyrazol-4-yl)methyl]-2H,3H, 4H-pyrido[3,2-b][1,4]oxazin-3-one Prepared from (1,3,5-trimethyl-1H-pyrazol-4-yl)methanol and Intermediate 56 in a similar manner to that described for Intermediate 143. $\delta_H$ (500 MHz, DMSO-$d_6$) 7.19 (s, 1H), 4.97 (d, J 14.7 Hz, 1H), 4.91-4.80 (m, 2H), 3.54 (s, 3H), 2.23 (s, 3H), 2.16 (s, 3H), 2.07 (s, 3H), 1.46 (d, J 6.8 Hz, 3H). Method B HPLC-MS: MH+ m/z 379, RT 2.04 minutes.

Intermediate 115

6-Bromo-4-[(3,5-dimethylpyridazin-4-yl)methyl]-8-methyl-2H,3H,4H-pyrido[3,2-b][1,4]-oxazin-3-one Prepared from Intermediates 4 and 189 in a similar manner to that described for Intermediate 143. $\delta_H$ (500 MHz, DMSO-$d_6$) 8.83 (s, 1H), 7.16 (s, 1H), 5.15 (s, 2H), 4.86 (s, 2H), 2.67 (s, 3H), 2.34 (s, 3H), 2.16 (s, 3H). Method D HPLC-MS: MH+ m/z 363, RT 1.66 minutes.

Intermediate 116

(2R)-6-Bromo-4-[(3,5-dimethylpyridazin-4-yl)methyl]-8-fluoro-2-methyl-3,4-dihydro-2H-1,4-benzoxazin-3-one Prepared from Intermediates 4 and 57 in a similar manner to that described for Intermediate 143. $\delta_H$ (500 MHz, CDCl$_3$) 8.83 (s, 1H), 7.02 (dd, J 9.2, 2.0 Hz, 1H), 6.65 (t, J 1.8 Hz, 1H), 5.23 (d, J 16.1 Hz, 1H), 5.06 (d, J 16.0 Hz, 1H), 4.68 (q, J 6.8 Hz, 1H), 2.72 (s, 3H), 2.34 (s, 3H), 1.62 (d, J 6.8 Hz, 3H). Method B HPLC-MS: MH+ m/z 380/382, RT 1.79 minutes.

Intermediate 117

(2R)-6-Bromo-8-fluoro-2-methyl-4-[(2-methylimidazo[1,2-a]pyridin-3-yl)methyl]-3,4-dihydro-2H-1,4-benzoxazin-3-one Prepared from (2-methylimidazo[1,2-a]pyridin-3-yl)methanol and Intermediate 57 in a similar manner to that described for Intermediate 143. $\delta_H$ (500 MHz, CDCl$_3$) 8.14 (d, J 6.9 Hz, 1H), 7.70-7.62 (m, 1H), 7.21-7.15 (m, 1H), 7.11 (t, J 1.9 Hz, 1H), 6.96 (dd, J 9.2, 2.1 Hz, 1H), 6.80 (t, J 6.8 Hz, 1H), 5.52 (d, J 16.3 Hz, 1H), 5.38 (d, J 16.2 Hz, 1H), 4.74 (q, J 6.8 Hz, 1H), 2.64 (s, 3H), 1.64 (d, J 6.8 Hz, 3H). Method B HPLC-MS: MH+ m/z 404/406, RT 1.46 minutes.

Intermediate 118

(2R)-6-Bromo-4-({1,3-dimethyl-5-[(oxetan-3-yloxy)methyl]-1H-pyrazol-4-yl}methyl)-8-fluoro-2-methyl-3,4-dihydro-2H-1,4-benzoxazin-3-one Prepared from Intermediates 21 and 57 in a similar manner to that described for Intermediate 143. $\delta_H$ (500 MHz, CDCl$_3$) 6.97 (dd, J 9.2, 2.0 Hz, 1H), 6.92 (t, J 1.8 Hz, 1H), 4.99 (m, 2H), 4.71 (m, 3H), 4.56 (m, 3H), 4.39 (m, 2H), 3.79 (s, 3H), 2.23 (s, 3H), 1.61 (d, J 6.8 Hz, 3H). Method B HPLC-MS: MH+ m/z 454/456, RT 1.85 minutes.

Intermediate 119

(2R)-6-Bromo-8-fluoro-4-({3-[(methoxymethoxy)methyl]-1,5-dimethyl-1H-pyrazol-4-yl}methyl)-2-methyl-3,4-dihydro-2H-1,4-benzoxazin-3-one Prepared from Intermediates 57 and 199 in a similar manner to that described for Intermediate 143. Method B HPLC-MS: MH+ m/z 442/444, RT 2.02 minutes.

Intermediate 120

6-Bromo-8-fluoro-4-({5-[(methoxymethoxy)methyl]-1,3-dimethyl-1H-pyrazol-4-yl}-methyl)-3,4-dihydro-2H-1,4-benzoxazin-3-one Prepared from 6-bromo-8-fluoro-4H-1,4-benzoxazin-3-one and Intermediate 6 in a similar manner to that described for Intermediate 143. Method B HPLC-MS: MH+ m/z 428/430, RT 1.92 minutes.

Intermediate 121

(2R)-6-Bromo-4-{[1,3-dimethyl-5-({[2-(morpholin-4-yl)pyrimidin-5-yl]oxy}methyl)-1H-pyrazol-4-yl]methyl}-8-fluoro-2-methyl-3,4-dihydro-2H-1,4-benzoxazin-3-one Prepared from Intermediates 23 and 57 in a similar manner to that described for Intermediate 143. Method B HPLC-MS: MH+ m/z 561/563, RT 2.12 minutes.

Intermediate 122

6-Bromo-4-[(3,5-dimethylpyridazin-4-yl)methyl]-8-fluoro-3,4-dihydro-2H-1,4-benzoxazin-3-one Prepared from 6-bromo-8-fluoro-4H-1,4-benzoxazin-3-one and Intermediate 4 in a similar manner to that described for Intermediate 143. Method B HPLC-MS: MH+ m/z 366/368, RT 1.68 minutes.

Intermediate 123

6-Bromo-8-fluoro-4-[(2-methylimidazo[1,2-a]pyridin-3-yl)methyl]-3,4-dihydro-2H-1,4-benzoxazin-3-one Prepared from 6-bromo-8-fluoro-4H-1,4-benzoxazin-3-one and (2-methyl-imidazo[1,2-a]pyridin-3-yl)methanol in a similar manner to that described for Intermediate 143. $\delta_H$ (500 MHz, CDCl$_3$) 8.22 (d, J 6.6 Hz, 1H), 7.71-7.63 (m, 1H), 7.50-7.42 (m, 1H), 7.12 (s, 1H), 6.99 (dd, J 9.2, 2.0 Hz, 1H), 6.93-6.85 (m, 1H), 5.47 (s, 2H), 4.74 (s, 2H), 2.69 (s, 3H). Method B HPLC-MS: MH+ m/z 390/392, RT 1.44 minutes.

Intermediate 124

(2R)-6-Chloro-2-methyl-4-[(2-methylpyridin-3-yl)methyl]-7-(trifluoromethyl)pyrido[3,2-b][1,4]oxazin-3-one and (2R)-6-Chloro-2-methyl-4-[(2-methylpyridin-3-yl)methyl]-8-(trifluoromethyl)pyrido[3,2-b][1,4]oxazin-3-one Prepared from (2-methylpyridin-3-yl)methanol and Intermediate 182 in a similar manner to that described for Intermediate 143 and obtained as a mixture of isomers. HPLC-MS: MH+ m/z 372, RT 2.07 minutes.

Intermediate 125

3-{[(2R)-6-Bromo-8-fluoro-2-methyl-3-oxo-1,4-benzoxazin-4-yl]methyl}-2-methyl-imidazo[1,2-a]pyridine-6-carbonitrile Prepared from Intermediates 24 and 57 in a similar manner to that described for Intermediate 143. HPLC-MS: MH+ m/z 429/431, RT 1.99 minutes.

Intermediate 126

(2R)-6-Bromo-8-fluoro-2-methyl-4-[(2-methylimidazo[1,2-a]pyrazin-3-yl)methyl]-3,4-dihydro-2H-1,4-benzoxazin-3-one Prepared from Intermediates 26 and 57 in a similar manner to that described for Intermediate 143. Method A HPLC-MS: MH+ m/z 405/407, RT 3.83 minutes (99%).

Intermediate 127

(2R)-6-Bromo-4-[(3,5-dimethyl-3H-triazol-4-yl)methyl]-8-fluoro-2-methyl-1,4-benzoxazin-3-one Prepared from Intermediates 2 and 57 in a similar manner to that described for Intermediate 143. $\delta_H$ (500 MHz, DMSO-d$_6$) 7.39 (dd, J 9.8, 2.0 Hz, 1H), 7.27 (d, J 1.7 Hz, 1H), 5.37 (d, J 16.7 Hz, 1H), 5.26 (d, J 16.7 Hz, 1H), 4.96

(q, J 6.7 Hz, 1H), 3.93 (s, 3H), 2.11 (s, 3H), 1.51 (d, J 6.7 Hz, 3H). Method B HPLC-MS: MH+ m/z 370, RT 1.91 minutes.

Intermediate 128

6-Bromo-4-[(3,5-dimethylisoxazol-4-yl)methyl]-2-methylpyrido[3,2-b][1,4]oxazin-3-one Prepared from Intermediate 46 and 4-(chloromethyl)-3,5-dimethylisoxazole in a similar manner to that described for Intermediate 101. LCMS (ES+) (M+H)$^+$ 352/354, RT 1.58 minutes.

Intermediate 129

6-Bromo-4-[(3,5-dimethylisoxazol-4-yl)methyl]-2-fluoro-2-methylpyrido[3,2-b][1,4]-oxazin-3-one To a solution of Intermediate 128 (0.183 g, 0.52 mmol) in THF at −78° C. was added LiHMDS (0.4 mL of a 2M solution in THF, 0.73 mmol). The solution was stirred for 10 minutes, then N-fluorobenzenesulfonimide (0.016 g, 1.04 mmol) was added. The mixture was stirred at 0° C. for 30 minutes, then quenched with saturated aqueous ammonium chloride solution (2 mL). The reaction mixture was poured into EtOAc/water. The layers were separated and the organic layer was washed three times with water, then dried over MgSO$_4$ and concentrated under vacuum. The residue was purified by gradient silica column chromatography, eluting with 0-80% EtOAc in DCM, to afford the title compound (0.04 g, 21%) as a white solid. Method B LCMS (ES+) (M+H)$^+$ 370/372, RT 1.61 minutes (Method 2).

Intermediate 130

(2R)-6-Bromo-4-[(3,5-dimethyl-3H-1,2,3-triazol-4-yl)methyl]-2-methyl-2H,3H,4H-pyrido[3,2-b][1,4]oxazin-3-one Prepared from Intermediates 2 and 46 in a similar manner to that described for Intermediate 143. δ$_H$ (500 MHz, DMSO-d$_6$) 7.41 (d, J 8.2 Hz, 1H), 7.28 (d, J 8.2 Hz, 1H), 5.23 (d, J 15.6 Hz, 1H), 5.17 (d, J 15.6 Hz, 1H), 5.00 (q, J 6.7 Hz, 1H), 4.06 (s, 3H), 2.20 (s, 3H), 1.52 (d, J 6.8 Hz, 3H). Method B HPLC-MS: MH+ m/z 352/354, RT 1.82 minutes.

Intermediate 131

6-Chloro-8-methyl-4-[(1,3,5-trimethyl-1H-pyrazol-4-yl)methyl]-2H,3H,4H-pyrido[3,2-b][1,4]oxazin-3-one Prepared from Intermediates 36 and 193 in a similar manner to that described for Intermediate 101. δ$_H$ (250 MHz, CDCl$_3$) 6.79 (s, 1H), 5.06 (s, 2H), 4.65 (s, 2H), 3.70 (s, 3H), 2.37 (s, 3H), 2.27 (s, 3H), 2.19 (s, 3H). Method B HPLC-MS: MH+ m/z 321, RT 1.84 minutes.

Intermediate 132

(2R)-6-Bromo-2-methyl-4-[(1,3,5-trimethyl-1H-pyrazol-4-yl)methyl]-2H,3H,4H-pyrido-[3,2-b][1,4]oxazin-3-one Prepared from Intermediates 36 and 46 in a similar manner to that described for Intermediate 101.

Intermediate 133

6-Bromo-2,2-difluoro-4-[(1,3,5-trimethylpyrazol-4-yl)methyl]pyrido[3,2-b][1,4]oxazin-3-one Prepared from Intermediates 36 and 139 in a similar manner to that described for Intermediate 101. δ$_H$ (500 MHz, DMSO-d$_6$) 7.80 (d, J 8.3 Hz, 1H), 7.51 (d, J 8.3 Hz, 1H), 5.00 (s, 2H), 3.58 (s, 3H), 2.28 (s, 3H), 2.11 (s, 3H). Method B HPLC-MS: MH+ m/z 387-389, RT 2.03 minutes.

Intermediate 134

6-Bromo-8-fluoro-4-[(1,2,4-trimethyl-1H-imidazol-5-yl)methyl]-3,4-dihydro-2H-1,4-benzoxazin-3-one Prepared from Intermediate 41 and 6-bromo-8-fluoro-4H-1,4-benzoxazin-3-one in a similar manner to that described for Intermediate 101. δ$_H$ (500 MHz, CDCl$_3$) 7.01 (dd, J 9.2, 2.0 Hz, 1H), 6.98 (s, 1H), 5.10 (s, 2H), 4.69 (s, 2H), 3.41 (s, 3H), 2.36 (s, 6H). Method B HPLC-MS: MH+ m/z 368/370, RT 1.29 minutes.

Intermediate 135

(2R)-6-Bromo-8-fluoro-2-methyl-4-[(1,3,5-trimethyl-1H-pyrazol-4-yl)methyl]-3,4-dihydro-2H-1,4-benzoxazin-3-one Prepared from Intermediates 36 and 57 in a similar manner to that described for Intermediate 101. δ$_H$ (500 MHz, DMSO-d$_6$) 7.31 (dd, J 9.7, 2.0 Hz, 1H), 7.15-7.11 (m, 1H), 5.10 (d, J 15.8 Hz, 1H), 4.91 (q, J 6.7 Hz, 1H), 4.85 (d, J 15.8 Hz, 1H), 3.57 (s, 3H), 2.19 (s, 3H), 2.00 (s, 3H), 1.50 (d, J 6.7 Hz, 3H). Method B HPLC-MS: MH+ m/z 382/384, RT 1.94 minutes.

Intermediate 136

(2R)-6-Bromo-8-fluoro-4-({5-[(2-methoxyethoxy)methyl]-1,3-dimethyl-1H-pyrazol-4-yl}methyl)-2-methyl-3,4-dihydro-2H-1,4-benzoxazin-3-one Prepared from Intermediates 42 and 57 in a similar manner to that described for Intermediate 101. δ$_H$ (500 MHz, CDCl$_3$) 6.98-6.93 (m, 2H), 5.07-4.94 (m, 2H), 4.70 (q, J 6.8 Hz, 1H), 4.61-4.48 (m, 2H), 3.80 (s, 3H), 3.61-3.56 (m, 2H), 3.53 (m, 2H), 3.35 (s, 3H), 2.20 (s, 3H), 1.62 (d, J 6.8 Hz, 3H). Method B HPLC-MS: MH+ m/z 456/458, RT 1.95 minutes.

Intermediate 137

6-Bromo-8-fluoro-4-[(1,3,5-trimethyl-1H-pyrazol-4-yl)methyl]-3,4-dihydro-2H-1,4-benzoxazin-3-one Prepared from Intermediate 36 and 6-bromo-8-fluoro-4H-1,4-benzoxazin-3-one in a similar manner to that described for Intermediate 101. δ$_H$ (500 MHz, DMSO-d$_6$) 7.30 (dd, J 9.8, 2.1 Hz, 1H), 7.13 (t, J 1.8 Hz, 1H), 4.97 (s, 2H), 4.82 (s, 2H), 3.58 (s, 3H), 2.20 (s, 3H), 2.02 (s, 3H). Method B HPLC-MS: MH+ m/z 368/370, RT 1.91 minutes.

Intermediate 138

6-Bromo-8-fluoro-4-({6-[4-(methanesulfonyl)phenyl]-2-methylimidazo[1,2-a]pyridin-3-yl}methyl)-3,4-dihydro-2H-1,4-benzoxazin-3-one Prepared from Intermediate 43 and 6-bromo-8-fluoro-4H-1,4-benzoxazin-3-one in a similar manner to that described for Intermediate 101. $\delta_H$ (500 MHz, DMSO-$d_6$) 8.77 (s, 1H), 8.06 (d, J 8.4 Hz, 2H), 7.95 (d, J 8.4 Hz, 2H), 7.67 (dd, J 9.3, 1.7 Hz, 1H), 7.59 (d, J 9.3 Hz, 1H), 7.50 (s, 1H), 7.35 (dd, J 9.7, 2.0 Hz, 1H), 5.68 (s, 2H), 4.91 (s, 2H), 3.28 (s, 3H), 2.45 (s, 3H). Method B HPLC-MS: MH+ m/z 544/546, RT 1.57 minutes.

Intermediate 139

6-Bromo-2,2-difluoro-4H-pyrido[3,2-b][1,4]oxazin-3-one

A solution of 2-amino-6-bromopyridin-3-ol (500 mg, 2.29 mmol) in DMF (5 mL) was treated with potassium carbonate (367.5 mg, 2.66 mmol). 2-Bromo-2,2-difluoro-acetyl chloride (566 mg, 2.93 mmol) was added dropwise over 10 minutes with cooling in an ice-water bath. The reaction mixture was warmed to room temperature over 3 h, then heated at 50° C. for 18 h. The resulting mixture was concentrated under reduced pressure, then EtOAc (5 mL) and water (5 mL) were added. The organic layer was separated and washed with 2M aqueous HCl (5 mL), saturated aqueous NaHCO$_3$ solution and brine, then dried (MgSO$_4$). The crude material was concentrated under reduced pressure. Trituration of the resulting brown oil with DCM afforded the title compound (180 mg, 26%) as an orange solid. Method B HPLC-MS: MH+ m/z 264/266, RT 1.91 minutes (100%).

Intermediate 140

6-Bromo-4-[(2,4-dimethylpyridin-3-yl)methyl]spiro[1,4-benzoxazine-2,1'-cyclopropane]-3-one Prepared from Intermediates 35 and 196 in a similar manner to that described for Intermediate 101. LCMS (ES+) (M+H)+ 372/374, RT 2.42 minutes.

Intermediate 141

7-Bromo-1-[(3,5-dimethylisoxazol-4-yl)methyl]quinolin-2-one

Prepared from 7-bromo-1H-quinolin-2-one and 4-(chloromethyl)-3,5-dimethyl-isoxazole in a similar manner to that described for Intermediate 101. Method B LCMS (ES+) (M+H)+ 333/335, RT 1.33 minutes.

Intermediate 142

5-Bromo-3-[(3,5-dimethylisoxazol-4-yl)methyl]-1a,7b-dihydro-1H-cyclopropa[c]-quinolin-2-one To a solution of trimethylsulfoxonium iodide (0.21 g, 0.95 mmol) in DMSO (4 mL) was added potassium tert-butoxide (1M solution in THF, 1 mL, 0.11 g, 0.95 mmol). The solution was stirred for 1 h at r.t., then Intermediate 141 (0.3 g, 0.90 mmol) in DMSO (4 mL) was added and the solution was heated at 60° C. for 24 h. The reaction mixture was poured into EtOAc/water. The layers were separated and the organic layer was washed three times with water, then dried over MgSO$_4$ and concentrated under vacuum. The residue was purified by gradient silica column chromatography, eluting with 0-80% EtOAc in DCM, to afford the title compound (0.23 g, 74%) as a white solid. LCMS (ES+) (M+H)+ 347/349, RT 1.33 minutes.

Intermediate 143

(2R)-6-Bromo-2-methyl-4-[(1,2,4-trimethyl-1H-imidazol-5-yl)methyl]-2H,3H,4H-pyrido-[3,2-b][1,4]oxazin-3-one A mixture of Intermediate 46 (420 mg, 1.73 mmol), Intermediate 3 (242 mg, 1.73 mmol) and triphenylphosphine (504 mg, 1.9 mmol) in DCM (20 mL) was stirred at r.t. for 10 minutes, then cooled to 0° C., and a solution of DIAD (0.4 mL, 1.9 mmol) in DCM (5 mL) was added dropwise. After 5 minutes, the solution was allowed to warm to r.t. over 2 h. Water (30 mL) was added, the layers were separated and the aqueous phase was extracted with DCM (50 mL). The combined organic layers were washed with water (20 mL) and brine (20 mL), then dried over MgSO$_4$. The crude material was purified by column chromatography, with a gradient of 0-100% EtOAc in heptane, followed by a gradient of 0-10% NH$_3$ (7N in MeOH) in EtOAc, to give the title compound (631 mg, 54%). $\delta_H$ (500 MHz, CDCl$_3$) 7.10 (d, J 8.2 Hz, 1H), 7.07 (d, J 8.2 Hz, 1H), 5.26 (d, J 15.3 Hz, 1H), 5.15 (d, J 15.3 Hz, 1H), 4.68 (q, J 6.8 Hz, 1H), 3.60 (s, 3H), 2.35 (s, 3H), 2.31 (s, 3H), 1.58 (d, J 6.8 Hz, 3H). Method B HPLC-MS: MH+ m/z 365/367, RT 1.32 minutes.

Intermediate 144

2-Methyl-6-(4,4,5,5-tetramethyl-1,3,2-dioxaborolan-2-yl)-4-[(1,3,5-trimethyl-1H-pyrazol-4-yl)methyl]-2H,3H,4H-pyrido[3,2-b][1,4]oxazin-3-one Intermediate 107 (1 g, 2.74 mmol) and bis(pinacolato)diboron (1.95 g, 7.67 mmol) were dissolved in 1,4-dioxane (40 mL) under an atmosphere of nitrogen gas. Potassium acetate (0.80 g, 8.21 mmol) was added and the reaction mixture was degassed for 5 minutes. Pd(dppf)Cl$_2$ (0.11 g, 0.14 mmol) was added and the reaction mixture was heated at 110° C. for 90 minutes. The reaction mixture was cooled to r.t. and diluted with DCM, then filtered through a pad of celite and washed with DCM. The filtrate was concentrated in vacuo. The resulting crude thick oil was triturated in heptane (~20 mL) and diethyl ether (~10 mL) and sonicated for 5 minutes. A white solid and a black sticky solid both formed in the solution. The white solid was separated from the black solid, then dried by filtration, to afford the title compound (493.4 mg, 41%). $\delta_H$ (250 MHz, DMSO-$d_6$) 7.40 (d, J 7.8 Hz, 1H), 7.31 (d, J 7.8 Hz, 1H), 5.09 (d, J 14.4 Hz, 1H), 5.00 (d, J 14.4 Hz, 1H), 4.88 (q, J 6.6 Hz, 1H), 3.52 (s, 3H), 2.25 (s, 3H), 2.07 (s, 3H), 1.46 (d, J 6.8 Hz, 3H), 1.30 (s, 12H).

Intermediate 145

8-Fluoro-6-(4,4,5,5-tetramethyl-1,3,2-dioxaborolan-2-yl)-4-[(1,3,5-trimethyl-1H-pyrazol-4-yl)methyl]-3,4-dihydro-2H-1,4-benzoxazin-3-one Prepared from Intermediate 137 in a similar manner to that described for Intermediate 144. $\delta_H$ (500 MHz, DMSO-d$_6$) 7.15 (s, 1H), 7.08 (d, J 10.0 Hz, 1H), 4.98 (s, 2H), 4.85 (s, 2H), 3.57 (d, J 4.4 Hz, 3H), 2.25 (s, 3H), 2.03 (s, 3H), 1.28 (s, 12H). Method D HPLC-MS: MH+ m/z 416, RT 2.12 minutes.

Intermediate 146

4-[(2,4-Dimethylpyridin-3-yl)methyl]-6-(4,4,5,5-tetramethyl-1,3,2-dioxaborolan-2-yl)-2H,3H,4H-pyrido[3,2-b][1,4]oxazin-3-one Prepared from Intermediate 102 in a similar manner to that described for Intermediate 144. δ$_H$ (500 MHz, DMSO-d$_6$) 8.08 (d, J 4.9 Hz, 1H), 7.33 (d, J 7.9 Hz, 1H), 7.31 (d, J 7.9 Hz, 1H), 6.93 (d, J 4.9 Hz, 1H), 5.27 (s, 2H), 4.83 (s, 2H), 2.50 (s, 3H), 2.43 (s, 3H), 1.28 (s, 12H). Method B HPLC-MS: MH+ m/z 314 (boronic acid), RT 1.02 minutes.

Intermediate 147

6-(4,4,5,5-Tetramethyl-1,3,2-dioxaborolan-2-yl)-4-[(,3,5-trimethyl-1H-pyrazol-4-yl)-methyl]-2H,3H,4H-pyrido[3,2-b][1,4]oxazin-3-one Prepared from Intermediate 112 in a similar manner to that described for Intermediate 144. δ$_H$ (500 MHz, DMSO-d$_6$) 7.41 (d, J 7.8 Hz, 1H), 7.32 (d, J 7.9 Hz, 1H), 5.07 (s, 2H), 4.80 (s, 2H), 3.55 (s, 3H), 2.28 (s, 3H), 2.11 (s, 3H), 1.32 (s, 12H).

Intermediate 148

4-[(2-Methylimidazo[1,2-a]pyridin-3-yl)methyl]-6-(4,4,5,5-tetramethyl-1,3,2-dioxaborolan-2-yl)-2H-pyrido[3,2-b][1,4]oxazin-3-one Prepared from Intermediate 111 in a similar manner to that described for Intermediate 144.

Intermediate 149

(2R)-4-[(3,5-Dimethyl-3H-1,2,3-triazol-4-yl)methyl]-8-fluoro-2-methyl-6-(4,4,5,5-tetramethyl-1,3,2-dioxaborolan-2-yl)-3,4-dihydro-2H-1,4-benzoxazin-3-one Prepared from Intermediate 127 in a similar manner to that described for Intermediate 144. δ$_H$ (500 MHz, DMSO-d$_6$) 7.15 (m, J 7.9 Hz, 2H), 5.41 (d, J 16.5 Hz, 1H), 5.30 (d, J 16.5 Hz, 1H), 5.00 (q, J 6.8 Hz, 1H), 3.90 (s, 3H), 2.23 (s, 3H), 1.53 (d, J 6.7 Hz, 3H), 1.29 (s, 12H). Method B HPLC-MS: MH+ m/z 417, RT 2.14 minutes.

Intermediate 150

(2R)-8-Fluoro-2-methyl-6-(4,4,5,5-tetramethyl-1,3,2-dioxaborolan-2-yl)-4-[(1,3,5-trimethyl-1H-pyrazol-4-yl)methyl]-3,4-dihydro-2H-1,4-benzoxazin-3-one Prepared from Intermediate 135 in a similar manner to that described for Intermediate 144. δ$_H$ (500 MHz, DMSO-d$_6$) 7.15 (s, 1H), 7.08 (d, J 10.0 Hz, 1H), 5.10 (d, J 15.8 Hz, 1H), 4.94 (q, J 6.7 Hz, 1H), 4.87 (d, J 15.7 Hz, 1H), 3.56 (s, 3H), 2.24 (s, 3H), 2.02 (s, 3H), 1.50 (d, J 6.7 Hz, 3H), 1.29 (s, 12H). Method B HPLC-MS: MH+ m/z 430, RT 2.22 minutes.

Intermediate 151

(2R)-2-Methyl-6-(4,4,5,5-tetramethyl-1,3,2-dioxaborolan-2-yl)-4-[(1,3,5-trimethyl-1H-pyrazol-4-yl)methyl]-2H,3H,4H-pyrido[3,2-b][1,4]oxazin-3-one Prepared from Intermediate 132 in a similar manner to that described for Intermediate 144. δ$_H$ (500 MHz, CDCl$_3$) 7.47 (d, J 7.8 Hz, 1H), 7.15 (d, J 7.8 Hz, 1H), 5.29-5.16 (m, 2H), 4.67 (q, J 6.8 Hz, 1H), 3.63 (s, 3H), 2.33 (s, 3H), 2.25 (s, 3H), 1.54 (d, J 6.8 Hz, 3H), 1.36 (s, 12H).

Intermediate 152

(2R)-6-Ethenyl-8-fluoro-2-methyl-4-[(1,3,5-trimethyl-1H-pyrazol-4-yl)methyl]-3,4-dihydro-2H-1,4-benzoxazin-3-one To a solution of Intermediate 101 (1.09 g, 3.23 mmol) in anhydrous 1,4-dioxane (15 mL) was added vinylboronic anhydride pyridine complex (932 mg, 3.87 mmol), followed by 2M aqueous Na$_2$CO$_3$ solution (4.84 mL). The mixture was degassed under N$_2$ for 5 minutes before the addition of (1E,4E)-1,5-diphenylpenta-1,4-dien-3-one-palladium (3:2) (147 mg, 0.16 mmol) and dicyclohexyl[2',4',6'-tri(propan-2-yl)biphenyl-2-yl]phosphane (153 mg, 0.32 mmol). The mixture was further degassed under N$_2$ for 5 minutes, then placed in a pressure tube and heated at 110° C. for 18 h. The mixture was cooled to r.t., EtOAc (20 mL) and water (20 mL) were added, then the organic layer was washed with water and brine. The aqueous layers were extracted with EtOAc (2×20 mL), then the combined organic layers were dried (Na$_2$SO$_4$) and the solvent was removed in vacuo. The residue was purified by column chromatography (SiO$_2$; gradient: heptanes to 100% EtOAc) to give the title compound (1.06 g, 91%). δ$_H$ (DMSO-d$_6$) 7.13 (dd, J 11.4, 1.5 Hz, 1H), 7.01 (s, 1H), 6.60 (dd, J 17.6, 10.9 Hz, 1H), 5.76 (d, J 17.6 Hz, 1H), 5.26 (d, J 10.9 Hz, 1H), 5.12 (d, J 15.7 Hz, 1H), 4.95-4.80 (m, 2H), 3.55 (s, 3H), 2.18 (s, 3H), 1.98 (s, 3H), 1.48 (d, J 6.7 Hz, 3H). Method B HPLC-MS: MH+ m/z 330, RT 1.90 minutes (97%).

Intermediate 153

(2R)-6-(1-Benzylpyrrolidin-3-yl)-8-fluoro-2-methyl-4-[(1,3,5-trimethyl-1H-pyrazol-4-yl)-methyl]-3,4-dihydro-2H-1,4-benzoxazin-3-one To a stirred solution of Intermediate 152 (600 mg, 1.82 mmol) and N-(methoxy-methyl)-N-(trimethylsilylmethyl)benzylamine (0.7 mL, 2.73 mmol) in dry DCM (16 mL) at 0° C. under nitrogen was added a solution of trifluoroacetic acid (15 µL) in DCM (4 mL) dropwise over 4 minutes. The reaction mixture was stirred at 0° C. for 20 minutes, then allowed to warm to r.t. Stirring was continued for 18 h. An additional portion of N-(methoxymethyl)-N-(trimethylsilylmethyl)benzylamine (0.45 mL, 1.78 mmol) and a solution of trifluoroacetic acid (15 µL) in DCM (2 mL) were added at 0° C., then the mixture was warmed to r.t. and stirred for 2 h. A further portion of N-(methoxymethyl)-N-(trimethylsilylmethyl)benzylamine (0.45 mL, 1.78 mmol) and a solution of trifluoro-acetic acid (15 µL) in DCM (2 mL) were added at 0° C. After stirring at r.t. for 18 h, the reaction mixture was concentrated in vacuo. The residue was purified by column chromatography (SiO$_2$; 100% heptane to 100% EtOAc, then 0-10% MeOH/DCM) to afford the title compound (718 mg, 88%).

Intermediate 154

6-Ethenyl-4-[(1,3,5-trimethyl-1H-pyrazol-4-yl)methyl]-2H,3H,4H-pyrido[3,2-b][1,4]-oxazin-3-one Prepared from Intermediate 112 and vinylboronic anhydride pyridine complex in a similar manner to that described for Intermediate 152. $\delta_H$ (500 MHz, DMSO-$d_6$) 7.35 (d, J 8.1 Hz, 1H), 7.14 (d, J 8.1 Hz, 1H), 6.74 (dd, J 17.4, 10.8 Hz, 1H), 6.09 (dd, J 17.4, 1.5 Hz, 1H), 5.39 (dd, J 10.8, 1.5 Hz, 1H), 5.06 (s, 2H), 4.73 (s, 2H), 3.53 (s, 3H), 2.19 (s, 3H), 2.02 (s, 3H). Method B HPLC-MS: MH+ m/z 299.0, RT 1.80 minutes (99%).

Intermediate 155

6-(1-Benzylpyrrolidin-3-yl)-4-[(1,3,5-trimethyl-1H-pyrazol-4-Yl)methyl]-2H,3H,4H-pyrido[3,2-b][1,4]oxazin-3-one Prepared from Intermediate 154 in a similar manner to that described for Intermediate 153 to give the title compound (39%). $\delta_H$ (500 MHz, DMSO-$d_6$) 7.34-7.26 (m, 5H), 7.23 (dq, J 6.3, 3.3, 2.8 Hz, 1H), 6.96 (d, J 8.1 Hz, 1H), 5.01 (d, J 1.8 Hz, 2H), 4.69 (s, 2H), 3.67-3.56 (m, 2H), 3.54 (s, 3H), 3.49-3.38 (m, 1H), 2.90 (t, J 8.4 Hz, 1H), 2.70 (q, J 8.1 Hz, 1H), 2.66-2.56 (m, 1H), 2.53 (1H, obs), 2.17 (m, 4H), 2.00 (s, 3H), 1.93 (ddt, J 12.7, 8.5, 6.4 Hz, 1H). Method B HPLC-MS: MH+ m/z 432, RT 1.26 minutes (99%).

Intermediate 156

Methyl 2-(4-methoxyphenyl)ethylcarbamate

At 0° C., under a nitrogen atmosphere, methyl chloroformate (235 mL, 3.04 mol) was added to a solution of 2-(4-methoxyphenyl)ethylamine (90 g, 595 mmol) and triethylamine (99 mL, 714 mmol) in dry THF (2.7 L). The mixture was stirred at r.t. overnight, then water (360 mL) was added. The layers were separated and the aqueous phase was extracted with diethyl ether. The combined organic layers were washed with 1M aqueous HCl, water and brine, then dried ($Na_2SO_4$) and evaporated in vacuo, to afford the title compound (120.7 g, 90%). $\delta_H$ (300 MHz, CDCl$_3$) 7.10 (d, J 8.6 Hz, 2H), 6.84 (d, J 8.7 Hz, 2H), 3.79 (s, 3H), 3.66 (s, 3H), 3.40 (q, J 6.6 Hz, 2H), 2.74 (t, J 7.0 Hz, 2H).

Intermediate 157

7-Methoxy-3,4-dihydroisoquinolin-1(2H)-one

Phosphorus pentoxide (126 g, 890 mmol) was added to methanesulfonic acid (445 mL, 6.86 mol) in portions and heated at 130° C. for 1 h. Intermediate 156 (93.15 g, 445 mmol) was added and the mixture was heated at 140° C. until gas evolution ceased. The reaction mixture was allowed to cool and quenched by pouring onto ice. The resulting mixture was extracted with EtOAc. The combined organic layers were washed with brine, dried ($Na_2SO_4$) and evaporated in vacuo. The residue was coevaporated from toluene and purified by column chromatography (silica; eluent: 50-100% EtOAc in heptane) to afford the title compound (38.16 g, 48%). $\delta_H$ (300 MHz, CDCl$_3$) 7.60 (d, J 2.8 Hz, 1H), 7.13 (d, J 8.3 Hz, 1H), 7.01 (dd, J 8.3, 2.8 Hz, 1H), 6.14 (s, 1H), 3.85 (s, 3H), 3.55 (td, J 6.6, 2.9 Hz, 2H), 2.94 (t, J 6.6 Hz, 2H).

Intermediate 158

7-Hydroxy-3,4-dihydroisoquinolin-1(2H)-one

Under a nitrogen atmosphere, Intermediate 157 (19 g, 107 mmol) was dissolved in DCM (250 mL) and cooled to −78° C. Boron tribromide (1M in DCM, 430 mL, 430 mmol) was added dropwise to the resulting suspension within 1.5 h. After 30 min, the cooling bath was removed and the reaction mixture was allowed to warm to r.t., then stirred overnight. The reaction mixture was quenched by careful dropwise addition of MeOH (114 mL, 2.81 mol) and the resulting solution was stirred for 1.5 h, then concentrated in vacuo. The residue was coevaporated from MeOH and crystallized from water, then filtered, washed with water and dried, to afford the title compound (14.6 g, 81%). $\delta_H$ (300 MHz, DMSO-$d_6$) 9.47 (s, 1H), 7.83 (s, 1H), 7.25 (d, J 2.7 Hz, 1H), 7.09 (d, J 8.2 Hz, 1H), 6.85 (dd, J 8.1, 2.7 Hz, 1H), 3.31 (td, J 6.6, 2.8 Hz, 2H), 2.76 (t, J 6.6 Hz, 2H).

Intermediate 159

1-Oxo-1,2,3,4-tetrahydroisoquinolin-7-yl trifluoromethanesulfonate

Under a nitrogen atmosphere, Intermediate 158 (38.3 g, 235 mmol) was suspended in DCM (1 L), then N-phenyl-bis(trifluoromethanesulfonimide) (84 g, 235 mmol) and triethylamine (33 mL, 235 mmol) were added. The mixture was stirred overnight, diluted with water, and the layers were separated. The aqueous layer was extracted with DCM (500 mL). The combined organic layers were washed with aqueous HCl (1M) and water, then dried ($Na_2SO_4$) and evaporated in vacuo. The residue was crystallised from diisopropyl ether, then dried in vacuo at 40° C. for 2 days, to afford the title compound (37.9 g, 55%). $\delta_H$ (300 MHz, CDCl$_3$) 7.97 (s, 1H), 7.42-7.29 (m, 2H), 7.02 (s, 1H), 3.61 (td, J 6.7, 2.9 Hz, 2H), 3.04 (t, J 6.6 Hz, 2H).

Intermediate 160

7-(4,4,5,5-Tetramethyl-1,3,2-dioxaborolan-2-yl)-3,4-dihydroisoquinolin-1(2H)-one A suspension of Intermediate 159 (48.38 g, 164 mmol), bis(pinacolato)diboron (54.1 g, 213 mmol) and potassium acetate (80 g, 819 mmol) in 1,4-dioxane (2 L) was purged with argon, then heated to 80° C. Pd(dppf)Cl$_2$ (1.7 g, 2.08 mmol) was added and the mixture was stirred overnight. After cooling to r.t., the reaction mixture was purified by column chromatography (silica; eluent: 30-100% EtOAc in heptane), then triturated from diisopropyl ether, to afford the title compound (33.5 g, 73%). $\delta_H$ (300 MHz, CDCl$_3$) 8.53 (s, 1H), 7.86 (d, J 7.5 Hz, 1H), 7.22 (d, J 7.5 Hz, 1H), 6.38 (s, 1H), 3.56 (td, J 6.6, 2.8 Hz, 2H), 3.01 (t, J 6.6 Hz, 2H), 1.33 (s, 12H).

Intermediates 161 & 162

7-Bromo-5-fluoro-1,2,3,4-tetrahydroisoquinolin-1-one and 7-Bromo-5-fluoro-1,2,3,4-tetrahydroquinolin-2-one A solution of 6-bromo-4-fluoro-2,3-dihydro-1H-inden-1-one (500 mg, 2.18 mmol) in a mixture of DCM (13 mL) and methanesulfonic acid (6.5 mL) at 0° C. was treated slowly with sodium azide (115.32 µL, 3.27 mmol). The resulting mixture warmed to r.t. and stirred for 1.5 h. Ceric ammonium nitrate solution (5.5% in water, 25 mL) was added slowly and the mixture was partitioned between DCM (50 mL) and water (25 mL). The aqueous layer was extracted with DCM (50 mL), and the combined organic layers were washed with water (25 mL) and brine (25 mL), then dried (MgSO$_4$). The solvent was removed in vacuo to give a mixture (1:1) of the title compounds (410 mg), that was used without separation.

Intermediate 163

7-(4,4,5,5-Tetramethyl-1,3,2-dioxaborolan-2-yl)-1,2-dihydrophthalazin-1-one

A mixture of 7-bromo-1,2-dihydrophthalazin-1-one (4.1 g, 18.22 mmol) and bis(pinacolato)diboron (12.95 g, 51.01 mmol) was dissolved in 1,4-dioxane (150 mL) under nitrogen. Potassium acetate (5.36 g, 54.66 mmol) was added, and the reaction mixture was degassed with N$_2$ for 5 minutes. Pd(dppf)Cl$_2$ (0.74 g, 0.91 mmol) was added and the mixture was heated at 110° C. for 1.5 h, then cooled and diluted with DCM. The solids were removed by filtration through celite. The residue was washed with DCM and the combined organic phases were concentrated in vacuo. The resulting solid was triturated in heptane (30 mL) and diethyl ether (15 mL). The solid was further triturated with heptane (30 mL) and diethyl ether (15 mL), then the precipitate was collected by filtration, to give the title compound (5.1 g, 81%). $\delta_H$ (250 MHz, DMSO-d$_6$) 12.68 (s, 1H), 8.50 (s, 1H), 8.37 (s, 1H), 8.10 (dd, J 7.8, 1.1 Hz, 1H), 7.88 (d, J 7.8 Hz, 1H), 1.30 (s, 12H). Method B: HPLC-MS MH+ m/z 273, RT 1.78 minutes (97%).

Intermediate 164

6-(4,4,5,5-Tetramethyl-1,3,2-dioxaborolan-2-yl)-2,3-dihydro-1,2-benzothiazole 1,1-dioxide Prepared from Intermediate 171 and bis(pinacolato)diboron in a similar manner to that described for Intermediate 163 to afford the title compound (74%). $\delta_H$ (500 MHz, DMSO-d$_6$) 7.91 (d, J 7.7 Hz, 1H), 7.89 (s, 1H), 7.62-7.53 (m, 2H), 4.43 (s, 2H), 1.31 (s, 12H).

Intermediate 165

3-(4,4,5,5-Tetramethyl-1,3,2-dioxaborolan-2-yl)benzene-1-sulfonamide

Prepared from 3-bromobenzene-1-sulfonamide and bis(pinacolato)diboron in a similar manner to that described for Intermediate 163 to afford the title compound (100%) as a dark brown-grey solid. Method B HPLC-MS: MH+ m/z 284, RT 1.74 minutes (94%).

Intermediate 166

6-(4,4,5,5-Tetramethyl-1,3,2-dioxaborolan-2-yl)-1,2,3,4-tetrahydroquinazoline-2,4-dione 6-Bromoquinazoline-2,4(1H,3H)-dione (350 mg, 1.45 mmol) and bis(pinacolato)-diboron (1.03 g, 4.07 mmol) were dissolved in 1,4-dioxane (12 mL) under nitrogen. Potassium acetate (855 mg, 8.71 mmol) was added and the reaction mixture was degassed for 10 minutes. Bis[3-(diphenylphosphanyl)cyclopenta-2,4-dien-1-yl]iron DCM dichloropalladium (119 mg, 0.145 mmol) was added and the reaction mixture was heated at 100° C. for 4 h. The reaction mixture was diluted with DCM (30 mL), then filtered through celite and concentrated to dryness. The crude material was purified by column chromatography, with a gradient of 0-100% EtOAc in heptane, to afford the title compound (200 mg, 29% yield, 60% purity). Method B HPLC-MS: MH+ m/z 289, RT 1.60 minutes (60%).

Intermediate 167

2-Bromo-5,6,7,8-tetrahydrothiazolo[4,5-c]azepin-4-one

A solution of 2-bromo-6,7-dihydro-5H-1,3-benzothiazol-4-one (0.36 g, 1.55 mmol) in DCM:methanesulfonic acid (2:1) at 0° C. was treated slowly with sodium azide. The resulting mixture was allowed to warm to r.t. and stirred for 3 h. The reaction mixture was partitioned between DCM and aqueous sodium hydroxide solution (1. ON, 10 mL). The aqueous layer was extracted with DCM. The combined organic layers were washed sequentially with water and brine, then dried over Na$_2$SO$_4$ and concentrated in vacuo. The residue was dissolved in DCM and purified via column chromatography (silica), eluting with EtOAc/DCM then DCM/MeOH, to afford the title compound (230 mg, 60%) as a pale orange solid as a single regioisomer. LCMS (ES+) (M+H)$^+$ 247/249, RT 0.96 minutes (Method 2).

Intermediates 168 & 169

6-Bromo-1-methyl-1H-pyrazolo[4,3-b]pyridine and 6-Bromo-2-methyl-2H-pyrazolo[4,3-b]pyridine A solution of 6-bromo-1H-pyrazolo[4,3-b]pyridine (500 mg, 2.52 mmol) and cesium carbonate (1234.04 mg, 3.79 mmol) in DMF (7.5 mL) was stirred at r.t. Iodomethane (189 µL, 3.03 mmol) was added and the reaction mixture was stirred for 1.5 h. The reaction mixture was concentrated in vacuo and the residue was partitioned between water (25 mL) and EtOAc (25 mL). The aqueous phase was further extracted with EtOAc (25 mL). The combined organic phase was washed with brine (25 mL), then dried over MgSO$_4$ and filtered. The solvent was removed in vacuo to give the title compounds (584.8 mg) as a 7:3 mixture of regioisomers, which was used in the next step without further separation. Method B HPLC-MS: MH+ m/z 212/214, RT 1.47 minutes (26%) and 1.56 minutes (72%).

Intermediate 170

5-Bromo-2-(bromomethyl)benzene-1-sulfonamide

Under nitrogen, a mixture of 5-bromo-2-methylbenzene-1-sulfonamide (950 mg, 3.8 mmol) and N-bromosuccinimide (709.84 mg, 3.99 mmol) in anhydrous acetonitrile (9.5 mL) was stirred at 90° C. for 5 minutes. AIBN (124.74 mg, 0.76 mmol) was added and the reaction mixture was heated at 90° C. for another 80 minutes. The solvent was removed in vacuo and the residue was partitioned between water (20 mL) and DCM (40 mL). The organic phase was dried over MgSO$_4$ and filtered, then the solvent removed in vacuo. The residue was twice triturated in DCM (3 mL), and the resulting precipitates were filtered off and combined, to afford the title compound (614.8 mg, 40%). $\delta_H$ (500 MHz, DMSO-d$_6$) 8.00 (d, J 2.1 Hz, 1H), 7.84 (dd, J 8.3, 2.1 Hz, 1H), 7.77 (s, 2H), 7.63 (d, J 8.3 Hz, 1H), 5.00 (s, 2H).

Intermediate 171

6-Bromo-2,3-dihydro-1,2-benzothiazole 1,1-dioxide

Under an atmosphere of nitrogen gas, Intermediate 170 (2.50 g, 4.03 mmol) and NaHCO$_3$ (1.01 g, 12.1 mmol) in acetonitrile (75 mL) were stirred at 90° C. for 24 h. The reaction mixture was cooled to r.t. A precipitate which formed was filtered off and the the filtrate was concentrated in vacuo. The residue was purified on silica (Biotage), using an eluent of 0-100% EtOAc in heptane, to afford the title compound (473.7 mg, 47%) as a white solid. δ$_H$ (500 MHz, DMSO-d$_6$) 8.11 (d, J 1.6 Hz, 1H), 7.95 (s, 1H), 7.87 (dd, J 8.2, 1.8 Hz, 1H), 7.53 (d, J 8.2 Hz, 1H), 4.37 (s, 2H). Method B HPLC-MS: MH+ m/z 248/250, RT 1.51 minutes (100%).

Intermediate 172

6-Chloro-4-(methanesulfonyl)-1H-indazole

To a solution of 4-bromo-6-chloro-1H-indazole (100 mg, 0.43 mmol) in DMSO (7 mL) were added sodium methanesulfinate (165 mg, 1.62 mmol), CuI (8.2 mg, 0.04 mmol), N,N'-dimethylethylenediamine (0.01 mL, 0.09 mmol) and K$_2$CO$_3$ (119.41 mg, 0.86 mmol). The reaction mixture was heated at 100° C. for 3.75 h, then at 140° C. for 16.25 h, then at 160° C. for 3.5 h. The reaction mixture was retreated with another portion of sodium methanesulfinate (165 mg, 1.62 mmol), CuI (24.68 mg, 0.13 mmol) and N,N'-dimethylethylenediamine (0.03 mL, 0.26 mmol) and the resulting mixture was heated at 160° C. for 2 h. The reaction mixture was extracted with EtOAc (2×15 mL), washed with water (10 mL) and brine (10 mL), and dried over MgSO$_4$, then concentrated in vacuo. The resulting crude product was purified by column chromatography, using a heptane/EtOAc gradient followed by a DCM/MeOH gradient, to give the title compound (24.6 mg, 19%). δ$_H$ (500 MHz, DMSO-d$_6$) 13.85 (s, 1H), 8.40 (s, 1H), 8.08 (s, 1H), 7.65 (s, 1H), 3.38 (s, 3H). Method B HPLC-MS: MH+ m/z 231, RT 1.42 minutes (81%).

Intermediate 173

2-Bromo-4,5,6,7-tetrahydro-1-benzothiophen-4-one

To a suspension of N-bromosuccinimide (547 mg, 3.08 mmol) in hexane (3 mL) was added 4,5,6,7-tetrahydrobenzo[b]thiophen-4-one (468 mg, 3.08 mmol), followed by 70% perchloric acid (10 mol %, 0.026 mL). The reaction mixture was stirred at r.t. overnight. Saturated aqueous NaHCO$_3$ solution (5 mL) was added and the reaction mixture was extracted with EtOAc (3×10 mL). The combined organic layers were washed with brine (5 mL), dried over anhydrous Na$_2$SO$_4$ and filtered, then the filtrate was concentrated in vacuo. The crude residue was purified by column chromatography, with a gradient of 20-80% EtOAc in heptane, to afford the title compound (450 mg, 63%). δ$_H$ (500 MHz, DMSO-d$_6$) 7.34 (s, 1H), 2.97 (t, J 6.1 Hz, 2H), 2.47 (m, 2H), 2.10 (p, J 6.2 Hz, 2H). Method B HPLC-MS: MH+ m/z 231/233, RT 1.87 minutes (95%).

Intermediate 174

2-Bromo-4H,5H,6H,7H,8H-thieno[3,2-c]azepin-4-one

To a solution of Intermediate 173 (310 mg, 1.34 mmol) in DCM (8.1 mL) and methanesulfonic acid (3.9 mL) at 0° C. was added sodium azide (130.8 mg, 2.01 mmol) portionwise, then the resulting mixture was allowed to warm to r.t. and stirred overnight. The reaction mixture was partitioned between DCM and aqueous sodium hydroxide (1.0N, 4.0 mL). The aqueous layer was extracted with DCM. The combined organic layers were washed sequentially with water and brine, then dried over Na$_2$SO$_4$ and concentrated in vacuo. The crude residue was purified by column chromatography, with a gradient of 5-100% EtOAc in heptane, to afford the title compound (82 mg, 25%) as a white solid. Method B HPLC-MS: MH+ m/z 246/248, RT 1.61 minutes (100%).

Intermediate 175

2-Methylimidazo[1,2-a]pyrazine-6-carbonitrile

To a solution of 5-aminopyrazine-2-carbonitrile (0.6 g, 4.99 mmol) in dry EtOH (9 mL) were added sodium bromide (0.257 g, 2.49 mmol) and chloroacetone (2.01 mL, 24.95 mmol) portionwise. The reaction mixture was heated at 80° C. for 16 h with stirring, then allowed to cool to r.t. The solvent was removed in vacuo, then the solids were taken up in DCM (100 mL) and washed with saturated aqueous NaHCO$_3$ solution (50 mL). The phases were separated and the aqueous phase was extracted with DCM (2×50 mL). The combined organic layers were washed with brine (50 mL), then dried (MgSO$_4$), filtered and concentrated. Purification by column chromatography, eluting with EtOAc/heptane (20-100%), yielded the title compound (220 mg, 28%).

Intermediate 176

3-(Hydroxymethyl)-2-methylimidazo[1,2-a]pyrazine-6-carbonitrile

Prepared from Intermediate 175 in a similar manner to that described for Intermediate 21. Method C HPLC-MS: MH+ m/z 188.9, RT 0.46 minutes (100%).

Intermediate 177

(6-Fluoro-2-methylimidazo[1,2-a]pyridin-3-yl)methanol

Prepared from 6-fluoro-2-methylimidazo[1,2-a]pyridine in a similar manner to that described for Intermediate 21. δ$_H$ (500 MHz, DMSO-d$_6$) 8.46 (dd, J 4.7, 2.4 Hz, 1H), 7.52 (dd, J 9.8, 5.3 Hz, 1H), 7.28 (ddd, J 9.8, 8.4, 2.5 Hz, 1H), 5.09 (t, J 5.4 Hz, 1H), 4.76 (d, J 5.2 Hz, 2H), 2.34 (s, 3H). Method E HPLC-MS: MH+ m/z 181, RT 0.17 minutes (96%).

Intermediate 178

(6-Methoxy-2-methylimidazo[1,2-a]pyrazin-3-yl)methanol

To a solution of (6-bromo-2-methylimidazo[1,2-a]pyrazin-3-yl)methanol (0.3 g, 1.24 mmol) in MeOH (4 mL)

was added 10% NaOH in water (2.07 mL). The mixture was heated under microwave irradiation, whilst stirring, at 100° C. for 30 minutes. The reaction mixture was concentrated in vacuo, then purified by reverse-phase column chromatography, using 0-100% MeCN in water, to give the title compound (167 mg, 70%). $\delta_H$ (500 MHz, DMSO-$d_6$) 8.68 (d, J 1.3 Hz, 1H), 7.92 (d, J 1.3 Hz, 1H), 4.79 (s, 2H), 3.89 (s, 3H), 2.40 (s, 3H). Method E HPLC-MS: MH+ m/z 194.2, RT 0.91 minutes (100%).

Intermediate 179

(2R)-6-(2,2-Difluoroethenyl)-8-fluoro-2-methyl-4-[(1,3,5-trimethyl-1H-pyrazol-4-yl)-methyl]-3,4-dihydro-2H-1,4-benzoxazin-3-one An aqueous solution of tripotassium phosphate (1.27M, 1.43 mL) was added to a solution of 2,2-difluoroethenyl 4-methylbenzene-1-sulfonate (prepared according to the procedure described in *J. Org. Chem.*, 2008, 73, 3404) (250 mg, 1.07 mmol) and Intermediate 150 (76%, 603 mg, 1.07 mmol) in 1,4-dioxane (7 mL). The mixture was degassed with a stream of bubbling nitrogen whilst being sonicated for 10 minutes. Tris(dibenzylidineacetone)dipalladium(0) (24.44 mg, 0.03 mmol) and tricyclohexyl-phosphonium tetrafluoroborate (19.65 mg, 0.05 mmol) were added under nitrogen and the mixture was heated, whilst stirring, at 105° C. in a sealed tube for 4 h. The mixture was allowed to cool to r.t., then partitioned between saturated aqueous $Na_2CO_3$ solution (30 mL) and EtOAc (30 mL). The organic phase was separated and the aqueous layer was extracted with EtOAc (2×30 mL). The combined organic extracts were washed with brine (20 mL), dried over $MgSO_4$, filtered and concentrated in vacuo. Purification of the crude residue by column chromatography, using 0-100% EtOAc in heptane, gave the title compound (322 mg, 55%). $\delta_H$ (500 MHz, DMSO-$d_6$) 6.98 (dd, J 11.4, 1.7 Hz, 1H), 6.87 (s, 1H), 5.72 (dd, J 27.3, 3.9 Hz, 1H), 5.08 (d, J 15.9 Hz, 1H), 4.90 (q, J 6.7 Hz, 1H), 4.84 (d, J 15.8 Hz, 1H), 3.57 (s, 3H), 2.17 (s, 3H), 1.96 (s, 3H), 1.50 (d, J 6.7 Hz, 3H). Method B HPLC-MS: MH+ m/z 366.1, RT 2.01 minutes (100%).

Intermediate 180

(2R)-6-(1-Benzyl-4,4-difluoropyrrolidin-3-yl)-8-fluoro-2-methyl-4-[(1,3,5-trimethyl-1H-pyrazol-4-yl)methyl]-3,4-dihydro-2H-1,4-benzoxazin-3-one Prepared from Intermediate 179 in a similar manner to that described for Intermediate 153 to give the title compound (15%). Method B HPLC-MS: MH+ m/z 499.2, RT 1.94 minutes (77%).

Intermediate 181

(2R)-6-Bromo-4-[(6-bromo-7-fluoro-2-methylimidazo[1,2-a]pyridin-3-yl)methyl]-8-fluoro-2-methyl-1,4-benzoxazin-3-one Prepared from Intermediates 27 and 57 in a similar manner to that described for Intermediate 143.

Intermediate 182

(2R)-6-Chloro-2-methyl-7-(trifluoromethyl)-4H-pyrido[3,2-b][1,4]oxazin-3-one and (2R)-6-Chloro-2-methyl-8-(trifluoromethyl)-4H-pyrido[3,2-b][1,4]oxazin-3-one Potassium phosphate (dibasic) (1.3 g, 7.6 mmol) and Ir(fppy)$_3$ (0.096 g, 0.13 mmol) were added to an oven-dried round bottom flask which was degassed and flushed with nitrogen. A solution of (2R)-6-chloro-2-methyl-4H-pyrido[3,2-b][1,4]oxazin-3-one (0.5 g, 2.52 mmol) in acetonitrile (1 mL) was added via septum. The mixture was cooled in an acetone/dry ice bath, degassed and flushed with nitrogen, then allowed to warm to r.t. Trifluoromethanesulfonyl chloride (3.4 g, 20 mmol) was added. A fluorescent bulb (25 W bell) was placed 2 cm away from the flask and foil was placed loosely around the area. The mixture was stirred overnight. Further trifluoromethanesulfonyl chloride (3.4 g, 20 mmol) was added. The reaction mixture was separated between EtOAc (20 mL) and aqueous $NaHCO_3$ solution (20 mL). The organic layer was dried (phase separator) and evaporated in vacuo. The residue was purified by column chromatography ($SiO_2$, 0-10% MeOH:DCM) to give the title compounds (80 mg, 2%) as a 4:1 mixture of the 7-CF$_3$ and 8-CF$_3$ isomers respectively as off-white solids. HPLC-MS: MH− m/z 266, RT 0.86 minutes.

Intermediate 183

(2R)-2-Methyl-6-[3-(methylsulfonyl)phenyl]-7-(trifluoromethyl)-4H-pyrido[3,2-b][1,4]-oxazin-3-one and (2R)-2-Methyl-6-[3-(methylsulfonyl)phenyl]-8-(trifluoromethyl)-4H-pyrido[3,2-b][1,4]oxazin-3-one 3-(Methylsulfonyl)phenylboronic acid (0.38 g, 1.8 mmol), [1,1'-bis(diphenyl-phosphino)ferrocene]palladium (II) dichloride DCM complex (0.098 g, 0.12 mmol), $Na_2CO_3$ (0.25 g, 2.4 mmol) and Intermediate 182 (340 mg, 1.35 mmol) were suspended in 1,4-dioxane (25 mL) and stirred overnight at reflux. The reaction mixture was separated between EtOAc and water. The water was extracted with EtOAc (25 mL), then the combined organic layers were dried ($Na_2SO_4$) and evaporated in vacuo. The residue was purified by column chromatography ($SiO_2$, 1-100% Et$_2$O:DCM) to afford the title compounds (260 mg, 54%) as a 3:1 mixture of the 7-CF$_3$ and 8-CF$_3$ isomers respectively. Isomer A HPLC-MS: MH+ m/z 387, RT 0.88 minutes. Isomer B HPLC-MS: MH+ m/z 387, RT 0.84 minutes.

Intermediate 184

(2R)-8-Fluoro-2-methyl-6-[3-(methylsulfanyl)phenyl]-4H-1,4-benzoxazin-3-one

To 3-(methylsulfanyl)phenylboronic acid (1.3 g, 7.7 mmol) in 1,4-dioxane (30 mL) were added $Na_2CO_3$ (0.83 g, 7.8 mmol) in water (1 mL), Intermediate 57 (1.0 g, 3.8 mmol) and [1,1'-bis(diphenylphosphino)ferrocene]palladium(II) dichloride DCM complex (0.14 g, 0.17 mmol). The reaction mixture was degassed, flushed with nitrogen and heated at reflux for 3 h. On cooling, the mixture was separated between EtOAc (25 mL) and brine (25 mL). The aqueous layer was further extracted with EtOAc. The combined organic layers were washed with brine, then dried ($Na_2SO_4$) and concentrated in vacuo. The residue was purified by column chromatography ($SiO_2$, 10-30% EtOAc: hexane) to afford the title compound (0.81 g, 69%). HPLC-MS: MH+ m/z 304, RT 2.16 minutes.

Intermediate 185

(2R)-8-Fluoro-2-methyl-6-[3-(methylsulfonyl)phenyl]-4H-1,4-benzoxazin-3-one 3-(Methylsulfonyl)phenylboronic acid (0.60 g, 2.9 mmol), [1,1'-bis(diphenyl-phosphino)ferrocene]palladium (II) dichloride DCM complex (0.16 g, 0.19 mmol) and Intermediate 57 (0.5 g, 1.92 mmol) were dissolved in degassed 1,4-dioxane (5 mL) and treated with $Na_2CO_3$ (0.41 g, 3.8 mmol) dissolved in water (2 mL). The mixture was heated at reflux for 7 h, then separated between EtOAc (25 mL) and brine (25 mL). The organic phase was dried (phase separator) and evaporated in vacuo, then purified by column chromatography ($SiO_2$, 10-100% EtOAc:DCM), to afford the title compound (375 mg, 58%) as a yellow sold. HPLC-MS: MH+ m/z 336, RT 1.50 minutes.

Intermediate 186

(2R)-8-Fluoro-2-methyl-6-[3-(methylsulfinyl)phenyl]-4H-1,4-benzoxazin-3-one

To Intermediate 184 (0.49 g, 1.60 mmol) in DCM (15 mL) at 0° C. was added 3-chloroperoxybenzoic acid (0.24 g, 1.42 mmol). The mixture was left to stir under nitrogen overnight, then diluted with DCM (25 mL) and washed twice with aqueous $Na_2CO_3$ solution (2×25 mL) The residue was dried (phase separator), then concentrated in vacuo, to afford the title compound (0.43 g, 76%). HPLC-MS: MH+ m/z 320, RT 1.41 minutes.

Intermediate 187

2,2,2-Trifluoro-N-[{3-[(2R)-8-fluoro-2-methyl-3-oxo-4H-1,4-benzoxazin-6-yl]phenyl}-(methyl)(oxo)-$\lambda^6$-sulfanylidene]acetamide Intermediate 186 (0.43 g, 1.22 mmol) was dissolved in DCM (20 mL) and 2,2,2-trifluroacetamide (0.28 g, 2.49 mmol), magnesium oxide (0.21 g, 5.1 mmol), rhodium(II) acetate dimer (0.028 g, 0.064 mmol) and iodobenzene I,I-diacetate (0.53 g, 1.65 mmol) were added. After 18 h at r.t. the pink solution was filtered through a pad of celite and concentrated in vacuo. The residue was purified by column chromatography ($SiO_2$, 20-60% EtOAc:DCM) to yield the title compound (0.39 g, 90%). HPLC-MS: MH+ m/z 431, RT 2.00 minutes.

Intermediate 188

Methyl 2-[(6-bromo-4-methyl-2-nitropyridin-3-yl)oxy]acetate

Prepared from Intermediate 64 and methyl glycolate in a similar manner to that described for Intermediate 45. $\delta_H$ (500 MHz, $CDCl_3$) 7.60 (d, J 0.7 Hz, 1H), 4.62 (s, 2H), 3.81 (s, 3H), 2.47 (d, J 0.6 Hz, 3H). Method B HPLC-MS: MH+ m/z 306.8, RT 1.80 minutes (96%).

Intermediate 189

6-Bromo-8-methyl-2H,3H,4H-pyrido[3,2-b][1,4]oxazin-3-one

Prepared from Intermediate 188 in a similar manner to that described for Intermediate 46. $\delta_H$ (500 MHz, DMSO-$d_6$) 11.38 (s, 1H), 7.12 (s, 1H), 4.66 (s, 2H), 2.16 (s, 3H). Method B HPLC-MS: MH+ m/z 243, RT 1.63 minutes (99%).

Intermediate 190

6-Chloro-4-methylpyridin-3-ol

An aqueous solution of sodium nitrite (0.5M, 50.5 mL) was added to a cold (0-5°° C.) solution of 6-chloro-4-methylpyridin-3-amine (3 g, 21.04 mmol) in 50% aqueous $H_2SO_4$ (75 mL) over 1 h, maintaining a temperature of 0-5° C. The reaction mixture was allowed to stir for 20 minutes, then added to acetic acid (60 mL) at 100° C. over 30 minutes. Stirring was continued for 2 h, then the reaction mixture was cooled and neutralised with saturated aqueous $NaHCO_3$ solution, followed by solid $NaHCO_3$, to pH 7. The residue was extracted with EtOAc (4×200 mL) and dried ($Na_2SO_4$), then filtered and concentrated. Purification by Biotage (eluent 0-100% EOAc:heptanes; $R_F$ 0.33 in 1:1 EtOAc:heptane) afforded the title compound (1.47 g, 48.8%). $\delta_H$ (500 MHz, DMSO-$d_6$) 10.05 (s, 1H), 7.83 (s, 1H), 7.23 (s, 1H), 2.14 (s, 3H). Method B HPLC-MS: MH+ m/z 143.9/145.9, RT 1.48 minutes (100%).

Intermediate 191

6-Chloro-4-methyl-2-nitropyridin-3-ol

Prepared from Intermediate 190 using the method described for Intermediate 48 to afford the title compound (73%). Method B HPLC-MS: MH+ m/z 189/191, RT 1.59 minutes (97%).

Intermediate 192

Methyl 2-[(6-chloro-4-methyl-2-nitropyridin-3-yl)oxy]acetate

Prepared from Intermediate 191 and methyl glycolate in a similar manner to that described for Intermediate 45. $\delta_H$ (500 MHz, $CDCl_3$) 7.45 (s, 1H), 4.63 (s, 2H), 3.81 (s, 3H), 2.48 (s, 3H). Method B HPLC-MS: MH+ m/z 261, RT 1.80 minutes (96%).

Intermediate 193

6-Chloro-8-methyl-2H,3H,4H-pyrido[3,2-b][1,4]oxazin-3-one

Prepared from Intermediate 192 in a similar manner to that described for Intermediate 46. $\delta_H$ (500 MHz, DMSO-$d_6$) 11.36 (s, 1H), 6.99 (s, 1H), 4.66 (s, 2H), 2.17 (s, 3H). Method B HPLC-MS: MH+ m/z 199, RT 1.52 minutes (97%).

Intermediate 194

7-Fluoro-2-methylimidazo[1,2-a]pyridine-6-carbonitrile

Intermediate 33 (0.6 g, 2.6 mmol) was heated with copper(I) cyanide (0.19 g, 2.2 mmol) in 1-methyl-2-pyrrolidinone (2 mL) under microwave irradiation at 150° C. for 1 h, then at 175° C. for a further 2 h. The reaction mixture was treated with EtOAc (20 mL), then washed with dilute aqueous ammonia solution (2×20 mL) and brine (20 mL). The residue was purified by preparative HPLC to afford the title compound (150 mg, 33%) as a white solid. HPLC-MS: MH− m/z 176, RT 1.0 minute.

Intermediate 195

7-Fluoro-3-(hydroxymethyl)-2-methylimidazo[1,2-a]pyridine-6-carbonitrile

Intermediate 194 (0.15 g, 0.86 mmol) was suspended in water (5.0 mL) and warmed to 40° C., then a solution of formaldehyde in water (37 mass %, 0.7 mL, 9 mmol) was added. The resulting suspension was heated at 80° C. for 12 h, then cooled. The resulting white precipitate was isolated by filtration, washed with water and dried in vacuo, to afford the title compound (110 mg, 63%) as a white powder. HPLC-MS: MH⁻ m/z 206, RT 0.6 minutes.

Intermediate 196

6-Bromospiro[4H-1,4-benzoxazine-2,1'-cyclopropane]-3-one

Prepared from 2-amino-4-bromophenol and 1-bromocyclopropanecarbonyl chloride in a similar manner to that described for Intermediate 139 to give the title compound. Method B HPLC-MS: MH+ m/z 254/256; RT 1.35 minutes.

Intermediate 197

(2R)-6-(1-Acetyl-1,4,5,6-tetrahydropyridin-3-yl)-2-methyl-4-[(1,3,5-trimethyl-1H-pyrazol-4-yl)methyl]-2H,3H,4H-pyrido[3,2-b][1,4]oxazin-3-one Prepared from Intermediate 151 and 1-(5-bromo-1,2,3,4-tetrahydropyridin-1-yl)-ethan-1-one following the procedure described for Example 154 to provide the title compound in 51% yield. Method B HPLC-MS: MH+ m/z 410, RT 1.77 minutes (96%).

Intermediate 198

Ethyl 3-[(methoxymethoxy)methyl]-1,5-dimethyl-1H-pyrazole-4-carboxylate

To a solution of ethyl 3-(hydroxymethyl)-1,5-dimethyl-1H-pyrazole-4-carboxylate (*J. Heterocycl. Chem.*, 1979, 16, 1117) (91%, 0.58 g, 2.67 mmol) and DIPEA (0.93 mL, 5.33 mmol) in anhydrous DCM (13 mL) at 0° C. was added chloromethyl methyl ether (0.3 mL, 4 mmol) dropwise over approximately 2 minutes. The mixture was allowed to warm to room temperature overnight, then more DIPEA (0.93 mL, 5.33 mmol) and chloro-methyl methyl ether (0.3 mL, 4 mmol) were added. The reaction mixture was stirred at r.t. overnight, then quenched by thee addition of water (25 mL). The mixture was extracted with DCM (25 mL), and the organic phase was washed with water (25 mL). The combined aqueous washes were further extracted with DCM (10 mL). The combined organic extracts were dried over MgSO₄, then filtered and concentrated in vacuo. The resulting crude yellow oil (0.736 g) was purified using column chromatography (SiO₂, with a gradient of 15-100% EtOAc/heptane) to give the title compound (0.55 g, 84.6%) as a clear oil. $\delta_H$ (500 MHz, CDCl₃) 4.80 (s, 2H), 4.77 (s, 2H), 4.30 (q, J 7.1 Hz, 2H), 3.79 (s, 3H), 3.43 (s, 3H), 2.51 (s, 3H), 1.35 (t, J 7.1 Hz, 3H). Method B HPLC-MS: MH+ m/z 243, RT 1.69 minutes (100%).

Intermediate 199

{3-[(Methoxymethoxy)methyl]-1,5-dimethyl-1H-pyrazol-4-yl}methanol

To a solution of Intermediate 198 (0.54 g, 2.22 mmol) in anhydrous THF (46 mL) at 0° C. was added diisobutylaluminium hydride(1.0M in heptane, 6.67 mL). The reaction mixture was stirred at 0° C. for 7 h, then quenched with saturated aqueous potassium tartrate solution (50 mL). The mixture was allowed to warm to room temperature overnight. The phases were separated and the aqueous phase was extracted with DCM (50 mL), followed by a 1:2 mixture of EtOH/CHCl₃ (50 mL). The combined organic extracts were dried over MgSO₄, then filtered and concentrated in vacuo. The resulting crude light yellow liquid (0.727 g) was purified using a Biotage Isolera 4 flash purification system using column chromatography (SiO₂, with a gradient of MeOH/DCM), yielding the title compound (0.46 g, 103%) as a light yellow oil. $\delta_H$ (500 MHz, CDCl₃) 4.71 (s, 2H), 4.62 (s, 2H), 4.48 (s, 2H), 3.75 (s, 3H), 3.41 (s, 3H), 2.26 (s, 3H). Method B HPLC-MS: MH+ m/z 201, RT 1.15 minutes (97%).

Intermediate 200

1-Chloro-3-fluoro-5-(methylsulfanyl)benzene

3-Chloro-5-fluorothiophenol (1.0 g, 6.1 mmol) was dissolved in acetone (20 mL) and potassium carbonate (0.93 g, 6.76 mmol) was added. The mixture was cooled in an ice bath, then iodomethane (0.96 g, 6.76 mmol) was added dropwise. The reaction mixture was separated between ethyl acetate and brine. The organic layer was washed with water and passed through a phase separator, then evaporated in vacuo, to obtain the title compound (0.90 g, 82%) as a yellow oil. $\delta_H$ (400 MHz, DMSO-d₆) 7.16 (m, 3H), 2.53 (s, 3H).

Intermediate 201

1-Chloro-3-fluoro-5-(methylsulfinyl)benzene

Intermediate 200 (0.51 g, 2.83 mmol) was dissolved in dichloromethane (50 mL) and cooled in an ice bath. 3-Chloroperoxybenzoic acid (0.51 g, 2.83 mmol) was added and the mixture was stirred at room temperature. After 90 minutes, the reaction mixture was diluted with dichloromethane (25 mL), then washed with aqueous sodium carbonate solution (2×50 mL) and water (50 mL). The organic layer was passed through a phase separator, then evaporated in vacuo, to obtain the title compound (550 mg, 93%). HPLC-MS: MH+ m/z 193, RT 1.65 minutes.

Intermediate 202

3-({(2R)-8-Fluoro-6-[3-fluoro-5-(methylsulfinyl)phenyl]-2-methyl-3-oxo-1,4-benzoxazin-4-yl}methyl)-2-methylimidazo[1,2-a]pyridine-6-carbonitrile To a solution of Intermediate 201(0.25 g, 1.30 mmol) in 1,4-dioxane (2 mL) was added bis(pinacolato)diboron (0.98 g, 3.76 mmol), followed by potassium acetate hydrate (386 mg, 3.94 mmol), palladium dibenzyl acetate (12 mg, 0.013 mmol) and X-Phos (25 mg, 0.05 mmol) The mixture was heated under microwave irradiation for 1 h, then Intermediate 125 (200 mg, 0.47 mmol) was added, followed by sodium carbonate (89 mg, 0.84 mmol) dissolved in water (1 mL). The mixture was heated for 3 h at 100° C. under microwave irradiation. On cooling, the reaction mixture was separated between ethyl acetate (20 mL) and water (20 mL). The aqueous layer was extracted with further ethyl acetate (25 mL). The combined organic layers were washed with water (2×25 mL) and dried (phase separator), then evaporated in vacuo. The residue was purified by preparative HPLC to afford the title compound (148 mg, 69%) as a white powder. HPLC-MS: MH+ m/z 507, RT 2.22 minutes.

Intermediate 203

[4-Bromo-2-(methylsulfanyl)phenyl]methanol

4-Bromo-2-(methylsulfanyl)benzaldehyde (0.5 g, 2.16 mmol) was dissolved in tetrahydrofuran (5 mL) and cooled in an ice bath. Lithium borohydride (0.071 g, 3.25 mmol) was added and the mixture was allowed to warm to room temperature over 1 h. After 2 h, the mixture was cooled in an ice bath and 2M hydrochloric acid (3 mL) was added, followed by water (5 mL). The resulting white precipitate was removed by filtration to give the title compound (440 mg, 88%). $\delta_H$ (300 MHz, DMSO-$d_6$) 7.34 (m, 3H), 5.33 (t, 1H, J 5.5 Hz), 4.42 (d, 2H, J 5.5 Hz), 2.50 (s, 3H).

Intermediate 204

[4-Bromo-2-(methylsulfinyl)phenyl]methanol

Intermediate 203 (0.24 g, 1.03 mmol) was dissolved in dichloromethane (20 mL) and cooled in an ice bath. 3-Chloroperoxybenzoic acid (0.19 g, 1.03 mmol) was added and the mixture was stirred at room temperature. After 1 h, additional 3-chloroperoxy-benzoic acid (100 mg) was added. After a further 30 minutes, the reaction mixture was diluted with DCM (50 mL), then washed with sodium carbonate solution (2×50 mL) and water (50 mL). The organic layer was passed through a phase separator, then evaporated in vacuo, to afford the title compound (0.25 g, 97%) as a white solid. $\delta_H$ (300 MHz, DMSO-$d_6$) 7.95 (d, 1H, J 2.1 Hz), 7.71 (dd, 1H, J 8.1, 2.1 Hz), 7.43 (d, 1H, J 8.1 Hz), 5.56 (t, 1H, J 5.4 Hz), 4.54 (d, 2H, J 5.3 Hz), 2.76 (s, 3H). HPLC-MS: MH− m/z 247 249, RT 1.70 minutes.

Intermediate 205

[2-(Methylsulfinyl)-4-(4,4,5,5-tetramethyl-1,3,2-dioxaborolan-2-yl)phenyl]methanol Intermediate 204 (0.2 g, 0.80 mmol) in 1,4-dioxane (25 mL) was treated with bis(pinacolato)diboron (0.31 g, 1.20 mmol), potassium acetate (0.096 g, 0.96 mmol) and [1,1'-bis(diphenylphosphino)ferrocene]dichloropalladium(II) dichloromethane complex (0.066 g, 0.080 mmol). The mixture was degassed and flushed with nitrogen before heating at reflux for 2.5 h. The resulting material was used without further purification.
HPLC-MS: MH+ m/z 297, RT 1.10 minutes.

Intermediate 206

3-({(2R)-8-Fluoro-6-[4-(hydroxymethyl)-3-(methylsulfinyl)phenyl]-2-methyl-3-oxo-1,4-benzoxazin-4-yl}methyl)-2-methylimidazo[1,2-a]pyridine-6-carbonitrile Prepared from Intermediates 125 and 205 in a similar manner to that described for
Intermediate 202. The resulting material was purified by column chromatography (SiO$_2$, MeOH:DCM, 1-10% gradient) to afford the title compound (0.28 g, 83%). $\delta_H$ (400 MHz, DMSO-$d_6$) 9.20 (m, 1H), 8.07 (dd, 1H, J 6.3, 2.0 Hz), 7.54 (m, 6H), 5.73 (m, 2H), 5.51 (m, 1H), 5.03 (m, 1H), 4.63 (m, 2H), 2.80 (s, 3H), 2.33 (m, 3H), 1.56 (d, 3H, J 6.6 Hz). HPLC-MS: MH+ m/z 519, RT 1.78 minutes.

Example 1

4-[(2,4-Dimethylpyridin-3-yl)methyl]-6-(1-oxo-1,2,3,4-tetrahydroisoquinolin-7-yl)-2H-pyrido[3,2-b][1,4]oxazin-3(4H)-one To a stirred solution of Intermediate 102 (180 mg, 0.52 mmol) and Intermediate 160 (155 mg, 0.57 mmol) in anhydrous 1,4-dioxane (4 mL) was added 2M aqueous Na$_2$CO$_3$ solution (0.80 mL, 1.60 mmol) and the reaction mixture was degassed with N$_2$ for 10 minutes. Bis[3-(diphenylphosphanyl)cyclopenta-2,4-dien-1-yl]iron DCM dichloropalladium (21 mg, 0.030 mmol) was added and the reaction mixture was degassed with N$_2$ for another 5 minutes. The reaction mixture was heated in a pressure tube at 100° C. for 2 h, then cooled to ambient temperature. EtOAc (20 mL) and water (20 mL) were added. The aqueous phase was extracted with EtOAc (20 mL) and the combined organic phases were washed with brine (15 mL), then dried (Na$_2$SO$_4$). The solvent was removed in vacuo. The residue was purified by column chromatography (SiO$_2$: DCM/MeOH) to afford the title compound (135 mg, 63%) as a cream solid. $\delta_H$ (500 MHz, DMSO-$d_6$) 8.32 (d, J 1.9 Hz, 1H), 8.14 (d, J 4.9 Hz, 1H), 8.03 (s, 1H), 7.87 (dd, J 7.9, 2.0 Hz, 1H), 7.58 (d, J 8.3 Hz, 1H), 7.51 (d, J 8.2 Hz, 1H), 7.38 (d, J 8.0 Hz, 1H), 7.04 (d, J 5.0 Hz, 1H), 5.38 (s, 2H), 4.82 (s, 2H), 3.43-3.37 (m, 2H), 2.94 (t, J 6.8 Hz, 2H), 2.46 (s, 3H), 2.33 (s, 3H). Method A HPLC-MS: MH+ m/z 415, RT 2.71 minutes (100%).

Example 2

7-{4-[(2-Methylimidazo[1,2-a]pyridin-3-yl)methyl]-3-oxo-2H,3H,4H-pyrido[3,2-b][1,4]-oxazin-6-yl}-1,2,3,4-tetrahydroisoquinolin-1-one A solution of Intermediate 148 (120 mg, 0.32 mmol) in anhydrous 1,4-dioxane (3 mL) was treated with 7-bromo-3,4-dihydroisoquinolin-1(2H)-one (99.78 mg, 0.44 mmol) and 2N aqueous Na$_2$CO$_3$ solution (0.77 mL). The reaction mixture was degassed with N$_2$ for 5 minutes, then bis[3-(diphenylphosphanyl)cyclopenta-2,4-dien-1-yl]iron DCM dichloropalladium (18 mg, 0.016 mmol) was added. The mixture was degassed with N$_2$ for 10 minutes and heated with stirring for 2.5 h at 130° C. under microwave irradiation. Further portions of 7-bromo-3,4-dihydroisoquinolin-1(2H)-one (50 mg, 0.22 mmol), 1,4-dioxane (3 mL), 2N aqueous Na$_2$CO$_3$ solution (0.5 mL) and bis[3-(diphenylphosphanyl)-cyclopenta-2,4-dien-1-yl]iron DCM dichloropalladium (18 mg, 0.016 mmol) were added. The mixture was degassed and heated with stirring for 1 h at 130° C. under microwave irradiation. The mixture was cooled, then EtOAc (10 mL) and water (10 mL) were added. The organic layer was washed with water (10 mL) and brine (10 mL), then dried (Na$_2$SO$_4$). The solvent was removed in vacuo. The residue was purified using preparative HPLC (Method A) to afford the title compound (10 mg, 5%) as a white solid. $\delta_H$ (500 MHz, DMSO-$d_6$) 8.62 (d, J 6.9 Hz, 1H), 8.48 (d, J 1.8 Hz, 1H), 8.09 (dd, J 7.9, 1.9 Hz, 1H), 8.05 (s, 1H), 7.65 (d, J 8.2 Hz, 1H), 7.51 (d, J 8.2 Hz, 1H), 7.41 (t, J 7.9 Hz, 2H), 7.18-7.12 (m, 1H), 6.74 (t, J 6.5 Hz, 1H), 5.73 (s, 2H), 4.86 (s, 2H), 3.42 (td, J 6.6, 2.6 Hz, 2H), 2.98 (t, J 6.5 Hz, 2H), 2.31 (s, 3H). Method D (uPLC): MH+ m/z 440.1, RT 1.68 minutes (100%).

Example 3

7-{2-Methyl-4-[(2-methylpyridin-3-yl)methyl]-3-oxo-2H,3H,4H-pyrido[3,2-b][1,4]-oxazin-6-yl}-1,2,3,4-tetrahydroisoquinolin-1-one Prepared from Intermediates 106 and 160 in a similar manner to that described for Example 1. $\delta_H$ (500 MHz, DMSO-$d_6$) 8.17 (d, J 1.9 Hz, 1H), 8.08 (d, J 3.5 Hz, 1H), 7.76 (s, 1H), 7.70 (dd, J 7.9, 2.0 Hz, 1H), 7.44 (d, J 8.3 Hz, 1H), 7.35 (d, J 8.2 Hz, 1H), 7.16 (dd, J 13.9, 7.6 Hz, 2H), 6.92 (dd, J 7.7, 4.8 Hz, 1H), 5.16 (d, J 15 Hz, 1H), 5.11 (d, J 15 Hz, 1H), 4.88 (q, J 6.7 Hz, 1H), 2.72 (t, J 6.5 Hz, 2H), 2.44 (s, 3H), 1.38 (d, J 6.8 Hz, 3H), 2H obscured by DMSO peaks. Method A HPLC-MS: MH+ m/z 415, RT 3.10 minutes (100%).

Example 4

7-{2-Methyl-3-oxo-4-[(1,3,5-trimethyl-1H-pyrazol-4-yl)methyl]-2H,3H,4H-pyrido[3,2-b][1,4]oxazin-6-yl}-1,2,3,4-tetrahydroisoquinolin-1-one Prepared from Intermediates 107 and 160 in a similar manner to that described for Example 1. $\delta_H$ (500 MHz, DMSO-$d_6$) 8.37 (d, J 1.9 Hz, 1H), 8.01 (dd, J 7.9, 2.0 Hz, 1H), 7.91 (s, 1H), 7.53 (d, J 8.2 Hz, 1H), 7.41 (d, J 8.2 Hz, 1H), 7.33 (d, J 8.0 Hz, 1H), 5.07 (d, J 15 Hz, 1H), 5.04 (d, J 15 Hz, 1H), 4.79 (q, J 6.7 Hz, 1H), 3.44 (s, 3H), 3.30 (2H, obscured by DMSO), 2.87 (t, J 6.5 Hz, 2H), 2.06 (s, 3H), 1.87 (s, 3H), 1.40 (d, J 6.8 Hz, 3H). Method A HPLC-MS: MH+ m/z 432, RT 3.94 minutes (100%).

Example 5

6-(2-Methyl-1-oxo-1,2,3,4-tetrahydroisoquinolin-7-yl)-4-[(1,3,5-trimethyl-1H-pyrazol-4-yl)methyl]-2H-pyrido[3,2-b][1,4]oxazin-3(4H)-one Prepared from 7-bromo-2-methyl-3,4-dihydroisoquinolin-1-one and Intermediate 147 in a similar manner to that described for Example 2. $\delta_H$ (500 MHz, DMSO-$d_6$) 8.48 (d, J 1.8 Hz, 1H), 8.37 (s, 1H, formate), 8.08 (dd, J 1.9, 8.2 Hz, 1H), 7.60 (d, J 8.2 Hz, 1H), 7.48 (d, J 8.2 Hz, 1H), 7.40 (d, J 7.9 Hz, 1H), 5.15 (s, 2H), 4.79 (s, 2H), 3.58 (t, J 6.7 Hz, 2H), 3.53 (s, 3H), 3.05 (s, 3H), 3.03 (t, J 6.6 Hz, 2H), 2.15 (s, 3H), 1.97 (s, 3H). Method A HPLC-MS: MH+ m/z 432.10, RT 3.67 minutes (100%).

Example 6

(2R)-8-Fluoro-2-methyl-4-[(2-methylpyridin-3-yl)methyl]-6-(1-oxo-1,2,3,4-tetrahydro-isoquinolin-7-yl)-3,4-dihydro-2H-1,4-benzoxazin-3-one Prepared from Intermediates 103 and 160 in a similar manner to that described for Example 1. $\delta_H$ (500 MHz, DMSO-$d_6$) 8.32 (d, J 3.8 Hz, 1H), 7.97 (s, 1H), 7.94 (d, J 1.9 Hz, 1H), 7.61 (dd, J 7.9, 2.1 Hz, 1H), 7.36-7.30 (m, 3H), 7.15 (dd, J 7.7, 4.8 Hz, 1H), 6.96 (s, 1H), 5.30 (d, J 17.2 Hz, 1H), 5.23 (d, J 17.1 Hz, 1H), 5.09 (q, J 6.7 Hz, 1H), 3.40 (m, 2H), 2.90 (t, J 6.5 Hz, 2H), 2.57 (s, 3H), 1.58 (d, J 6.7 Hz, 3H). Column: Chiralcel OD-H 25 cm; Mobile phase: 18% EtOH: 82% $CO_2$; Flow rate: 4 mL/minute; Runtime: 20 minutes; UV at 215 nm; RT 12.4 minutes. Method D HPLC-MS: MH+ m/z 432.1, RT 2.00 minutes (97%).

Example 7

7-{(2R)-2-Methyl-4-[(2-methylpyridin-3-yl)methyl]-3-oxo-2H,3H,4H-pyrido[3,2-b][1,4]-oxazin-6-yl}-1,2,3,4-tetrahydroisoquinolin-1-one Prepared from Intermediates 105 and 160 in a similar manner to that described for Example 1. $\delta_H$ (500 MHz, DMSO-$d_6$) 8.17 (d, J 1.9 Hz, 1H), 8.08 (d, J 3.5 Hz, 1H), 7.76 (s, 1H), 7.70 (dd, J 7.9, 2.0 Hz, 1H), 7.44 (d, J 8.3 Hz, 1H), 7.35 (d, J 8.2 Hz, 1H), 7.16 (dd, J 13.9, 7.6 Hz, 2H), 6.92 (dd, J 7.7, 4.8 Hz, 1H), 5.16 (d, J 15 Hz, 1H), 5.11 (d, J 15 Hz, 1H), 4.88 (q, J 6.7 Hz, 1H), 2.72 (t, J 6.5 Hz, 2H), 2.44 (s, 3H), 1.38 (d, J 6.8 Hz, 3H), 2H obscured by DMSO peaks. Column: Chiralpak OD-H; Mobile phase: 15% EtOH: 85% heptane; Runtime: 40 minutes; RT 25.0 minutes. Method A HPLC-MS: MH+ m/z 415, RT 3.10 minutes (100%).

Example 8

7-{3-Oxo-4-[(1,3,5-trimethyl-1H-pyrazol-4-yl)methyl]-2H,3H,4H-pyrido[3,2-b][1,4]-oxazin-6-yl}-1,2,3,4-tetrahydroisoquinolin-1-one Prepared from 7-bromo-3,4-dihydroisoquinolin-1-one and Intermediate 147 in a similar manner to that described for Example 2. $\delta_H$ (500 MHz, DMSO-$d_6$) 8.45 (d, J 1.8 Hz, 1H), 8.10 (dd, J 7.9, 1.9 Hz, 1H), 8.02 (s, 1H), 7.61 (d, J 8.2 Hz, 1H), 7.48 (d, J 8.2 Hz, 1H), 7.42 (d, J 8.0 Hz, 1H), 5.15 (s, 2H), 4.79 (s, 2H), 3.53 (s, 3H), 3.40 (td, J 6.5, 2.5 Hz, 2H), 2.95 (t, J 6.5 Hz, 2H), 2.15 (s, 3H), 1.97 (s, 3H). Method A HPLC-MS: MH+m/z 418.15, RT 3.42 minutes (100%).

Example 9

4-[(4,6-Dimethylpyrimidin-5-yl)methyl]-8-fluoro-6-(1-oxo-1,2,3,4-tetrahydroisoquinolin-7-yl)-3,4-dihydro-2H-1,4-benzoxazin-3-one Prepared from Intermediates 113 and 160 in a similar manner to that described for Example 1. $\delta_H$ (500 MHz, DMSO-$d_6$) 8.71 (s, 1H), 8.07 (d, J 2.1 Hz, 1H), 8.02 (s, 1H), 7.70 (dd, J 7.9, 2.1 Hz, 1H), 7.41 (d, J 8.0 Hz, 1H), 7.37 (dd, J 11.4, 1.8 Hz, 1H), 7.21 (s, 1H), 5.34 (s, 2H), 4.82 (s, 2H), 3.40 (td, J 6.6, 2.8 Hz, 2H), 2.94 (t, J 6.5 Hz, 2H), 2.48 (s, 6H). Method A HPLC-MS: MH+ m/z 433, RT 3.50 minutes (97%).

Example 10

7-{2-Methyl-4-[(2-methylimidazo[2-a]pyridin-3-yl)methyl]-3-oxo-2H,3H,4H-pyrido-[3,2-b][1,4]oxazin-6-yl}-1,2,3,4-tetrahydroisoquinolin-1-one Prepared from Intermediates 110 and 160 in a similar manner to that described for Example 1. $\delta_H$ (500 MHz, DMSO-$d_6$) 8.62 (d, J 6.9 Hz, 1H), 8.48 (d, J 1.6 Hz, 1H), 8.07 (dd, J 7.9, 1.8 Hz, 1H), 8.03 (s, 1H), 7.65 (d, J 8.2 Hz, 1H), 7.52 (d, J 8.2 Hz, 1H), 7.39 (t, J 7.4 Hz, 2H), 7.14 (t, J 7.6 Hz, 1H), 6.74 (t, J 6.8 Hz, 1H), 5.71 (s, 2H), 4.94 (q, J 6.7 Hz, 1H), 2.96 (t, J 6.5 Hz, 2H), 2.29 (s, 3H), 1.49 (d, J 6.7 Hz, 3H); 2H obscured by DMSO peak. Method A HPLC-MS: MH+ m/z 454.20, RT 2.95 minutes (99%).

Example 11

7-{8-Methyl-3-oxo-4-[(1,3,5-trimethyl-1H-pyrazol-4-yl)methyl]-2H,3H,4H-pyrido[3,2-b][1,4]oxazin-6-yl}-1,2,3,4-tetrahydroisoquinolin-1-one Prepared from Intermediates 131 and 160 in a similar manner to that described for Example 1. $\delta_H$ (500 MHz, DMSO-$d_6$) 8.47 (d, J 1.9 Hz, 1H), 8.12 (dd, J 7.9, 2.0 Hz, 1H), 8.01 (s, 1H), 7.59 (s, 1H), 7.42 (d, J 8.0 Hz, 1H), 5.16 (s, 2H), 4.80 (s, 2H), 3.53 (s, 3H), 3.42 (td, J 6.6, 2.7 Hz, 2H), 2.96 (t, J 6.5 Hz, 2H), 2.28 (s, 3H), 2.15 (s, 3H), 1.98 (s, 3H). Method A HPLC-MS: MH+ m/z 432.05, RT 3.68 minutes (98%).

Example 12

7-{4-[(2-Methylpyridin-3-yl)methyl]-3-oxo-2H,3H,4H-pyrido[3,2-b][1,4]oxazin-6-yl}-1,2,3,4-tetrahydroisoquinolin-1-one Prepared from Intermediates 109 and 160 in a similar manner to that described for Example 1. $\delta_H$ (500 MHz, DMSO-$d_6$) 8.35 (d, J 1.8 Hz, 1H), 8.28 (d, J 3.6 Hz, 1H), 7.95 (s, 1H), 7.87 (dd, J 7.9, 1.9 Hz, 1H), 7.62 (d, J 8.3 Hz, 1H), 7.51 (d, J 8.2 Hz, 1H), 7.44 (d, J 7.5 Hz, 1H), 7.33 (d, J 8.0 Hz, 1H), 7.09 (dd, J 7.7, 4.8 Hz, 1H), 5.33 (s, 2H), 4.96 (s, 2H), 3.37 (td, J 6.6, 2.7 Hz, 2H), 2.90 (t, J 6.5 Hz, 2H), 2.63 (s, 3H). Method A HPLC-MS: MH+ m/z 401.05, RT 2.75 minutes (96%).

Example 13

8-Fluoro-6-(1-oxo-1,2,3,4-tetrahydroisoquinolin-7-yl)-4-[(1,3,5-trimethyl-1H-pyrazol-4-yl)methyl]-3,4-dihydro-2H-1,4-benzoxazin-3-one Prepared from Intermediates 137 and 160 in a similar manner to that described for Example 1. $\delta_H$ (500 MHz, DMSO-$d_6$) 8.02 (s, 1H), 7.91 (d, J 1.9 Hz, 1H), 7.70 (dd, J 7.9, 2.1 Hz, 1H), 7.41 (d, J 7.9 Hz, 1H), 7.30 (dd, J 11.5, 1.7 Hz, 1H), 7.07 (s, 1H), 5.08 (s, 2H), 4.86 (s, 2H), 3.62 (s, 3H), 3.41 (td, J 6.6, 2.6 Hz, 2H), 2.94 (t, J 6.5 Hz, 2H), 2.28 (s, 3H), 1.98 (s, 3H). Method D HPLC-MS: MH+ m/z 435.2, RT 2.60 minutes (99%).

Example 14

7-{2,2-Difluoro-3-oxo-4-[(1,3,5-trimethyl-1H-pyrazol-4-yl)methyl]-2H,3H,4H-pyrido-[3,2-b][1,4]oxazin-6-yl}-1,2,3,4-tetrahydroisoquinolin-1-one Prepared from Intermediates 133 and 160 in a similar manner to that described for Example 1. $\delta_H$ (500 MHz, DMSO-$d_6$) 8.48 (d, J 1.9 Hz, 1H), 8.15 (dd, J 7.9, 2.0 Hz, 1H), 8.04 (s, 1H), 7.97-7.83 (m, 2H), 7.47 (d, J 8.0 Hz, 1H), 5.24 (s, 2H), 3.58 (s, 3H), 3.41 (td, J 6.7, 2.8 Hz, 2H), 2.98 (t, J 6.6 Hz, 2H), 2.19 (s, 3H), 1.99 (s, 3H). Method A HPLC-MS: MH+ m/z 453.95, RT 3.92 minutes (99%).

Example 15

7-{(2R)-4-[(3,5-Dimethylpyridazin-4-yl)methyl]-2-methyl-3-oxo-2H,3H,4H-pyrido[3,2-b][1,4]oxazin-6-yl}-1,2,3,4-tetrahydroisoquinolin-1-one Prepared from Intermediates 108 and 160 in a similar manner to that described for Example 1. $\delta_H$ (500 MHz, DMSO-$d_6$) 8.87 (s, 1H), 8.27 (d, J 1.9 Hz, 1H), 8.00 (s, 1H), 7.82 (dd, J 7.9, 2.0 Hz, 1H), 7.61 (d, J 8.2 Hz, 1H), 7.55 (d, J 8.2 Hz, 1H), 7.37 (d, J 8.0 Hz, 1H), 5.38 (s, 2H), 4.97 (q, J 6.8 Hz, 1H), 3.40 (dt, J 6.5, 2.8 Hz, 2H), 2.94 (t, J 6.5 Hz, 2H), 2.59 (s, 3H), 2.30 (s, 3H), 1.50 (d, J 6.8 Hz, 3H). Chiral analysis: 91% ee, (R) isomer at 8.86 minutes; Column: Chiralcel OD-H 25 cm; Mobile phase: 25% MeOH: 75% $CO_2$; Flow rate: 4 mL/minute; Runtime: 15 minutes; UV at 215 nm. Method D HPLC-MS: MH+ m/z 430, RT 2.20 minutes (98%).

Example 16

8-Fluoro-4-[(2-methylimidazo[1,2-a]pyridin-3-yl)methyl]-6-(1-oxo-1,2,3,4-tetrahydro-isoquinolin-7-yl)-3,4-dihydro-2H-1,4-benzoxazin-3-one Prepared from Intermediates 123 and 160 in a similar manner to that described for Example 1. $\delta_H$ (500 MHz, DMSO-$d_6$) 8.32 (d, J 6.9 Hz, 1H), 8.07 (d, J 1.9 Hz, 1H), 8.01 (s, 1H), 7.59 (dd, J 7.9, 2.1 Hz, 1H), 7.42 (d, J 9.0 Hz, 1H), 7.37 (d, J 7.9 Hz, 1H), 7.35-7.27 (m, 2H), 7.24-7.17 (m, 1H), 6.95 (t, J 6.8 Hz, 1H), 5.71 (s, 2H), 4.91 (s, 2H), 3.40 (td, J 6.5, 2.6 Hz, 2H), 2.94 (t, J 6.5 Hz, 2H), 2.39 (s, 3H). Method A HPLC-MS: MH+m/z 456.95, RT 2.94 minutes (98%).

Example 17

(2R)-4-[(3,5-Dimethylpyridazin-4-yl)methyl]-8-fluoro-2-methyl-6-(1-oxo-1,2,3,4-tetrahydroisoquinolin-7-yl)-3,4-dihydro-2H-1,4-benzoxazin-3-one Prepared from Intermediates 116 and 160 in a similar manner to that described for Example 1. $\delta_H$ (500 MHz, DMSO-$d_6$) 8.88 (s, 1H), 8.02 (s, 1H), 7.96 (d, J 2.1 Hz, 1H), 7.68 (dd, J 7.9, 2.1 Hz, 1H), 7.39 (d, J 8.0 Hz, 1H), 7.36 (dd, J 11.4, 1.8 Hz, 1H), 7.10 (s, 1H), 5.40 (d, J 16.1 Hz, 1H), 5.27 (d, J 16.1 Hz, 1H), 4.93 (q, J 6.7 Hz, 1H), 3.39 (td, J 6.6, 2.7 Hz, 2H), 2.93 (t, J 6.5 Hz, 2H), 2.57 (s, 3H), 2.32 (s, 3H), 1.49 (d, J 6.7 Hz, 3H). Method A HPLC-MS: MH+ m/z 447, RT 3.45 minutes (99%).

Example 18

(2R)-8-Fluoro-2-methyl-6-(1-oxo-1,2,3,4-tetrahydroisoquinolin-7-yl)-4-[(1,3,5-trimethyl-1H-pyrazol-4-yl)methyl]-3,4-dihydro-2H-1,4-benzoxazin-3-one Prepared from Intermediates 135 and 160 in a similar manner to that described for Example 1. $\delta_H$ (500 MHz, DMSO-$d_6$) 8.02 (s, 1H), 7.90 (d, J 2.0 Hz, 1H), 7.70 (dd, J 7.9, 2.1 Hz, 1H), 7.40 (d, J 7.9 Hz, 1H), 7.29 (dd, J 11.4, 1.8 Hz, 1H), 7.06 (s, 1H), 5.17 (d, J 15.8 Hz, 1H), 5.03-4.87 (m, 2H), 3.61 (s, 3H), 3.40 (d, J 1.9 Hz, 2H underneath water peak), 2.94 (t, J 6.6 Hz, 2H), 2.26 (s, 3H), 1.96 (s, 3H), 1.53 (d, J 6.7 Hz, 3H). Method A HPLC-MS: MH+ m/z 449, RT 3.80 minutes (100%).

Example 19

4-[(3,5-Dimethylpyridazin-4-yl)methyl]-8-fluoro-6-(1-oxo-1,2,3,4-tetrahydroisoquinolin-7-yl)-3,4-dihydro-2H-1,4-benzoxazin-3-one Prepared from Intermediates 122 and 160 in a similar manner to that described for Example 1. $\delta_H$ (500 MHz, DMSO-d$_6$) 8.89 (s, 1H), 8.03 (br s, 1H), 7.97 (d, J 2.0 Hz, 1H), 7.69 (dd, J 7.9, 2.1 Hz, 1H), 7.40 (d, J 8.0 Hz, 1H), 7.37 (dd, J 11.4, 1.7 Hz, 1H), 7.11 (s, 1H), 5.33 (s, 2H), 4.84 (s, 2H), 3.45-3.37 (m, 2H), 2.94 (t, J 6.5 Hz, 2H), 2.60 (s, 3H), 2.34 (s, 3H). Method D HPLC-MS: MH+ m/z 433, RT 3.29 minutes (99%).

Example 20

7-{4-[(3,5-Dimethylpyridazin-4-yl)methyl]-8-methyl-3-oxo-2H,3H,4H-pyrido[3,2-b]-[1,4]oxazin-6-yl}-1,2,3,4-tetrahydroisoquinolin-1-one Prepared from Intermediates 115 and 160 in a similar manner to that described for Example 1. δ$_H$ (500 MHz, DMSO-d$_6$) 8.87 (s, 1H), 8.28 (d, J 1.9 Hz, 1H), 8.01 (s, 1H), 7.82 (dd, J 7.9, 2.0 Hz, 1H), 7.57 (s, 1H), 7.37 (d, J 7.9 Hz, 1H), 5.38 (s, 2H), 4.86 (s, 2H), 3.40 (dt, J 6.4, 3.2 Hz, 2H), 2.95 (t, J 6.5 Hz, 2H), 2.61 (s, 3H), 2.31 (s, 3H), 2.30 (s, 3H). Method A HPLC-MS: MH+ m/z 430.05, RT 3.36 minutes (96%).

Example 21

8-Fluoro-4-({5-[(methoxymethoxy)methyl]-1,3-dimethyl-1H-pyrazol-4-yl}methyl)-6-(1-oxo-1,2,3,4-tetrahydroisoquinolin-7-yl)-3,4-dihydro-2H-1,4-benzoxazin-3-one Prepared from Intermediates 120 and 160 in a similar manner to that described for Example 1. δ$_H$ (500 MHz, DMSO-d$_6$) 8.04 (s, 1H), 7.89 (d, J 1.8 Hz, 1H), 7.68 (dd, J 7.9, 1.9 Hz, 1H), 7.39 (d, J 7.9 Hz, 1H), 7.28 (dd, J 11.4, 1.4 Hz, 1H), 7.13 (s, 1H), 5.14 (s, 2H), 4.84 (s, 2H), 4.65 (s, 2H), 4.48 (s, 2H), 3.70 (s, 3H), 3.43-3.36 (m, 2H), 3.19 (s, 3H), 2.94 (t, J 6.5 Hz, 2H), 2.02 (s, 3H). Method A HPLC-MS: MH+ m/z 495, RT 3.96 minutes (100%).

Example 22

7-{(2R)-4-[(3,5-Dimethyl-3H-1,2,3-triazol-4-yl)methyl]-2-methyl-3-oxo-2H,3H,4H-pyrido[3,2-b][1,4]oxazin-6-yl}-1,2,3,4-tetrahydroisoquinolin-1-one Prepared from Intermediates 130 and 160 in a similar manner to that described for Example 1. δ$_H$ (500 MHz, DMSO-d$_6$) 8.44 (d, J 1.9 Hz, 1H), 8.06 (dd, J 7.9, 2.0 Hz, 1H), 8.02 (s, 1H), 7.68 (d, J 8.2 Hz, 1H), 7.56 (d, J 8.2 Hz, 1H), 7.42 (d, J 8.0 Hz, 1H), 5.44 (s, 2H), 4.99 (q, J 6.7 Hz, 1H), 4.03 (s, 3H), 3.41 (td, J 6.5, 2.6 Hz, 2H), 2.96 (t, J 6.5 Hz, 2H), 2.05 (s, 3H), 1.52 (d, J 6.8 Hz, 3H). Column: Chiralpak AS-H 25 cm; Mobile phase: 20% MeOH: 80% CO$_2$; Flow rate: 4 mL/minute; UV at 215 nm; Runtime: 10 minutes; e.e. 97%. Method D HPLC-MS: MH+ m/z 419.1, RT 2.46 minutes (96%).

Example 23

7-{(2R)-2-Methyl-3-oxo-4-[(1,2,4-trimethyl-1H-imidazol-5-yl)methyl]-2H,3H,4H-pyrido[3,2-b][1,4]oxazin-6-yl}-1,2,3,4-tetrahydroisoquinolin-1-one Prepared from Intermediates 143 and 160 in a similar manner to that described for Example 1. δ$_H$ (500 MHz, DMSO-d$_6$) 8.43 (d, J 1.9 Hz, 1H), 8.08 (d, J 7.9, 2.0 Hz, 1H), 8.02 (s, 1H), 7.63 (d, J 8.2 Hz, 1H), 7.52 (d, J 8.2 Hz, 1H), 7.42 (d, J 8.0 Hz, 1H), 5.30 (d, J 3.2 Hz, 2H), 4.91 (q, J 6.7 Hz, 1H), 3.45 (s, 3H), 3.40 (dt, J 6.6, 3.3 Hz, 2H), 2.95 (t, J 6.5 Hz, 2H), 2.16 (s, 3H), 1.92 (s, 3H), 1.49 (d, J 6.8 Hz, 3H). Column: Chiralcel OD-H 25 cm; Mobile phase: 30% MeOH+0.1% DEA: 70% CO$_2$; Flow rate: 4 mL/minute; Runtime: 10 minutes; UV at 215 nm. Method D HPLC-MS: MH+ m/z 432, RT 1.80 minutes (99%).

Example 24

(2R)-4-[(3,5-Dimethyl-3H-1,2,3-triazol-5-yl)methyl]-8-fluoro-2-methyl-6-(1-oxo-1,2,3,4-tetrahydroisoquinolin-7-yl)-3,4-dihydro-2H-1,4-benzoxazin-3-one Prepared from Intermediates 127 and 160 in a similar manner to that described for Example 1. δ$_H$ (500 MHz, DMSO-d$_6$) 8.05 (d, J 1.8 Hz, 1H), 8.02 (s, 1H), 7.72 (dd, J 7.9, 1.9 Hz, 1H), 7.41 (d, J 8.0 Hz, 1H), 7.38 (d, J 10.0 Hz, 1H), 7.22 (s, 1H), 5.49 (d, J 16.7 Hz, 1H), 5.40 (d, J 16.6 Hz, 1H), 5.00 (q, J 6.7 Hz, 1H), 3.96 (s, 3H), 3.40 (dt, J 6.4, 3.1 Hz, 2H), 2.94 (t, J 6.5 Hz, 2H), 2.12 (s, 3H), 1.55 (d, J 6.7 Hz, 3H). Column: Chiralcel OD-H 25 cm; Mobile phase: 22% MeOH+0.1% DEA: 78% CO$_2$; Flow rate: 4 mL/minute; Runtime: 10 minutes; UV at 215 nm. Method D HPLC-MS: MH+ m/z 436.1, RT 2.61 minutes (100%).

Example 25

8-Fluoro-4-({6-[4-(methanesulfonyl)phenyl]-2-methylimidazo[1,2-a]pyridin-3-yl}-methyl)-6-(1-oxo-1,2,3,4-tetrahydroisoquinolin-7-yl)-3,4-dihydro-2H-1,4-benzoxazin-3-one Prepared from Intermediates 138 and 160 in a similar manner to that described for Example 1. δ$_H$ (500 MHz, DMSO-d$_6$) 8.83 (s, 1H), 8.05 (d, J 1.9 Hz, 1H), 8.03-7.97 (m, 3H), 7.90 (d, J 8.4 Hz, 2H), 7.64 (dd, J 9.4, 1.6 Hz, 1H), 7.61-7.54 (m, 2H), 7.45 (s, 1H), 7.32 (dd, J 11.3, 1.6 Hz, 1H), 7.24 (d, J 7.9 Hz, 1H), 5.80 (s, 2H), 4.94 (s, 2H), 3.40-3.35 (m, 2H), 3.28 (s, 3H), 2.90 (t, J 6.5 Hz, 2H), 2.39 (s, 3H). Method D HPLC-MS: MH+m/z 611, RT 2.08 minutes (100%).

Example 26

(2R)-8-Fluoro-6-(5-fluoro-1-oxo-1,2,3,4-tetrahydroisoquinolin-7-yl)-2-methyl-4-[(1,3,5-trimethyl-1H-pyrazol-4-yl)methyl]-3,4-dihydro-2H-1,4-benzoxazin-3-one Prepared from Intermediates 150 and 161 in a similar manner to that described for Example 2. δ$_H$ (500 MHz, DMSO-d$_6$) 8.15 (s, 1H), 7.80 (d, J 1.6 Hz, 1H), 7.71 (dd, J 10.5, 1.7 Hz, 1H), 7.39 (dd, J 11.4, 1.8 Hz, 1H), 7.12 (s, 1H), 5.19 (d, J 15.8 Hz, 1H), 5.03-4.93 (m, 2H), 3.61 (s, 3H), 3.43 (td, J 6.6, 2.8 Hz, 2H), 2.93 (t, J 6.6 Hz, 2H), 2.27 (s, 3H), 1.96 (s, 3H), 1.54 (d, J 6.7 Hz, 3H). Column: Chiralcel OD-H 25 cm; Mobile phase: 25% EtOH: 75% CO$_2$; Flow rate: 4 mL/minute; UV at 254 nm; Runtime: 10 minutes; e.e. 98%. Method D HPLC-MS: MH+ m/z 467.5, RT 3.00 minutes (99%).

Example 27

(2R)-2-Methyl-4-[(2-methylpyridin-3-yl)methyl]-6-(1-oxo-3,4-dihydro-2H-isoquinolin-7-yl)-8-(trifluoromethyl)pyrido[3,2-b][1,4]oxazin-3-one Prepared from Intermediates 124 and 160 in a similar manner to that described for Example 1. δ$_H$ (400 MHz, DMSO-d$_6$) 8.41 (m, 1H), 8.30 (m, 1H), 7.98 (m, 2H), 7.84 (s, 1H), 7.44 (m, 1H), 7.37 (d, 1H, J 8.1 Hz), 7.11 (m, 1H), 5.33 (m, 3H), 3.40 (m, 2H), 2.94 (m, 2H), 2.48 (s, 3H), 1.61 (d, 3H, J 6.7 Hz). HPLC-MS: MH+ m/z 483, RT 2.13 minutes.

Example 28

(2R)-2-Methyl-4-[(2-methylpyridin-3-yl)methyl]-6-(1-oxo-3,4-dihydro-2H-isoquinolin-7-yl)-7-(trifluoromethyl)pyrido[3,2-b][1,4]oxazin-3-one Prepared from Intermediates 124 and 160 in a similar manner to that described for Example 1. δ$_H$ (400 MHz, DMSO-d$_6$) 8.29 (m, 1H), 7.99 (d, 1H, J 0.4 Hz), 7.91 (m, 2H), 7.41 (d, 1H, J 8.0 Hz), 7.36 (s, 2H), 7.13 (m, 1H), 5.22 (m, 3H), 3.41 (m, 2H), 2.96 (m, 2H), 2.48 (s, 3H), 1.61 (d, 3H, J 6.8 Hz). HPLC-MS: MH+ m/z 483, RT 2.07 minutes.

Example 29

(2R)-8-Fluoro-2-methyl-4-[(2-methylimidazo[1,2-a]pyrazin-3-yl)methyl]-6-(1-oxo-1,2,3,4-tetrahydroisoquinolin-7-yl)-3,4-dihydro-2H-1,4-benzoxazin-3-one Prepared from Intermediates 126 and 160 in a similar manner to that described for Example 1. δ$_H$ (500 MHz, DMSO-d$_6$) 8.95 (d, J 1.4 Hz, 1H), 8.53 (dd, J 4.7, 1.4 Hz, 1H), 8.14 (d, J 2.1 Hz, 1H), 8.07 (m, 1H), 8.02 (d, J 4.7 Hz, 1H), 7.68 (dd, J 7.9, 2.1 Hz, 1H), 7.46-7.36 (m, 3H), 5.84 (s, 1H), 5.78 (s, 1H), 5.06 (q, J 6.7 Hz, 1H), 3.46 (td, J 6.6, 2.7 Hz, 2H), 3.00 (t, J 6.5 Hz, 2H), 2.46 (s, 3H), 1.62 (s, 3H). Method D HPLC-MS: MH+m/z 472, RT 2.56 minutes (96%).

Example 30

(2R)-4-[(3,5-Dimethyl-3H-1,2,3-triazol-4-yl)methyl]-8-fluoro-6-(5-fluoro-1-oxo-1,2,3,4-tetrahydroisoquinolin-7-yl)-2-methyl-3,4-dihydro-2H-1,4-benzoxazin-3-one Prepared from Intermediates 149 and 161 in a similar manner to that described for Example 2. δ$_H$ (500 MHz, DMSO-d$_6$) 8.14 (s, 1H), 7.95 (d, J 1.7 Hz, 1H), 7.74 (dd, J 10.5, 1.8 Hz, 1H), 7.47 (dd, J 11.4, 1.8 Hz, 1H), 7.30 (s, 1H), 5.50 (d, J 16.6 Hz, 1H), 5.41 (d, J 16.6 Hz, 1H), 5.00 (q, J 6.7 Hz, 1H), 3.96 (s, 3H), 3.43 (td, J 6.6, 2.8 Hz, 2H), 2.93 (t, J 6.6 Hz, 2H), 2.12 (s, 3H), 1.55 (d, J 6.7 Hz, 3H). Column: Chiralcel OJ-H 25 cm; Mobile phase: 50:50 EtOH: MeOH; Flow rate: 1 mL/minute; UV at 254 nm; Runtime: 12 minutes; e.e. 97%. Method D HPLC-MS: MH+ m/z 454.1, RT 2.77 minutes (100%).

Example 31

(2R)-4-[(3,5-Dimethyl-3H-1,2,3-triazol-4-yl)methyl]-8-fluoro-6-(5-fluoro-2-oxo-1,2,3,4-tetrahydroquinolin-7-yl)-2-methyl-3,4-dihydro-2H-1,4-benzoxazin-3-one Prepared from Intermediates 149 and 162 in a similar manner to that described for Example 2. δ$_H$ (500 MHz, DMSO-d$_6$) 10.37 (s, 1H), 7.25 (dd, J 11.2, 1.7 Hz, 1H), 7.19 (s, 1H), 7.14-7.06 (m, 1H), 6.88 (s, 1H), 5.44 (d, J 16.7 Hz, 1H), 5.34 (d, J 16.6 Hz, 1H), 4.99 (q, J 6.7 Hz, 1H), 3.96 (s, 3H), 2.91 (t, J 7.6 Hz, 2H), 2.56-2.51 (m, 2H), 2.09 (s, 3H), 1.54 (d, J 6.7 Hz, 3H). Column: Chiralpak AD-H 25 cm; Mobile phase: 40% EtOH: 60% CO$_2$; Flow rate: 4 mL/minute; UV at 215 nm; Runtime: 10 minutes; e.e. 95%. Method D HPLC-MS: MH+ m/z 454.1, RT 2.85 minutes (96%).

Example 32

7-{2-Methyl-3-oxo-4-[(1,3,5-trimethyl-1H-pyrazol-4-yl)methyl]-2H,3H,4H-pyrido[3,2-b][1,4]oxazin-6-yl}-1,2,3,4-tetrahydroisoquinolin-1-one (Enantiomer A)

Prepared from Example 4 using chiral chromatography to separate the two enantiomers. δ$_H$ (500 MHz, DMSO-d$_6$) 8.37 (d, J 1.9 Hz, 1H), 8.01 (dd, J 7.9, 2.0 Hz, 1H), 7.91 (s, 1H), 7.53 (d, J 8.2 Hz, 1H), 7.41 (d, J 8.2 Hz, 1H), 7.33 (d, J 8.0 Hz, 1H), 5.07 (d, J 15 Hz, 1H), 5.04 (d, J 15 Hz, 1H), 4.79 (q, J 6.7 Hz, 1H), 3.44 (s, 3H), 3.30 (2H, obscured by DMSO peaks), 2.87 (t, J 6.5 Hz, 2H), 2.06 (s, 3H), 1.87 (s, 3H), 1.40 (d, J 6.8 Hz, 3H). Method A HPLC-MS: MH+ m/z 432, RT 3.94 minutes (100%).

Example 33

7-{2-Methyl-3-oxo-4-[(1,3,5-trimethyl-1H-pyrazol-4-yl)methyl]-2H,3H,4H-pyrido[3,2-b][1,4]oxazin-6-yl}-1,2,3,4-tetrahydroisoquinolin-1-one (Enantiomer B)

Prepared from Example 4 using chiral chromatography to separate the two enantiomers. δ$_H$ (500 MHz, DMSO-d$_6$) 8.37 (d, J 1.9 Hz, 1H), 8.01 (dd, J 7.9, 2.0 Hz, 1H), 7.91 (s, 1H), 7.53 (d, J 8.2 Hz, 1H), 7.41 (d, J 8.2 Hz, 1H), 7.33 (d, J 8.0 Hz, 1H), 5.14-4.98 (m, 2H), 4.79 (q, J 6.7 Hz, 1H), 3.44 (s, 3H), 3.30 (2H, obscured by DMSO peaks), 2.87 (t, J 6.5 Hz, 2H), 2.06 (s, 3H), 1.87 (s, 3H), 1.40 (d, J 6.7 Hz, 3H).

Example 34

8-Fluoro-4-{[5-(hydroxymethyl)-1,3-dimethyl-1H-pyrazol-4-yl]methyl}-6-(1-oxo-1,2,3,4-tetrahydroisoquinolin-7-yl)-3,4-dihydro-2H-1,4-benzoxazin-3-one A solution of Example 21 (233 mg, 0.47 mmol) in a 1:1 mixture of THF: 6M HCl (10 mL) was heated at 55° C. for 12 h, then cooled and quenched by the addition of saturated aqueous NaHCO$_3$ solution (5 mL). The mixture was extracted with DCM (3×10 mL) and the combined organic layers were dried (MgSO$_4$), then the solvent was removed in vacuo. The residue was purified by preparative HPLC (Method D), and the solid was washed with MeOH, to afford the title compound (35 mg, 17%) as an off-white solid. δ$_H$ (500 MHz, DMSO-d$_6$) 8.05 (s, 1H), 7.90 (d, J 1.9 Hz, 1H), 7.71 (dd, J 7.9, 2.0 Hz, 1H), 7.39 (d, J 8.0 Hz, 1H), 7.29 (dd, J 11.4, 1.6 Hz, 1H), 7.15 (s, 1H), 5.15 (s, 3H), 4.84 (s, 2H), 4.61 (s, 2H), 3.70 (s, 3H), 3.40 (td, J 6.5, 2.7 Hz, 2H), 2.94 (t, J 6.5 Hz, 2H), 1.99 (s, 3H). Method E HPLC-MS: MH+ m/z 451, RT 3.67 minutes (100%).

Example 35

8-Fluoro-4-{[5-(fluoromethyl)-1,3-dimethyl-1H-pyrazol-4-yl]methyl}-6-(1-oxo-1,2,3,4-tetrahydroisoquinolin-7-yl)-3,4-dihydro-2H-1,4-benzoxazin-3-one To a stirred suspension of Example 34 (25 mg, 0.051 mmol) in anhydrous DCM (1 mL) under nitrogen at r.t. was added (diethylamino)sulfur trifluoride (13.35 μL, 0.1 mmol). The mixture was stirred at r.t. for 2 h, then cooled to 0° C. and quenched by the addition of saturated aqueous NaHCO$_3$ solution (2 mL). The mixture was stirred at r.t. for 4 h, then the aqueous phase was extracted with DCM (3×2 mL), the combined organic extracts were dried (MgSO$_4$) and the solvent was removed in vacuo. The residue was purified by preparative HPLC (Method D) to afford the title compound (3.7 mg, 16%) as a white solid. $δ_H$ (500 MHz, DMSO-d$_6$) 8.04 (s, 1H), 7.90 (d, J 2.0 Hz, 1H), 7.71 (dd, J 7.9, 2.0 Hz, 1H), 7.39 (d, J 8.0 Hz, 1H), 7.30 (dd, J 11.4, 1.7 Hz, 1H), 7.15 (s, 1H), 5.63 (d, J 48.8 Hz, 2H), 5.21 (s, 2H), 4.85 (s, 2H), 3.75 (s, 3H), 3.40 (td, J 6.5, 2.9 Hz, 2H), 2.94 (t, J 6.6 Hz, 2H), 2.04 (s, 3H). Method D HPLC-MS: MH+ m/z 453, RT 2.69 minutes (100%).

Example 36

(2R)-6-[3-(Methanesulfonyl)phenyl]-2-methyl-4-[(1,3,5-trimethyl-1H-pyrazol-4-yl)-methyl]-2H,3H,4H-pyrido[3,2-b][1,4]oxazin-3-one To a solution of Intermediate 132 (150 mg, 0.41 mmol) in anhydrous 1,4-dioxane (5 mL) were added 3-(methanesulfonyl)phenylboronic acid (90.36 mg, 0.45 mmol) and 2M aqueous Na$_2$CO$_3$ solution (0.62 mL). The mixture was degassed with N$_2$ for 5 minutes before the addition of Pd(dppf)Cl$_2$ (16.77 mg, 0.02 mmol). The mixture was heated at 100° C. for 1 h. The mixture was cooled, then EtOAc (20 mL) and water (20 mL) were added. The aqueous phase was extracted with EtOAc (20 mL). The combined organic layers were washed with brine (20 mL) and dried (MgSO$_4$), then the solvent was removed in vacuo. The residue was purified by column chromatography (SiO$_2$; gradient 0-100% EtOAc in heptanes followed by 0-10% MeOH in DCM), then preparative HPLC (Method C), to give the title compound (135 mg, 73%) as a white solid. $δ_H$ (500 MHz, DMSO-d$_6$) 8.52 (s, 1H), 8.36 (d, J 7.9 Hz, 1H), 7.96 (d, J 8.4 Hz, 1H), 7.80-7.74 (m, 2H), 7.57 (d, J 8.2 Hz, 1H), 5.17 (s, 2H), 4.92 (q, J 6.7 Hz, 1H), 3.52 (s, 3H), 3.29 (s, 3H), 2.14 (s, 3H), 1.97 (s, 3H), 1.50 (d, J 6.8 Hz, 3H). Column: Chiralpak AD-H 25 cm; Mobile phase: 23% MeOH: 77% CO$_2$; Flow rate: 4 mL/minute, Runtime: 6 minutes, UV at 215 nm, e.e. 95%. Method D HPLC-MS: MH+ m/z 441.1, RT 1.76 minutes (100%).

Example 37

(2R)-6-[3-(Methanesulfonyl)phenyl]-2-methyl-4-[(2-methylimidazo[1,2-a]pyridin-3-yl)-methyl]-2H,3H,4H-pyrido[3,2-b][1,4]oxazin-3-one Prepared from Intermediate 110A and 3-(methanesulfonyl)phenylboronic acid in a similar manner to that described for Example 36. $δ_H$ (500 MHz, DMSO-d$_6$) 8.61 (d, J 6.9 Hz, 1H), 8.54 (t, J 1.6 Hz, 1H), 8.30 (d, J 8.0 Hz, 1H), 7.98 (d, J 7.8 Hz, 1H), 7.78 (d, J 8.2 Hz, 1H), 7.75 (t, J 7.8 Hz, 1H), 7.59 (d, J 8.2 Hz, 1H), 7.39 (d, J 9.0 Hz, 1H), 7.18-7.09 (m, 1H), 6.74 (td, J 6.8, 1.0 Hz, 1H), 5.74 (s, 2H), 4.98 (q, J 6.7 Hz, 1H), 3.30 (s, 3H), 2.29 (s, 3H), 1.52 (d, J 6.7 Hz, 3H). Chiral analysis: (R) isomer at 3.89 minutes; Column: Chiralpak AD-H 25 cm; Mobile phase: 35% MeOH+0.1% TEA: 65% CO$_2$; Flow rate: 4 mL/minute; Runtime: 10 minutes; UV: 254 nM. Method D HPLC-MS: MH+ m/z 463, RT 1.87 minutes (100%).

Example 38

(2R)-8-Fluoro-6-[3-(methanesulfonyl)phenyl]-2-methyl-4-[(1,3,5-trimethyl-1H-pyrazol-4-yl)methyl]-3,4-dihydro-2H-1,4-benzoxazin-3-one Prepared from Intermediate 135 and 3-(methanesulfonyl)phenylboronic acid in a similar manner to that described for Example 36. $δ_H$ (500 MHz, DMSO-d$_6$) 8.05 (s, 1H), 7.97 (d, J 7.8 Hz, 1H), 7.92 (d, J 7.9 Hz, 1H), 7.75 (t, J 7.8 Hz, 1H), 7.46 (dd, J 11.4, 1.7 Hz, 1H), 7.20 (s, 1H), 5.21 (d, J 15.8 Hz, 1H), 5.03-4.94 (m, 2H), 3.55 (s, 3H), 3.29 (s, 3H), 2.21 (s, 3H), 1.97 (s, 3H), 1.54 (d, J 6.7 Hz, 3H). Column: Chiralpak AD-H 25 cm; Mobile phase: 20% MeOH+80% CO$_2$; Flow rate: 4 mL/minute; Runtime: 7 minutes; UV at 215 nm. Method D HPLC-MS: MH+ m/z 458, RT 2.95 minutes (100%).

Example 39

8-Fluoro-6-[3-(methanesulfonyl)phenyl]-4-({5-[(methoxymethoxy)methyl]-1,3-dimethyl-1H-pyrazol-4-yl}methyl)-3,4-dihydro-2H-1,4-benzoxazin-3-one Prepared from Intermediate 120 and 3-(methanesulfonyl)phenylboronic acid in a similar manner to that described for Example 36. $δ_H$ (500 MHz, CDCl$_3$) 7.91 (d, J 7.7 Hz, 1H), 7.88 (s, 1H), 7.67 (d, J 7.7 Hz, 1H), 7.62 (t, J 7.7 Hz, 1H), 7.04 (dd, J 10.6, 1.4 Hz, 1H), 6.96 (s, 1H), 5.15 (s, 2H), 4.78 (s, 2H), 4.61 (s, 2H), 4.46 (s, 2H), 3.83 (s, 3H), 3.26 (s, 3H), 3.08 (s, 3H), 2.19 (s, 3H). Method A HPLC-MS: MH+ m/z 503.95, RT 3.67 minutes (100%).

Example 40

(2R)-6-[3-(Methanesulfonyl)phenyl]-2,8-dimethyl-4-[(1,3,5-trimethyl-1H-pyrazol-4-yl)-methyl]-2H,3H,4H-pyrido[3,2-b][1,4]oxazin-3-one Prepared from Intermediate 114 and 3-(methanesulfonyl)phenylboronic acid in a similar manner to that described for Example 36. $δ_H$ (500 MHz, DMSO-d$_6$) 8.52 (s, 1H), 8.36 (d, J 7.9 Hz, 1H), 7.95 (d, J 7.8 Hz, 1H), 7.78-7.72 (m, 2H), 5.16 (s, 2H), 4.88 (q, J 6.7 Hz, 1H), 3.51 (s, 3H), 3.29 (s, 3H), 2.30 (s, 3H), 2.13 (s, 3H), 1.96 (s, 3H), 1.49 (d, J 6.8 Hz, 3H). Column: Chiralpak AD-H 25 cm; Mobile phase: 20% MeOH: 80% CO$_2$; Flow rate: 4 mL/minute; UV at 215 nm; Runtime: 7 minutes. Method A HPLC-MS: MH+ m/z 455.05, RT 4.06 minutes (100%).

Example 41

8-Fluoro-6-[3-(methanesulfonyl)phenyl]-4-[(1,3,5-trimethyl-1H-imidazol-5-yl)methyl]-3,4-dihydro-2H-1,4-benzoxazin-3-one Prepared from Intermediate 134 and 3-(methanesulfonyl)phenylboronic acid in a similar manner to that described for Example 36.

Example 42

(2R)-8-Fluoro-6-[3-(methanesulfonyl)phenyl]-2-methyl-4-[(2-methylimidazo[1,2-a]-pyridin-3-yl)methyl]-3,4-dihydro-2H-1,4-benzoxazin-3-one Prepared from Intermediate 117 and 3-(methanesulfonyl)phenylboronic acid in a similar manner to that described for

Example 43

8-Fluoro-6-[3-(methanesulfonyl)phenyl]-4-({6-[4-(methanesulfonyl)phenyl]-2-methyl-imidazo[1,2-a]pyridin-3-yl}methyl)-3,4-dihydro-2H-1,4-benzoxazin-3-one Prepared from Intermediate 138 and 3-(methanesulfonyl)phenylboronic acid in a similar manner to that described for Example 36. $\delta_H$ (500 MHz, DMSO-$d_6$) 8.83 (s, 1H), 8.17 (s, 1H), 8.03 (d, J 8.4 Hz, 2H), 7.94-7.86 (m, 4H), 7.67-7.59 (m, 2H), 7.59-7.49 (m, 3H), 5.82 (s, 2H), 4.97 (s, 2H), 3.30-3.25 (m, 6H), 2.37 (s, 3H). Method A HPLC-MS: MH+ m/z 620, RT 2.10 minutes (98%).

Example 44

(2R)-4-({1,3-Dimethyl-5-[(oxetan-3-yloxy)methyl]-1H-pyrazol-4-yl}methyl)-8-fluoro-6-[3-(methanesulfonyl)phenyl]-2-methyl-3,4-dihydro-2H-1,4-benzoxazin-3-one Prepared from Intermediate 118 and 3-(methanesulfonyl)phenylboronic acid in a similar manner to that described for Example 36. $\delta_H$ (500 MHz, CDCl$_3$) 7.91 (dt, J 7.6, 1.4 Hz, 1H), 7.85 (t, J 1.7 Hz, 1H), 7.69 (dt, J 7.8, 1.4 Hz, 1H), 7.64 (t, J 7.7 Hz, 1H), 7.05 (dd, J 10.5, 1.9 Hz, 1H), 6.98-6.96 (m, 1H), 5.21-5.08 (m, 2H), 4.79 (q, J 6.8 Hz, 1H), 4.69-4.63 (m, 2H), 4.60-4.53 (m, 1H), 4.53-4.45 (m, 2H), 4.45-4.40 (m, 2H), 3.85 (s, 3H), 3.08 (s, 3H), 2.19 (s, 3H), 1.67 (d, J 6.8 Hz, 3H). Column: Chiralpak AD-H 25 cm; Mobile phase: 12% EtOH: 88% CO$_2$; Flow rate: 4 mL/minute; UV at 215 nm; Runtime: 20 minutes. Method A HPLC-MS: MH+ m/z 530.0, RT 3.61 minutes (100%).

Example 45

(2R)-8-Fluoro-6-[3-(methanesulfonyl)phenyl]-4-({3-[(methoxymethoxy)methyl]-1,5-dimethyl-1H-pyrazol-4-yl}methyl)-2-methyl-3,4-dihydro-2H-1,4-benzoxazin-3-one Prepared from Intermediate 119 and 3-(methanesulfonyl)phenylboronic acid in a similar manner to that described for Example 36. Method B HPLC-MS: MH+ m/z 518, RT 1.95 minutes (99%).

Example 46

(2R)-4-{[1,3-Dimethyl-5-({[2-(morpholin-4-yl)pyrimidin-5-yl]oxy}methyl)-1H-pyrazol-4-yl]methyl}-8-fluoro-6-[3-(methanesulfonyl)phenyl]-2-methyl-3,4-dihydro-2H-1,4-benzoxazin-3-one Prepared from Intermediate 121 and 3-(methanesulfonyl)phenylboronic acid in a similar manner to that described for Example 36. $\delta_H$ (500 MHz, DMSO-$d_6$) 8.05 (s, 2H), 8.04 (t, J 1.7 Hz, 1H), 7.94 (d, J 7.9 Hz, 1H), 7.85 (d, J 7.8 Hz, 1H), 7.62 (t, J 7.8 Hz, 1H), 7.41 (dd, J 11.3, 1.7 Hz, 1H), 7.34 (s, 1H), 5.29 (d, J 15.9 Hz, 1H), 5.15-5.05 (m, 3H), 4.86 (q, J 6.7 Hz, 1H), 3.70-3.63 (m, 7H), 3.61-3.55 (m, 4H), 3.29 (s, 3H), 2.06 (s, 3H), 1.44 (d, J 6.7 Hz, 3H). Column: Chiralcel OD-H 25 cm; Mobile phase: 15% EtOH+0.1% DEA: 85% CO$_2$; Flow rate: 4 mL/minute; UV at 254 nm; Runtime: 40 minutes; no baseline separation. Method A HPLC-MS: MH+ m/z 637, RT 4.19 minutes (100%).

Example 47

(2R)-8-Fluoro-6-[3-(methanesulfonyl)phenyl]-4-({5-[(2-methoxyethoxy)methyl]-1,3-dimethyl-1H-pyrazol-4-yl}methyl)-2-methyl-3,4-dihydro-2H-1,4-benzoxazin-3-one Prepared from Intermediate 136 and 3-(methanesulfonyl)phenylboronic acid in a similar manner to that described for Example 36. $\delta_H$ (500 MHz, CDCl$_3$) 7.93-7.89 (m, 1H), 7.89-7.87 (m, 1H), 7.70-7.67 (m, 1H), 7.62 (t, J 7.7 Hz, 1H), 7.04 (dd, J 10.6, 1.9 Hz, 1H), 7.00-6.97 (m, 1H), 5.22-5.09 (m, 2H), 4.79 (q, J 6.8 Hz, 1H), 4.64-4.55 (m, 2H), 3.83 (s, 3H), 3.56-3.51 (m, 2H), 3.43-3.38 (m, 2H), 3.26 (s, 3H), 3.08 (s, 3H), 2.17 (s, 3H), 1.67 (d, J 6.8 Hz, 3H). Column: Chiralpak IC 25 cm; Mobile phase: 30% EtOH: 70% CO$_2$; Flow rate: 4 mL/minute; UV at 215 nm; Runtime: 20 minutes. Method A HPLC-MS: MH+ m/z 531.95, RT 4.00 minutes (100%).

Example 48

(2R)-2-Methyl-4-[(2-methylpyridin-3-yl)methyl]-6-[3-(methylsulfonyl)phenyl]-8-(trifluoromethyl)pyrido[3,2-b][1,4]oxazin-3-one Prepared from Intermediate 183 and (2-methylpyridin-3-yl)methanol in a similar manner to that described for Intermediate 143. $\delta_H$ (300 MHz, DMSO-$d_6$) 8.41 (s, 1H), 8.29 (dd, 1H, J 4.9, 1.6 Hz), 8.23 (m, 1H), 8.04 (s, 1H), 7.93 (m, 1H), 7.70 (dd, 1H, J 7.8, 7.8 Hz), 7.44 (m, 1H), 7.10 (dd, 1H, J 7.8, 4.8 Hz), 5.35 (m, 3H), 3.24 (s, 3H), 2.62 (s, 3H), 1.62 (d, 3H, J 6.8 Hz). HPLC-MS: MH+ m/z 492, RT 2.18 minutes.

Example 49

(2R)-2-Methyl-4-[(2-methylpyridin-3-yl)methyl]-6-[3-(methylsulfonyl)phenyl]-7-(trifluoromethyl)pyrido[3,2-b][1,4]oxazin-3-one Prepared from Intermediate 183 and (2-methylpyridin-3-yl)methanol in a similar manner to that described for Intermediate 143. $\delta_H$ (300 MHz, DMSO-$d_6$) 8.29 (dd, 1H, J 4.7, 1.5 Hz), 8.01 (m, 1H), 7.97 (s, 1H), 7.82 (s, 1H), 7.73 (t, 1H, J 7.8 Hz), 7.64 (m, 1H), 7.42 (dd, 1H, J 7.8, 1.4 Hz), 7.12 (dd, 1H, J 7.7, 4.8 Hz), 5.23 (m, 3H), 3.24 (s, 3H), 2.45 (s, 3H), 1.61 (d, 3H, J 6.8 Hz). HPLC-MS: MH+ m/z 492, RT 2.22 minutes.

Example 50

(2R)-4-{[1,5-Dimethyl-3-(methylsulfanyl)pyrazol-4-yl]methyl}-8-fluoro-2-methyl-6-[3-(methylsulfonyl)phenyl]-1,4-benzoxazin-3-one Prepared from Intermediates 7 and 185 in a similar manner to that described for Intermediate 143. HPLC-MS: MH+ m/z 490, RT 2.23 minutes.

Example 51

7-Fluoro-3-({(2R)-8-fluoro-2-methyl-6-[3-(methylsulfonimidoyl)phenyl]-3-oxo-1,4-benzoxazin-4-yl}methyl)-2-methylimidazo[1,2-a]pyridine-6-carbonitrile Prepared from Intermediates 187 and 195 in a similar manner to that described for Intermediate 143. $\delta_H$ (300 MHz, DMSO-$d_6$) 9.31 (d, 1H, J 6.4 Hz), 8.10 (m, 1H), 7.93 (d, 1H, J 7.8 Hz), 7.87 (d, 1H, J 8.0 Hz), 7.69 (m, 1H), 7.63 (d, 1H, J 10.5 Hz), 7.49 (m, 2H), 5.71 (m, 2H), 5.02 (m, 1H), 4.25 (s, 1H), 3.14 (s, 3H), 2.26 (s, 3H), 1.55 (d, 3H, J 6.3 Hz). HPLC-MS: MH+ m/z 522, RT 2.00 minutes.

Example 52

(2R)-4-[(6-Bromo-7-fluoro-2-methylimidazo[1,2-a]pyridin-3-yl)methyl]-8-fluoro-2-methyl-6-[3-(methylsulfonimidoyl)phenyl]-1,4-benzoxazin-3-one Prepared from Intermediates 27 and 187 in a similar manner to that described for Intermediate 143. $\delta_H$ (400 MHz, DMSO-$d_6$) 8.82 (d, 1H, J 6.7 Hz), 8.15 (s, 1H), 7.94 (m, 1H), 7.84 (d, 1H, J 8.2 Hz), 7.68 (m, 1H), 7.54 (d, 1H, J 9.5 Hz), 7.48 (m, 2H), 5.72 (m, 2H), 5.03 (q, 1H, J 6.6 Hz), 4.27 (s, 1H), 3.15 (s, 3H), 2.50 (s, 3H) 2.29 (d, 3H, J 6.3 Hz). HPLC-MS: MH+ m/z 575/577, RT 2.15 minutes.

Example 53

(2R)-4-[(6-Bromo-7-fluoro-2-methylimidazo[2-a]pyridin-3-yl)methyl]-8-fluoro-2-methyl-6-[3-(methylsulfonyl)phenyl]-1,4-benzoxazin-3-one Prepared from Intermediates 27 and 185 in a similar manner to that described for Intermediate 143. $\delta_H$ (300 MHz, DMSO-$d_6$) 8.81 (d, 1H, J 6.7 Hz), 8.17 (s, 1H), 7.93 (m, 2H), 7.73 (m, 1H), 7.53 (m, 3H), 5.72 (m, 2H), 5.02 (m, 1H), 3.39 (s, 3H), 2.27 (s, 3H), 1.56 (d, 3H, J 6.7 Hz). HPLC-MS: MH+ m/z 576/578, RT 2.42 minutes.

Example 54

(2R)-4-[(5-Chloro-1,3-dimethyl-1H-pyrazol-4-yl)methyl]-8-fluoro-2-methyl-6-[3-(methylsulfonyl)phenyl]-1,4-benzoxazin-3-one Intermediate 185 (0.3 g, 0.89 mmol) was dissolved in DMF (25 mL) and cooled in an ice bath, then sodium hydride (0.054 g, 1.34 mmol) was added. The mixture was stirred for 10 minutes, then 5-chloro-4-(chloromethyl)-1,3-dimethyl-1H-pyrazole (0.19 g, 0.98 mmol) was added. After 18 h, the reaction mixture was poured onto iced water (25 mL) and extracted into EtOAc (2×50 mL). The resultant brown solid was purified by column chromatography (SiO$_2$, 1-100% EtOAc:DCM) to afford the title compound (0.24 g, 57%) as a white powder. $\delta_H$ (300 MHz, DMSO-$d_6$) 8.10 (s, 1H), 7.99 (m, 1H), 7.92 (m, 1H), 7.74 (dd, 1H, J 7.8, 7.8 Hz), 7.49 (dd, 1H, J 11.5, 1.9 Hz), 7.22 (s, 1H), 5.15 (m, 3H), 3.64 (s, 3H), 3.34 (s, 3H), 2.07 (m, 3H), 1.54 (d, 3H, J 6.7 Hz). HPLC-MS: MH+m/z 479, RT 2.21 minutes.

Example 55

(2R)-4-{[1,5-Dimethyl-3-(methylsulfonyl)-1H-pyrazol-4-yl]methyl}-8-fluoro-2-methyl-6-[3-(methylsulfonyl)phenyl]-1,4-benzoxazin-3-one Example 50 (0.06 g, 0.12 mmol) was dissolved in DCM (10 mL) and cooled in an ice bath. 3-Chloroperoxybenzoic acid (0.032 g, 0.18 mmol) was added, then the reaction mixture was allowed to warm to r.t. and stirred for 3 h. The reaction mixture was diluted with DCM (20 mL) and washed with aqueous Na$_2$CO$_3$ solution (3×20 mL). The organic layer was dried and evaporated in vacuo. The residue was purified by column chromatography (SiO$_2$, 20-100% EtOAc:DCM) to afford the title compound as a white powder. $\delta_H$ (400 MHz, DMSO-$d_6$) 8.07 (s, 1H), 7.97 (d, 1H, J 8.0 Hz), 7.90 (d, 1H, J 8.1 Hz), 7.71 (dd, 1H, J 7.8, 7.8 Hz), 7.49 (dd, 1H, J 11.4, 1.7 Hz), 7.43 (s, 1H), 5.51 (m, 1H), 5.30 (d, 1H, J 16.2 Hz), 4.98 (q, 1H, J 6.7 Hz), 3.76 (s, 3H), 3.30 (s, 3H), 3.19 (s, 3H), 2.13 (s, 3H), 1.56 (d, 3H, J 6.7 Hz). HPLC-MS: MH+ m/z 522, RT 2.00 minutes.

Example 56

(2R)-8-Fluoro-4-{[5-(6-methoxypyridin-3-yl)-1,3-dimethyl-1H-pyrazol-4-yl]methyl}-2-methyl-6-[3-(methylsulfonyl)phenyl]-1,4-benzoxazin-3-one Example 54 (0.09 g, 0.19 mmol), 2-methoxypyridin-5-ylboronic acid (0.06 g, 0.38 mmol), 1,1'-bis(di-tert-butylphosphino)ferrocene palladium dichloride (0.013 g, 0.019 mmol) and potassium fluoride (0.022 g, 0.38 mmol) were dissolved in DMF (3 mL, 38.7 mmol) and heated under microwave irradiation for 2.5 h at 110° C. The reaction mixture was separated between EtOAc (25 mL) and aqueous NaHCO$_3$ solution (25 mL). The organic layer was washed with water (10 mL) and dried (phase separator), then evaporated in vacuo. The residue was purified by column chromatography to afford the title compound (0.075 g, 65%) as an off white powder. $\delta_H$ (300 MHz, DMSO-$d_6$) 8.00 (m, 1H), 7.92 (m, 2H), 7.74 (m, 2H), 7.40 (m, 2H), 6.83 (s, 1H), 6.68 (dd, 1H, J 8.5, 0.6 Hz), 5.28 (d, 1H, J 15.9 Hz), 4.92 (d, 1H, J 15.9 Hz), 4.68 (1H, q, J 6.5 Hz), 3.83 (s, 3H), 3.44 (s, 3H), 3.31 (s, 3H), 2.18 (s, 3H), 1.38 (d, 3H, J 6.7 Hz). HPLC-MS: MH+ m/z 552, RT 2.22 minutes.

Example 57

(2R)-4-{[1,3-Dimethyl-5-(6-oxo-1H-pyridin-3-yl)pyrazol-4-yl]methyl}-8-fluoro-2-methyl-6-[3-(methylsulfonyl)phenyl]-1,4-benzoxazin-3-one Example 56 (0.055 g, 0.089 mmol) was heated with pyridine hydrochloride (1.0 g, 8.5 mmol) as a melt for 30 minutes at 145° C. On cooling, the residue was separated between EtOAc and aqueous NaHCO$_3$ solution. The organic layers were washed with aqueous ammonium chloride solution and dried (phase separator). The residue was purified by column chromatography (SiO$_2$, 0-20% MeOH EtOAc) to afford the title compound (25 mg, 52%) as a white powder. $\delta_H$ (400 MHz, DMSO-$d_6$) 11.83 (m, 1H), 8.02 (s, 1H), 7.92 (m, 1H), 7.82 (m, 1H), 7.73 (t, 1H, J 7.8 Hz), 7.41 (dd, 1H, J 11.3, 1.7 Hz), 7.27 (d, 1H, J 0.5 Hz), 7.08 (dd, 1H, J 9.4, 2.5 Hz), 6.93 (s, 1H), 6.16 (d, 1H, J 9.4 Hz), 5.29 (d, 1H, J 16.0 Hz), 4.93 (d, 1H, J 15.9 Hz), 4.76 (q, 1H, J 6.7 Hz), 3.47

(s, 3H), 3.31 (s, 3H), 2.15 (s, 3H), 1.44 (d, 3H, J 6.7 Hz). HPLC-MS: MH+ m/z 537, RT 1.67 minutes.

Example 58

(2R)-8-Fluoro-4-[(7-fluoro-2-methylimidazo[1,2-a] pyridin-3-yl)methyl]-2-methyl-6-[3-(methylsulfonyl) phenyl]-1,4-benzoxazin-3-one To a degassed solution of Example 53 (0.03 g, 0.05 mmol) and ammonium formate (0.5 g, 7.93 mmol) in EtOH (5 mL) was added palladium on charcoal (10 wt %, 0.005 g, 0.047 mmol). The mixture was stirred for 3 h at r.t., then filtered through celite and evaporated in vacuo. The residue was taken up into EtOAc and washed with aqueous NaHCO$_3$ solution (2×50 mL). The organic fraction was dried over Na$_2$SO$_4$ and evaporated in vacuo to give the title compound (19 mg, 73%) as an off white solid. $\delta_H$ (400 MHz, DMSO-d$_6$) 8.37 (dd, 1H, J 7.4, 5.9 Hz), 8.17 (s, 1H), 7.93 (m, 2H), 7.74 (dd, 1H, J 7.8, 7.8 Hz), 7.49 (m, 2H), 7.28 (dd, 1H, J 9.9, 2.5 Hz), 7.04 (td, 1H, J 7.6, 2.7 Hz), 5.78 (m, 1H), 5.65 (m, 1H), 5.02 (q, 1H, J 6.6 Hz), 3.30 (s, 3H), 2.31 (s, 3H), 1.57 (d, 3H, J 6.7 Hz). HPLC-MS: MH+ m/z 498, RT 2.08 minutes.

Example 59

7-Fluoro-3-({(2R)-8-fluoro-2-methyl-6-[3-(methylsulfonyl)phenyl]-3-oxo-1,4-benzoxazin-4-yl}methyl)-2-methylimidazo[1,2-a]pyridine-6-carbonitrile Example 53 (0.1 g, 0.17 mmol) was heated with copper(I) cyanide (0.3470 mmol) in 1-methyl-2-pyrrolidinone (2.5 mL) under microwave irradiation at 200° C. for 1 h, then at 210° C. for a further 2 h. The reaction mixture was diluted with EtOAc, and washed with water and brine, then dried over Na$_2$SO$_4$ and evaporated in vacuo. The residue was purified by preparative HPLC to obtain the title compound (10 mg, 11%) as a lyophilised white powder. $\delta_H$ (400 MHz, DMSO-d$_6$) 9.32 (d, 1H, J 6.4 Hz), 8.11 (s, 1H), 7.95 (m, 2H), 7.74 (dd, 1H, J 7.8, 7.8 Hz), 7.64 (d, 1H, J 10.4 Hz), 7.53 (m, 2H), 5.72 (m, 2H), 5.03 (q, 1H, J 6.7 Hz), 3.29 (s, 3H), 2.26 (s, 3H), 1.55 (d, 3H, J 6.7 Hz). HPLC-MS: MH+ m/z 523, RT 2.25 minutes.

Example 60

3-({(2R)-8-Fluoro-2-methyl-6-[3-(methylsulfanyl) phenyl]-3-oxo-1,4-benzoxazin-4-yl}-methyl)-2-methylimidazo[1,2-a]pyridine-6-carbonitrile To a solution of Intermediate 125 (2.0 g, 4.2 mmol) in 1,4 dioxane (5 mL) was added 3-(methylthio)phenylboronic acid (1.2 g, 6.8 mmol), followed by Na$_2$CO$_3$ (856 mg, 8.4 mmol) dissolved in water (1 mL). [1,1'-Bis(diphenylphosphino)ferrocene]-palladium(II) dichloride DCM complex (0.048 g, 0.059 mmol) was added and the mixture was heated at reflux under nitrogen for 5 h. On cooling, the reaction mixture was separated between EtOAc (50 mL) and water (25 mL). The water layer was further extracted with EtOAc (25 mL). The combined organic layers were washed with water (2×25 mL) and dried (phase separator), then evaporated in vacuo. The residue was purified by column chromatography (SiO$_2$, 10-100% EtOAc:DCM gradient) to afford the title compound (1.05 g). HPLC-MS: MH+ m/z 473, RT 2.44 minutes.

Example 61

3-({(2R)-8-Fluoro-2-methyl-6-[3-(methylsulfinyl) phenyl]-3-oxo-1,4-benzoxazin-4-yl}-methyl)-2-methylimidazo[1,2-a]pyridine-6-carbonitrile Example 60 (1.05 g, 2.22 mmol) was dissolved in DCM (10 mL) and cooled in an ice bath. To the mixture was added 3-chloroperoxybenzoic acid (498 mg, 2.22 mmol) and the reaction mixture was stirred at r.t. for 1 h. A further aliquot of 3-chloroperoxy-benzoic acid (150 mg) was added and reaction mixture was stirred for a further 30 minutes. The reaction mixture was diluted with DCM (20 mL), then washed with aqueous Na$_2$CO$_3$ solution (2×50 mL) and water (50 mL). The organic layer was dried through a phase separator, then evaporated in vacuo, to afford the title compound (1.1 g, 91%). HPLC-MS: MH+ m/z 489, RT 2.11 minutes.

Examples 62 & 63

3-({(2R)-8-Fluoro-2-methyl-6-[3-(methylsulfonimidoyl)phenyl]-3-oxo-1,4-benzoxazin-4-yl}methyl)-2-methylimidazo[1,2-a]pyridine-6-carbonitrile (Isomers A and B)

To Example 61 (1.1 g, 2.0 mmol) in DCM (20 mL) were added 2,2,2-trifluoro-acetamide (510 mg, 4.5 mmol) and magnesium oxide (370 mg, 9.0 mmol), followed by rhodium (II) acetate dimer (100 mg, 0.23 mmol). To the resulting pink suspension was added iodobenzene I,I-diacetate (1.1 g, 3.4 mmol), and the reaction mixture was left to stir under nitrogen for 7 h. The reaction mixture was evaporated in vacuo. The orange residue was treated with MeOH (5 mL) and Na$_2$CO$_3$ (50 mg) and stirred for 45 minutes. The solvent was removed in vacuo and the residue was taken up into DCM (20 mL), then filtered through celite, washed with water and dried using a phase separator. The residue was purified using preparative HPLC to afford a mixture of diastereoisomers (39 mg, 4%) as a white powder. HPLC-MS: MH+ m/z 505, RT 1.68 minutes. The diastereomers were separated by preparative HPLC (mobile phase: 100% MeOH+0.1% diethylamine; stationary phase: Chiralcel OD-H) to afford the individual title compounds.

Isomer A (Example 62)

$\delta_H$ (400 MHz, DMSO-d$_6$) 9.24 (s, 1H), 8.13 (s, 1H), 7.93 (dd, 1H, J 7.8, 1.5 Hz), 7.81 (m, 1H), 7.67 (m, 1H), 7.60 (dd, 1H, J 9.3, 0.8 Hz), 7.49 (m, 3H), 5.75 (m, 2H), 5.03 (m, 1H), 4.26 (s, 1H), 3.15 (d, 3H, J 0.8 Hz), 2.30 (s, 3H), 1.56 (d, 3H, J 6.7 Hz). HPLC-MS: MH+ m/z 505, RT 1.68 minutes.

Isomer B (Example 63)

$\delta_H$ (400 MHz, DMSO-d$_6$) 9.24 (s, 1H), 8.13 (s, 1H), 7.93 (m, 1H), 7.81 (m, 1H), 7.67 (m, 1H), 7.60 (dd, 1H, J 9.3, 0.7 Hz), 7.48 (m, 3H), 5.75 (m, 2H), 5.03 (m, 1H), 4.26 (s, 1H), 3.14 (d, 3H, J 0.8 Hz), 2.30 (s, 3H), 1.56 (d, 3H, J 6.7 Hz). HPLC-MS: MH+ m/z 505, RT 1.68 minutes.

Example 64

3-[(8-Fluoro-6-{3-[(imino)(methyl)(oxo)-$\lambda^6$-sulfanyl]phenyl}-3-oxo-3,4-dihydro-2H-1,4-benzoxazin-4-yl)methyl]-2-methylimidazo[1,2-a]pyridine-6-carbonitrile A solution of DIAD (82.09 μL, 0.42 mmol) was added slowly over 2 minutes to a stirred solution of Intermediate 99

(131.2 mg, 0.28 mmol), Intermediate 24 (92%, 84.64 mg, 0.42 mmol) and triphenylphosphine (109.1 mg, 0.42 mmol) in DCM (5.6 mL) at r.t. under nitrogen. The resultant mixture was stirred at r.t. under nitrogen for 18.5 h. The reaction mixture was concentrated in vacuo and the residue was purified by column chromatography, using a gradient of 0-100% EtOAc in heptane followed by a gradient of 0-10% MeOH in DCM. The isolated material was dissolved in MeOH (10 mL), then $Na_2CO_3$ (176.35 mg, 1.66 mmol) was added and the resulting suspension was stirred for 1 h at r.t. The reaction mixture was concentrated in vacuo and the residue was purified by column chromatography, using a gradient of 0-100% EtOAc in heptane followed by a gradient of 0-10% MeOH in DCM, to afford the title compound (46 mg, 33%) as a white solid. $\delta_H$ (500 MHz, DMSO-$d_6$) 9.25 (s, 1H), 8.13 (s, 1H), 7.93 (d, J 7.8 Hz, 1H), 7.81 (d, J 8.0 Hz, 1H), 7.67 (t, J 7.8 Hz, 1H), 7.60 (d, J 9.1 Hz, 1H), 7.52-7.42 (m, 3H), 5.75 (s, 2H), 4.94 (s, 2H), 4.27 (s, 1H), 3.14 (s, 3H), 2.32 (s, 3H). Method D HPLC-MS: MH+m/z 490, RT 2.19 minutes (98%).

Example 65

3-{[(2R)-6-{3-[(Imino)(methyl)(oxo)-$\lambda^6$-sulfanyl] phenyl}-2-methyl-3-oxo-2H,3H,4H-pyrido[3,2-b][1,4]oxazin-4-yl]methyl}-2-methylimidazo[1,2-a]pyridine-6-carbonitrile Prepared from Intermediates 24 and 100 in a similar manner to that described for Example 64. $\delta_H$ (500 MHz, DMSO-$d_6$) 9.47 (s, 1H), 8.52 (dt, J 3.8, 1.8 Hz, 1H), 8.21-8.19 (m, 1H), 7.98 (d, J 8.0 Hz, 1H), 7.77 (dd, J 8.2, 2.1 Hz, 1H), 7.68 (t, J 7.8 Hz, 1H), 7.64-7.55 (m, 2H), 7.43 (dd, J 9.3, 1.6 Hz, 1H), 5.80-5.73 (m, 2H), 4.99 (q, J 6.7 Hz, 1H), 4.32-4.20 (m, 1H), 3.13 (s, 3H), 2.34 (d, J 2.2 Hz, 3H), 1.51 (d, J 6.8 Hz, 3H). Method D HPLC-MS: MH+ m/z 487, RT 1.96 minutes (99%).

Example 66

(2R)-8-Fluoro-4-{[3-(hydroxymethyl)-1,5-dimethyl-1H-pyrazol-4-yl]methyl}-6-[3-(methanesulfonyl) phenyl]-2-methyl-3,4-dihydro-2H-1,4-benzoxazin-3-one A solution of Example 45 (180 mg, 0.348 mmol) in a 1:1 mixture of THF and 6N aqueous HCl solution (10 mL) was heated at 55° C. with stirring for 5 h. Saturated aqueous $NaHCO_3$ solution was added and the mixture was extracted with DCM (3×20 mL). The combined organic layers were dried ($Na_2SO_4$) and the solvent was removed in vacuo. The residue was purified by high pH preparative HPLC (Method D) to afford the title compound (145 mg, 88%). $\delta_H$ (500 MHz, $CDCl_3$) 8.05 (t, J 1.7 Hz, 1H), 7.90 (d, J 7.8 Hz, 1H), 7.76 (d, J 7.9 Hz, 1H), 7.62 (t, J 7.8 Hz, 1H), 7.30 (s, 1H), 7.09 (dd, J 10.7, 1.9 Hz, 1H), 5.21 (q, J 15.8 Hz, 2H), 4.81 (q, J 6.8 Hz, 1H), 4.65 (s, 2H), 3.73 (s, 3H), 3.10 (s, 3H), 2.20 (s, 3H), 1.68 (d, J 6.8 Hz, 3H). Method B HPLC-MS: MH+ m/z 474, RT 1.68 minutes (97%).

Example 67

(2R)-8-Fluoro-4-{[3-(fluoromethyl)-1,5-dimethyl-1H-pyrazol-4-yl]methyl}-6-[3-(methanesulfonyl) phenyl]-2-methyl-3,4-dihydro-2H-1,4-benzoxazin-3-one To a stirred suspension of Example 66 (100 mg, 0.211 mmol) in anhydrous DCM (5 mL) was added (diethylamino) sulfur trifluoride (0.056 mL, 0.422 mmol) and the mixture was stirred at r.t. for 2 h. The mixture was cooled to 0° C. and saturated aqueous $NaHCO_3$ solution (10 mL) was added. The reaction mixture was warmed to r.t. The phases were separated and the aqueous phase was extracted with DCM (3×20 mL). The combined organic extracts were dried ($MgSO_4$) and the solvent was removed in vacuo. The residue was purified by preparative HPLC (Method D) to afford the title compound (55 mg, 55%). $\delta_H$ (500 MHz, DMSO-$d_6$) 8.06 (t, J 1.6 Hz, 1H), 7.99 (d, J 7.9 Hz, 1H), 7.91 (d, J 7.8 Hz, 1H), 7.74 (t, J 7.8 Hz, 1H), 7.46 (dd, J 11.4, 1.8 Hz, 1H), 7.26 (s, 1H), 5.20 (m, 4H), 4.93 (q, J 6.7 Hz, 1H), 3.66 (d, J 1.8 Hz, 3H), 3.29 (s, 3H), 2.27 (s, 3H), 1.53 (d, J 6.7 Hz, 3H). Column: Chiralcel OD-H 25 cm; Mobile phase: 35% IPA: 65% $CO_2$; Flow rate: 4 mL/minute; UV at 215 nm; Runtime: 10 minutes, e.e. 99%. Method A HPLC-MS: MH+ m/z 476, RT 3.78 minutes (100%).

Example 68

(2R)-8-Fluoro-6-[4-(methanesulfonyl)-1H-indazol-6-yl]-2-methyl-4-[(1,3,5-trimethyl-1H-pyrazol-4-yl) methyl]-3,4-dihydro-2H-1,4-benzoxazin-3-one To a solution of Intermediate 150 (34.34 mg, 0.08 mmol) in anhydrous 1,4-dioxane (3 mL) were added Intermediate 172 (24.6 mg, 0.08 mmol) and 2M aqueous $Na_2CO_3$ solution (0.12 mL). The mixture was degassed for 5 minutes with $N_2$, then X-Phos (7.63 mg, 0.02 mmol) and $Pd_2(dba)_3$ (3.66 mg, 4 μmol) were added. The mixture was degassed with $N_2$ for 5 minutes, then heated at 110° C. with stirring in a sealed tube for 1 h. The reaction mixture was cooled, then EtOAc (20 mL) and water (20 mL) were added. The aqueous phase was extracted with EtOAc (20 mL). The combined organic fractions were washed with brine (20 mL) and dried ($Na_2SO_4$), then the solvent was removed in vacuo. The residue was purified by column chromatography ($SiO_2$; gradient 0-10% MeOH/DCM) and preparative HPLC (Method A) to give the title compound (5 mg, 11%). 8H (500 MHz, DMSO-$d_6$) 13.90 (s, 1H), 8.40 (s, 1H), 8.07 (s, 1H), 7.78 (s, 1H), 7.51 (d, J 10.6 Hz, 1H), 7.22 (s, 1H), 5.22 (d, J 15.7 Hz, 1H), 5.05-4.95 (m, 2H), 3.57 (s, 3H), 3.37 (s, 3H), 2.24 (s, 3H), 1.99 (s, 3H), 1.55 (d, J 6.7 Hz, 3H). Column: Chiralpak AD-H 25 cm; Mobile phase: 40% EtOH: 60% $CO_2$; Flow rate: 4 mL/minute; UV at 254 nm; Runtime: 5 minutes; e.e. 99%. Method D HPLC-MS: MH+ m/z 498.1, RT 2.68 minutes (98%).

Example 69

7-{(2R)-4-[(2,4-Dimethylpyridin-3-yl)methyl]-2-methyl-3-oxo-2H,3H,4H-pyrido[3,2-b]-[1,4]oxazin-6-yl}-1,2-dihydrophthalazin-1-one To a nitrogen degassed mixture of Intermediate 163 (139 mg, 0.38 mmol), Intermediate 104 (127 mg, 0.37 mmol) and 2M aqueous $Na_2CO_3$ solution (0.57 mL) in 1,4-dioxane (5.5 mL) was added Pd(dppf)$Cl_2$ (14 mg, 0.02 mmol). The reaction mixture was further degassed with $N_2$ and heated at 100° C. for 3 h. The mixture was cooled to 0° C. and saturated aqueous ammonium chloride solution (5 mL) was added. 1,4-Dioxane (10 mL) was added, and the mixture was sonicated. The solids were removed by filtration through Kieselguhr, and the residue was washed with 1,4-dioxane (2×10 mL). The filtrate was concentrated in vacuo. EtOAc (30 mL) and water (10 mL) were added and the mixture was sonicated. The solids were removed by filtration and the residue was washed with EtOAc (2×5 mL). The aqueous layer was extracted with EtOAc (2×5 mL) and the combined organic layers were washed with brine (2×5 mL), then dried (MgSO$_4$). The solvent was removed in vacuo. The residue was purified by column chromatography (SiO$_2$; gradient of 1-10% MeOH in DCM) to afford the title compound (25 mg, 15%). $\delta_H$ (500 MHz, DMSO-d$_6$) 12.71 (s, 1H), 8.65 (s, 1H), 8.40 (s, 1H), 8.32 (dd, J 8.3, 1.8 Hz, 1H), 8.15 (d, J 4.9 Hz, 1H), 7.99 (d, J 8.3 Hz, 1H), 7.80 (d, J 8.2 Hz, 1H), 7.59 (d, J 8.2 Hz, 1H), 7.05 (d, J 5.0 Hz, 1H), 5.42 (s, 2H), 4.97 (q, J 6.7 Hz, 1H), 2.46 (s, 3H), 2.34 (s, 3H), 1.50 (d, J 6.8 Hz, 3H). Column: Chiralpak AD-H 25 cm; Mobile phase: 50:50 EtOH:MeOH; Flow rate: 1 mL/minute; UV at 254 nm; Runtime 24.38 minutes; 88% e.e. Method D HPLC-MS: MH+ m/z 428, RT 1.71 minutes (98%).

Example 70

7-{4-[(2,4-Dimethylpyridin-3-yl)methyl]-3-oxo-2H,3H,4H-pyrido[3,2-b][1,4]oxazin-6-yl}-1,2-dihydrophthalazin-1-one Prepared from Intermediates 102 and 163 in a similar manner to that described for Example 69. $\delta_H$ (500 MHz, DMSO-d$_6$) 12.71 (s, 1H), 8.65 (s, 1H), 8.40 (s, 1H), 8.31 (dd, J 8.3, 1.6 Hz, 1H), 8.15 (d, J 4.9 Hz, 1H), 7.99 (d, J 8.3 Hz, 1H), 7.79 (d, J 8.2 Hz, 1H), 7.57 (d, J 8.2 Hz, 1H), 7.05 (d, J 4.9 Hz, 1H), 5.41 (s, 2H), 4.86 (s, 2H), 2.47 (s, 3H), 2.35 (s, 3H). Method D HPLC-MS: MH+ m/z 414, RT 1.53 minutes (98%).

Example 71

(2R)-8-Fluoro-2-methyl-6-(4-oxo-3,4-dihydrophthalazin-6-yl)-4-[(1,3,5-trimethyl-1H-pyrazol-4-yl)methyl]-3,4-dihydro-2H-1,4-benzoxazin-3-one Prepared from Intermediates 135 and 163 in a similar manner to that described for Example 69. $\delta_H$ (500 MHz, DMSO-d$_6$) 12.74 (s, 1H), 8.41 (s, 1H), 8.26 (s, 1H), 8.20 (dd, J 8.2, 2.0 Hz, 1H), 8.03 (d, J 8.3 Hz, 1H), 7.50 (dd, J 11.4, 1.8 Hz, 1H), 7.23 (s, 1H), 5.22 (d, J 15.9 Hz, 1H), 5.05-4.95 (m, 2H), 3.61 (s, 3H), 2.28 (s, 3H), 1.97 (s, 3H), 1.55 (d, J 6.7 Hz, 3H). Method A HPLC-MS: MH+ m/z 448, RT 3.60 minutes (98%).

Example 72

(2R)-4-[(3,5-Dimethylpyridazin-4-yl)methyl]-8-fluoro-2-methyl-6-(4-oxo-3,4-dihydro-phthalazin-6-yl)-3,4-dihydro-2H-1,4-benzoxazin-3-one Prepared from Intermediates 116 and 163 in a similar manner to that described for Example 69. $\delta_H$ (500 MHz, DMSO-d$_6$) 12.72 (s, 1H), 8.88 (s, 1H), 8.39 (s, 1H), 8.36 (d, J 1.8 Hz, 1H), 8.18 (dd, J 8.3, 1.9 Hz, 1H), 8.01 (d, J 8.3 Hz, 1H), 7.57 (dd, J 11.3, 1.7 Hz, 1H), 7.34 (s, 1H), 5.40 (d, J 16.0 Hz, 1H), 5.30 (d, J 16.0 Hz, 1H), 4.95 (q, J 6.7 Hz, 1H), 2.59 (s, 3H), 2.32 (s, 3H), 1.49 (d, J 6.7 Hz, 3H). Method D HPLC-MS: MH+ m/z 446, RT 2.32 minutes (98%).

Example 73

7-{(2R)-2-Methyl-4-[(2-methylimidazo[1,2-a]pyridin-3-yl)methyl]-3-oxo-2H,3H,4H-pyrido[3,2-b][1,4]oxazin-6-yl}-1,2-dihydrophthalazin-1-one Prepared from Intermediates 110A and 163 in a similar manner to that described for Example 69. $\delta_H$ (250 MHz, DMSO-d$_6$) 12.74 (s, 1H), 8.82 (d, J 1.6 Hz, 1H), 8.62 (d, J 7.0 Hz, 1H), 8.53 (dd, J 8.3, 1.9 Hz, 1H), 8.42 (s, 1H), 8.01 (d, J 8.3 Hz, 1H), 7.86 (d, J 8.3 Hz, 1H), 7.58 (d, J 8.3 Hz, 1H), 7.38 (d, J 9.0 Hz, 1H), 7.20-7.02 (m, 1H), 6.72 (td, J 6.8, 1.2 Hz, 1H), 5.74 (s, 2H), 4.98 (q, J 6.8 Hz, 1H), 2.27 (s, 3H), 1.50 (d, J 6.7 Hz, 3H). Chiral analysis SFC-MS: MH+ m/z 453, RT 2.93 minutes. Method A HPLC-MS: MH+m/z 453, RT 2.86 minutes (100%).

Example 74

3-{2-Methyl-4-[(2-methylimidazo[1,2-a]pyridin-3-yl)methyl]-3-oxo-2H,3H,4H-pyrido-[3,2-b][1,4]oxazin-6-yl}benzamide Prepared from Intermediate 110 and (3-carbamoylphenyl) boronic acid in a similar manner to that described for Example 69. $\delta_H$ (500 MHz, DMSO-d$_6$) 8.64 (d, J 6.91 Hz, 1H), 8.50 (s, 1H), 8.15 (s, 1H), 8.11 (d, J 7.82 Hz, 1H), 7.92 (d, J 7.76 Hz, 1H), 7.71 (d, J 8.24 Hz, 1H), 7.59-7.51 (m, 2H), 7.48 (s, 1H), 7.38 (d, J 8.97 Hz, 1H), 7.16-7.09 (m, 1H), 6.69 (t, J 6.79 Hz, 1H), 5.75 (d, J 2.50 Hz, 2H), 4.96 (q, J 6.71 Hz, 1H), 2.28 (s, 3H), 1.50 (d, J 6.74 Hz, 3H). Method A HPLC-MS: MH+ m/z 428, RT 2.80 minutes (100%).

Example 75

3-{4-[(2,4-Dimethylpyridin-3-yl)methyl]-3-oxospiro[1,4-benzoxazine-2,1'-cyclopropane]-6-yl}benzamide Prepared from Intermediate 140 and (3-carbamoylphenyl) boronic acid in a similar manner to that described for Example 69. $\delta_H$ (400 MHz, CDCl$_3$) 8.29 (d, 1H, J 5.0 Hz), 7.98 (d, 1H, J 7.3 Hz), 7.55-7.46 (m, 3H), 7.26 (s, 1H), 7.11 (d, 1H, J 8.3 Hz), 6.98 (d, 1H, J 4.9 Hz), 6.94 (d, 1H, J 8.3 Hz), 6.78 (d, 1H, J 1.4 Hz), 5.79 (m, 1H), 5.40 (s, 2H), 2.79 (s, 3H), 2.33 (s, 3H), 1.49 (m, 2H), 1.29 (m, 2H). LCMS (ES+) (M+H)$^+$ 414, RT 1.85 minutes (Method 2).

Example 76

3-{4-[(3,5-Dimethylisoxazol-4-yl)methyl]-2-fluoro-2-methyl-3-oxopyrido[3,2-b][1,4]-oxazin-6-yl}benzamide Prepared from Intermediate 129 and (3-carbamoylphenyl) boronic acid in a similar manner to that described for Example 69. $\delta_H$ (400 MHz, CD$_3$OD) 8.51 (t, 1H, J 1.7 Hz), 8.16 (m, 1H), 7.95 (m, 1H), 7.73 (m, 1H), 7.62 (m, 2H), 5.36 (m, 2H), 2.39 (s, 3H), 2.19 (s, 3H), 1.98 (d, 3H, J 18.7 Hz). LCMS (ES+) (M+H)$^+$ 411, RT 2.09 minutes (Method 2).

Example 77

3-[(3,5-Dimethylisoxazol-4-yl)methyl]-5-(3-methoxyphenyl)-1a,7b-dihydro-1H-cyclopropa[c]quinolin-2-one Prepared from Intermediate 142 and 3-methoxyphenyl-boronic acid in a similar manner to that described for Example 69. $\delta_H$ (400 MHz, CDCl$_3$) 7.45 (d, 1H, J 7.8 Hz), 7.35 (m, 1H), 7.24 (dd, 1H, J 7.8, 1.6 Hz), 7.00-6.98 (m, 1H), 6.95-6.87 (m, 3H), 5.22 (d, 1H, J 16.2 Hz), 4.86 (d, 1H, J 16.1 Hz), 3.88 (s, 3H), 2.63 (td, 1H, J 8.0, 5.1 Hz), 2.44 (m, 1H), 2.31 (s, 3H), 2.23 (s, 3H), 1.69 (m, 1H), 0.66 (q, 1H, J 4.8 Hz). LCMS (ES+) (M+H)+ 375, RT 2.41 minutes (Method 2).

Example 78

3-{(2R)-2-Methyl-4-[(2-methylimidazo[1,2-a]pyridin-3-yl)methyl]-3-oxo-2H,3H,4H-pyrido[3,2-b][1,4]oxazin-6-yl}benzene-1-sulfonamide Prepared from Intermediates 110A and 165 in a similar manner to that described for Example 69. $\delta_H$ (500 MHz, DMSO-$d_6$) 8.60 (d, J 6.9 Hz, 1H), 8.48 (s, 1H), 8.18 (d, J 7.9 Hz, 1H), 7.87 (d, J 7.8 Hz, 1H), 7.69 (t, J 8.2 Hz, 1H), 7.66 (d, J 15.7 Hz, 1H), 7.59 (d, J 8.2 Hz, 1H), 7.51 (br s, 2H), 7.40 (d, J 9.0 Hz, 1H), 7.18-7.10 (m, 1H), 6.78-6.69 (m, 1H), 5.83-5.66 (m, 2H), 4.98 (q, J 6.7 Hz, 1H), 2.29 (s, 3H), 1.51 (d, J 6.7 Hz, 3H). Chiral SFC-MS: MH+ m/z 464, RT 4.93 minutes. Method D HPLC-MS: MH+ m/z 464, RT 2.86 minutes (95%).

Example 79

3-{6-Oxo-5-[(1,3,5-trimethyl-1H-pyrazol-4-yl)methyl]-5,6,7,8-tetrahydro-1,5-naphthyridin-3-yl}benzamide Prepared from Intermediate 75 and 3-(4,4,5,5-tetramethyl-1,3,2-dioxaborolan-2-yl)benzamide in a similar manner to that described for Example 69. $\delta_H$ (400 MHz, DMSO-$d_6$) 8.42 (d, J 1.8 Hz, 1H), 8.12-8.00 (m, 2H), 7.92-7.82 (m, 1H), 7.77 (dt, J 7.9, 1.4 Hz, 1H), 7.59-7.50 (m, 2H), 7.45 (d, J 18.1 Hz, 1H), 5.03 (s, 2H), 3.52 (s, 3H), 3.01 (dd, J 8.7, 6.2 Hz, 2H), 2.77 (dd, J 8.7, 6.2 Hz, 2H), 2.18 (s, 3H), 1.94 (s, 3H). LCMS (ES+) (M+H)+ 390, RT 1.62 minutes (97%).

Example 80

7-[3-(Methylsulfonyl)phenyl]-1-[(1,3,5-trimethyl-1H-pyrazol-4-yl)methyl]-3,4-dihydro-1,5-naphthyridin-2(1H)-one Prepared from Intermediate 75 and 2-[3-(methylsulfonyl)phenyl]-4,4,5,5-tetramethyl-1,3,2-dioxaborolane in a similar manner to that described for Example 69. $\delta_H$ (400 MHz, DMSO-$d_6$) 8.49 (d, J 1.8 Hz, 1H), 8.08 (d, J 1.8 Hz, 1H), 8.03 (dt, J 7.9, 1.4 Hz, 1H), 7.97 (dt, J 7.9, 1.3 Hz, 1H), 7.79 (t, J 7.8 Hz, 1H), 7.60 (d, J 2.1 Hz, 1H), 5.08 (s, 2H), 3.54 (s, 3H), 3.30 (s, 3H), 3.06 (dd, J 8.6, 6.3 Hz, 2H), 2.81 (dd, J 8.7, 6.3 Hz, 2H), 2.21 (s, 3H), 1.98 (s, 3H). LCMS (ES+) (M+H)+ 425, RT 1.66 minutes (99%).

Example 81

7-(1-Oxo-1,2,3,4-tetrahydroisoquinolin-7-yl)-1-[(1,3,5-trimethyl-1H-pyrazol-4-yl)-methyl]-3,4-dihydro-1,5-naphthyridin-2(1H)-one Prepared from Intermediate 75 and 7-(4,4,5,5-tetramethyl-1,3,2-dioxaborolan-2-yl)-3,4-dihydroisoquinolin-1(2H)-one in a similar manner to that described for Example 69. $\delta_H$ (400 MHz, CDCl$_3$) 8.37 (d, J 2.4 Hz, 1H), 8.08 (s, 1H), 7.56 (d, J 7.4 Hz, 1H), 7.36-7.28 (m, 2H), 6.06 (s, 1H), 5.05 (s, 2H), 3.71 (s, 3H), 3.61 (d, J 6.7 Hz, 2H), 3.17 (t, J 7.7 Hz, 2H), 3.06 (t, J 6.7 Hz, 2H), 2.87 (t, J 7.9 Hz, 2H), 2.29 (s, 3H), 2.13 (s, 3H). LCMS (ES+) (M+H)+ 416, RT 1.69 minutes (100%).

Example 82

7-(3-Methoxyphenyl)-1-[(1,3,5-trimethyl-1H-pyrazol-4-yl)methyl]-3,4-dihydro-1,5-naphthyridin-2(1H)-one Prepared from Intermediate 75 and 2-(3-methoxyphenyl)-4,4,5,5-tetramethyl-1,3,2-dioxaborolane in a similar manner to that described for Example 69. $\delta_H$ (400 MHz, DMSO-$d_6$) 8.40 (d, J 1.8 Hz, 1H), 7.54 (d, J 2.1 Hz, 1H), 7.41 (t, J 7.9 Hz, 1H), 7.30-7.07 (m, 2H), 6.99 (dd, J 8.2, 2.5 Hz, 1H), 5.07 (s, 2H), 3.83 (s, 3H), 3.52 (s, 3H), 3.02 (dd, J 8.6, 6.3 Hz, 2H), 2.79 (dd, J 8.6, 6.2 Hz, 2H), 2.15 (s, 3H), 2.00 (s, 3H). LCMS (ES+) (M+H)+ 377, RT 1.89 minutes (100%).

Example 83

3-{7-Methyl-6-oxo-5-[(1,3,5-trimethyl-1H-pyrazol-4-yl)methyl]-7,8-dihydro-1,5-naphthyridin-3-yl}benzamide Prepared from Intermediate 76 and 3-(4,4,5,5-tetramethyl-1,3,2-dioxaborolan-2-yl)benzamide in a similar manner to that described for Example 69. $\delta_H$ (400 MHz, DMSO-$d_6$) 8.57-8.32 (m, 2H), 8.19-8.00 (m, 1H), 7.91 (dt, J 7.9, 1.3 Hz, 1H), 7.80 (dt, J 8.0, 1.3 Hz, 1H), 7.70-7.31 (m, 2H), 5.25 (d, J 15.8 Hz, 1H), 4.91 (d, J 15.8 Hz, 1H), 3.55 (s, 3H), 3.12 (q, J 11.6 Hz, 2H), 2.96-2.73 (m, 2H), 2.20 (s, 3H), 1.96 (s, 3H), 1.23 (d, J 5.8 Hz, 3H). LCMS (ES+) (M+H)+ 404, RT 1.61 minutes (99%).

Example 84

3-Methyl-7-[3-(methylsulfonyl)phenyl]-1-[(1,3,5-trimethyl-1H-pyrazol-4-yl)methyl]-3,4-dihydro-1,5-naphthyridin-2-one Prepared from Intermediate 76 and 2-[3-(methylsulfonyl)phenyl]-4,4,5,5-tetramethyl-1,3,2-dioxaborolane in a similar manner to that described for Example 69. $\delta_H$ (400 MHz, CDCl$_3$) 8.36 (d, J 1.9 Hz, 1H), 8.06-7.84 (m, 2H), 7.83-7.53 (m, 2H), 7.25 (m, 1H), 5.23 (d, J 15.9 Hz, 1H), 4.90 (d, J 15.8 Hz, 1H), 3.70 (s, 3H), 3.26 (dd, J 15.5, 5.2 Hz, 1H), 3.09 (s, 3H), 3.03-2.76 (m, 2H), 2.24 (s, 3H), 2.12 (s, 3H), 1.37 (d, J 6.6 Hz, 3H). LCMS (ES+) (M+H)+ 439, RT 1.89 minutes (96%).

Example 85

3-Methyl-7-(1-oxo-3,4-dihydro-2H-isoquinolin-7-yl)-1-[(1,3,5-trimethyl-1H-pyrazol-4-yl)methyl]-3,4-dihydro-1,5-naphthyridin-2-one Prepared from Intermediate 76 and 7-(4,4,5,5-tetramethyl-1,3,2-dioxaborolan-2-yl)-3,4-dihydroisoquinolin-1(2H)-one in a similar manner to that described for Example 69. $\delta_H$ (400 MHz, DMSO-$d_6$) 8.39 (d, J 1.8 Hz, 1H), 8.05 (t, J 2.8 Hz, 1H), 7.93 (d, J 2.1 Hz, 1H), 7.76 (dd, J 7.8, 2.1 Hz, 1H), 7.45 (d, J 7.7 Hz, 2H), 5.24 (d, J 15.8 Hz, 1H), 4.90 (d, J 15.8 Hz, 1H), 3.59 (s, 3H), 3.41 (td, J 6.3, 2.5 Hz, 2H), 3.11 (t, J 10.8 Hz, 1H), 2.96 (t, J 6.6 Hz, 2H), 2.84 (qd, J 10.2, 9.1, 5.1 Hz, 2H), 2.26 (s, 3H), 1.95 (s, 3H), 1.23 (d, J 5.6 Hz, 3H). LCMS (ES+) (M+H)+ 430, RT 1.73 minutes (97%).

Example 86

7-(3-Methoxyphenyl)-3-methyl-1-[(1,3,5-trimethyl-1H-pyrazol-4-yl)methyl]-3,4-dihydro-1,5-naphthyridin-2-one Prepared from Intermediate 76 and 2-(3-methoxyphenyl)-4,4,5,5-tetramethyl-1,3,2-dioxaborolane in a similar manner to that described for Example 69. $\delta_H$ (400 MHz, DMSO-$d_6$) 8.51-8.25 (m, 1H), 7.54 (d, J 1.9 Hz, 1H), 7.41 (t, J 7.9 Hz, 1H), 7.26-7.11 (m, 2H), 6.99 (dd, J 8.3, 2.5 Hz, 1H), 5.24 (d, J 15.8 Hz, 1H), 4.92 (d, J 15.8 Hz, 1H), 3.83 (s, 3H), 3.52 (s, 3H), 3.24-2.96 (m, 2H), 2.97-2.66 (m, 2H), 2.14 (s, 3H), 1.99 (s, 3H), 1.22 (d, J 5.8 Hz, 3H). LCMS (ES+) (M+H)$^+$ 391, RT 2.15 minutes (98%).

Example 87

3-Methyl-7-(pyridin-3-yl)-1-[(1,3,5-trimethyl-1H-pyrazol-4-yl)methyl]-3,4-dihydro-1,5-naphthyridin-2-one Prepared from Intermediate 76 and 3-(4,4,5,5-tetramethyl-1,3,2-dioxaborolan-2-yl)pyridine in a similar manner to that described for Example 69. $\delta_H$ (400 MHz, DMSO-$d_6$) 8.88 (d, J 2.3 Hz, 1H), 8.62 (dd, J 4.9, 1.5 Hz, 1H), 8.47 (d, J 1.8 Hz, 1H), 8.08 (dt, J 8.0, 2.0 Hz, 1H), 7.64 (d, J 1.8 Hz, 1H), 7.54 (dd, J 7.9, 4.8 Hz, 1H), 5.25 (d, J 15.8 Hz, 1H), 4.91 (d, J 15.8 Hz, 1H), 3.51 (s, 3H), 3.22-2.97 (m, 1H), 2.94-2.73 (m, 2H), 2.14 (s, 3H), 1.98 (s, 3H), 1.22 (d, J 5.9 Hz, 3H). LCMS (ES+) (M+H)$^+$ 362, RT 1.69 minutes (100%).

Example 88

7-(Pyridin-3-yl)-1-[(1,3,5-trimethyl-1H-pyrazol-4-yl)methyl]-3,4-dihydro-1,5-naphthyridin-2-one Prepared from Intermediate 75 and 3-(4,4,5,5-tetramethyl-1,3,2-dioxaborolan-2-yl)pyridine in a similar manner to that described for Example 69. $\delta_H$ (400 MHz, DMSO-$d_6$) 8.92 (s, 1H), 8.61 (d, 1H), 8.43 (s, 1H), 8.10 (m, 1H), 7.63 (s, 1H), 6.93 (m, 1H), 5.08 (s, 2H), 3.58 (s, 3H), 3.02 (dd, J 8.6, 6.3 Hz, 2H), 2.79 (dd, J 8.6, 6.2 Hz, 2H), 2.15 (s, 3H), 2.00 (s, 3H). LCMS (ES+) (M+H)$^+$ 348, RT 1.54 minutes (98%).

Example 89

7-(6-Methoxypyridin-3-yl)-3-methyl-1-[(1,3,5-trimethyl-1H-pyrazol-4-yl)methyl]-3,4-dihydro-1,5-naphthyridin-2-one Prepared from Intermediate 76 and (6-methoxypyridin-3-yl)boronic acid in a similar manner to that described for Example 69. $\delta_H$ (400 MHz, DMSO-$d_6$) 8.48 (d, J 2.5 Hz, 1H), 8.41 (d, J 1.8 Hz, 1H), 8.01 (dd, J 8.6, 2.6 Hz, 1H), 7.57 (d, J 1.9 Hz, 1H), 6.97 (d, J 8.7 Hz, 1H), 5.24 (d, J 15.8 Hz, 1H), 4.90 (d, J 15.8 Hz, 1H), 3.91 (s, 3H), 3.51 (s, 3H), 3.08 (t, J 10.8 Hz, 1H), 2.93-2.65 (m, 2H), 2.14 (s, 3H), 1.98 (s, 3H), 1.21 (d, J 6.1 Hz, 3H). LCMS (ES+) (M+H)$^+$ 392, RT 1.98 minutes (97%).

Example 90

3-{7-Oxo-8-[(1,3,5-trimethyl-1H-pyrazol-4-yl)methyl]-5,6,7,8-tetrahydro-1,8-naphthyridin-2-yl}benzamide Prepared from Intermediate 74 and 3-(4,4,5,5-tetramethyl-1,3,2-dioxaborolan-2-yl)benzamide in a similar manner to that described for Example 69. LCMS (ES+) (M+H)$^+$ 390.2, RT 1.88 minutes (96%).

Example 91

7-[3-(Methylsulfonyl)phenyl]-1-[(1,3,5-trimethyl-1H-pyrazol-4-yl)methyl]-3,4-dihydro-1,8-naphthyridin-2(1H)-one Prepared from Intermediate 74 and 2-[3-(methylsulfonyl)phenyl]-4,4,5,5-tetramethyl-1,3,2-dioxaborolane in a similar manner to that described for Example 69. $\delta_H$ (400 MHz, CDCl$_3$) 8.51 (t, J 1.8 Hz, 1H), 8.27 (dt, J 7.9, 1.4 Hz, 1H), 7.98 (ddd, J 7.9, 1.9, 1.1 Hz, 1H), 7.68 (t, J 7.8 Hz, 1H), 7.58-7.50 (m, 1H), 7.43 (d, J 7.6 Hz, 1H), 5.31 (s, 2H), 3.61 (s, 3H), 3.11 (s, 3H), 2.89 (dd, J 8.7, 6.1 Hz, 2H), 2.73 (dd, J 8.7, 6.0 Hz, 2H), 2.20 (s, 3H), 2.05 (s, 3H). LCMS (ES+) (M+H)$^+$ 425.2, RT 2.01 minutes (96%).

Example 92

7-(1-Oxo-1,2,3,4-tetrahydroisoquinolin-7-yl)-1-[(1,3,5-trimethyl-1H-pyrazol-4-yl)-methyl]-3,4-dihydro-1,8-naphthyridin-2(1H)-one Prepared from Intermediate 74 and 7-(4,4,5,5-tetramethyl-1,3,2-dioxaborolan-2-yl)-3,4-dihydroisoquinolin-1(2H)-one in a similar manner to that described for Example 69. $\delta_H$ (400 MHz, DMSO-$d_6$) 8.49 (d, J 2.0 Hz, 1H), 8.13 (dd, J 7.9, 2.0 Hz, 1H), 8.02 (t, J 2.7 Hz, 1H), 7.72 (d, J 7.7 Hz, 1H), 7.59 (d, J 7.7 Hz, 1H), 7.43 (d, J 8.0 Hz, 1H), 5.18 (s, 2H), 3.51 (s, 3H), 3.41 (td, J 6.6, 2.8 Hz, 2H), 2.96 (t, J 6.5 Hz, 2H), 2.85 (dd, J 8.6, 6.1 Hz, 2H), 2.69-2.63 (m, 2H), 2.11 (s, 3H), 1.93 (s, 3H). LCMS (ES+) (M+H)$^+$ 416.3, RT 1.81 minutes (99%).

Example 93

7-(3-Methoxyphenyl)-1-[(1,3,5-trimethyl-1H-pyrazol-4-yl)methyl]-3,4-dihydro-1,8-naphthyridin-2(1H)-one Prepared from Intermediate 74 and 2-(3-methoxyphenyl)-4,4,5,5-tetramethyl-1,3,2-dioxaborolane in a similar manner to that described for Example 69. $\delta_H$ (400 MHz, DMSO-$d_6$) 7.70 (d, J 7.7 Hz, 1H), 7.64-7.50 (m, 3H), 7.39 (t, J 8.0 Hz, 1H), 7.05-6.94 (m, 1H), 5.17 (s, 2H), 3.82 (s, 3H), 3.50 (s, 3H), 2.84 (t, J 7.0 Hz, 2H), 2.65 (t, J 7.2 Hz, 2H), 2.10 (s, 3H), 1.94 (s, 3H). LCMS (ES+) (M+H)$^+$ 377.2, RT 2.23 minutes (97%).

Example 94

7-(Pyridin-3-yl)-1-[(1,3,5-trimethyl-1H-pyrazol-4-yl)methyl]-3,4-dihydro-1,8-naphthyridin-2(1H)-one Prepared from Intermediate 74 and 3-(4,4,5,5-tetramethyl-1,3,2-dioxaborolan-2-yl)pyridine in a similar manner to that described for Example 69. $\delta_H$ (400 MHz, CDCl$_3$)

9.16 (d, J 2.3 Hz, 1H), 8.64 (dd, J 4.9, 1.7 Hz, 1H), 8.24 (dt, J 8.1, 2.0 Hz, 1H), 7.54 (d, J 7.6 Hz, 1H), 7.44-7.34 (m, 2H), 5.30 (s, 2H), 3.60 (s, 3H), 2.87 (dd, J 8.8, 5.9 Hz, 2H), 2.72 (dd, J 8.7, 5.9 Hz, 2H), 2.18 (s, 3H), 2.05 (s, 3H). LCMS (ES+) (M+H)$^+$ 348.2, RT 1.80 minutes (98%).

Example 95

7-(6-Methoxypyridin-3-yl)-1-[(1,3,5-trimethyl-1H-pyrazol-4-yl)methyl]-3,4-dihydro-1,8-naphthyridin-2(1H)-one Prepared from Intermediate 74 and (6-methoxypyridin-3-yl)boronic acid in a similar manner to that described for Example 69. $\delta_H$ (400 MHz, CDCl$_3$) 8.75 (dd, J 2.4, 0.8 Hz, 1H), 8.16 (dd, J 8.7, 2.5 Hz, 1H), 7.49 (dt, J 7.7, 0.9 Hz, 1H), 7.27 (d, J 7.7 Hz, 1H), 6.83 (dd, J 8.6, 0.7 Hz, 1H), 5.29 (s, 2H), 4.00 (s, 3H), 3.60 (s, 3H), 2.84 (dd, J 8.9, 5.8 Hz, 2H), 2.70 (dd, J 8.5, 5.7 Hz, 2H), 2.19 (s, 3H), 2.06 (s, 3H). LCMS (ES+) (M+H)$^+$ 378.2, RT 2.10 minutes (99%).

Example 96

3-{6-Methyl-7-oxo-8-[(1,3,5-trimethyl-1H-pyrazol-4-yl)methyl]-5,6,7,8-tetrahydro-1,8-naphthyridin-2-yl}benzamide Prepared from Intermediate 77 and 3-(4,4,5,5-tetramethyl-1,3,2-dioxaborolan-2-yl)benzamide in a similar manner to that described for Example 69. $\delta_H$ (400 MHz, CDCl$_3$) 8.18 (t, J 1.8 Hz, 1H), 8.12-8.02 (m, 1H), 7.90 (ddd, J 7.8, 1.9, 1.1 Hz, 1H), 7.60-7.48 (m, 2H), 7.37 (d, J 7.6 Hz, 1H), 6.64 (s, 1H), 5.79 (s, 1H), 5.25 (d, J 8.2 Hz, 2H), 3.62 (s, 3H), 3.01-2.88 (m, 1H), 2.80-2.56 (m, 2H), 2.16 (s, 3H), 2.07 (s, 3H), 1.30 (d, J 6.4 Hz, 3H). LCMS (ES+) (M+H)$^+$ 404.3, RT 1.86 minutes (100%).

Example 97

3-Methyl-7-[3-(methylsulfonyl)phenyl]-1-[(1,3,5-trimethyl-1H-pyrazol-4-yl)methyl]-3,4-dihydro-1,8-naphthyridin-2(1H)-one Prepared from Intermediate 77 and 2-[3-(methylsulfonyl)phenyl]-4,4,5,5-tetramethyl-1,3,2-dioxaborolane in a similar manner to that described for Example 69. $\delta_H$ (400 MHz, CDCl$_3$) 8.52 (t, J 1.8 Hz, 1H), 8.27 (ddd, J 8.0, 1.8, 1.1 Hz, 1H), 7.98 (ddd, J 7.9, 1.9, 1.1 Hz, 1H), 7.67 (t, J 7.8 Hz, 1H), 7.56 (dd, J 7.6, 1.3 Hz, 1H), 7.42 (d, J 7.6 Hz, 1H), 5.31 (s, 2H), 3.61 (s, 3H), 3.11 (s, 3H), 3.00-2.88 (m, 1H), 2.75-2.58 (m, 2H), 2.20 (s, 3H), 2.04 (s, 3H), 1.30 (d, J 6.4 Hz, 3H). LCMS (ES+) (M+H)$^+$ 439.2, RT 2.03 minutes (99%).

Example 98

3-Methyl-7-(1-oxo-1,2,3,4-tetrahydroisoquinolin-7-yl)-1-[(1,3,5-trimethyl-1H-pyrazol-4-yl)methyl]-3,4-dihydro-1,8-naphthyridin-2(1H)-one Prepared from Intermediate 77 and 7-(4,4,5,5-tetramethyl-1,3,2-dioxaborolan-2-yl)-3,4-dihydroisoquinolin-1(2H)-one in a similar manner to that described for Example 69. $\delta_H$ (400 MHz, CDCl$_3$) 8.60 (d, J 2.0 Hz, 1H), 8.18 (dd, J 7.9, 2.0 Hz, 1H), 7.51 (d, J 7.7 Hz, 1H), 7.46 (d, J 7.6 Hz, 1H), 7.33 (d, J 8.0 Hz, 1H), 5.32 (d, J 2.8 Hz, 2H), 3.70-3.54 (m, 5H), 3.08 (q, J 7.6, 6.6 Hz, 2H), 2.91 (dd, J 14.1, 4.3 Hz, 1H), 2.80-2.46 (m, 2H), 2.21 (s, 3H), 2.06 (s, 3H), 1.28 (d, J 6.4 Hz, 3H). LCMS (ES+) (M+H)$^+$ 430.3, RT 1.95 minutes (98%).

Example 99

7-(3-Methoxyphenyl)-3-methyl-1-[(1,3,5-trimethyl-1H-pyrazol-4-yl)methyl]-3,4-dihydro-1,8-naphthyridin-2(1H)-one Prepared from Intermediate 77 and 2-(3-methoxyphenyl)-4,4,5,5-tetramethyl-1,3,2-dioxaborolane in a similar manner to that described for Example 69. $\delta_H$ (400 MHz, DMSO-d$_6$) 7.70 (d, J 7.7 Hz, 1H), 7.65-7.52 (m, 2H), 7.40 (t, J 7.9 Hz, 1H), 7.00 (dd, J 8.3, 2.6 Hz, 1H), 5.17 (d, J 9.1 Hz, 2H), 3.82 (s, 3H), 3.50 (s, 3H), 2.95 (dd, J 14.9, 4.9 Hz, 2H), 2.80-2.55 (m, 2H), 2.10 (s, 3H), 1.93 (s, 3H), 1.17 (d, J 6.5 Hz, 3H). LCMS (ES+) (M+H)$^+$ 391.2, RT 2.49 minutes (99%).

Example 100

3-Methyl-7-(pyridin-3-yl)-1-[(1,3,5-trimethyl-1H-pyrazol-4-yl)methyl]-3,4-dihydro-1,8-naphthyridin-2(1H)-one Prepared from Intermediate 77 and 3-(4,4,5,5-tetramethyl-1,3,2-dioxaborolan-2-yl)pyridine in a similar manner to that described for Example 69. $\delta_H$ (400 MHz, CDCl$_3$) 9.16 (d, J 3.0 Hz, 1H), 8.73-8.53 (m, 1H), 8.25 (d, J 7.9 Hz, 1H), 7.54 (d, J 7.6 Hz, 1H), 7.46-7.31 (m, 2H), 5.29 (s, 2H), 3.60 (s, 3H), 3.01-2.85 (m, 1H), 2.77-2.54 (m, 2H), 2.18 (s, 3H), 2.04 (s, 3H), 1.29 (d, J 6.3 Hz, 3H). LCMS (ES+) (M+H)$^+$ 362.3, RT 1.88 minutes (98%).

Example 101

7-(6-Methoxypyridin-3-yl)-3-methyl-1-[(1,3,5-trimethyl-1H-pyrazol-4-yl)methyl]-3,4-dihydro-1,8-naphthyridin-2(1H)-one Prepared from Intermediate 77 and (6-methoxypyridin-3-yl)boronic acid in a similar manner to that described for Example 69. $\delta_H$ (400 MHz, CD$_3$OD) 8.79 (m, 1H), 8.32 (d, J 7.6 Hz, 1H), 7.05 (m, 1H), 7.48 (m, 1H), 6.92 (m, 1H), 5.13 (m, 2H), 4.08 (s, 3H), 3.60 (s, 3H), 3.01 (m, 1H), 2.81-2.60 (m, 2H), 2.20 (s, 3H), 2.00 (s, 3H), 1.20 (d, 3H). LCMS (ES+) (M+H)$^+$ 392.2, RT 1.20 minutes (98%).

Example 102

7-Fluoro-5-(2-fluoro-4-methoxyphenyl)-3-[(1,3,5-trimethyl-1H-pyrazol-4-yl)methyl]-1,3-benzoxazol-2(3H)-one Prepared from Intermediate 78 and (2-fluoro-4-methoxyphenyl)boronic acid in a similar manner to that described for Example 69. $\delta_H$ (400 MHz, CD$_3$OD) 7.26 (ddd, J 8.3, 6.6, 1.3 Hz, 1H), 7.04 (dd, J 11.4, 1.8 Hz, 1H), 6.89 (dt, J 11.4, 1.8 Hz, 1H), 6.76 (ddd, J 8.6, 6.7, 1.9 Hz, 2H), 4.86 (s, 2H), 3.80 (s, 3H), 3.70 (s, 3H), 2.30 (s, 3H), 2.20 (s, 3H). LCMS (ES+) (M+H)$^+$ 400.2, RT 2.48 minutes (100%).

Example 103

7-Fluoro-5-(6-methoxypyridin-3-yl)-3-[(1,3,5-trimethyl-1H-pyrazol-4-yl)methyl]-1,3-benzoxazol-2(3H)-one Prepared from Intermediate 78 and (6-methoxypyridin-3-yl)boronic acid in a similar manner to that described for Example 69. δ$_H$ (400 MHz, CD$_3$OD) 8.31 (d, J 2.6 Hz, 1H), 7.87 (dd, J 8.8, 2.5 Hz, 1H), 7.22 (d, J 11.3 Hz, 1H), 7.05 (s, 1H), 6.89 (d, J 8.7 Hz, 1H), 4.93 (s, 2H), 3.95 (s, 3H), 3.69 (s, 3H), 2.34 (s, 3H), 2.22 (s, 3H). LCMS (ES+) (M+H)$^+$ 383.2, RT 2.27 minutes (97%).

Example 104

7-Fluoro-5-(1H-indol-4-yl)-3-[(1,3,5-trimethyl-1H-pyrazol-4-yl)methyl]-1,3-benzoxazol-2(3H)-one Prepared from Intermediate 78 and 4-(4,4,5,5-tetramethyl-1,3,2-dioxaborolan-2-yl)-1H-indole in a similar manner to that described for Example 69. δ$_H$ (400 MHz, DMSO-d$_6$) 11.35 (s, 1H), 7.50-7.40 (m, 2H), 7.18 (t, J 7.7 Hz, 1H), 7.17-7.07 (m, 3H), 6.34 (s, 1H), 4.90 (s, 2H), 3.63 (s, 3H), 2.24 (s, 3H), 2.08 (s, 3H). LCMS (ES+) (M+H)$^+$ 391.2, RT 2.32 minutes (99%).

Example 105

7-Fluoro-5-(pyridin-3-yl)-3-[(1,3,5-trimethyl-1H-pyrazol-4-yl)methyl]-1,3-benzoxazol-2(3H)-one Prepared from Intermediate 78 and pyridine-3-boronic acid in a similar manner to that described for Example 69. δ$_H$ (400 MHz, CD$_3$OD) 8.76 (s, 1H), 8.56 (d, J 4.8 Hz, 1H), 8.05 (dd, J 8.0, 2.2 Hz, 1H), 7.67-7.42 (m, 1H), 7.33 (d, J 11.1 Hz, 1H), 7.16 (s, 1H), 4.95 (d, J 1.5 Hz, 2H), 3.69 (s, 3H), 2.34 (s, 3H), 2.22 (s, 3H). LCMS (ES+) (M+H)$^+$ 353.1, RT 1.96 minutes (99%).

Example 106

5-[3-(Difluoromethoxy)phenyl]-7-fluoro-3-[(1,3,5-trimethyl-1H-pyrazol-4-yl)methyl]-1,3-benzoxazol-2(3H)-one Prepared from Intermediate 78 and 3-(difluoromethoxy)phenylboronic acid in a similar manner to that described for Example 69. δ$_H$ (400 MHz, CD$_3$OD) 7.49 (t, J 7.9 Hz, 1H), 7.41 (d, J 7.8 Hz, 1H), 7.34-6.67 (m, 5H), 4.93 (s, 2H), 3.69 (s, 3H), 2.34 (s, 3H), 2.22 (s, 3H). LCMS (ES+) (M+H)$^+$ 418.2, RT 2.71 minutes (97%).

Example 107 tert-Butyl 4-{7-fluoro-2-oxo-3-[(1,3,5-trimethyl-1H-pyrazol-4-yl)methyl]-2,3-dihydro-1,3-benzoxazol-5-yl}-3,6-dihydropyridine-1(2H)-carboxylate Prepared from Intermediate 78 and tert-butyl 4-(4,4,5,5-tetramethyl-1,3,2-dioxaborolan-2-yl)-5,6-dihydropyridine-1(2H)-carboxylate in a similar manner to that described for Example 69. δ$_H$ (400 MHz, CD$_3$OD) 7.05 (d, J 11.8 Hz, 1H), 6.88 (s, 1H), 6.08 (s, 1H), 4.88 (s, 2H), 4.06 (s, 2H), 3.70 (s, 3H), 3.61 (m, 2H), 2.46 (t, J 5.5 Hz, 2H), 2.38 (s, 3H), 2.21 (s, 3H), 1.49 (s, 9H). LCMS (ES+) (M+H)$^+$ 457.3, RT 2.77 minutes (98%).

Example 108

7-Fluoro-5-[2-(morpholin-4-yl)pyrimidin-5-yl]-3-[(1,3,5-trimethyl-1H-pyrazol-4-yl)-methyl]-1,3-benzoxazol-2(3H)-one Prepared from Intermediate 78 and 2-(morpholin-4-yl)pyrimidin-5-ylboronic acid in a similar manner to that described for Example 69. δ$_H$ (400 MHz, CD$_3$OD) 8.56 (s, 2H), 7.21 (d, J 11.4 Hz, 1H), 7.02 (s, 1H), 4.86 (s, 2H), 3.83 (q, J 4.4, 4.0 Hz, 4H), 3.76 (q, J 4.3 Hz, 4H), 3.69 (s, 3H), 2.34 (s, 3H), 2.22 (s, 3H). LCMS (ES+) (M+H)$^+$ 439.2, RT 2.30 minutes (97%).

Example 109

7-Fluoro-5-(6-methoxypyridin-2-yl)-3-[(1,3,5-trimethyl-1H-pyrazol-4-yl)methyl]-1,3-benzoxazol-2(3H)-one Prepared from Intermediate 78 and 6-methoxypyridine-2-boronic acid in a similar manner to that described for Example 69. δ$_H$ (400 MHz, CD$_3$OD) 7.76-7.64 (m, 2H), 7.59 (d, J 1.7 Hz, 1H), 7.39 (d, J 7.7 Hz, 1H), 6.74 (d, J 8.2 Hz, 1H), 4.94 (d, J 1.6 Hz, 2H), 4.00 (d, J 1.6 Hz, 3H), 3.68 (s, 3H), 2.34 (s, 3H), 2.27 (s, 3H). LCMS (ES+) (M+H)$^+$ 383.2, RT 2.49 minutes (98%).

Example 110

7-Fluoro-5-(2-methoxypyridin-4-yl)-3-[(1,3,5-trimethyl-1H-pyrazol-4-yl)methyl]-1,3-benzoxazol-2(3H)-one Prepared from Intermediate 78 and 2-methoxypyridine-4-boronic acid in a similar manner to that described for Example 69. δ$_H$ (400 MHz, CD$_3$OD) 8.22-8.15 (m, 1H), 7.35 (dt, J 11.4, 1.7 Hz, 1H), 7.15 (dd, J 8.1, 2.4 Hz, 2H), 6.96 (s, 1H), 4.94 (d, J 1.4 Hz, 2H), 3.98 (s, 3H), 3.69 (s, 3H), 2.34 (s, 3H), 2.23 (s, 3H). LCMS (ES+) (M+H)$^+$ 383.2, RT 2.20 minutes (98%).

Example 111

5-(3-Acetylphenyl)-7-fluoro-3-[(1,3,5-trimethyl-1H-pyrazol-4-yl)methyl]-1,3-benzoxazol-2(3H)-one Prepared from Intermediate 78 and 3-acetylphenylboronic acid in a similar manner to that described for Example 69. δ$_H$ (400 MHz, CD$_3$OD) 8.12 (d, J 2.1 Hz, 1H), 8.01 (d, J 7.6 Hz, 1H), 7.81 (d, J 7.7 Hz, 1H), 7.60 (t, J 7.8 Hz, 1H), 7.30 (d, J 11.3 Hz, 1H), 7.10 (s, 1H), 4.94 (s, 2H), 3.71 (s, 3H), 2.66 (s, 3H), 2.36 (s, 3H), 2.22 (s, 3H). LCMS (ES+) (M+H)$^+$ 394.2, RT 2.45 minutes (98%).

Example 112

7-Fluoro-5-(1-methyl-1H-pyrazol-5-yl)-3-[(1,3,5-trimethyl-1H-pyrazol-4-yl)methyl]-1,3-benzoxazol-2(3H)-one Prepared from Intermediate 78 and 1-methyl-1H-pyrazole-5-ylboronic acid in a similar manner to that described for Example 69. δ$_H$ (400 MHz, CD$_3$OD) 7.50 (t, J 1.9 Hz, 1H), 7.14 (d, J 10.7 Hz, 1H), 6.91 (s, 1H), 6.39 (m, 1H), 4.92 (s, 2H), 3.81 (s, 3H), 3.69 (s, 3H), 2.31 (s, 3H), 2.19 (s, 3H). LCMS (ES+) (M+H)$^+$ 356.2, RT 2.16 minutes (100%).

Example 113

7-Fluoro-5-[3-(1H-pyrazol-1-yl)phenyl]-3-[(1,3,5-trimethyl-1H-pyrazol-4-yl)methyl]-1,3-benzoxazol-2(3H)-one Prepared from Intermediate 78 and [3-(1H-pyrazol-1-yl)phenyl]boronic acid in a similar manner to that described for Example 69. δ$_H$ (400 MHz, CD$_3$OD) 8.38 (s, 1H), 7.97 (s, 1H), 7.79-7.67 (m, 2H), 7.63-7.41 (m, 2H), 7.35 (d, J 11.4 Hz, 1H), 7.16 (s, 1H), 6.57 (s, 1H), 4.95 (s, 2H), 3.70 (s, 3H), 2.36 (s, 3H), 2.23 (s, 3H). LCMS (ES+) (M+H)$^+$ 418.2, RT 2.46 minutes (99%).

Example 114

7-Fluoro-5-[3-(1H-pyrazol-5-yl)phenyl]-3-[(1,3,5-trimethyl-1H-pyrazol-4-yl)methyl]-1,3-benzoxazol-2(3H)-one Prepared from Intermediate 78 and [3-(1H-pyrazol-5-yl)phenyl]boronic acid in a similar manner to that described for Example 69. δ$_H$ (400 MHz, CD$_3$OD) 7.97 (s, 1H), 7.78 (t, J 4.6 Hz, 1H), 7.70 (s, 1H), 7.51 (d, J 4.4 Hz, 2H), 7.31 (d, J 11.4 Hz, 1H), 7.13 (s, 1H), 6.75 (d, J 2.3 Hz, 1H), 4.94 (s, 2H), 3.69 (s, 3H), 2.35 (s, 3H), 2.24 (s, 3H). LCMS (ES+) (M+H)$^+$ 418.2, RT 2.29 minutes (99%).

Example 115

7-Fluoro-5-(2-fluoropyridin-3-yl)-3-[(1,3,5-trimethyl-1H-pyrazol-4-yl)methyl]-1,3-benzoxazol-2(3H)-one Prepared from Intermediate 78 and (2-fluoropyridin-3-yl)boronic acid in a similar manner to that described for Example 69. δ$_H$ (400 MHz, CD$_3$OD) 8.21 (dq, J 4.5, 2.5, 2.0 Hz, 1H), 8.04 (ddd, J 9.8, 7.5, 2.1 Hz, 1H), 7.42 (ddt, J 7.6, 4.6, 2.2 Hz, 1H), 7.25 (dd, J 11.4, 2.6 Hz, 1H), 7.09 (q, J 1.9 Hz, 1H), 4.92 (s, 2H), 3.69 (s, 3H), 2.33 (s, 3H), 2.20 (s, 3H). LCMS (ES+) (M+H)$^+$ 371.1, RT 2.22 minutes (99%).

Example 116

7-Fluoro-5-(6-fluoropyridin-3-yl)-3-[(1,3,5-trimethyl-1H-pyrazol-4-yl)methyl]-1,3-benzoxazol-2(3H)-one Prepared from Intermediate 78 and (6-fluoropyridin-3-yl)boronic acid in a similar manner to that described for Example 69. δ$_H$ (400 MHz, CD$_3$OD) 8.40 (d, J 2.6 Hz, 1H), 8.18-8.07 (m, 1H), 7.29 (d, J 11.1 Hz, 1H), 7.21-7.10 (m, 2H), 4.93 (s, 2H), 3.69 (s, 3H), 2.34 (s, 3H), 2.21 (s, 3H). LCMS (ES+) (M+H)$^+$ 371.2, RT 2.36 minutes (99%).

Example 117

7-Fluoro-5-(quinolin-8-yl)-3-[(1,3,5-trimethyl-1H-pyrazol-4-yl)methyl]-1,3-benzoxazol-2(3H)-one Prepared from Intermediate 78 and quinolin-8-ylboronic acid in a similar manner to that described for Example 69. δ$_H$ (400 MHz, CD$_3$OD) 8.84 (dd, J 4.2, 2.0 Hz, 1H), 8.44 (m, 1H), 7.98 (d, J 8.0 Hz, 1H), 7.80-7.48 (m, 3H), 7.23 (d, J 11.2 Hz, 1H), 7.19 (s, 1H), 4.91 (s, 2H), 3.65 (s, 3H), 2.23 (s, 3H), 2.19 (s, 3H). LCMS (ES+) (M+H)$^+$ 403.2, RT 2.41 minutes (100%).

Example 118

7-Fluoro-5-(3-methoxyphenyl)-3-[(1,3,5-trimethyl-1H-pyrazol-4-yl)methyl]-1,3-benzoxazol-2(3H)-one Prepared from Intermediate 78 and 3-methoxyphenylboronic acid in a similar manner to that described for Example 69. δ$_H$ (400 MHz, CD$_3$OD) 7.35 (t, J 8.0 Hz, 1H), 7.21 (dd, J 11.4, 1.9 Hz, 1H), 7.09 (d, J 7.6 Hz, 1H), 7.04 (d, J 3.6 Hz, 2H), 6.94 (dd, J 8.4, 2.3 Hz, 1H), 4.92 (s, 2H), 3.85 (s, 3H), 3.68 (s, 3H), 2.33 (s, 3H), 2.23 (s, 3H). LCMS (ES+) (M+H)$^+$ 382.2, RT 2.62 minutes (99%).

Example 119

3-{(2R)-2-Methyl-4-[(2-methylimidazo[1,2-a]pyridin-3-yl)methyl]-3-oxo-2H,3H,4H-pyrido[3,2-b][1,4]oxazin-6-yl}benzamide Prepared from racemic Example 74 (300 mg) by separation of the enantiomers using chiral preparative HPLC (Column: Chiralcel OD-H 25 cm; Mobile phase: 90:10 heptane:EtOH; Flow rate: 18 mL/minute; UV at 215 nm) to afford the title compound (147 mg) and the corresponding (S)-isomer (50 mg). δ$_H$ (500 MHz, DMSO-d$_6$) 8.64 (d, J 6.9 Hz, 1H), 8.50 (m, 1H), 8.12 (m, 2H), 7.92 (m, 1H), 7.71 (d, J 8.2 Hz, 1H), 7.55 (m, 2H), 7.46 (s, 1H), 7.38 (d, J 9.0 Hz, 1H), 7.12 (m, 1H), 6.69 (td, J 6.8, 1.0 Hz, 1H), 5.75 (m, 2H), 4.96 (q, J 6.7 Hz, 1H), 2.29 (s, 3H), 1.51 (d, J 6.7 Hz, 3H). SFC-MS: MH+ m/z 428, RT 56.65 minutes (99% e.e.). Method D HPLC-MS: MH+ m/z 428, RT 2.75 minutes (100%).

Example 120

7-(Piperidin-3-yl)-1-[(1,3,5-trimethyl-1H-pyrazol-4-yl)methyl]-3,4-dihydro-1,8-naphthyridin-2-one To a solution of Example 94 (1.6 g, 0.045 mol) in EtOH (25 mL) and 1N HCl (16 mL) was added PtO$_2$. The reaction mixture was stirred at 60 psi under a hydrogen atmosphere at ambient temperature for 8 h, then filtered through Celite. The organic layer was concentrated and the crude residue was dissolved in DCM (25 mL), then the pH was adjusted to 7 using saturated aqueous NaHCO$_3$ solution. The organic layer was separated, dried and concentrated. The crude residue was purified using column chromatography (silica: 100-200 mesh; 2% MeOH in DCM) to afford the title compound (1.2 g, 75%). δ$_H$ (400 MHz, CDCl$_3$) 7.42 (dd, J 7.5, 1.1 Hz, 1H), 6.82 (d, J 7.5 Hz, 1H), 5.13 (d, J 1.3 Hz, 2H), 3.68 (s, 3H), 3.56-3.42 (m, 1H), 3.39-3.27 (m, 1H), 3.20-3.09 (m, 1H), 2.83 (t, J 7.6 Hz, 2H), 2.67 (td, J 7.6, 7.0, 2.4 Hz, 2H), 2.27 (s, 3H), 2.07 (t, J 12.8 Hz, 2H), 2.00 (s, 3H), 1.95-1.83 (m, 2H), 1.80-1.70 (m, 2H). LCMS (ES+) (M+H)$^+$ 354.4, RT 1.39 minutes (91%).

Example 121

3-{7-Oxo-8-[(1,3,5-trimethyl-1H-pyrazol-4-yl)methyl]-5,6,7,8-tetrahydro-1,8-naphthyridin-2-yl}piperidine-1-carboxamide To a solution of Example 120 (0.2 g, 0.00054 mol) in AcOH (3 mL), maintained at 0° C., was added KOCN (0.883 g, 0.01 mol). The reaction mixture was stirred at r.t. for 1 h, then dissolved in EtOAc (15 mL). The pH was adjusted to 7 using saturated aqueous NaHCO$_3$ solution. The organic layer was separated, dried and concentrated. The crude residue was purified by preparative TLC (100% EtOAc) to afford the title compound (5.9 mg, 32%). δ$_H$ (400 MHz, DMSO-d$_6$) 7.55 (d, J 7.5 Hz, 1H), 6.92 (d, J 7.5 Hz, 1H), 5.91 (s, 2H), 5.05 (s, 2H), 4.00 (dd, 1H), 3.54 (s, 3H), 2.85-2.73 (m, 2H), 2.68 (t, J 11.7 Hz, 2H), 2.60 (dd, J 8.7, 6.0 Hz, 2H), 2.17 (s, 3H), 1.97 (s, 3H), 1.91 (q, J 7.1, 4.6 Hz, 2H), 1.71-1.57 (m, 2H), 1.53-1.38 (m, 2H). LCMS (ES+) (M+H)+ 397, RT 1.80 minutes (98%).

Example 122

3-Methyl-7-(piperidin-3-yl)-1-[(1,3,5-trimethyl-1H-pyrazol-4-yl)methyl]-3,4-dihydro-1,5-naphthyridin-2-one Prepared from Example 87 in a similar manner to that described for Example 120 to afford the title compound (52 mg). $\delta_H$ (400 MHz, DMSO-$d_6$) 8.00 (s, 1H), 7.19 (s, 1H), 5.20 (m, 1H), 4.80 (m, 1H), 4.10 (br s, 1H), 3.58 (s, 3H), 3.19 (s, 1H), 3.00 (m, 3H), 2.78 (m, 2H), 2.72-2.48 (m, 3H), 2.19 (s, 3H), 1.99 (s, 3H), 1.80-1.75 (m, 2H), 1.95 (d, J 5.9 Hz, 3H).

Example 123

3-{7-Methyl-6-oxo-5-[(1,3,5-trimethyl-1H-pyrazol-4-yl)methyl]-5,6,7,8-tetrahydro-1,5-naphthyridin-3-yl}piperidine-1-carboxamide Prepared from Example 122 in a similar manner to that described for Example 121 to afford the title compound (18 mg, 8%). $\delta_H$ (400 MHz, CD$_3$OD) 8.05 (s, 1H), 7.27 (s, 1H), 5.21 (d, J 15.8 Hz, 1H), 4.94 (d, J 15.9 Hz, 1H), 4.02 (t, J 11.0 Hz, 2H), 3.63 (s, 3H), 3.11 (t, J 10.7 Hz, 1H), 3.00-2.53 (m, 5H), 2.23 (d, J 3.2 Hz, 3H), 2.09 (d, J 2.5 Hz, 3H), 1.95 (d, J 10.8 Hz, 2H), 1.79 (dd, J 10.7, 5.2 Hz, 2H), 1.64 (q, J 12.4 Hz, 2H), 1.27 (d, J 5.8 Hz, 3H). LCMS (ES+) (M+H)+ 411, RT 1.35 minutes (97%).

Example 124

7-(1-Acetylpiperidin-3-yl)-1-[(1,35-trimethyl-1H-pyrazol-4-yl)methyl]-3,4-dihydro-1,8-naphthyridin-2(1H)-one To a solution of Example 120 (0.2 g, 0.00056 mol) in DCM (3 mL), maintained at 0° C., was added pyridine (0.134 mL, 0.0016 mol), followed by acetyl chloride (0.048 mL, 0.00067 mol). The reaction mixture was stirred at r.t. for 3 h, then concentrated and purified by preparative HPLC, to afford the title compound (34 mg, 15%). $\delta_H$ (400 MHz, DMSO-$d_6$) 7.57 (t, J 7.4 Hz, 1H), 6.94 (dd, J 17.0, 7.5 Hz, 1H), 5.06 (d, J 15.0 Hz, 2H), 4.43 (dd, 1H), 3.85 (t, J 15.2 Hz, 1H), 3.54 (s, 3H), 3.20 (t, J 12.3 Hz, 1H), 3.04 (t, J 13.0 Hz, 1H), 2.78 (t, J 7.4 Hz, 2H), 2.72-2.55 (m, 2H), 2.16 (s, 3H), 2.07-1.89 (m, 6H), 1.73 (t, J 11.9 Hz, 1H), 1.52 (d, J 13.0 Hz, 1H), 1.39 (d, J 12.7 Hz, 1H), 1.23 (s, 2H). LCMS (ES+) (M+H)+ 396.3, RT 1.73 minutes (100%).

Example 125

7-[1-(Methylsulfonyl)piperidin-3-yl]-1-[(1,3,5-trimethyl-1H-pyrazol-4-yl)methyl]-3,4-dihydro-1,8-naphthyridin-2(1H)-one To a solution of Example 120 (0.2 g, 0.00056 mol) in DCM (3 mL), maintained at 0° C., was added pyridine (0.134 mL, 0.0016 mol), followed by mesyl chloride (0.078 mL, 0.00078 mol). The reaction mixture was stirred at r.t. for 3 h, then concentrated and purified by preparative HPLC, to afford the title compound (36 mg, 15%). $\delta_H$ (400 MHz, CDCl$_3$) 7.39 (d, J 7.6 Hz, 1H), 6.82 (d, J 7.4 Hz, 1H), 5.18 (q, J 14.6 Hz, 2H), 4.01-3.74 (m, 2H), 3.65 (s, 3H), 2.97 (d, J 10.7 Hz, 1H), 2.81 (d, J 13.2 Hz, 5H), 2.67 (q, J 8.2, 7.4 Hz, 3H), 2.26 (s, 3H), 2.05 (s, 3H), 1.91 (d, 1H), 1.72 (dt, 4H). LCMS (ES+) (M+H)+ 432.3, RT 1.90 minutes (98%).

Example 126

3-{6-Methyl-7-oxo-8-[(1,3,5-trimethyl-1H-pyrazol-4-yl)methyl]-5,6-dihydro-1,8-naphthyridin-2-yl}piperidine-1-carboxamide Prepared from Example 100 in a similar manner to that described for Example 120, then Example 121, to afford the title compound (30 mg, 18%). $\delta_H$ (400 MHz, CD$_3$OD) 7.53 (d, J 7.5 Hz, 1H), 6.94 (d, J 7.6 Hz, 1H), 5.35-5.05 (m, 2H), 4.08 (dd, J 63.1, 11.9 Hz, 2H), 3.62 (s, 3H), 3.14-2.73 (m, 3H), 2.73-2.48 (m, 2H), 2.23 (s, 3H), 2.13-1.94 (m, 5H), 1.78 (t, J 12.4 Hz, 2H), 1.63 (t, J 13.3 Hz, 1H), 1.21 (dd, J 6.3, 2.0 Hz, 3H). LCMS (ES+) (M+H)+ 411.3, RT 1.68 minutes (99%).

Example 127

7-(1-Acetylpiperidin-3-yl)-3-methyl-1-[(1,3,5-trimethyl-1H-pyrazol-4-yl)methyl]-3,4-dihydro-1,8-naphthyridin-2(1H)-one Prepared from Example 100 in a similar manner to that described for Example 120, then Example 124, to afford the title compound (8 mg). LCMS (ES+) (M+H)+ 410.3, RT 2.05 minutes (96%).

Example 128

3-Methyl-7-[1-(methylsulfonyl)piperidin-3-yl]-1-[(1,3,5-trimethyl-1H-pyrazol-4-yl)-methyl]-3,4-dihydro-1,8-naphthyridin-2(1H)-one Prepared from Example 100 in a similar manner to that described for Example 120, then Example 125, to afford the title compound (25%). $\delta_H$ (400 MHz, CDCl$_3$) 7.38 (d, J 7.4 Hz, 1H), 6.94-6.68 (m, 1H), 5.36-4.97 (m, 2H), 4.08-3.75 (m, 2H), 3.65 (d, J 2.0 Hz, 3H), 3.07-2.92 (m, 1H), 2.91-2.74 (m, 4H), 2.74-2.45 (m, 4H), 2.25 (d, J 5.9 Hz, 4H), 2.06 (d, J 6.7 Hz, 4H), 1.78-1.65 (m, 2H), 1.25 (dd, J 6.5, 3.5 Hz, 3H). LCMS (ES+) (M+H)+ 446.3, RT 2.00 minutes (97%).

Example 129

6-{2-Methyl-3-oxo-4-[(1,3,5-trimethyl-1H-pyrazol-4-yl)methyl]-2H,3H,4H-pyrido[3,2-b][1,4]oxazin-6-yl}-2,3-dihydro-1,2-benzothiazole 1,1-dioxide To a solution of Intermediate 144 (250 mg, 0.57 mmol) in anhydrous 1,4-dioxane (5 mL) were added 6-bromo-2,3-dihydro-1,2-benzothiazole 1,1-dioxide (162 mg, 0.63 mmol) and 2M aqueous Na$_2$CO$_3$ solution (0.85 mL) and mixture was degassed with N$_2$ for 5 minutes. Pd(dppf)Cl$_2$ (23.27 mg, 0.03 mmol) was added and the mixture was degassed with N$_2$ for 5 minutes, then heated in a sealed tube at 100° C. for 1 h. After cooling, EtOAc (20 mL) and water (20 mL) were added. The aqueous layer was extracted with EtOAc (20 mL) and the combined organic layers were washed with brine (20 mL), then dried (Na$_2$SO$_4$). The solvent was removed in vacuo. The residue was purified by preparative HPLC (Method D) to give the title compound (145 mg, 55%) as a light brown solid. $\delta_H$ (500 MHz, DMSO-$d_6$) 8.35 (s, 1H), 8.34 (d, J 8.3 Hz, 1H), 7.88 (s, 1H), 7.79 (d, J 8.2

Hz, 1H), 7.67 (d, J 8.1 Hz, 1H), 7.54 (d, J 8.2 Hz, 1H), 5.16 (s, 2H), 4.93 (q, J 6.7 Hz, 1H), 4.47 (s, 2H), 3.54 (s, 3H), 2.17 (s, 3H), 1.96 (s, 3H), 1.51 (d, J 6.7 Hz, 3H). Method D HPLC-MS: MH+ m/z 454.3, RT 2.56 minutes (98%).

Example 130

6-{4-[(2,4-Dimethylpyridin-3-yl)methyl]-3-oxo-2H,3H,4H-pyrido[3,2-b][1,4]oxazin-6-yl}-2,3-dihydro-1,2-benzothiazole 1,1-dioxide Prepared from Intermediate 146 and 6-bromo-2,3-dihydro-1,2-benzothiazole 1,1-dioxide in a similar manner to that described for Example 129. $\delta_H$ (500 MHz, DMSO-$d_6$) 8.15 (d, J 4.9 Hz, 1H), 8.09 (dd, J 6.2, 1.8 Hz, 2H), 7.86 (s, 1H), 7.71 (d, J 8.2 Hz, 1H), 7.61 (d, J 8.6 Hz, 1H), 7.54 (d, J 8.2 Hz, 1H), 7.06 (d, J 5.0 Hz, 1H), 5.37 (s, 2H), 4.85 (s, 2H), 4.44 (s, 2H), 2.44 (s, 3H), 2.35 (s, 3H). Method A HPLC-MS: MH+ m/z 437.1, RT 2.98 minutes (99%).

Example 131

6-{2-Methyl-4-[(2-methylpyridin-3-yl)methyl]-3-oxo-2H,3H4H-pyrido[3,2-b][1,4]-oxazin-6-yl}-2,3-dihydro-1,2-benzothiazole 1,1-dioxide Prepared from Intermediates 146 and 164 in a similar manner to that described for Example 129. $\delta_H$ (500 MHz, DMSO-$d_6$) 8.16-8.10 (m, 3H), 7.83 (s, 1H), 7.80 (d, J 8.3 Hz, 1H), 7.57 (dd, J 8.2, 4.1 Hz, 2H), 7.39 (d, J 7.0 Hz, 1H), 7.10 (dd, J 7.8, 4.8 Hz, 1H), 5.36 (d, J 15.8 Hz, 1H), 5.30 (d, J 15.8 Hz, 1H), 5.12 (q, J 6.7 Hz, 1H), 4.41 (s, 2H), 2.62 (s, 3H), 1.58 (d, J 6.8 Hz, 3H). Method D HPLC-MS: MH+ m/z 437.1, RT 1.69 minutes (98%).

Example 132

6-{8-Fluoro-3-oxo-4-[(1,3,5-trimethyl-1H-pyrazol-4-yl)methyl]-3,4-dihydro-2H-1,4-benzoxazin-6-yl}-2,3-dihydro-1,2-benzothiazole 1,1-dioxide Prepared from Intermediate 145 and 6-bromo-2,3-dihydro-1,2-benzothiazole 1,1-dioxide in a similar manner to that described for Example 129. $\delta_H$ (500 MHz, DMSO-$d_6$) 8.03 (d, J 1.2 Hz, 1H), 7.94 (dd, J 8.1, 1.7 Hz, 1H), 7.89 (s, 1H), 7.65 (d, J 8.1 Hz, 1H), 7.47 (dd, J 11.5, 1.8 Hz, 1H), 7.26 (s, 1H), 5.12 (s, 2H), 4.87 (s, 2H), 4.45 (s, 2H), 3.54 (s, 3H), 2.19 (s, 3H), 1.99 (s, 3H). Method D HPLC-MS: MH+ m/z 457, RT 2.52 minutes (98%).

Example 133

8-Fluoro-6-(4-oxo-5,6,7,8-tetrahydrothiazolo[4,5-c]azepin-2-yl)-4-[(1,3,5-trimethyl-1H-pyrazol-4-yl)methyl]-1,4-benzoxazin-3-one Prepared from Intermediates 145 and 167 in a similar manner to that described for Example 129. $\delta_H$ (400 MHz, CDCl$_3$) 7.45 (s, 1H), 7.36 (dd, 1H, J 10.4, 1.8 Hz), 6.52-6.46 (m, 1H), 5.08 (s, 2H), 4.78 (s, 2H), 3.69 (s, 3H), 3.40 (m, 2H), 3.18 (t, 2H, J 7.1 Hz), 2.37 (s, 3H), 2.24-2.16 (m, 5H). LCMS (ES+) (M+H)+ 456, RT 1.66 minutes (Method 2).

Example 134

8-Fluoro-6-(4-oxo-4,5,6,7-tetrahydro-1-benzothiophen-2-yl)-4-[(1,3,5-trimethyl-1H-pyrazol-4-yl)methyl]-3,4-dihydro-2H-1,4-benzoxazin-3-one Prepared from Intermediate 145 and 2-bromo-6,7-dihydro-5H-benzothiophen-4-one in a similar manner to that described for Example 129. Method D HPLC-MS: MH+m/z 440, RT 3.97 minutes (98%).

Example 135

8-Fluoro-6-(4-oxo-3H-pyrrolo[2,1-f][1,2,4]triazin-6-yl)-4-[(1,3,5-trimethyl-1H-pyrazol-4-yl)methyl]-1,4-benzoxazin-3-one Prepared from Intermediate 145 and 6-bromo-3H-pyrrolo[2,1-f][1,2,4]triazin-4-one in a similar manner to that described for Example 129. LCMS (ES+) (M+H)+ 423, RT 1.21 minutes (Method 3).

Example 136

(2R)-8-Fluoro-2-methyl-6-(1-methyl-1H-pyrazolo[4,3-b]pyridin-6-yl)-4-[(1,3,5-trimethyl-1H-pyrazol-4-yl)methyl]-3,4-dihydro-2H-1,4-benzoxazin-3-one Prepared from Intermediates 150 and 168 in a similar manner to that described for Example 129. $\delta_H$ (500 MHz, DMSO-$d_6$) 8.83 (d, J 1.9 Hz, 1H), 8.41-8.36 (m, 1H), 8.31 (s, 1H), 7.55 (dd, J 11.4, 1.7 Hz, 1H), 7.38 (s, 1H), 5.25 (d, J 15.8 Hz, 1H), 5.02 (d, J 15.7 Hz, 1H), 4.97 (q, J 6.7 Hz, 1H), 4.13 (s, 3H), 3.52 (s, 3H), 2.18 (s, 3H), 2.00 (s, 3H), 1.55 (d, J 6.7 Hz, 3H). Column: Chiralpak AS-H 25 cm; Mobile phase: 15% EtOH: 85% CO$_2$; Flow rate: 4 mL/minute; UV at 215 nm; Runtime: 6 minutes. Method D HPLC-MS: MH+ m/z 435.2, RT 2.72 minutes (100%).

Example 137

(2R)-8-Fluoro-2-methyl-6-(2-methyl-2H-pyrazolo[4,3-b]pyridin-6-yl)-4-[(1,3,5-trimethyl-1H-pyrazol-4-yl)methyl]-3,4-dihydro-2H-1,4-benzoxazin-3-one Prepared from Intermediates 150 and 169 in a similar manner to that described for Example 129. $\delta_H$ (500 MHz, DMSO-$d_6$) 8.79 (d, J 2.0 Hz, 1H), 8.68 (s, 1H), 8.31-8.23 (m, 1H), 7.50 (dd, J 11.4, 1.7 Hz, 1H), 7.32 (s, 1H), 5.24 (d, J 15.8 Hz, 1H), 5.02 (d, J 15.8 Hz, 1H), 4.96 (q, J 6.7 Hz, 1H), 4.25 (s, 3H), 3.52 (s, 3H), 2.17 (s, 3H), 2.00 (s, 3H), 1.54 (d, J 6.7 Hz, 3H). Column: Chiralcel OD-H 25 cm; Mobile phase: 32% EtOH: 68% CO$_2$; Flow rate: 2 mL/minute; UV at 215 nm; Runtime: 10 minutes. Method D HPLC-MS: MH+ m/z 435.2, RT 2.54 minutes (97%).

Example 138

(2R)-8-Fluoro-2-methyl-6-(1H-pyrazolo[4,3-b]pyridin-6-yl)-4-[(1,3,5-trimethyl-1H-pyrazol-4-yl)methyl]-3,4-dihydro-2H-1,4-benzoxazin-3-one Prepared from Intermediate 150 and 6-bromo-1H-pyrazolo[4,3-b]pyridine in a similar manner to that described for Example 129. $\delta_H$ (500 MHz, DMSO-$d_6$) 13.52 (s, 1H), 8.77 (d, J 2.0 Hz, 1H), 8.33 (s, 1H), 8.12 (s, 1H), 7.50 (dd, J 11.3, 1.8 Hz, 1H), 7.29 (s, 1H), 5.22 (d, J 15.8 Hz, 1H), 5.00 (d, J 15.8 Hz, 1H), 4.95 (q, J 6.7 Hz, 1H), 3.52 (s, 3H), 2.16 (s, 3H), 1.99 (s, 3H), 1.53 (d, J 6.7 Hz, 3H). Method A HPLC-MS: MH+ m/z 421.05, RT=3.48 minutes (99%).

Example 139

8-Fluoro-6-(4-methoxy-1H-indazol-6-yl)-4-[(1,3,5-trimethyl-1H-pyrazol-4-yl)methyl]-3,4-dihydro-2H-1,4-benzoxazin-3-one Prepared from Intermediate 145 and 6-bromo-4-methoxy-1H-indazole in a similar manner to that described for Example 129. $\delta_H$ (500 MHz, DMSO-$d_6$) 13.22 (s, 1H), 8.05 (s, 1H), 7.40 (d, J 11.4 Hz, 1H), 7.21 (s, 1H), 7.20 (s, 1H), 6.72 (s, 1H), 5.12 (s, 2H), 4.86 (s, 2H), 4.01 (s, 3H), 3.55 (s, 3H), 2.20 (s, 3H), 2.03 (s, 3H). Method D HPLC-MS: MH+m/z 436.1, RT 2.83 minutes (100%).

Example 140

4-[(2,4-Dimethylpyridin-3-yl)methyl]-6-(4-oxo-4H,5H,6H,7H,8H-thieno[3,2-c]azepin-2-yl)-2H,3H,4H-pyrido[3,2-b][1,4]oxazin-3-one Prepared from Intermediates 146 and 174 in a similar manner to that described for Example 129. $\delta_H$ (500 MHz, DMSO-$d_6$) 8.20 (d, J 4.9 Hz, 1H), 7.98 (t, J 5.2 Hz, 1H), 7.81 (s, 1H), 7.64 (d, J 8.2 Hz, 1H), 7.53 (d, J 8.2 Hz, 1H), 7.07 (d, J 5.0 Hz, 1H), 5.39 (s, 2H), 4.83 (s, 2H), 3.25-3.18 (m, 2H), 3.13 (t, J 6.9 Hz, 2H), 2.54 (s, 3H), 2.39 (s, 3H), 2.05 (dt, J 12.6, 6.9 Hz, 2H). Method A HPLC-MS: MH+ m/z 435, RT 2.97 minutes (97%).

Example 141

8-Fluoro-6-(4-oxo-4H,5H,6H,7H,8H-thieno[3,2-c]azepin-2-yl}-4-[(1,3,5-trimethyl-1H-pyrazol-4-yl)methyl]-3,4-dihydro-2H-1,4-benzoxazin-3-one Prepared from Intermediates 145 and 174 in a similar manner to that described for Example 129. $\delta_H$ (500 MHz, DMSO-$d_6$) 7.94 (t, J 5.4 Hz, 1H), 7.57 (s, 1H), 7.26 (dd, J 11.2, 1.8 Hz, 1H), 7.08 (s, 1H), 5.07 (s, 2H), 4.83 (s, 2H), 3.57 (s, 3H), 3.17 (q, J 5.5 Hz, 2H), 3.08 (t, J 6.9 Hz, 2H), 2.24 (s, 3H), 2.03 (s, 3H), 2.02-1.98 (m, 2H). Method D HPLC-MS: MH+ m/z 455, RT 3.53 minutes (99%).

Example 142

6-(7,7-Dimethyl-4-oxo-6,8-dihydro-5H-thiazolo[5,4-c]azepin-2-yl)-4-[(1,3,5-trimethyl-1H-pyrazol-4-yl)methyl]pyrido[3,2-b][1,4]oxazin-3-one Prepared from Intermediate 146 and 2-bromo-7,7-dimethyl-6,8-dihydro-5H-thiazolo[5,4-c]azepin-4-one in a similar manner to that described for Example 129. $\delta_H$ (400 MHz, DMSO-$d_6$) 7.33 (d, 1H, J 8.2 Hz), 6.50 (t, 1H, J 4.8 Hz), 5.25 (s, 2H), 4.70 (s, 2H), 3.68 (s, 3H), 3.17 (d, 2H, J 5.3 Hz), 3.05 (s, 2H), 2.34 (s, 3H), 2.16 (s, 3H), 1.16 (s, 6H). LCMS (ES+) (M+H)+ 467, RT 1.92 minutes (Method 2).

Example 143

(2R)-8-Fluoro-2-methyl-6-(6-methylpyridin-3-yl)-4-[(1,3,5-trimethyl-1H-pyrazol-4-yl)-methyl]-3,4-dihydro-2H-1,4-benzoxazin-3-one A solution of Intermediate 101(340 mg, 1.01 mmol), (6-methylpyridin-3-yl)-boronic acid (165 mg, 1.21 mmol), 2M aqueous Na$_2$CO$_3$ solution (1.51 mL) and X-Phos (24 mg, 0.05 mmol) in 1,4-dioxane (10 mL) was degassed with N$_2$ for 10 minutes. Pd$_2$(dba)$_3$ (23 mg, 0.025 mmol) was added and the mixture was heated at 100° C. for 3 h, then cooled. The residue was diluted with EtOAc (10 mL) and the solids were removed by filtration through Kieselguhr. The filtrate was evaporated under reduced pressure. The resulting yellow solid was purified by column chromatography (SiO$_2$; gradient 0-6% MeOH/DCM) to give the title compound (168 mg, 38%). Method B HPLC-MS: MH+ m/z 395, RT 1.49 minutes (85%).

Example 144

6-(3-Methoxyphenyl)-4-[1-(2-methylimidazo[1,2-a]pyridin-3-yl)ethyl]pyrido[3,2-b][1,4]-oxazin-3-one To a solution of Intermediate 79 (0.15 g, 0.59 mmol) in DMF at 0° C. was added portionwise sodium hydride and the mixture was stirred for 10 minutes. 3-(1-Chloro-ethyl)-2-methylimidazo[1,2-a]pyridine (0.13 g, 0.67 mmol) in DMF (2 mL) was added dropwise. The mixture was stirred for an extra 30 minutes at 0° C. The reaction mixture was poured into EtOAc/water. The layers were separated and the organic layer was washed three times with water, then dried over MgSO$_4$ and concentrated under vacuum. The residue was purified by gradient silica column chromatography, eluting with 0-80% EtOAc in DCM, followed by preparative chromatography, to afford the title compound (10 mg, 4%) as a white solid. $\delta_H$ (400 MHz, CDCl$_3$) 8.20 (d, 1H, J 7.0 Hz), 7.54-7.43 (m, 2H), 7.45-7.41 (m, 3H), 7.34 (d, 1H, J 8.2 Hz), 7.10 (dt, 1H, J 1.1, 6.8 Hz), 7.07-6.93 (m, 2H), 6.64 (dt, 1H, J 1.2, 6.8 Hz), 4.59 (dd, 2H, J 15.1 Hz), 3.90 (s, 3H), 2.66 (s, 3H), 2.17 (d, 3H, J 7.3 Hz). LCMS (ES+) (M+H)+ 415, RT 2.05 minutes (Method 2).

Example 145

4-[(6-Bromo-2-methylimidazo[1,2-a]pyridin-3-yl)methyl]-6-(3-methoxyphenyl)-2H,3H,4H-pyrido[3,2-b][1,4]oxazin-3-one A solution of Intermediate 40 in DMF (2 mL) was added dropwise to a suspension of Intermediate 79 (250.85 mg, 0.98 mmol) in DMF (10 mL). The mixture was treated with sodium hydride (60% oil dispersion, 117.46 g, 2.94 mmol) and stirred at r.t. for 2 h, then heated at 50° C. and stirred for 16 h. The mixture was cooled, quenched with saturated aqueous NH$_4$Cl solution and extracted with EtOAc. Solids were removed by filtration and the filtrate was concentrated to dryness in vacuo. The residue was purified by preparative chromatography (Method C) to give the title compound (31 mg, 7%) as a white solid. $\delta_H$ (250 MHz, DMSO-$d_6$) 8.95 (d, J 1.1 Hz, 1H), 7.65 (d, J 8.3 Hz, 1H), 7.55-7.46 (m, 3H), 7.41-7.31 (m, 2H), 7.25 (dd, J 9.5, 1.9 Hz, 1H), 6.97 (dd, J 7.2, 2.4 Hz, 1H), 5.68 (s, 2H), 4.83 (s, 2H), 3.80 (s, 3H), 2.31 (s, 3H). Method B HPLC-MS: MH+ m/z 478, RT 1.70 minutes (100%).

Example 146

6-(3-Methoxyphenyl)-4-{[6-(6-methoxypyridin-3-yl)-2-methylimidazo[1,2-a]pyridin-3-yl]methyl}-2H,3H,4H-pyrido[3,2-b][1,4]oxazin-3-one A mixture of Example 145 (31 mg, 0.07 mmol), (6-methoxypyridin-3-yl)boronic acid (10.19 mg, 0.07 mmol) and 2M aqueous Na₂CO₃ solution (0.1 mL) in 1,4-dioxane (1 mL) was degassed with nitrogen for 10 minutes. [1,1'-bis(diphenylphosphino)ferrocene]-dichloropalladium(II) (0.003 mmol, 0.002 mmol) was added. The mixture was heated at 100° C. for 18 h, then cooled and diluted with EtOAc. The solids were removed by filtration through Celite. The filtrate was concentrated in vacuo to give the crude title compound, which was used without further purification. Method B HPLC-MS: MH+ m/z 508, RT 1.73 minutes (82%).

Example 147

5-(3-{[6-(3-Methoxyphenyl)-3-oxo-2H,3H,4H-pyrido[3,2-b][1,4]oxazin-4-yl]methyl}-2-methylimidazo[1,2-a]pyridin-6-yl)-1,2-dihydropyridin-2-one A solution of Example 146 (33 mg, 65 µmol) in 1,4-dioxane (1 mL) was treated with 6M aqueous HCl (0.108 mL) and the mixture was heated at 70° C. for 16 h. The solvent was removed under reduced pressure and the residue was purified by neutral preparative chromatography (Method C) to give the title compound (5.5 mg, 62%). $\delta_H$ (250 MHz, CD₃OD) 9.03 (s, 1H), 7.64-7.33 (m, 9H), 7.29 (t, J 7.9 Hz, 1H), 6.87 (d, J 8.3 Hz, 1H), 6.29 (d, J 9.4 Hz, 1H), 5.81 (s, 2H), 4.74 (s, 2H), 3.77 (s, 3H), 2.55 (s, 3H). Method B HPLC-MS: MH+ m/z 494, RT 1.42 minutes (99%).

Example 148

(2R)-6-(1-Acetylpyrrolidin-3-yl)-8-fluoro-2-methyl-4-[(1,3,5-trimethyl-1H-pyrazol-4-yl)-methyl]-3,4-dihydro-2H-1,4-benzoxazin-3-one To a solution of Intermediate 153 (580 mg, 1.25 mmol) in dry DCM (15 mL) were added acetic anhydride (0.118 mL, 1.25 mmol) and acetic acid (0.035 mL, 1.88 mmol). Palladium on carbon (10%, 134 mg, 0.13 mmol) was added and the reaction mixture was stirred under an atmosphere of H₂ at r.t. for 18 h. The mixture was treated with more catalyst (10% Pd/C, 100 mg) and was stirred under H₂ for a further 6 h, then diluted with DCM. The solids were removed by filtration through celite. The residue was washed with MeOH and the filtrate was concentrated in vacuo. Purification by column chromatography (SiO₂; 0-10% MeOH in DCM) afforded the title compound (405 mg, 75%) as a mixture of diastereoisomers. Method B HPLC-MS: MH+ m/z 415, RT 2.40 minutes (99%).

Example 149

(2R)-6-(1-Acetylpyrrolidin-3-yl)-8-fluoro-2-methyl-4-[(1,3,5-trimethyl-1H-pyrazol-4-yl)-methyl]-3,4-dihydro-2H-1,4-benzoxazin-3-one (Isomer A)

Prepared from Example 148 by separation of the mixture of diastereoisomers using SFC (10% IPA+0.1% DEA: 90% CO₂ with Chiralpak AD-H). $\delta_H$ (DMSO-d₆) 6.94 (m, 1H), 6.83 (m, 1H), 5.12 (m, 1H), 4.89-4.78 (m, 2H), 3.80 (m, 1H), 3.65-3.58 (m, 0.5H), 3.56 (s, 3H+0.5H), 3.47 (m, 0.5H), 3.36 (s, 0.5H), 3.31-3.19 (m, 1.5H), 3.07-2.98 (m, 0.5H), 2.19 (m, 0.5H), 2.19 (s, 3H), 2.14 (m, 0.5H), 2.00-1.90 (m, 6H), 1.90 (m, 0.5H), 1.86-1.76 (m, 0.5H), 1.48 (d, J 6.7 Hz, 3H). Chiral analysis: d.e. 100%; Column: Chiralpak AS-H 25 cm; Mobile phase: 15% IPA+0.1% DEA: 85% CO₂; Flow rate: 4 mL/minute; UV at 215 nm; Runtime: 40 minutes. Method A HPLC-MS: MH+ m/z 415, RT 3.45 minutes (100%).

Example 150

(2R)-6-(1-Acetylpyrrolidin-3-yl)-8-fluoro-2-methyl-4-[(1,3,5-trimethyl-1H-pyrazol-4-yl)-methyl]-3,4-dihydro-2H-1,4-benzoxazin-3-one (Isomer B)

Prepared from Example 148 by separation of the mixture of diastereoisomers using SFC (10% IPA+0.1% DEA: 90% CO₂ with Chiralpak AD-H). $\delta_H$ (DMSO-d₆) 6.95 (m, 1H), 6.84 (m, 1H), 5.10 (dd, J 15.7, 5.7 Hz, 1H), 4.85 (m, 2H), 3.86-3.74 (m, 1H), 3.62 (t, J 8.1 Hz, 0.5H), 3.54 (s, 3H+0.5H), 3.50-3.44 (m, 0.5H), 3.37 (s, 0.5H), 3.30-3.20 (m, 1.5H), 3.08-2.98 (m, 0.5H), 2.24 (m, 0.5H), 2.19 (s, 3H), 2.17-2.11 (m, 0.5H), 1.99-1.94 (m, 6H), 1.92 (m, 0.5H), 1.88-1.76 (m, 1.5H), 1.48 (dd, J 6.7, 1.6 Hz, 3H). Chiral analysis: d.e. 92%; Column: Chiralpak AS-H 25 cm; Mobile phase: 15% IPA+0.1% DEA: 85% CO₂; Flow rate: 4 mL/minute; UV at 215 nm; Runtime: 40 minutes. Method A HPLC-MS: MH+ m/z 415, RT 3.47 minutes (100%).

Example 151

(2R)-6-(1-Benzyl-1,2,5,6-tetrahydropyridin-3-yl)-2-methyl-4-[(1,3,5-trimethyl-1H-pyrazol-4-yl)methyl]-2H,3H,4H-pyrido[3,2-b][1,4]oxazin-3-one A solution of Intermediate 132 (300 mg, 0.82 mmol), 1-benzyl-5-(4,4,5,5-tetramethyl-1,3,2-dioxaborolan-2-yl)-1,2,3,6-tetrahydropyridine (245.78 mg, 0.82 mmol) and 2M aqueous Na₂CO₃ solution (1.23 mL) in 1,4-dioxane (10 mL) was degassed with N₂ for 10 minutes, then Pd(dppf)Cl₂ (67.08 mg, 0.08 mmol) was added. The mixture was heated at 60° C. for 1 h, then cooled to r.t. and partitioned between EtOAc (50 mL) and water (20 mL). The aqueous layer was extracted with EtOAc (2×25 mL), then the combined organic layers were dried (Na₂SO₄) and the solvent was removed in vacuo. The residue was purified by column chromatography (SiO₂; 0-10% MeOH/EtOAc) to give the title compound (300 mg, 80%). $\delta_H$ (500 MHz, CDCl₃) 7.39 (s, 2H), 7.31 (t, J 7.4 Hz, 2H), 7.26 (s, 1H, includes chloroform peak), 7.16 (d, J 8.2 Hz, 1H), 6.97 (d, J 8.2 Hz, 1H), 6.58 (d, J 3.9 Hz, 1H), 5.11 (q, J 14.5 Hz, 2H), 4.59 (q, J 6.8 Hz, 1H), 3.72 (s, 2H), 3.65 (s, 3H), 3.48 (s, 2H), 2.64 (s, 2H), 2.36 (d, J 37.3 Hz, 2H), 2.19 (s, 3H), 2.08 (s, 3H), 1.57 (d, J 12.3 Hz, 2H), 1.52 (d, J 6.8 Hz, 3H). Method B HPLC-MS: MH+ m/z 458, RT 1.38 minutes (99%).

Example 152

(2R)-2-Methyl-6-(piperidin-3-yl)-4-[(1,3,5-trimethyl-1H-pyrazol-4-yl)methyl]-2H,3H,4H-pyrido[3,2-b][1,4]oxazin-3-one A solution of Example 151 (299.8 mg, 0.66 mmol) in EtOH (20 mL) was treated with Pearlman's catalyst (10% on carbon, 180 mg, 0.14 mmol) and stirred under a hydrogen atmosphere for 1 day at r.t. The catalyst was removed by filtration through Kieselguhr, washed with EtOH and concentrated under reduced pressure. The residue was purified by column chromatography (SiO₂; 0-10% MeOH/DCM) to give the title compound (63 mg, 24%). Method D HPLC-MS: MH+ m/z 398, RT 1.52 minutes (91%).

Example 153

(2R)-6-[1-(Methanesulfonyl)piperidin-3-yl]-2-methyl-4-[(1,3,5-trimethyl-1H-pyrazol-4-yl)methyl]-2H,3H,4H-pyrido[3,2-b][1,4]oxazin-3-one To a solution of Example 152 (133.8 mg, 0.23 mmol) and triethylamine (64.61 µL, 0.46 mmol) in DCM (1 mL) at 0° C. was added a solution of methanesulfonyl chloride (36 µL, 0.46 mmol) in DCM (0.5 mL). The mixture was stirred for 2 h at 0° C. Saturated aqueous NaHCO₃ solution (5 mL) was added and the mixture was extracted with DCM (3×5 mL). The combined organic layers were dried ($Na_2SO_4$) and concentrated under reduced pressure. The residue was purified by column chromatography ($SiO_2$; 0-10% MeOH/DCM) to give the title compound (56 mg, 52%). $\delta_H$ (500 MHz, $CDCl_3$) 7.26 (s, 2H), 7.17 (d, J 8.0 Hz, 1H), 6.82 (d, J 8.0 Hz, 1H), 5.22-5.04 (m, 2H), 4.68-4.54 (m, 1H), 3.93-3.85 (m, 1H), 3.85-3.78 (m, 1H), 3.67 (2×s, 3H), 3.05-2.90 (m, 1H), 2.82-2.62 (m, 5H), 2.27 (2×s, 3H), 2.14 (2×s, 3H), 2.08-1.96 (m, 1H), 1.91 (dd, J 10.2, 3.1 Hz, 1H), 1.83-1.48 (m, 5H). Method D HPLC-MS: MH+ m/z 448.1, RT 2.76 minutes (96%).

Example 154

6-(1-Acetyl-1,4,5,6-tetrahydropyridin-3-yl)-4-[(1,3,5-trimethyl-1H-pyrazol-4-yl)methyl]-2H,3H,4H-pyrido[3,2-b][1,4]oxazin-3-one A solution of Intermediate 147 (0.81 g, 1.8 mmol), 1-(5-bromo-1,2,3,4-tetrahydro-pyridin-1-yl)ethan-1-one (0.43 g, 1.8 mmol) in 1,4-dioxane (20 mL) and 2M aqueous $Na_2CO_3$ solution (2.76 mL, 5.5 mmol) in 1,4-dioxane (10 mL) was degassed with nitrogen, then Pd(dppf)Cl₂ (0.074 g, 0.09 mmol) was added. The mixture was degassed with nitrogen and heated at 60° C. for 2 h, then cooled and filtered through celite. The residue was washed with EtOAc (20 mL) and the combined organic layers were washed with water (20 mL) and brine (20 mL), then dried ($Na_2SO_4$). The solvent was removed in vacuo. The residue was purified by column chromatography ($SiO_2$; 0-10% MeOH/DCM) to afford the title compound (216 mg, 28%). $\delta_H$ (500 MHz, DMSO-d₆) 7.69 (s, 1H), 7.35 (dd, J 11.0, 8.3 Hz, 1H), 7.15 (d, J 8.2 Hz, 1H), 5.08 (d, J 7.0 Hz, 2H), 4.71 (s, 2H), 3.63 (dt, J 16.5, 5.6 Hz, 2H), 3.55 (s, 3H), 2.24 (s, 2H), 2.18 (s, 3H), 1.99 (d, J 7.6 Hz, 3H), 1.90 (dt, J 33.8, 5.7 Hz, 2H). Method B HPLC-MS: MH+ m/z 396, RT 1.69 minutes (89%).

Example 155

6-(1-Benzyl-1,2,5,6-tetrahydropyridin-3-yl)-8-fluoro-4-[(1,3,5-trimethyl-1H-pyrazol-4-yl)methyl]-3,4-dihydro-2H-1,4-benzoxazin-3-one A suspension of Intermediate 137 (1.5 g, 4.07 mmol) in 1,4-dioxane (15 mL) was treated with 1-benzyl-5-(4,4,5,5-tetramethyl-1,3,2-dioxaborolan-2-yl)-1,2,3,6-tetrahydropyridine (1.34 g, 4.48 mmol) and 2M aqueous $Na_2CO_3$ solution (6.1 mL, 12.2 mmol). The mixture was degassed with N₂ for 5 minutes, then Pd(dppf)Cl₂ DCM (333 mg, 0.41 mmol) was added. The mixture was heated at 60° C. for 3 h, then cooled and partitioned between EtOAc (50 mL) and water (50 mL). The aqueous layer was extracted with EtOAc (2×30 mL) and the combined organic layers were washed with brine (40 mL), then dried ($MgSO_4$). The solvent was removed in vacuo. The residue was purified by column chromatography ($SiO_2$; 0-10% MeOH/EtOAc) to afford the title compound (983 mg, 51%). 6H (500 MHz, $CDCl_3$) 7.46-7.27 (m, 5H), 6.74 (dd, J 11.3, 1.6 Hz, 1H), 6.62 (s, 1H), 5.96 (s, 1H), 4.96 (s, 2H), 4.67 (s, 2H), 3.69 (s, 2H), 3.64 (s, 3H), 3.21 (s, 2H), 2.60 (s, 2H), 2.32 (s, 2H), 2.15 (s, 3H), 2.12 (s, 3H). Method B HPLC-MS: MH+ m/z 461, RT 1.52 minutes (98%).

Example 156

6-(1-Acetylpiperidin-3-yl)-4-[(6-bromo-2-methyl-imidazo[1,2-a]pyridin-3-yl)methyl]-8-fluoro-3,4-dihydro-2H-1,4-benzoxazin-3-one Intermediate 25 (86 mg, 0.36 mmol) in DCM (2 mL) was treated with thionyl chloride (0.2 mL, 2.76 mmol) and heated to reflux for 1 h. The mixture was cooled, then the volatiles were removed in vacuo. The resulting material was dissolved in DMF (1 mL), then added to a mixture of Intermediate 82 (40 mg, 0.14 mmol) and $Cs_2CO_3$ (186 mg, 0.57 mmol) in dry DMF (1 mL). The mixture was stirred for 18 h at r.t., then water (10 mL) was added. The precipitate was collected by filtration, washed with water (2×2 mL), dissolved in MeOH and concentrated under vacuum, to afford the title compound (45 mg, 64%). Method B HPLC-MS: MH+ m/z 517, RT 1.50 minutes (94%).

Example 157

6-(1-Acetylpiperidin-3-yl)-8-fluoro-4-({6-[4-(methanesulfonyl)phenyl]-2-methyl-imidazo[1,2-a]pyridin-3-yl}methyl)-3,4-dihydro-2H-1,4-benzoxazin-3-one Pd(dppf)Cl₂ (4 mg, 4.9 µmol) was added to a mixture of Example 156 (45 mg, 0.09 mmol), 4-(methylsulfonyl)phenylboronic acid (22 mg, 0.11 mmol) and 2M aqueous $Na_2CO_3$ solution (0.15 mL) in 1,4-dioxane (2 mL). The reaction mixture was degassed with nitrogen and heated at 100° C. for 3 h, then cooled. The volatiles were removed in vacuo. DMSO (1.25 mL) and water (0.25 mL) were added, and the solid was removed by filtration. The filtrate was purified by preparative HPLC (Method C) to afford the title compound (20 mg, 39%). $\delta_H$ (500 MHz, $CDCl_3$) 8.63-8.57 (m, 1H), 8.09-8.02 (m, 2H), 7.78-7.71 (m, 2H), 7.64-7.57 (m, 1H), 7.51-7.43 (m, 1H), 6.90-6.80 (m, 1H), 6.76-6.69 (m, 1H), 5.75-5.32 (m, 2H), 4.78-4.59 (m, 3H), 3.88-3.70 (m, 1H), 3.11 (s, 3H), 3.10-2.92 (m, 1H), 2.66 (s, 3H), 2.63-2.55 (m, 1H), 2.55-2.44 (m, 1H), 2.15-2.06 (m, 3H), 2.00-1.91 (m, 1H), 1.87-1.78 (m, 1H), 1.65-1.50 (m, 2H). Method D HPLC-MS: MH+ m/z 591, RT 1.95 minutes (100%).

Example 158

(2R)-6-(1-Acetylpiperidin-3-yl)-2-methyl-4-[(1,3,5-trimethyl-1H-pyrazol-4-yl)methyl]-2H,3H,4H-pyrido[3,2-b][1,4]oxazin-3-one Pearlman's catalyst (15 mg) was added to a solution of Intermediate 197 (58.9 mg, 0.14 mmol) in EtOH (2 mL) and the mixture was stirred under a hydrogen atmosphere for 22 h at r.t. Additional Pearlman's catalyst (15 mg) was added and the mixture was stirred under a hydrogen atmosphere for a further 18 h at r.t. The catalyst was removed by filtration through kieselguhr and the reaction mixture was concentrated in vacuo. The residue was purified by column chromatography (SiO$_2$; gradient 0-5% MeOH/DCM) to afford the title compound (19.3 mg, 34%). Method D HPLC-MS: MH+m/z 412, RT 2.5 minutes (99%).

Example 159

(2R)-6-[1-(Methanesulfonyl)piperidin-3-yl]-2-methyl-4-[(1,3,5-trimethyl-1H-pyrazol-4-yl)methyl]-2H,3H4H-pyrido[3,2-b][1,4]oxazin-3-one (Isomer A)

Prepared from Example 153 (40 mg) by separation of the mixture of diastereomers using chiral SCF chromatography (Chiralpak AD-H 25 cm, eluting with 8% EtOH in supercritical CO$_2$) to give the title compound (14.1 mg, 35.4%). $\delta_H$ (500 MHz, CDCl$_3$) 7.19 (d, J 8.0 Hz, 1H), 6.84 (d, J 8.0 Hz, 1H), 5.14 (dd, J 18.3 Hz, 2H), 4.64 (q, J 6.8 Hz, 1H), 3.93-3.87 (m, 1H), 3.84 (d, J 11.8 Hz, 1H), 3.68 (s, 3H), 2.99 (tt, J 11.0, 3.8 Hz, 1H), 2.83-2.76 (m, 4H), 2.71 (td, J 11.6, 2.8 Hz, 1H), 2.29 (s, 3H), 2.15 (s, 3H), 2.10-2.02 (m, 1H), 1.93 (dt, J 13.0, 3.2 Hz, 1H), 1.77 (m, 2H), 1.57 (d, J 6.8 Hz, 3H). Method D HPLC-MS: MH+ m/z 448, RT 2.76 minutes (100%).

Example 160

6-(1-Acetylpiperidin-3-yl)-4-[(1,3,5-trimethyl-1H-pyrazol-4-yl)methyl]-2H,3H,4H-pyrido[3,2-b][1,4]oxazin-3-one A solution of Example 154 (216 mg, 0.52 mmol) in EtOH/dichloroethane (1:1, 30 mL) was treated with palladium (5% on carbon, 52 mg, 0.02 mmol) in a pressure vessel under a hydrogen atmosphere and stirred at 50° C. for 24 h. The solid was removed by filtration through Celite, then the residue was washed with EtOAc (3×20 mL) and the solvent was removed in vacuo. The residue was purified by column chromatography (SiO$_2$; gradient 0-10% MeOH/DCM, then 20-100% EtOAc/DCM/0.5% TEA, then 0-5% MeOH/EtOAc/0.5% TEA) to give the title compound (67 mg, 34%). $\delta_H$ (500 MHz, CDCl$_3$) 7.17 (dd, J 16.0, 8.0 Hz, 1H), 6.80 (d, J 8.0 Hz, 1H), 5.30-5.05 (m, 2H), 4.77-4.62 (m, 1H), 4.60 (d, J 6.9 Hz, 2H), 4.01-3.79 (m, 1H), 3.67 (d, J 3.8 Hz, 3H), 3.30-3.01 (m, 1H), 2.87-2.53 (m, 2H), 2.28 (d, J 4.3 Hz, 3H), 2.15 (d, J 3.8 Hz, 3H), 2.11 (d, J 17.3 Hz, 3H), 2.08-2.03 (m, 1H), 1.88-1.70 (m, 2H), 1.70-1.53 (m, 1H). Method D HPLC-MS: MH+ m/z 398, RT 2.27 minutes (96%).

Examples 161 & 162

6-(1-Acetylpiperidin-3-yl)-4-[(1,3,5-trimethyl-1H-pyrazol-4-yl)methyl]-2H,3H,4H-pyrido[3,2-b][1,4]oxazin-3-one (Isomers A and B)

Prepared from racemic Example 160 (60 mg) by separation of the enantiomers using SFC chiral HPLC (85% CO$_2$/15% IPA/0.1% DEA on 25 cm AD-H column; Runtime 25 minutes; RT 15.6 & 19.2 minutes) to afford enantiomer A (20 mg) and enantiomer B (20 mg). Method D HPLC-MS: MH+ m/z 398, RT 2.27 minutes (98%).

Example 163

6-(1-Acetylpiperidin-3-yl)-8-fluoro-4-[(1,3,5-trimethyl-1H-pyrazol-4-yl)methyl]-3,4-dihydro-2H-1,4-benzoxazin-3-one A solution of Example 155 (400 mg, 0.85 mmol), acetic anhydride (100 μL, 1.06 mmol) and acetic acid (73 μL, 1.28 mmol) in DCM (8 mL) was treated with palladium (10% on carbon, 91 mg, 0.09 mmol) and stirred under an atmosphere of hydrogen for 18 h at r.t. The mixture was treated with palladium (10% on carbon, 45 mg, 0.04 mmol) and stirred at r.t. under an atmosphere of hydrogen for a further 24 h. The solids were removed by filtration through Celite and the residue was washed with DCM (10 mL). The organic layers were washed with saturated aqueous NaHCO$_3$ solution (2×15 mL) and brine (15 mL), then dried (MgSO$_4$). The residue was concentrated in vacuo. The resulting yellow gum was purified by preparative HPLC (Method A) to afford the title compound (193 mg, 55%). Method D HPLC-MS: MH$^+$ m/z 415, RT 2.43 minutes (100%).

Example 164

3-{[(2R)-6-(1-Acetylpiperidin-3-yl)-8-fluoro-2-methyl-3-oxo-3,4-dihydro-2H-1,4-benzoxazin-4-yl]methyl}-2-methylimidazo[1,2-a]pyridine-6-carbonitrile (Isomer A)

A solution of DIAD (0.14 mL, 0.68 mmol) in DCM (2 mL) was slowly added to a mixture of Intermediate 84A (191 mg, 0.62 mmol), Intermediate 24 (126.85 mg, 0.68 mmol) and triphenylphosphine (179.53 mg, 0.68 mmol) in anhydrous DCM (4 mL) at −20° C. The mixture was warmed to r.t. and stirring was continued for 90 h. Solvent was removed in vacuo. The residue was purified by column chromatography (SiO$_2$; gradient 0-100% EtOAc/heptane followed by 0-10% MeOH/DCM), then by preparative HPLC (Method A), to give the title compound (12 mg, 4%). $\delta_H$ (500 MHz, DMSO-d$_6$) 9.45-9.23 (m, 1H), 7.68-7.56 (m, 1H), 7.56-7.40 (m, 1H), 7.10-6.88 (m, 2H), 5.80-5.63 (m, 1H), 5.60-5.43 (m, 1H), 4.96-4.84 (m, 1H), 4.53-4.22 (m, 1H), 3.93-3.59 (m, 1H), 3.08-2.89 (m, 1H), 2.62-2.53 (m, 1H), 2.47-2.40 (m, 1H), 2.30-2.25 (m, 3H), 2.04-1.94 (m, 3H), 1.68 (s, 2H), 1.55-1.27 (m, 5H). Column: Chiralpak AS-H 25 cm; Mobile phase: 20% EtOH: 80% CO$_2$; Flow rate: 4 mL/minute; UV at 215 nm; Runtime: 10 minutes; 90% d.e. Method D HPLC-MS: MH+ m/z 476.2, RT 2.46 minutes (98%).

Example 165

(2R)-6-(1-Acetylpiperidin-3-yl)-4-[(3,5-dimethyl-3H-1,2,3-triazol-4-yl)methyl]-8-fluoro-2-methyl-3,4-dihydro-2H-1,4-benzoxazin-3-one A solution of Intermediate 44 (1.7 mmol) in DMF (10 mL) was added to a suspension of Intermediate 84 (400 mg, 1.3 mmol) and Cs$_2$CO$_3$ (1.28 g, 3.92 mmol) in DMF (10 mL). The mixture was stirred for 2 h at r.t., then diluted with water (30 mL) and brine (10 mL). The solid residue was collected by filtration and purified by column chromatography (SiO$_2$; 0-5% MeOH/DCM) to give the title compound (400 mg, 74%). 6H (500 MHz, DMSO-d$_6$) 7.01 (dd, J 32.6, 11.3 Hz, 1H), 6.93 (d, J 27.9 Hz, 1H), 5.44-5.32 (m, 1H), 5.30-5.21 (m, 1H), 4.94-4.85 (m, 1H), 4.38 (dd, J 61.1, 12.0 Hz, 1H), 3.95 (s, 3H), 3.87-3.66 (m, 1H), 3.09-2.97 (m, 1H), 2.71-2.53 (m, 2H), 2.12-2.05 (m, 3H), 2.05-1.97 (m, 3H), 1.87-1.78 (m, 1H), 1.78-1.68 (m, 1H), 1.68-1.58 (m, 1H), 1.52-1.48 (m, 3H), 1.42-1.30 (m, 1H). Method D HPLC-MS: MH+ m/z 416.1, RT 2.46 minutes (96%).

Example 166

3-{[(2R)-6-(1-Acetylpiperidin-3-yl)-8-fluoro-2-methyl-3-oxo-3,4-dihydro-2H-1,4-benzoxazin-4-yl]methyl}-2-methylimidazo[1,2-a]pyridine-6-carbonitrile (Isomer B)

Prepared from Intermediates 24 and 84B in a similar manner to that described for Example 164. $\delta_H$ (500 MHz, DMSO-d$_6$) 9.42-9.31 (m, 1H), 7.68-7.57 (m, 1H), 7.57-7.46 (m, 1H), 7.05-7.01 (m, 1H), 7.01-6.91 (m, 1H), 5.75-5.66 (m, 1H), 5.59-5.49 (m, 1H), 4.94-4.86 (m, 1H), 4.48-4.21 (m, 1H), 3.86-3.58 (m, 1H), 3.05-2.80 (m, 1H), 2.63-2.56 (m, 1H), 2.46-2.39 (m, 1H), 2.27 (s, 3H), 2.04-1.93 (m, 3H), 1.77-1.64 (m, 2H), 1.61-1.27 (m, 5H). Column: Chiralpak AS-H 25 cm; Mobile phase: 20% EtOH: 80% CO$_2$; Flow rate: 4 mL/minute; UV at 215 nm; Runtime: 10 minutes; 97% e.e. Method D HPLC-MS: MH+ m/z 476.2, RT 2.48 minutes (100%).

Example 167

(2R)-6-(1-Acetylpiperidin-3-yl)-8-fluoro-2-methyl-4-[(2-methylpyridin-3-yl)methyl]-3,4-dihydro-2H-1,4-benzoxazin-3-one Prepared from Intermediate 84 and (2-methylpyridin-3-yl)methanol in a similar manner to that described for Example 164. Column: Chiralcel OD-H 25 cm; Mobile phase: 15% EtOH+0.1% TEA: 85% CO$_2$; Flow rate: 0.3 mL/minute; UV at 254 nm; Runtime: 80 minutes; RT 44.4 & 59.3 minutes (diastereomeric mixture). Method D HPLC-MS: MH+ m/z 412, RT 1.87 minutes (95%).

Example 168

(2R)-6-(1-Acetylpiperidin-3-yl)-8-fluoro-2-methyl-4-[(2-methylimidazo[1,2-a]pyrazin-3-yl)methyl]-3,4-dihydro-2H-1,4-benzoxazin-3-one Prepared from Intermediates 26 and 84 in a similar manner to that described for Example 164. $\delta_H$ (500 MHz, CD$_3$OD) 8.89 (d, J 4.0 Hz, 1H), 8.48 (d, J 4.3 Hz, 1H), 7.96 (t, J 4.3 Hz, 1H), 6.93 (m, 1H), 6.88 (m, 1H), 5.84-5.44 (m, 2H), 4.78 (m, 1H), 4.63-4.40 (m, 1H), 4.00-3.71 (m, 1H), 3.23-2.91 (m, 1H), 2.72-2.54 (m, 2H), 2.52 (m, 3H), 2.14 (s, 2H), 2.08 (s, 1H), 1.97-1.72 (m, 2H), 1.68-1.44 (m, 5H). Method A HPLC-MS: MH+ m/z 452, RT 3.47 minutes (95%).

Example 169

(2R)-6-(1-Acetylpyrrolidin-3-yl)-4-[(6-bromo-7-fluoro-2-methylimidazo[1,2-a]pyridin-3-yl)methyl]-8-fluoro-2-methyl-3,4-dihydro-2H-1,4-benzoxazin-3-one Prepared from Intermediates 27 and 88 in a similar manner to that described for Example 164. $\delta_H$ (500 MHz, DMSO-d$_6$) 8.99-8.86 (m, 1H), 7.60-7.51 (m, 1H), 7.09-7.02 (m, 1H), 7.01-6.93 (m, 1H), 5.72-5.63 (m, 1H), 5.53-5.44 (m, 1H), 4.94-4.86 (m, 1H), 3.80-3.71 (m, 1H), 3.63-3.51 (m, 1H), 3.50-2.85 (m, 3H), 2.29-2.21 (m, 3H), 2.20-2.03 (m, 1H), 1.97-1.89 (m, 3H), 1.88-1.70 (m, 1H), 1.50 (d, J 6.7 Hz, 3H). Column: Chiralcel OD-H 25 cm; Mobile phase: 10% MeOH: 90% CO$_2$; Flow rate: 2 mL/minute; UV at 215 nm; Runtime: 60 minutes; 1:1 mixture of diastereomers. Method D HPLC-MS: MH+ m/z 533, RT 2.27 minutes (97%).

Example 170

(2R)-6-(1-Acetylpyrrolidin-3-yl)-8-fluoro-2-methyl-4-[(2-methylimidazo[1,2-a]pyridin-3-yl)methyl]-3,4-dihydro-2H-1,4-benzoxazin-3-one Prepared from Intermediate 88 and (2-methylimidazo[1,2-a]pyridin-3-yl)methanol in a similar manner to that described for Example 164. $\delta_H$ (500 MHz, DMSO-d$_6$) 8.41-8.31 (m, 1H), 7.44 (dd, J 9.0, 4.8 Hz, 1H), 7.24-7.18 (m, 1H), 7.04-6.91 (m, 3H), 5.69 (dd, J 16.5, 8.7 Hz, 1H), 5.52 (dd, J 16.3, 7.2 Hz, 1H), 4.94-4.86 (m, 1H), 3.80-3.71 (m, 1H), 3.62-3.43 (m, 2H), 3.31-2.98 (m, 2H), 2.39-2.33 (m, 3H), 2.19-2.02 (m, 1H), 1.96-1.90 (m, 3H), 1.89-1.68 (m, 1H), 1.52 (d, J 6.7 Hz, 3H). Column: Chiralpak AS-H 25 cm; Mobile phase: 85:15 heptane:EtOH+0.1% formic acid; Flow rate: 1 mL/minute; UV at 254 nm; Runtime: 80 minutes; 1:1 mixture of diastereomers. Method D HPLC-MS: MH+ m/z 436.9, RT 2.84 minutes (100%).

Example 171

6-(1-Acetylpyrrolidin-3-yl)-4-[(6-bromo-7-fluoro-2-methylimidazo[1,2-a]pyridin-3-yl)-methyl]-8-fluoro-3,4-dihydro-2H-1,4-benzoxazin-3-one Prepared from Intermediates 27 and 92 in a similar manner to that described for Example 164. $\delta_H$ (500 MHz, DMSO-d$_6$) 9.01-8.94 (m, 1H), 7.60-7.51 (m, 1H), 7.07-7.01 (m, 1H), 7.00-6.93 (m, 1H), 5.58 (s, 2H), 4.82 (s, 2H), 3.79-3.71 (m, 1H), 3.63-3.51 (m, 1H), 3.49-3.28 (m, 1H), 3.26-3.16 (m, 1H), 3.16-2.91 (m, 1H), 2.27 (s, 3H), 2.19-2.04 (m, 1H), 1.97-1.90 (m, 3H), 1.90-1.72 (m, 1H). Method D HPLC-MS: MH+ m/z 519.1, RT 2.03 minutes (100%).

Example 172

6-(1-Acetylpyrrolidin-3-yl)-4-[(6-bromo-7-fluoro-2-methylimidazo[1,2-a]pyridin-3-yl)methyl]-3,4-dihydro-2H-1,4-benzoxazin-3-one Prepared from Intermediates 27 and 96 in a similar manner to that described for Example 164. $\delta_H$ (500 MHz, DMSO-d$_6$) 9.05-8.93 (m, 1H), 7.60-7.49 (m, 1H), 7.22-7.13 (m, 1H), 6.99-6.86 (m, 2H), 5.58 (s, 2H), 4.71 (s, 2H), 3.78-3.70 (m, 1H), 3.62-3.52 (m, 1H), 3.49-3.16 (m, 2H), 3.13-2.90 (m, 1H), 2.27 (s, 3H), 2.18-2.02 (m, 1H), 1.97-1.89 (m, 3H), 1.88-1.70 (m, 1H). Method A HPLC-MS: MH+ m/z 501, 503, RT 3.04 minutes (100%).

Example 173

3-{[(2R)-6-(1-Acetylpyrrolidin-3-yl)-8-fluoro-2-methyl-3-oxo-3,4-dihydro-2H-1,4-benzoxazin-4-yl]methyl}-2-methylimidazo[1,2-a]pyridine-6-carbonitrile Prepared from Intermediates 24 and 88A in a similar manner to that described for Example 164. Column: Chiralcel OD-H 25 cm, Mobile phase: 12% MeOH: 88% CO$_2$; Flow rate: 4 mL/minute; UV at 215 nm; Runtime: 10

Example 174

(2R)-6-(1-Acetylpyrrolidin-3-yl)-4-[(2,4-dimethylpyridin-3-yl)methyl]-8-fluoro-2-methyl-3,4-dihydro-2H-1,4-benzoxazin-3-one Prepared from Intermediates 1 and 88A in a similar manner to that described for Example 164. Column: Chiralcel OD-H 25 cm; Mobile phase: 15% MeOH: 85% $CO_2$; Flow rate: 4 mL/minute; UV at 215 nm; Runtime: 10 minutes; RT 6.44 minutes. Method A HPLC-MS: MH+ m/z 412, RT 1.63 minutes (100%).

Example 175

6-(1-Acetylpiperidin-3-yl)-4-[(2,4-dimethylpyridin-3-yl)methyl]-8-fluoro-3,4-dihydro-2H-1,4-benzoxazin-3-one Prepared from Intermediates 1 and 82 in a similar manner to that described for Example 164. $\delta_H$ (500 MHz, DMSO-$d_6$) 8.20-8.12 (m, 1H), 7.06-6.99 (m, 1H), 6.98-6.84 (m, 1H), 6.69-6.58 (m, 1H), 5.31-5.13 (m, 2H), 4.83-4.65 (m, 2H), 4.47-4.37 (m, 0.5H), 4.30-4.20 (m, 0.5H), 3.87-3.73 (m, 0.5H), 3.63-3.48 (m, 0.5H), 3.03-2.91 (m, 0.5H), 2.91-2.76 (m, 0.5H), 2.59-2.51 (m, 1H), 2.47-2.43 (m, 3H), 2.42-2.37 (m, 1H), 2.31-2.25 (m, 3H), 2.04-1.94 (m, 3H), 1.77-1.63 (m, 2H), 1.58-1.21 (m, 2H). Method A HPLC-MS: MH+ m/z 412, RT 1.64 minutes (100%).

Examples 176 & 177

6-(1-Acetylpiperidin-3-yl)-8-fluoro-4-[(1,3,5-trimethyl-1H-pyrazol-4-yl)methyl]-3,4-dihydro-2H-1,4-benzoxazin-3-one (Isomers A and B)

Prepared from racemic Example 163 (170 mg) by separation of the enantiomers using SFC chiral HPLC (Column: Chiralpak AD-H 25 cm; mobile phase: 12% EtOH: 88% $CO_2$; flow rate: 15 mL/minute) to afford the title compounds. Chiral analysis was performed using SFC chiral HPLC. $\delta_H$ (500 MHz, DMSO-$d_6$) 6.97 (d, J 11.4 Hz, 0.5H), 6.91-6.83 (m, 1H), 6.79 (s, 0.5H), 5.13-4.85 (m, 2H), 4.75 (d, J 2.3 Hz, 2H), 4.44 (d, J 11.8 Hz, 0.5H), 4.30 (d, J 8.6 Hz, 0.5H), 3.82 (d, J 13.2 Hz, 0.5H), 3.70 (d, J 11.3 Hz, 0.5H), 3.56 (d, J 6.5 Hz, 3H), 3.05-2.92 (m, 1H), 2.68-2.56 (m, 0.5H), 2.48-2.44 (m, 1.5H), 2.22 (d, J 11.2 Hz, 3H), 2.06-1.91 (m, 6H), 1.82 (d, J 13.0 Hz, 1H), 1.72 (t, J 13.2 Hz, 1H), 1.67-1.57 (m, 1H), 1.55-1.42 (m, 0.5H), 1.41-1.25 (m, 0.5H).

Example 178

(2R)-6-(1-Acetylpiperidin-3-yl)-4-[(3,5-dimethyl-3H-1,2,3-triazol-4-yl)methyl]-8-fluoro-2-methyl-3,4-dihydro-2H-1,4-benzoxazin-3-one (Isomer A)

Prepared from Example 165 by separation of the mixture of diastereomers using chiral SCF chromatography (Column: Chiralpak OD-H 25 cm, eluting with 85% heptane: 15% EtOH) to give the title compound. $\delta_H$ (500 MHz, DMSO-$d_6$) 7.08-6.95 (m, 1H), 6.93 (d, J 28.3 Hz, 1H), 5.39 (dd, J 16.6, 6.7 Hz, 1H), 5.33-5.18 (m, 1H), 4.89 (qd, J 6.6, 3.4 Hz, 1H), 4.50-4.38 (m, 0.5H), 4.36-4.24 (m, 0.5H), 3.95 (s, 3H), 3.88-3.76 (m, 0.5H), 3.72-3.64 (m, 0.5H), 3.14-2.85 (m, 1H), 2.72-2.62 (m, 0.5H), 2.62-2.53 (m, 1H), 2.48-2.43 (m, 0.5H), 2.09 (d, J 2.9 Hz, 3H), 2.01 (d, J 8.6 Hz, 3H), 1.87-1.78 (m, 1H), 1.78-1.68 (m, 1H), 1.68-1.56 (m, 1H), 1.50 (d, J 6.7 Hz, 3H), 1.48-1.30 (m, 1H). Chiral SFC Column: Chiralpak OD-H 25 cm, eluting with 85% heptane: 15% EtOH, 96% d.e. Method D HPLC-MS: MH+ m/z 416.1, RT 2.46 minutes (100%).

Example 179

(2R)-6-(1-Acetylpiperidin-3-yl)-4-[(3,5-dimethyl-3H-1,2,3-triazol-4-yl)methyl]-8-fluoro-2-methyl-3,4-dihydro-2H-1,4-benzoxazin-3-one (Isomer B)

Prepared from Example 165 by separation of the mixture of diastereomers using chiral SCF chromatography (Column: Chiralpak OD-H 25 cm, eluting with 85% heptane: 15% EtOH) to give the title compound. $\delta_H$ (500 MHz, DMSO-$d_6$) 7.07-6.97 (m, 1H), 6.93 (d, J 27.6 Hz, 1H), 5.37 (d, J 16.6 Hz, 1H), 5.26 (dd, J 16.5, 4.9 Hz, 1H), 4.89 (qd, J 6.6, 3.4 Hz, 1H), 4.48-4.40 (m, 0.5H), 4.36-4.28 (m, 0.5H), 3.95 (d, J 1.8 Hz, 3H), 3.86-3.77 (m, 0.5H), 3.75-3.66 (m, 0.5H), 3.02 (t, J 12.5 Hz, 1H), 2.71-2.55 (m, 1H), 2.49-2.43 (m, 1H), 2.09 (d, J 8.8 Hz, 3H), 2.01 (d, J 6.7 Hz, 3H), 1.86-1.78 (m, 1H), 1.75-1.68 (m, 1H), 1.68-1.57 (m, 1H), 1.50 (d, J 6.7 Hz, 3H), 1.48-1.31 (m, 1H). Chiral SFC Column: Chiralpak OD-H 25 cm, eluting with 85% heptane: 15% EtOH, 99% d.e. Method D HPLC-MS: MH+ m/z 416.1, RT 2.46 minutes (96%).

Example 180

(2R)-6-(1-Acetylpiperidin-3-yl)-8-fluoro-2-methyl-4-[(2-methylpyridin-3-yl)methyl]-3,4-dihydro-2H-1,4-benzoxazin-3-one (Isomer A)

Prepared from Example 167 by separation of the mixture of diastereomers using preparative chiral SCF (Column: Chiralpak AD-H 25 cm; Eluent: 10% IPA+0.1% TEA: 90% $CO_2$; Flow rate: 4 mL/minute; Runtime: 40 minutes; RT 24.8 minutes) to give the title compound. $\delta_H$ (500 MHz, DMSO-$d_6$) 8.32 (d, J 4.3 Hz, 1H), 7.31-7.22 (m, 1H), 7.16-7.11 (m, 1H), 7.02-6.92 (m, 1H), 6.72-6.62 (m, 1H), 5.21-5.06 (m, 2H), 5.03-4.95 (m, 1H), 4.41-4.19 (m, 1H), 3.80-3.57 (m, 1H), 3.03-2.91 (m, 1H), 2.65-2.40 (m, 2H), 2.55 (s, 3H), 1.99-1.90 (m, 3H), 1.73 (d, J 11.7 Hz, 1H), 1.69-1.61 (m, 1H), 1.60-1.48 (m, 4H), 1.47-1.20 (m, 1H). Method D HPLC-MS: MH+ m/z 412.2, RT 1.86 minutes (99%).

Example 181

(2R)-6-(1-Acetylpiperidin-3-yl)-8-fluoro-2-methyl-4-[(2-methylpyridin-3-yl)methyl]-3,4-dihydro-2H-1,4-benzoxazin-3-one (Isomer B)

Prepared from Example 167 by separation of the mixture of diastereomers using preparative chiral SCF (Column: Chiralpak AD-H 25 cm; Eluent: 15% EtOH: 85% heptane+ 0.1% TEA; Flow rate: 0.3 mL/minute; Runtime: 80 minutes; RT 45.9 minutes) to give the title compound. $\delta_H$ (500 MHz, DMSO-$d_6$) 8.35-8.30 (m, 1H), 7.31-7.22 (m, 1H), 7.17-7.10 (m, 1H), 7.03-6.91 (m, 1H), 6.72-6.61 (m, 1H), 5.23-5.15 (m, 1H), 5.10-5.03 (m, 1H), 5.03-4.96 (m, 1H), 4.41-4.15 (m, 1H), 3.79-3.54 (m, 1H), 3.03-2.91 (m, 1H), 2.65-2.53 (m, 1H), 2.55 (s, 3H), 2.53-2.40 (m, 1H), 1.97-1.90 (m, 3H), 1.75 (d, J 12.3 Hz, 1H), 1.68-1.61 (m, 1H), 1.60-1.48 (m, 1H), 1.53 (d, J 6.7 Hz, 3H), 1.47-1.21 (m, 1H). Method D HPLC-MS: MH+ m/z 412.2, RT 1.88 minutes (100%).

Example 182

Ethyl (3S)-3-methyl-1-{3-oxo-4-[(1,3,5-trimethyl-1H-pyrazol-4-yl)methyl]pyrido[3,2-b]-[1,4]oxazin-6-yl}piperidine-3-carboxylate A solution of 2-dicyclohexylphosphino-2',6'-diisopropoxybiphenyl (0.024 g, 0.052 mmol) and palladium(II) acetate (0.0058 g, 0.026 mmol) in 1,4-dioxane was degassed and heated under nitrogen for 5 minutes at 60° C. The mixture was cooled to r.t., then Intermediate 112 (0.13 g, 0.52 mmol), (S)-ethyl 3-methylpiperidine-3-carboxylate (0.094 g, 0.55 mmol) and cesium carbonate (0.51 g, 1.56 mmol) were added. The mixture was again degassed, then heated to reflux under nitrogen for 2 h. The reaction mixture was poured into EtOAc/water. The layers were separated and the organic layer was washed three times with water, then dried over MgSO$_4$ and concentrated under vacuum. The residue was purified by gradient silica column chromatography, eluting with 0-80% EtOAc in DCM, to afford the title compound (0.060 g, 30%) as a pale yellow oil. LCMS (ES+) (M+H)$^+$ 442, RT 1.53 minutes.

Example 183

(3S)-3-Methyl-1-{3-oxo-4-[(1,3,5-trimethyl-1H-pyrazol-4-yl)methyl]pyrido[3,2-b][1,4]-oxazin-6-yl}piperidine-3-carboxamide To a solution of Example 182 (0.06 g, 0.14 mmol) in THF/MeOH was added 2M aqueous NaOH solution (1 mL). The mixture was heated for 30 minutes at 50° C., then cooled to r.t. and neutralized with a 2M aqueous HCl solution. The organic layer was concentrated in vacuo, then the remaining water was removed by freeze drying. The crude residue was taken up in DMF at r.t., then ammonium chloride (0.073 g, 1.36 mmol), HATU (0.067 g, 0.18 mmol) and triethylamine (0.14 g, 1.36 mmol) were added. The mixture was stirred for 30 minutes, then quenched with saturated aqueous NaHCO$_3$ solution. The reaction mixture was poured into EtOAc/water. The layers were separated and the organic layer was washed three times with water, then dried over MgSO$_4$ and concentrated under vacuum. The residue was purified by gradient silica column chromatography, eluting with 0-80% EtOAc in DCM, to afford the title compound (0.017 g, 30%) as a white solid. $\delta_H$ (400 MHz, CDCl$_3$) 7.19 (d, 1H, J 8.5 Hz), 6.76 (s, 1H), 6.32 (d, 1H, J 8.6 Hz), 5.26 (s, 1H), 5.18-5.05 (m, 2H), 4.60-4.50 (m, 2H), 4.33 (d, 1H, J 13.3 Hz), 3.83-3.78 (m, 1H), 3.68 (s, 3H), 2.89-2.78 (m, 1H), 2.71 (d, 1H, J 13.4 Hz), 2.26 (m, 3H), 2.11 (s, 3H), 1.78-1.62 (m, 3H), 1.31 (m, 1H), 1.22 (s, 3H). LCMS (ES+) (M+H)$^+$ 413, RT 1.66 minutes.

Example 184

6-(1-Acetylpyrrolidin-3-yl)-8-fluoro-4-({7-fluoro-6-[2-(2-hydroxypropan-2-yl)pyrimidin-5-yl]-2-methyl-imidazo[1,2-a]pyridin-3-yl}methyl)-3,4-dihydro-2H-1,4-benzoxazin-3-one Aqueous Na$_2$CO$_3$ solution (2M, 0.3 mL) was added to a mixture of Example 171 (114 mg, 0.2 mmol) and 2-[5-(4,4,5,5-tetramethyl-1,3,2-dioxaborolan-2-yl)pyrimidin-2-yl] propan-2-ol (58 mg, 0.22 mmol) in 1,4-dioxane (2 mL). The mixture was degassed by bubbling through nitrogen for 10 minutes whilst sonicating. Pd(dppf)Cl$_2$ (8.1 mg, 0.01 mmol) was added in one portion and the mixture was degassed by bubbling through nitrogen for 5 minutes whilst sonicating. The reaction was heated, whilst stirring, at 100° C. under nitrogen in a sealed tube for 90 minutes before standing at r.t. overnight. The mixture was partitioned between EtOAc (30 mL) and saturated aqueous Na$_2$CO$_3$ solution (30 mL), then the organic phase was separated and the aqueous layer was extracted with EtOAc (2×30 mL). The combined organic extracts were washed with brine (20 mL) and dried over MgSO$_4$, then filtered and concentrated in vacuo. The crude residue was separated by preparative HPLC (Method A) to yield the title compound (41.8 mg, 37%). $\delta_H$ (500 MHz, DMSO-d$_6$) 9.06-8.98 (m, 2H), 8.89-8.83 (m, 1H), 7.61-7.51 (m, 1H), 7.12-7.05 (m, 1H), 7.02-6.93 (m, 1H), 5.68-5.58 (m, 2H), 5.19 (s, 1H), 4.82 (s, 2H), 3.78-3.68 (m, 1H), 3.54-3.40 (obs m, 2H), 3.23-2.91 (obs m, 2H), 2.35-2.31 (m, 3H), 2.17-2.00 (m, 1H), 1.92-1.88 (m, 3H), 1.87-1.67 (m, 1H), 1.56 (s, 6H). Method D HPLC-MS: MH+ m/z 577.3, RT 1.82 minutes (100%).

Example 185

6-(1-Acetylpyrrolidin-3-yl)-4-({7-fluoro-6-[2-(2-hydroxypropan-2-yl)pyrimidin-5-yl]-2-methylimidazo[1,2-a]pyridin-3-yl}methyl)-3,4-dihydro-2H-1,4-benzoxazin-3-one Prepared from Example 172 and 2-[5-(4,4,5,5-tetramethyl-1,3,2-dioxaborolan-2-yl)pyrimidin-2-yl]propan-2-ol in a similar manner to that described for Example 184 to afford the title compound. $\delta_H$ (500 MHz, DMSO-d$_6$) 9.04-8.98 (m, 2H), 8.91-8.84 (m, 1H), 7.60-7.50 (m, 1H), 7.26-7.18 (m, 1H), 6.98-6.88 (m, 2H), 5.63 (s, 2H), 5.18 (s, 1H), 4.72 (s, 2H), 3.77-3.67 (m, 1H), 3.53-3.38 (m, 2H), 3.23-2.90 (m, 2H), 2.35-2.31 (m, 3H), 2.16-1.98 (m, 1H), 1.93-1.87 (m, 3H), 1.87-1.66 (m, 1H), 1.56 (s, 6H). Method D HPLC-MS: MH+ m/z 559.2, RT 1.75 minutes (100%).

Example 186

6-(1-Acetylpyrrolidin-3-yl)-8-fluoro-4-{[7-fluoro-2-methyl-6-(1-methyl-1H-pyrazol-4-yl)imidazo[1,2-a]pyridin-3-yl]methyl}-3,4-dihydro-2H-1,4-benzoxazin-3-one Prepared from Example 171 and 1-methyl-4-(4,4,5,5-tetramethyl-1,3,2-dioxaborolan-2-yl)-1H-pyrazole in a similar manner to that described for Example 184 to afford the title compound (51%). Method A HPLC-MS: MH+ m/z 521.1, RT 2.83 minutes (100%).

Example 187

6-(Pyrrolidin-3-yl)-4-[(1,3,5-trimethyl-1H-pyrazol-4-yl)methyl]-2H,3H,4H-pyrido[3,2-b]-[1,4]oxazin-3-one Intermediate 155 (187 mg, 0.42 mmol) in dry DCM (5 mL) was flushed with nitrogen twice. Palladium (150 mg, 1.18 mmol) was added and the solution was flushed with nitrogen, followed by hydrogen, then stirred at r.t. for 60 h under hydrogen. The reaction mixture was diluted with DCM, filtered through a Celite cake, and washed with MeOH. Concentration in vacuo gave the title compound (136 mg, 83%). $\delta_H$ (500 MHz, CDCl$_3$) 9.95 (s, 1H), 7.13 (d, J 8.0 Hz, 1H), 6.80 (d, J 8.0 Hz, 1H), 5.14-4.97 (m, 2H), 4.55 (s, 2H), 3.69-3.61 (m, 1H), 3.60 (s, 3H), 3.58-3.53 (m, 1H), 3.52-3.44 (m, 1H), 3.41-3.32 (m, 2H), 2.40-2.28 (m, 1H), 2.20 (s, 3H), 2.19-2.09 (m, 1H), 2.01 (s, 3H). Method B HPLC-MS: MH+ m/z 342, RT 1.09 minutes (88%).

Example 188

6-[1-(Methanesulfonyl)pyrrolidin-3-yl]-4-[(1,3,5-trimethyl-1H-pyrazol-4-yl)methyl]-2H,3H,4H-pyrido[3,2-b][1,4]oxazin-3-one Triethylamine (0.1 mL, 0.701 mmol) was added to a solution of Example 187 (136 mg, 0.351 mmol) in DCM (3 mL). The resulting mixture was cooled to 0° C., then methanesulfonyl chloride (0.054 mL, 0.701 mmol) in DCM (0.5 mL) was added dropwise. The reaction mixture was stirred at r.t. for 1.5 h, then diluted with DCM and washed twice with water and once with brine. The organic phases were combined, dried over $Na_2SO_4$ and concentrated in vacuo. The crude residue was purified by preparative HPLC (Method C) to give the title compound (75 mg, 51%). $\delta_H$ (500 MHz, DMSO-$d_6$) 7.36 (d, J 8.0 Hz, 1H), 7.01 (d, J 8.1 Hz, 1H), 5.08-4.97 (m, 2H), 4.73 (s, 2H), 3.65 (dd, J 9.5, 7.9 Hz, 1H), 3.56 (s, 3H), 3.56-3.49 (m, 1H), 3.49-3.41 (m, 1H), 3.35 (m, 1H), 3.27 (t, J 9.3 Hz, 1H), 2.92 (s, 3H), 2.23 (m, 1H), 2.19 (s, 3H), 2.14-2.02 (m, 1H), 1.99 (s, 3H). Method A HPLC-MS: MH+ m/z 420, RT 3.24 minutes (100%).

Example 189 tert-Butyl 4-{7-fluoro-2-oxo-3-[(1,3,5-trimethyl-1H-pyrazol-4-yl)methyl]-1,3-benzoxazol-5-yl}piperidine-1-carboxylate To a solution of Example 107 (500 mg, 1.096 mmol) in EtOH (10 mL) was added 10% Pd/C (300 mg). The reaction mixture was stirred under a hydrogen atmosphere at r.t. for 6 h, then filtered through Celite. The organic layer was concentrated to afford the title compound (450 mg, 80%). LCMS: m/z 459.4 (97%).

Example 190

7-Fluoro-5-(piperidin-4-yl)-3-[(1,3,5-trimethyl-1H-pyrazol-4-yl)methyl]-1,3-benzoxazol-2-one To a solution of Example 189 (450 mg, 0.982 mmol) in 1,4-dioxane (2 mL), maintained at 0° C., was added 4N HCl in 1,4-dioxane (3 mL). The reaction mixture was stirred at r.t. for 12 h, then concentrated. The solid residue was dissolved in DCM (10 mL). The organic layer was washed with saturated $NaHCO_3$ solution. The organic layer was separated, then concentrated, to afford the title compound (0.25 g, 71%). $\delta_H$ (400 MHz, DMSO-$d_6$) 7.02-6.91 (m, 2H), 4.81 (s, 2H), 3.61 (s, 3H), 3.15-3.06 (m, 2H), 2.68 (m, 2H), 2.27 (s, 3H), 2.11 (s, 3H), 2.01 (m, 3H), 1.75 (m, 2H). LCMS: m/z 359 (98%).

Example 191

7-Fluoro-5-(piperidin-3-yl)-3-[(1,3,5-trimethyl-1H-pyrazol-4-yl)methyl]-1,3-benzoxazol-2(3H)-one To a solution of Example 105 (0.5 g, 1.42 mmol) in EtOH (100 mL) were added 1N HCl (5 mL) and $PtO_2$ (0.2 g). The reaction mixture was stirred under a hydrogen atmosphere at 60 psi at r.t. for 6 h, then filtered through Celite. The filtrate was concentrated. The crude residue was dissolved in DCM and the organic layer was washed with saturated aqueous $NaHCO_3$ solution. The organic layer was dried over $Na_2SO_4$, then concentrated, to afford the title compound (450 mg, 88%). $\delta_H$ (400 MHz, DMSO-$d_6$) 7.18-7.00 (m, 2H), 4.80 (s, 2H), 3.61 (s, 3H), 2.82 (m, 2H), 2.80 (m, 1H), 2.27 (s, 3H), 2.11 (s, 3H), 1.89 (m, 2H), 1.75 (s, 3H), 1.68 (m, 1H). LCMS: m/z 359.3 (98%).

Example 192

5-(1-Acetylpiperidin-3-yl)-7-fluoro-3-[(1,3,5-trimethyl-1H-pyrazol-4-yl)methyl]-1,3-benzoxazol-2-one To a solution of Example 191 (0.2 g, 0.558 mmol) in DCM (5 mL) were added acetyl chloride (0.052 g, 0.67 mmol) and triethylamine (0.2 mL, 1.676 mmol) at 0° C. The reaction mixture was stirred at r.t. for 12 h, then quenched with $H_2O$ (5 mL). The aqueous layer was extracted with DCM, then the organic layer was concentrated. The crude residue was purified by preparative TLC to afford the title compound (19 mg). $\delta_H$ (400 MHz, $CD_3OD$) 7.15 (d, J 30.8 Hz, 1H), 7.01 (dd, J 15.6, 11.5 Hz, 1H), 5.00 (d, J 3.8 Hz, 2H), 4.57 (t, J 13.8 Hz, 1H), 3.94 (s, 3H), 3.27-3.09 (m, 2H), 2.96-2.60 (m, 3H), 2.49 (d, J 7.8 Hz, 4H), 2.16 (d, J 4.4 Hz, 2H), 2.04 (m, 2H), 1.86 (m, 2H), 1.74-1.54 (m, 2H). LCMS: m/z 401.2, RT 2.15 minutes (100%).

Example 193

7-Fluoro-5-[1-(methylsulfonyl)piperidin-3-yl]-3-[(1,3,5-trimethyl-1H-pyrazol-4-yl)-methyl]-1,3-benzoxazol-2(3H)-one To a solution of Example 191 (0.2 g, 0.558 mmol) in DCM (5 mL) were added mesyl chloride (0.1 mL, 0.67 mmol) and triethylamine (0.2 mL, 1.676 mmol) at 0° C. The reaction mixture was stirred at r.t. for 12 h, then quenched with $H_2O$ (~7 mL). The aqueous layer was extracted with DCM, then the organic layer was concentrated. The crude residue was purified by preparative TLC to afford the title compound (9 mg). $\delta_H$ (400 MHz, DMSO-$d_6$) 7.10-7.07 (m, 2H), 4.80 (s, 2H), 3.61 (s, 3H), 3.57 (m, 2H), 2.89 (s, 3H), 2.79-2.62 (m, 3H), 2.28 (s, 3H), 2.10 (s, 3H), 1.85 (m, 2H), 1.60 (m, 2H). LCMS: m/z 437.2, RT 2.13 minutes (99%).

Example 194

3-{7-Fluoro-2-oxo-3-[(1,3,5-trimethyl-1H-pyrazol-4-yl)methyl]-1,3-benzoxazol-5-yl}-piperidine-1-carboxamide To a solution of Example 191 (0.2 g, 0.558 mmol) in THF (10 mL) were added AcOH (0.1 mL, 1.674 mmol) and potassium cyanate (0.678 g, 8.37 mmol) at 0° C. The reaction mixture was stirred at r.t. for 12 h, then concentrated. The crude residue was purified by preparative HPLC to afford the title compound (33 mg) $\delta_H$ (400 MHz, $CD_3OD$) 7.06-6.86 (m, 1H), 6.80 (d, J 8.1 Hz, 1H), 4.87 (s, 2H), 4.18-3.91 (m, 2H), 3.81 (s, 3H), 2.80 (ddd, J 42.6, 21.5, 11.2 Hz, 2H), 2.43 (s, 3H), 2.20 (s, 3H), 2.10-1.91 (m, 2H), 1.91-1.45 (m, 3H). LCMS: m/z 402.3, RT 1.73 minutes (100%).

Example 195

7-Fluoro-5-[1-(methylsulfonyl)piperidin-4-yl]-3-[(1,3,5-trimethyl-1H-pyrazol-4-yl)-methyl]-1,3-benzoxazol-2(3H)-one

Prepared from Example 190 in a similar manner to that described for Example 193 to give the title compound. $\delta_H$ (400 MHz, DMSO-$d_6$) 7.05-7.00 (m, 2H), 4.80 (s, 2H), 3.67 (dt, J 11.5, 2.4 Hz, 2H), 3.61 (s, 3H), 2.90 (s, 3H), 2.83 (d, J 2.4 Hz, 2H), 2.80 (d, J 2.5 Hz, 1H), 2.27 (s, 3H), 2.11 (s, 3H), 1.91-1.76 (m, 2H), 1.67 (qd, J 12.5, 4.1 Hz, 2H). LCMS: m/z 437.2, RT 2.11 minutes (99%).

Example 196

(2R)-6-(1-Acetylpiperidin-3-yl)-4-[(2,4-dimethyl-pyridin-3-yl)methyl]-8-fluoro-2-methyl-1,4-benzoxazin-3-one (Isomer A)

Prepared from Intermediates 1 and 84A in a similar manner to that described for Example 164. $\delta_H$ (500 MHz, DMSO-$d_6$) 8.17-8.12 (m, 1H), 7.03-7.00 (m, 1H), 6.98-6.86 (m, 1H), 6.62 (s, 1H), 5.42-5.30 (m, 1H), 5.18-5.07 (m, 1H), 4.86-4.79 (m, 1H), 4.45-4.19 (m, 1H), 3.82-3.58 (m, 1H), 3.00-2.78 (m, 1H), 2.47-2.38 (m, 5H), 2.31-2.26 (m, 3H), 2.02-1.96 (m, 3H), 1.78-1.66 (m, 2H), 1.47 (m, 5H). Method D uPLC-MS: MH+ m/z 426.3, RT 1.82 minutes (98%).

Example 197

(2R)-6-(1-Acetylpiperidin-3-yl)-4-[(6-bromo-7-fluoro-2-methylimidazo[1,2-a]pyridin-3-yl)methyl]-8-fluoro-2-methyl-1,4-benzoxazin-3-one

Prepared from Intermediates 27 and 84A in a similar manner to that described for Example 164. $\delta_H$ (500 MHz, DMSO-$d_6$) 9.03-8.91 (m, 1H), 7.60-7.53 (m, 1H), 7.02-6.91 (m, 2H), 5.74-5.67 (m, 1H), 5.53-5.46 (m, 1H), 4.93-4.87 (m, 1H), 4.48-4.25 (m, 1H), 3.87-3.60 (m, 1H), 3.04-2.82 (m, 1H), 2.63-2.54 (m, 1H), 2.48-2.39 (m, 1H), 2.30-2.25 (m, 3H), 2.03-1.95 (m, 3H), 1.74-1.65 (m, 2H), 1.55-1.27 (m, 5H). Method D uPLC-MS: MH+ m/z 549.1, RT 2.48 minutes (97%).

Example 198

(2R)-6-(1-Acetyl-4,4-difluoropyrrolidin-3-yl)-8-fluoro-2-methyl-4-[(1,3,5-trimethyl-1H-pyrazol-4-yl)methyl]-3,4-dihydro-2H-1,4-benzoxazin-3-one

A suspension of Intermediate 180 (74.5 mg, 0.12 mmol), 10% palladium on carbon (50% water wet) (12.25 mg, 0.01 mmol), acetic anhydride (15.3 µL, 0.16 mmol) and acetic acid (15.3 µL, 0.27 mmol) in DCM (3 mL) was stirred under an atmosphere of hydrogen for 17.5 h. The mixture was filtered through a Celite pad, washing with 1:1 DCM/MeOH (100 mL). The filtrate was concentrated in vacuo, then the residue was partitioned between saturated aqueous $Na_2CO_3$ solution (30 mL) and EtOAc (30 mL). The organic phase was separated and the aqueous layer was extracted with EtOAc (2×30 mL). The combined organic extracts were washed with brine (30 mL), dried over $MgSO_4$, filtered and concentrated in vacuo. Purification of the crude residue (46 mg) by column chromatography (0-100% EtOAc in heptane, then 0-10% MeOH in DCM), followed by HPLC (Method C), afforded the title compound (4.6 mg, 9%). $\delta_H$ (500 MHz, DMSO-$d_6$) 7.09-6.97 (m, 1H), 6.90-6.80 (m, 1H), 5.18-5.03 (m, 1H), 4.96-4.78 (m, 2H), 4.10-3.76 (m, 4H), 3.56 (s, 3H), 3.53-3.36 (m, 1H), 2.20-2.16 (m, 3H), 2.04-1.99 (m, 3H), 1.96-1.92 (m, 3H), 1.53-1.47 (m, 3H). Method E uPLC-MS: MH+ m/z 451.2, RT 2.51 minutes (99%).

Example 199

(2R)-6-(1-Acetylpiperidin-3-yl)-4-[(2,4-dimethyl-pyridin-3-yl)methyl]-8-fluoro-2-methyl-1,4-benzoxazin-3-one (Isomer B)

Prepared from Intermediates 1 and 84B in a similar manner to that described for Example 164. $\delta_H$ (500 MHz, DMSO-$d_6$) 8.19-8.11 (m, 1H), 7.05-6.98 (m, 1H), 6.98-6.82 (m, 1H), 6.62 (s, 1H), 5.46-5.27 (m, 1H), 5.19-5.04 (m, 1H), 4.83 (q, J 6.6 Hz, 1H), 4.48-4.20 (m, 1H), 3.87-3.48 (m, 1H), 3.04-2.80 (m, 1H), 2.59-2.53 (m, 1H), 2.47-2.42 (m, 3H), 2.42-2.36 (m, 1H), 2.32-2.26 (m, 3H), 2.03-1.96 (m, 3H), 1.76-1.65 (m, 2H), 1.57-1.24 (m, 5H). Method D uPLC-MS: MH+ m/z 426.3, RT 1.80 minutes (100%).

Example 200

(2R)-6-(1-Acetylpiperidin-3-yl)-8-fluoro-2-methyl-4-[(2-methylimidazo[1,2-a]pyrazin-3-yl)methyl]-1,4-benzoxazin-3-one

Prepared from Intermediates 26 and 84A in a similar manner to that described for Example 164. $\delta_H$ (500 MHz, $CD_3OD$) 8.89 (d, J 4.0 Hz, 1H), 8.48 (d, J 4.3 Hz, 1H), 7.96 (t, J 4.3 Hz, 1H), 6.93 (m, 1H), 6.88 (m, 1H), 5.84-5.44 (m, 2H), 4.78 (m, 1H), 4.63-4.40 (m, 1H), 4.00-3.71 (m, 1H), 3.23-2.91 (m, 1H), 2.72-2.54 (m, 2H), 2.52 (m, 3H), 2.14 (s, 2H), 2.08 (s, 1H), 1.97-1.72 (m, 2H), 1.68-1.44 (m, 5H). Method A HPLC-MS: MH+ m/z 452, RT 3.47 minutes (95%).

Example 201

3-{[6-(1-Acetylpiperidin-3-yl)-8-fluoro-3-oxo-1,4-benzoxazin-4-yl]methyl}-2-methyl-imidazo[1,2-a]pyridine-6-carbonitrile

Prepared from Intermediates 24 and 82 in a similar manner to that described for Example 164. $\delta_H$ (500 MHz, DMSO-$d_6$) 9.37 (s, 1H), 7.62 (dd, J 9.3, 5.4 Hz, 1H), 7.54-7.44 (m, 1H), 7.04-6.90 (m, 2H), 5.62 (d, J 4.0 Hz, 2H), 4.82 (s, 2H), 4.50-4.25 (m, 1H), 3.73 (m, 1H), 3.00 (t, J 12.2 Hz, 1H), 2.91 (t, J 12.4 Hz, 0H), 2.31 (s, 3H), 1.99 (s, 3H), 1.69 (d, J 8.5 Hz, 2H), 1.51 (m, 2H), 1.25 (s, 2H). Method A HPLC-MS: MH+ m/z 462.0, RT 3.43 minutes (96%).

Example 202

(2R)-8-Fluoro-4-[(6-fluoro-2-methylimidazo[1,2-a]pyridin-3-yl)methyl]-2-methyl-6-[3-(methylsulfonimidoyl)phenyl]-1,4-benzoxazin-3-one

Prepared from Intermediates 177 and 187 in a similar manner to that described for Example 64. $\delta_H$ (500 MHz, DMSO-$d_6$) 8.57 (dd, J 5.0, 2.2 Hz, 1H), 8.14 (s, 1H), 7.93 (d, J 7.1 Hz, 1H), 7.79 (d, J 7.9 Hz, 1H), 7.66 (t, J 7.8 Hz, 1H), 7.50 (dd, J 9.8, 5.4 Hz, 1H), 7.46 (d, J 11.3, 1.6 Hz, 1H), 7.42 (s, 1H), 7.30 (ddd, J 10.3, 8.3, 2.4 Hz, 1H), 5.81-5.72 (m, 1H), 5.68-5.61 (m, 1H), 5.07-5.00 (m, 1H), 4.27 (s, 1H), 3.15 (s, 3H), 2.33-2.27 (m, 3H), 1.57 (d, J 6.7 Hz, 3H). Method D HPLC-MS: MH+ m/z 497.2, RT 1.90 minutes (100%).

Example 203

3-({(2R)-8-Fluoro-2-methyl-6-[3-(methylsulfonimidoyl)phenyl]-3-oxo-1,4-benzoxazin-4-yl}methyl)-2-methylimidazo[1,2-a]pyrazine-6-carbonitrile Prepared from Intermediates 176 and 187 in a similar manner to that described for Example 64. $\delta_H$ (500 MHz, CDCl$_3$) 9.04-8.94 (m, 1H), 8.92 (s, 1H), 8.39-8.28 (m, 1H), 8.03 (d, J 6.7 Hz, 1H), 7.71-7.64 (m, 2H), 7.25-7.19 (m, 1H), 7.16-7.10 (m, 1H), 5.72-5.54 (m, 2H), 4.88-4.77 (m, 1H), 3.36-3.26 (m, 3H), 2.61-2.55 (m, 3H), 1.74-1.67 (m, 3H). Method A HPLC-MS: MH+ m/z 505.0, RT 3.60 minutes (95%).

Example 204

(2R)-8-Fluoro-2-methyl-6-[3-(methylsulfonimidoyl)phenyl]-4-[(1,3,5-trimethyl-1H-pyrazol-4-yl)methyl]-1,4-benzoxazin-3-one Prepared from Intermediate 187 and (1,3,5-trimethyl-1H-pyrazol-4-yl)methanol in a similar manner to that described for Example 64. $\delta_H$ (500 MHz, DMSO-d$_6$) 8.05-8.02 (m, 1H), 7.93 (d, J 7.9 Hz, 1H), 7.89 (d, J 8.0 Hz, 1H), 7.70 (t, J 7.8 Hz, 1H), 7.42 (d, J 11.4 Hz, 1H), 7.18 (s, 1H), 5.24-5.18 (m, 1H), 5.02-4.94 (m, 2H), 4.31 (s, 1H), 3.57-3.56 (m, 3H), 3.14 (s, 3H), 2.23 (m, 3H), 1.97 (s, 3H), 1.54 (m, 3H). Method D HPLC-MS: MH+ m/z 457.2, RT 2.48 minutes (96%).

Example 205

(2R)-4-[(2,4-Dimethylpyridin-3-yl)methyl]-8-fluoro-2-methyl-6-[3-(methyl-sulfonimidoyl)phenyl]-1,4-benzoxazin-3-one Prepared from Intermediates 1 and 187 in a similar manner to that described for Example 64. $\delta_H$ (500 MHz, DMSO-d$_6$) 8.15-8.16 (m, 1H), 7.96 (s, 1H), 7.91 (d, J 7.7 Hz, 1H), 7.79 (d, J 7.9 Hz, 1H), 7.67 (t, J 7.8 Hz, 1H), 7.43 (d, J 11.1 Hz, 1H), 7.06-7.03 (m, 2H), 5.46-5.42 (m, 1H), 5.27-5.24 (m, 1H), 4.95 (q, J 6.7 Hz, 1H), 4.30 (s, 1H), 3.14 (s, 3H), 2.46 (s, 3H), 2.34 (s, 3H), 1.52 (d, J 6.7 Hz, 3H). Method D uPLC-MS: MH+ m/z 454.2, RT 1.70 minutes (100%).

Example 206

(2R)-8-Fluoro-4-[(6-methoxy-2-methylimidazo[1,2-a]pyrazin-3-yl)methyl]-2-methyl-6-[3-(methylsulfonimidoyl)phenyl]-1,4-benzoxazin-3-one Prepared from Intermediates 178 and 187 in a similar manner to that described for Example 64. $\delta_H$ (500 MHz, DMSO-d$_6$) 8.66 (s, 1H), 8.14 (s, 1H), 8.03 (s, 1H), 7.92 (d, J 7.8 Hz, 1H), 7.80 (d, J 7.6 Hz, 1H), 7.65 (t, J 7.8 Hz, 1H), 7.48 (d, J 11.3 Hz, 1H), 7.43 (s, 1H), 5.80 (d, J 16.6 Hz, 1H), 5.69 (d, J 16.5 Hz, 1H), 5.04 (q, J 6.6 Hz, 1H), 4.30 (s, 1H), 3.83 (s, 3H), 3.15 (s, 3H), 2.35 (s, 3H), 1.56 (d, J 6.7 Hz, 3H). Method D uPLC-MS: MH+ m/z 510.1, RT 3.58 minutes (98%).

Example 207

3-({(2R)-6-[3-(Cyclopropylsulfanyl)phenyl]-8-fluoro-2-methyl-3-oxo-1,4-benzoxazin-4-yl}methyl)-2-methylimidazo[1,2-a]pyridine-6-carbonitrile Prepared from Intermediate 125 and 3-(cyclopropylsulfanyl)phenylboronic acid in a similar manner to that described for Example 60 to give the title compound. $\delta_H$ (400 MHz, DMSO-d$_6$) 9.26 (m, 1H), 7.62 (dd, 1H, J 9.3, 0.8 Hz), 7.52 (d, 1H, J 1.6 Hz), 7.34 (m, 6H), 5.72 (m, 2H), 5.02 (m, 1H), 2.34 (m, 1H), 2.27 (s, 3H), 1.56 (d, 3H, J 6.7 Hz), 1.08 (m, 2H), 0.59 (m, 2H). HPLC-MS: MH+ m/z 499, RT 2.88 minutes.

Example 208

(2R)-4-[(6-Bromo-7-fluoro-2-methylimidazo[1,2-a]pyridin-3-yl)methyl]-8-fluoro-2-methyl-6-[3-(methylsulfinyl)phenyl]-1,4-benzoxazin-3-one Prepared from Intermediate 181 and 3-(methylsulfanyl)phenylboronic acid in a similar manner to that described for Example 60, followed by oxidation as described for Example 61, to give the title compound. $\delta_H$ (400 MHz, DMSO-d$_6$) 8.85 (d, 1H, J 4.3 Hz), 7.87 (d, 1H, J 8.3 Hz), 7.71 (m, 3H), 7.55 (d, 1H, J 9.6 Hz), 7.45 (m, 2H), 5.69 (m, 2H), 5.02 (q, 1H, J 6.7 Hz), 2.81 (s, 3H), 2.27 (s, 3H), 1.56 (d, 3H, J 6.7 Hz). HPLC-MS: MH+ m/z 560 6, RT 2.30 minutes.

Example 209

3-{[(2R)-8-Fluoro-6-(4-fluoro-3-sulfamoylphenyl)-2-methyl-3-oxo-1,4-benzoxazin-4-yl]-methyl}-2-methylimidazo[1,2-a]pyridine-6-carbonitrile Bis(pinacolato)diboron was added to 5-bromo-2-fluorobenzenesulfonamide in the presence of Pd(dppf)Cl$_2$ as described for Intermediate 144. The resulting material was reacted with Intermediate 125 in a similar manner to that described in Example 36 to provide the title compound. $\delta_H$ (400 MHz, DMSO-d$_6$) 9.22 (s, 1H), 7.91 (m, 2H), 7.61 (dd, 1H, J 9.3, 0.7 Hz), 7.50 (m, 4H), 7.36 (dd, 1H, J 11.2, 1.7 Hz), 5.72 (m, 2H), 5.01 (m, 1H), 2.30 (s, 3H), 1.55 (d, 3H, J 6.7 Hz). HPLC-MS: MH+ m/z 524, RT 1.98 minutes.

Example 210

3-({(2R)-6-[3-(Cyclopropylsulfonyl)phenyl]-8-fluoro-2-methyl-3-oxo-1,4-benzoxazin-4-yl}methyl)-2-methylimidazo[1,2-a]pyridine-6-carbonitrile Prepared from Example 207 in a similar manner to that described for Example 61 to give the title compound. $\delta_H$ (300 MHz, DMSO-d$_6$) 9.21 (m, 1H), 8.09 (s, 1H), 7.89 (m, 2H), 7.72 (m, 1H), 7.60 (dd, 1H, J 9.3, 0.8 Hz), 7.50 (m, 3H), 5.75 (m, 2H), 5.03 (m, 1H), 2.95 (m, 1H), 2.29 (s, 3H), 1.55 (d, 3H, J 6.7 Hz), 1.10 (m, 4H). HPLC-MS: MH+ m/z 531, RT 2.30 minutes.

Example 211

3-({(2R)-6-[3-(Cyclopropylsulfinyl)phenyl]-8-fluoro-2-methyl-3-oxo-1,4-benzoxazin-4-yl}methyl)-2-methylimidazo[1,2-a]pyridine-6-carbonitrile Prepared from Example 207 in a similar manner to that described for Example 61 to give the title compound. $\delta_H$ (300 MHz, DMSO-$d_6$) 9.25 (d, 1H, J 1.2 Hz), 7.84 (d, 1H, J 7.0 Hz), 7.55 (m, 7H), 5.73 (m, 2H), 5.02 (m, 1H), 2.49 (m, 1H), 2.27 (s, 3H), 1.55 (d, 3H, J 6.7 Hz), 0.90 (m, 4H). HPLC-MS: MH+ m/z 515, RT 2.11 minutes.

Example 212

3-({(2R)-8-Fluoro-6-[3-fluoro-5-(methylsulfonimidoyl)phenyl]-2-methyl-3-oxo-1,4-benzoxazin-4-yl}methyl)-2-methylimidazo[1,2-a]pyridine-6-carbonitrile Prepared from Intermediate 202 in a similar manner to that described for Example 62 to give the title compound. $\delta_H$ (400 MHz, DMSO-$d_6$) 9.22 (s, 1H), 8.02 (m, 1H), 7.74 (m, 2H), 7.54 (m, 4H), 5.75 (m, 2H), 5.03 (q, 1H, J 6.5 Hz), 4.43 (s, 1H), 3.19 (s, 3H), 2.29 (s, 3H), 1.55 (d, 3H, J 6.7 Hz). HPLC-MS: MH+ m/z 522, RT 1.99 minutes.

Example 213

3-{[(2R)-8-Fluoro-6-{4-(hydroxymethyl)-3-[(R)-methylsulfinyl]phenyl}-2-methyl-3-oxo-1,4-benzoxazin-4-yl]methyl}-2-methylimidazo[1,2-a]pyridine-6-carbonitrile Prepared from Intermediate 206 in a similar manner to that described for Example 62 to give the title compound. $\delta_H$ (400 MHz, DMSO-$d_6$) 9.20 (m, 1H), 8.07 (dd, 1H, J 6.3, 2.0 Hz), 7.54 (m, 6H), 5.73 (m, 2H), 5.51 (m, 1H), 5.03 (m, 1H), 4.63 (m, 2H), 2.80 (s, 3H), 2.33 (m, 3H), 1.56 (d, 3H, J 6.6 Hz). HPLC-MS: MH+ m/z 519, RT 1.78 minutes.

Example 214

7-{7-Fluoro-2-oxo-3-[(1,3,5-trimethyl-1H-pyrazol-4-yl)methyl]-2,3-dihydro-1,3-benzoxazol-5-yl}-1,2,3,4-tetrahydroisoquinolin-1-one Prepared from Intermediates 78 and 160 in a similar manner to that described for Example 1. $\delta_H$ (500 MHz, DMSO-$d_6$) 8.08 (d, J 1.9 Hz, 1H), 8.04 (s, 1H), 7.77 (dd, J 7.9, 2.0 Hz, 1H), 7.46-7.42 (m, 2H), 7.31 (d, J 1.2 Hz, 1H), 4.91 (s, 2H), 3.64 (s, 3H), 3.42 (td, J 6.5, 2.6 Hz, 2H), 2.96 (t, J 6.5 Hz, 2H), 2.32 (s, 3H), 2.12 (s, 3H). Method D uPLC-MS: MH+ m/z 421.1, RT 2.76 minutes (98%).

The invention claimed is:
1. A compound of formula (I):

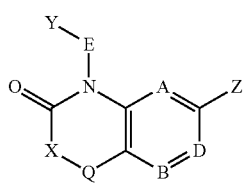

(I)

or an N-oxide or a pharmaceutically acceptable salt thereof,
wherein,
A represents C—$R^0$ or N;
B represents C—$R^1$;
D represents C—$R^2$;
E represents —$CH_2$— or —$CH(CH_3)$—;
Q represents —O—;
X represents —$C(R^{6a})(R^{6b})$—;
Y represents pyrazolyl, isoxazolyl, imidazolyl, imidazo[1,2-a]pyridinyl, imidazo[1,2-a]pyrazinyl, triazolyl, pyridinyl, pyridazinyl or pyrimidinyl, any of which groups may be optionally substituted by one, two or three substituents independently selected from halogen, $C_{1-6}$ alkyl, halo($C_{1-6}$)alkyl, $C_{1-6}$ alkoxy, ($C_{1-6}$)alkoxy($C_{1-6}$)alkoxy($C_{1-6}$)alkyl, $C_{1-6}$ alkylthio, $C_{1-6}$ alkylsulfonyl, $C_{1-6}$ alkylsulfonylphenyl, hydroxy($C_{1-6}$)alkyl, cyano, oxetanyloxy($C_{1-6}$)alkyl, ($C_{1-6}$)alkylheteroaryl, ($C_{1-6}$)alkoxyheteroaryl, hydroxy($C_{1-6}$)alkylheteroaryl and morpholinylheteroaryloxy($C_{1-6}$)alkyl;
Z represents phenyl, pyrrolidinyl, dihydrobenzoisothiazolyl, piperidinyl, 1,2,3,4-tetrahydroquinolinyl, 1,2,3,4-tetrahydro-isoquinolinyl, 1,2,3,6-tetrahydropyridinyl, 4,5,6,7-tetrahydro-benzothienyl, 4,5,6,7,8-pentahydrothieno[3,2-c]azepinyl, indolyl, pyrrolo[2,1-f][1,2,4]triazinyl, pyrazolyl, indazolyl, pyrazolo[4,3-b]pyridinyl, 4,5,6,7,8-pentahydrothiazolo[4,5-c]-azepinyl, 4,5,6,7,8-pentahydrothiazolo[5,4-c]azepinyl, pyridinyl, quinolinyl, phthalazinyl or pyrimidinyl, any of which groups may be optionally substituted by one, two or three substituents independently selected from halogen, $C_{1-6}$ alkyl, $C_{1-6}$ alkoxy, difluoromethoxy, $C_{1-6}$ alkylthio, $C_{1-6}$ alkylsulfinyl, $C_{1-6}$ alkyl-sulfonyl, cyclopropylthio, cyclopropylsulfinyl, cyclopropyl-sulfonyl, hydroxy($C_{1-6}$)alkyl, oxo, $C_{2-6}$ alkylcarbonyl, $C_{2-6}$ alkoxycarbonyl, aminocarbonyl, aminosulfonyl, ($C_{1-6}$)alkyl-sulphoximinyl, benzyl, morpholinyl and heteroaryl;
$R^0$ represents hydrogen, halogen or $C_{1-6}$ alkyl;
$R^1$ and $R^2$ independently represent hydrogen, halogen, cyano, $C_{1-6}$ alkyl, fluoromethyl, difluoromethyl, trifluoromethyl, hydroxy, hydroxy($C_{1-6}$)alkyl, $C_{1-6}$ alkoxy, difluoromethoxy, trifluoromethoxy, pentafluorothio, $C_{1-6}$ alkylthio, $C_{1-6}$ alkylsulphinyl, $C_{1-6}$ alkylsulphonyl, amino, amino($C_{1-6}$)alkyl, $C_{1-6}$ alkylamino, di($C_{1-6}$)alkylamino, formyl, $C_{2-6}$ alkylcarbonyl, carboxy, $C_{2-6}$ alkoxycarbonyl, aminocarbonyl, $C_{1-6}$ alkyl-aminocarbonyl, di($C_{1-6}$)alkylaminocarbonyl, aminosulphonyl, $C_{1-6}$ alkylaminosulphonyl, di($C_{1-6}$)alkylaminosulphonyl, ($C_{1-6}$)alkylsulphoximinyl or [($C_{1-6}$)alkyl][N—($C_{1-6}$)alkyl]-sulphoximinyl;
$R^{6a}$ represents hydrogen, halogen, trifluoromethyl or methyl; and
$R^{6b}$ represents hydrogen, fluoro or methyl.
2. The compound as claimed in claim 1, wherein the compound is represented by formula (IIA):

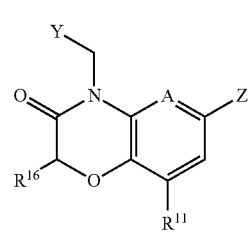

(IIA)

or an N-oxide or a pharmaceutically acceptable salt thereof, wherein:

$R^{11}$ represents hydrogen, halogen or $C_{1-6}$ alkyl; and $R^{16}$ represents hydrogen, halogen or methyl.

3. A pharmaceutical composition comprising a compound as claimed in claim 1, or an N-oxide or a pharmaceutically acceptable salt thereof, in association with a pharmaceutically acceptable carrier.

4. The pharmaceutical composition as claimed in claim 3, wherein the pharmaceutical composition further comprises an additional pharmaceutically active ingredient.

5. A method for modulating tumor necrosis factor alpha activity in a patient, which comprises administering to a patient in need of such treatment an effective amount of a compound as claimed in claim 1, or an N-oxide or a pharmaceutically acceptable salt thereof.

6. The method as claimed in claim 5, wherein the patient has a disorder selected from the group consisting of an inflammatory disorder, an autoimmune disorder, a neurological disorder, a neurodegenerative disorder, pain, a nociceptive disorder, a cardiovascular disorder, a metabolic disorder, an ocular disorder and an oncological disorder.

* * * * *